(12) United States Patent
Duchateau et al.

(10) Patent No.: US 11,186,824 B2
(45) Date of Patent: Nov. 30, 2021

(54) METHODS FOR ENGINEERING ALLOGENEIC T CELL TO INCREASE THEIR PERSISTENCE AND/OR ENGRAFTMENT INTO PATIENTS

(71) Applicant: Cellectis, Paris (FR)

(72) Inventors: Philippe Duchateau, Draveil (FR); Jean-Pierre Cabaniols, Saint Lau la Foret (FR); Julien Valton, New York, NY (US); Laurent Poirot, Paris (FR)

(73) Assignee: CELLECTIS, Paris (FR)

( * ) Notice: Subject to any disclaimer, the term of this patent is extended or adjusted under 35 U.S.C. 154(b) by 792 days.

(21) Appl. No.: 15/556,558

(22) PCT Filed: Mar. 11, 2016

(86) PCT No.: PCT/EP2016/055332
§ 371 (c)(1),
(2) Date: Mar. 9, 2018

(87) PCT Pub. No.: WO2016/142532
PCT Pub. Date: Sep. 15, 2016

(65) Prior Publication Data
US 2018/0291343 A1    Oct. 11, 2018

(30) Foreign Application Priority Data
Mar. 11, 2015   (DK) .............................. PA201570138

(51) Int. Cl.
| | | |
|---|---|---|
| *A61K 35/17* | (2015.01) | |
| *A61K 48/00* | (2006.01) | |
| *C12N 5/0783* | (2010.01) | |
| *C12N 5/00* | (2006.01) | |
| *C07K 14/005* | (2006.01) | |
| *C07K 14/705* | (2006.01) | |
| *C07K 14/74* | (2006.01) | |
| *C07K 16/28* | (2006.01) | |
| *C12N 9/22* | (2006.01) | |
| *C12N 15/11* | (2006.01) | |
| *A61K 39/00* | (2006.01) | |

(52) U.S. Cl.
CPC ............ *C12N 5/0638* (2013.01); *A61K 35/17* (2013.01); *C07K 14/005* (2013.01); *C07K 14/70503* (2013.01); *C07K 14/70532* (2013.01); *C07K 14/70539* (2013.01); *C07K 16/2818* (2013.01); *C07K 16/2827* (2013.01); *C12N 5/0006* (2013.01); *C12N 9/22* (2013.01); *C12N 15/11* (2013.01); *A01K 2207/12* (2013.01); *A61K 2039/505* (2013.01); *A61K 2039/5156* (2013.01); *A61K 2039/5158* (2013.01); *C07K 2319/00* (2013.01); *C12N 2310/20* (2017.05); *C12N 2501/48* (2013.01); *C12N 2501/51* (2013.01); *C12N 2501/599* (2013.01); *C12N 2510/00* (2013.01); *C12N 2710/16122* (2013.01); *C12N 2710/16133* (2013.01); *C12N 2710/16171* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 2005/0214313 A1 * | 9/2005 | Peach .................... | C07H 21/04 424/185.1 |
| 2006/0222633 A1 | 10/2006 | Shlomchik et al. | |
| 2013/0315884 A1 * | 11/2013 | Gaietto .................... | A61P 5/38 424/93.71 |

FOREIGN PATENT DOCUMENTS

| | | |
|---|---|---|
| WO | 95/17911 A1 | 7/1995 |
| WO | 2005/097160 A2 | 10/2005 |
| WO | 2011/064779 A2 | 6/2011 |
| WO | 2011/109789 A2 | 9/2011 |
| WO | 2014/184744 A1 | 11/2014 |
| WO | 2014184741 A1 | 11/2014 |
| WO | 2014/191128 A1 | 12/2014 |

OTHER PUBLICATIONS

Rong et al., Cell Stem Cell, Jan. 2, 2014, 14: 121-130.*
Riolobos et al., Mol. Ther., 2013, 21: 1232-1241.*
Favier et al., PLoS One, 2011,6: 1-8.*
Reyburn et al., Nature, 1997, 386: 514-517.*
Mincheva-Nilsson et al., J. Immunol., 2006, 176: 3585-3592.*
Dotti et al., Blood, 2009, 114: 1457-1458.*
Blast Alignment, 2020.*
Sequence alignment_16, 2020.*
Sequence alignment_17, 2020.*
Sequence alignment_18, 2020.*
Pardoll, Nat. Rev. Cancer, 2012, 12: 252-264.*
Blazar, J. Immunol., 2003, 171: 1272-1277.*

(Continued)

*Primary Examiner* — Ileana Popa
(74) *Attorney, Agent, or Firm* — Arrigo, Lee, Guttman & Mouta-Bellum LLP

(57) ABSTRACT

The present invention relates to methods for developing engineered immune cells such as T-cells for immunotherapy that have a higher potential of persistence and/or engraftment in host organism. IN particular, this method involves an inactivation of at least one gene involved in self/non self recognition, combined with a step of contact with at least one non-endogenous immunosuppressive polypeptide. The invention allows the possibility for a standard and affordable adoptive immunotherapy, whereby the risk of GvH is reduced.

Figure 1:
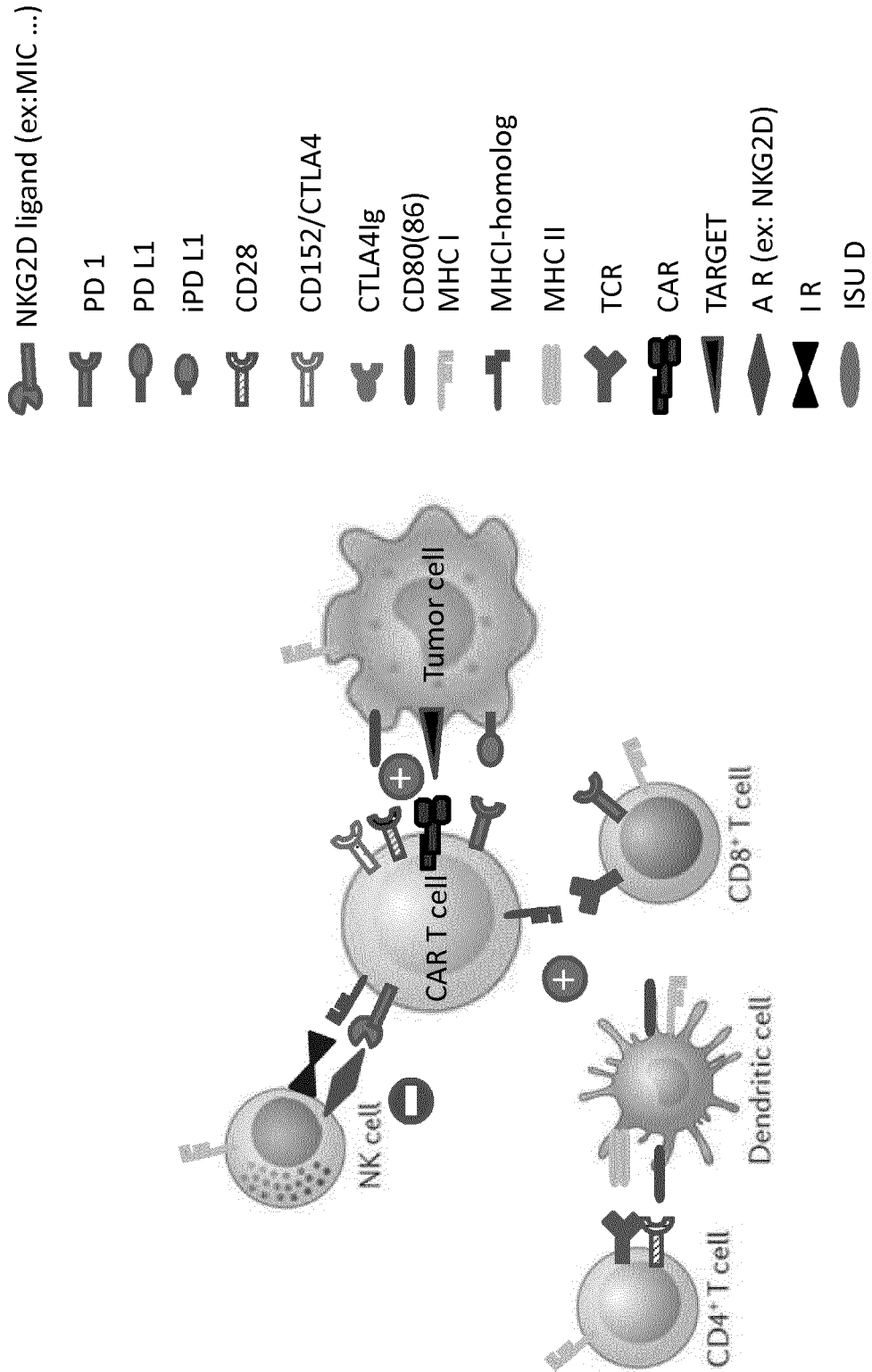

22 Claims, 27 Drawing Sheets
Specification includes a Sequence Listing.

(56) References Cited

OTHER PUBLICATIONS

Torikai et al: "A foundation for universal T-cell based immunotherapy: T cells engineered to express a CD19-specific chimeric-antigen-receptor and eliminate expression of endogenous TCR", Blood, vol. 119, No. 24, Jun. 14, 2012, pp. 5697-5705.
Cooper et al: "Combining checkpoint inhibitors and BRAF-targeted agents against metastatic melanoma", Oncoimmunology, vol. 2, No. 5, May 1, 2013, p. e24320.
Wilkinson et al: "Modulation of natural killer cells by human cytomegalovirus", Journal of Clinical Virology, Elsevier, Amsterdam, NL, vol. 41, No. 3, Feb. 15, 2008, pp. 206-212.
European Patent Office, International Search Report for International Appln. PCT/EP2016/055332, dated May 31, 2016.
Curran et al: "PD-1 and CTLA-4 combination blockade expands infiltrating T cells and reduces regulatory T and myeloid cells within B16 melanoma tumors", Proceedings of the National Academy of Sciences, vol. 107, No. 9, Mar. 2, 2010, pp. 4275-4280.
John et al: "Anti-PD-1 antibody therapy potently enhances the eradication of established tumors by gene-modified T cells", Clinical Cancer Research, The American Association for Cancer Research, US, vol. 19, No. 20, Oct. 15, 2013, pp. 5636-5646.
Thell et al., "Immunosuppressive peptides and their therapeutic applications", Drug Discov. Today., May 2014; 19(5): 645-653.
Rong et al., "An Effective Approach to Prevent Immune Rejection of Human ESC-Derived Allografts" Cell Stem Cell 14, 121-130, Jan. 2, 2014.
Moon et al., Multifactorial T cell Hypofunction that is Reversible Can Limit the Efficacy of Chimeric Antibody Receptor-transduced Human T cells in Solid Tumors, Clin Cancer Res. Aug. 15, 2014; 20(16): 4262-4273.

* cited by examiner

| Group | % CAR+ cells | % PDL1+ cells | CTLA4Ig concentration (pg/µl) |
|---|---|---|---|
| CAR CD123 | 98.3 | n.a. | n.a. |
| CAR CD123/PDL1 | 97.3 | 96.6 | n.a. |
| CAR CD123/CTLA4Ig | 97.7 | n.a. | 250 |
| CAR CD123/PDL1/CTLA4Ig | 97.1 | 91.9 | 275 |

Figure 22

METHODS FOR ENGINEERING ALLOGENEIC T CELL TO INCREASE THEIR PERSISTENCE AND/OR ENGRAFTMENT INTO PATIENTS

FIELD OF THE INVENTION

The present invention relates to methods for developing engineered non-alloreactive T-cells for immunotherapy and more specifically to methods for increasing the persistence and/or the engraftment of allogeneic immune cells. This method involves at least a step of inactivation of a gene implicated in the self/non-selfrecognition by the use of preferably specific rare-cutting endonuclease, followed by a step of contact of said engineered immune cells with at least one non-endogenous immunosuppressive polypeptide (such as PD-L1 ligand and/or CTLA-4 Ig). This invention also relates to engineered immune cells and functional derivatives thereof, Chimeric Antigen Receptor (CAR), multichain CAR and their use thereof to enhance the efficiency of immunotherapy. The invention opens the way to a safer strategy by reducing the risk of graft versus host disease GvHD and allows an affordable adoptive immunotherapy.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010).

The current protocol for treatment of patients using adoptive immunotherapy is based on autologous cell transfer. In this approach, T lymphocytes are recovered from patients, genetically modified or selected ex vivo, cultivated in vitro in order to amplify the number of cells if necessary and finally infused into the patient. In addition to lymphocyte infusion, the host may be manipulated in other ways that support the engraftment of the T cells or their participation in an immune response, for example pre-conditioning (with radiation or chemotherapy) and administration of lymphocyte growth factors (such as IL-2). Each patient receives an individually fabricated treatment, using the patient's own lymphocytes (i.e. an autologous therapy). Autologous therapies face substantial technical and logistic hurdles to practical application, their generation requires expensive dedicated facilities and expert personnel, they must be generated in a short time following a patient's diagnosis, and in many cases, pretreatment of the patient has resulted in degraded immune function, such that the patient's lymphocytes may be poorly functional and present in very low numbers. Because of these hurdles, each patient's autologous cell preparation is effectively a new product, resulting in substantial variations in efficacy and safety. Ideally, one would like to use a standardized therapy in which allogeneic therapeutic cells could be pre-manufactured, characterized in detail, and available for immediate administration to patients. By allogeneic it is meant that the cells are obtained from individuals belonging to the same species but are genetically dissimilar. However, the use of allogeneic cells presently has many drawbacks. In immune-competent hosts allogeneic cells are rapidly rejected, a process termed host versus graft rejection (HvG), and this substantially limits the efficacy of the transferred cells. In immune-incompetent hosts, allogeneic cells are able to engraft, but their endogenous TCR specificities recognize the host tissue as foreign, resulting in graft versus host disease (GvHD), which can lead to serious tissue damage and death. In order to effectively use allogeneic cells, both of these problems must be overcome.

In immunocompetent hosts, allogeneic cells are rapidly rejected by the host immune system. It has been demonstrated that, allogeneic leukocytes present in non-irradiated blood products will persist for no more than 5 to 6 days. (Boni, Muranski et al. 2008). Thus, to prevent rejection of allogeneic cells, the host's immune system must be effectively suppressed. Glucocorticoidsteroids are widely used therapeutically for immunosuppression (Coutinho and Chapman 2011). This class of steroid hormones binds to the glucocorticoid receptor (GR) present in the cytosol of T cells resulting in the translocation into the nucleus and the binding of specific DNA motifs that regulate the expression of a number of genes involved in the immunologic process. Treatment of T cells with glucocorticoid steroids results in reduced levels of cytokine production leading to T cell anergy and interfering in T cell activation. Alemtuzumab, also known as CAMPATH1-H, is a humanized monoclonal antibody targeting CD52, a 12 amino acid glycosylphosphatidyl-inositol-(GPI) linked glycoprotein (Waldmann and Hale 2005). CD52 is expressed at high levels on T and B lymphocytes and lower levels on monocytes while being absent on granulocytes and bone marrow precursors. Treatment with Alemtuzumab, a humanized monoclonal antibody directed against CD52, has been shown to induce a rapid depletion of circulating lymphocytes and monocytes. It is frequently used in the treatment of T cell lymphomas and in certain cases as part of a conditioning regimen for transplantation. However, in the case of adoptive immunotherapy the use of immunosuppressive drugs will also have a detrimental effect on the introduced therapeutic T cells. Therefore, to effectively use an adoptive immunotherapy approach in these conditions, the introduced cells would need to be resistant to the immunosuppressive treatment.

On the other hand, T cell receptors (TCR) are cell surface receptors that participate in the activation of T cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable region of the alpha and beta chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of GVHD. It has been shown that normal surface expression of the TCR depends on the coordinated synthesis and assembly of all seven components of the complex (Ashwell and Klusner 1990). The inactivation of TCRalpha or TCRbeta can result in the elimination of the TCR from the surface of T cells preventing recognition of alloantigen and thus GVHD. However, TCR disruption results in the elimination of the CD3 signaling component and alters the means of further T cell expansion.

Adaptive immune response is a complex biological system where numerous cellular components interact. Professional Antigen Presenting Cells (APC) are able to process foreign bodies and expose them to helper T cells in the context of MHC Class II molecules. Activated helper T cells will in turn stimulate B cells response and cytotoxic T (CTL) cells response. CTL recognize foreign peptides presented by MHC Class I molecules but in the case of alloreactivity, recognize and kill cells bearing foreign MHC Class I. MHC Class I molecules are composed of 2 entities: the highly polymorphic, transmembrane heavy chain and a small invariant polypeptide, the β2-microglobuline (β2-m) encoded by B2M gene. The expression of the MHC Class I heavy chain at the cell surface requires its association with the β2-m. Hence, abrogation of β2-m expression in CAR T cells will impair MHC Class I expression and make them invisible to host CTL. However, MHC Class I deficient CAR T cells are susceptibe to lysis by host NK cells, which target cells lacking MHC Class I molecules [Ljunggren H G et al. (1990), Immunl Today. 11:237-244].

NK cells exert cytotoxic functions towards the cells they interact with based on the balance between activating and inhibitory signals they received through different monomorphic or polymorphic receptors. One central activating receptor on human NK cells is NKG2D and its ligands include proteins such as MICA, MICB, ULBP1, ULBP2, ULBP3 [Raulet D H, (2003), Nature Reviews Immunology 3 (10): 781-79]. On the other hand, the inhibitory signal is mediated through the interaction between NK receptors like LIR-1/ILT2 and MHC Class I molecules [Ljunggren H G et al. (1990), Immunl Today. 11:237-244]. Some viruses such as cytomegaloviruses have aquired mechanisms to avoid NK cell mediate immune surveillance. HCMV genome encodes proteins that are able to prevent MHC Class I surface expression (i.e. US2, US3, US6 and US11) while expressing a MHC class I homolog protein (UL18) that acts as a decoy to block NK-mediated cell lysis [Kim, Y et al. (2008), PLOS Pathogens. 4: e1000123, and Wilkinson G. et al. (2010). J Clin Virol. 41(3):206-212]. Moreover, HCMV interferes with the NKG2D pathway by secreting a protein able to bind NKG2D ligands and prevent their surface expression [Welte S A et al. (2003), Eur J Immunol 33 (1): 194-203]. In tumor cells, some mechanisms have evolved to evade NKG2D response by secreting NKG2D ligands such as ULBP2, MICB or MICA (Waldhauer I, Steinle A (2003). Proteolytic release of soluble UL16-binding protein 2 from tumor cells. Cancer Res 2006; 66(5): 2520-2526; Salih H R et al. (2006), Hum Immunol. 2006 March; 67(3):188-95; Salih H R et al. (2003) Blood. 2003 Aug. 15; 102(4):1389-96; Salih H R et al. (2002) J Immunol.; 169(8):4098-102].

Many strategies are used by viruses to escape host immune system Tumor cells expressing a retroviral envelope escape immune rejection in vivo [Mangeney M et al. (1998). Proc. Natl. Acad. Sci. 95: 14920; Quintana F. et al. (2005). J. Clin. Invest. 115:2149; Bloch I. et al. (2007), FASEB J. 21:393]. It has been shown that retroviruses like Moloney murine leukemia virus as well as lentiviruses (HIV 1 and HIV 2) exert immunosuppressive activity through their envelope protein gp41 [Morozov V. et al. (2012), Retrovorology. 9:67; Denner J. et al. (2013), PLOS ONE. 8:e55199; Schlecht-Louf G et al (2014). J. Virology. 88:992). Although the primary function of this viral protein is to promote fusion between viral and cell membrane, different domains of gp41 can inhibit T cell activation and proliferation. The first one, termed ISU (for ImmunoSuppressive Unit) is located in the C-terminal part of the N-helical repeat of gp41 (Mangeney M et al. (1998). Proc. Natl. Acad. Sci. 95: 14920; Morozov V. et al. (2012), Retrovorology. 9:67; Denner J. et al. (2013), PLOS ONE. 8:e55199; Schlecht-Louf G et al (2014). J. Virology. 88:992). Its mode of action is not well established but it seems to interfere with calcium influx and PKC (protein Kinase C) function. The second one, termed FP (fusion peptide) is located in the N terminal part of the protein and interacts directly with TCRalpha chain, preventing TCR complex assembly [Cohen T et al (2010), PLOS Pathogens. 6:e1001085; Faingold O et al, (2012), J. Biol. Chem. 287:33503]. Both ISU and FP have been shown to be inmunosuppressive as whole protein transmembrane protein, truncated transmembrane protein or synthetic peptides.

T-cell mediated immunity includes multiple sequential steps regulated by a balance between co-stimulatory and inhibitory signals that fine-tune the immunity response. The inhibitory signals referred to as immune checkpoints are crucial for the maintenance of self-tolerance and also to limit immune-mediated collateral tissue damage. The expression of immune checkpoints protein can be deregulated by tumours. The ability of tumours to co-opt these inhibitory pathways represents an important mechanism in immune resistance and limits the success of immunotherapy. One of promising approaches to activating therapeutic T-cell immune response is the blockade of these immune checkpoints (Pardoll 2012). Immune checkpoints represent significant barriers to activation of functional cellular immunity in cancer, and antagonistic antibodies specific for inhibitory ligands on T cells including CTLA4 and programmed death-1 (PD-1) are examples of targeted agents being evaluated in the clinics.

Cytotoxic-T-lymphocyte-associated antigen 4 (CTLA-4; also known as CD152) downregulates the amplitude of T cell activation and treatment with antagonist CTLA4 antibodies (ipilimumab) has shown a survival benefit in patients with melanoma (Robert and Mateus 2011). Programmed cell death protein 1 (PD1 or PDCD1 also known as CD279) represent another very promising target for immunotherapy (Pardoll and Drake 2012; Pardoll 2012). In contrast to CTLA-4, PD1 limits T cell effector functions in peripheral tissue at the time of an inflammatory response to infection and to limit autoimmunity. The first clinical trial with PD1 antibody shows some cases of tumour regression (Brahmer, Drake et al. 2010). Multiple additional immune checkpoint protein represent promising targets for therapeutic blockade based on recently studies.

WO2013/173223A application describes a method for immunotherapy wherein the PD-1-PD-L1 pathway is disrupted by the administration of antibodies against PD-1 and/or PD-L1. This inhibitory immunoregulator is used as biomarker to enable patient selection and guide on-treatment management.

Pegram et al. (2012) have shown that tumor-targeted T cells modified to secrete the interferon IL-12 can eradicate systemic tumors in murine model, without the need of prior conditioning such as irradiation, lymphodepleting chemotherapy and/or additional cytokine support.

Rong et al. (2014) have demonstrated that the expression of both CTLA-4 Ig and PD-L1 are required in human embryonic stem cells (hESCs) to confer immune protection as neither was sufficient on their own. This approach has been used to support allograft of human Embryonic Stem Cells into mice.

In all 3 above prior art (WO2013/173223A, Pegram et al., and Rong Z et al), self-recognition systems, such as TCR, were maintained functional, which limited the persistence of the engrafted cells into the host. However, to be able to use allogeneic CAR T cells as treatment in cancer immunotherapy or other indications, one must mitigate the risk of graft vs. host disease (GvHD) as well as the risk of rejection of therapeutic cells by the patient. Allogenic cells can survive in patients having received lymphodepletion regimen but their therapeutic activity is limited by the duration of the lymphodepletion.

To extend their survival and enhance their therapeutic activity, the inventors describe here a method to prevent the rejection of therapeutic allogeneic T cells, while the patient's immune system may be still active. This method consists in creating a local immune protection by engineering therapeutic cells to ectopically express and/or secrete immunosuppressive polypeptides at or through the cell membrane. They found that a various panel of such polypeptides in particular antagonists of immune checkpoints, or derived from viral envelope or NKG2D ligand could enhance persistence and/or an engraftment of allogeneic immune cells into the host. For a better efficacy, this local immunosuppressive effect is completed by the inactivation of gene involved in the self/non-self recognition, making these engineered immune cell for engraftment, available as an "off the shelf" product.

SUMMARY OF THE INVENTION

The present invention discloses methods to engineer immune cell, such as T cells, to make them suitable for immunotherapy purposes by increasing their persistence and/or easing their engraftment in host organism, reducing thereby the risk of graft versus host disease (GvHD). More particularly, the invention relates to a method, wherein at least one endogenous gene encoding a polypeptide involved in the self and non-self antigen recognition is inactivated in one immune cells, followed by contacting said engineered immune cells with at least one non-endogenous immunosuppressive polypeptide.

In one aspect, the inactivation is performed on TCR and/or beta2M gene, preferably by using a specific rare-cutting endonuclease, such as a TALE-nuclease.

In a further aspect, in order to prevent depletion of adoptively transferred allogeneic immune cells by host-versus-graft (HvG)—i.e. host immune cells attacking those allogeneic transferred immune cells—the contacting step is realized by the expression of inactive PD1 and/or CTLA-4 ligand by the immune cell itself. Other alternatives according to the invention provide with the expression of viral MHC homolog, NKG2D ligand, and/or viral env immune suppressive domain (ISU) or the viral FP protein.

Also, still within the scope of the present invention, the incubation of engineered immune cells with at least one non-endogenous immunosuppressive polypeptide may be used instead of the expression of immunosuppressive polypeptides. CD80/CD86 antibodies are preferred as immune suppressive polypeptide to be used in said incubation.

The modified immune cells relevant for immunotherapy may further comprise exogenous recombinant polynucleotides encoding Chimeric Antigen Receptors (CAR) for specific cell recognition. The resulting isolated cells or cell lines comprising any of the proteins, polypeptides or vectors described in this specification are dedicated for use as therapeutic products, ideally as "off the shelf" products with reduced graft-versus-host disease (GvHD) risk and extended life span.

Methods for treating or preventing cancer or infections in a patient by administrating such engineered immune cells area also described.

BRIEF DESCRIPTION OF THE FIGURES AND TABLES

In addition to the above, the invention further comprises features which will emerge from the description that follows, as well as to the appended drawings. A more complete appreciation of the invention and many of the attendant advantages thereof will be readily obtained as the same becomes better understood by reference to the following figures in conjunction with the detailed description below.

Legends of the Figures

FIG. 1: Schematic representation of the potential interactions between an allogeneic CAR T cell with diverse host immune cells (CD8+ and CD4+ T cell, APC such as dendritic cell and NK cell), the CAR T cell having no additional genetic modification. Sign (+) represents activation and sign (−) inhibition. CAR T cell is activated by encountering targeted tumor cell which displays an antigen cell surface recognized by the scFvs of the CAR. Interaction between allogeneic CAR T cell and host NK cell is inhibited by the recognition of the MHC I by the inhibitor of the NK cell. Activation of the host cytotoxic T cell (CD8+ T cell) takes place by the binding by TCR of the MHC I components of the CAR T cell. Also, the action of host NK cell on allogeneic T CAR cell is inhibited via the MHCI recognition.

Figure 2:
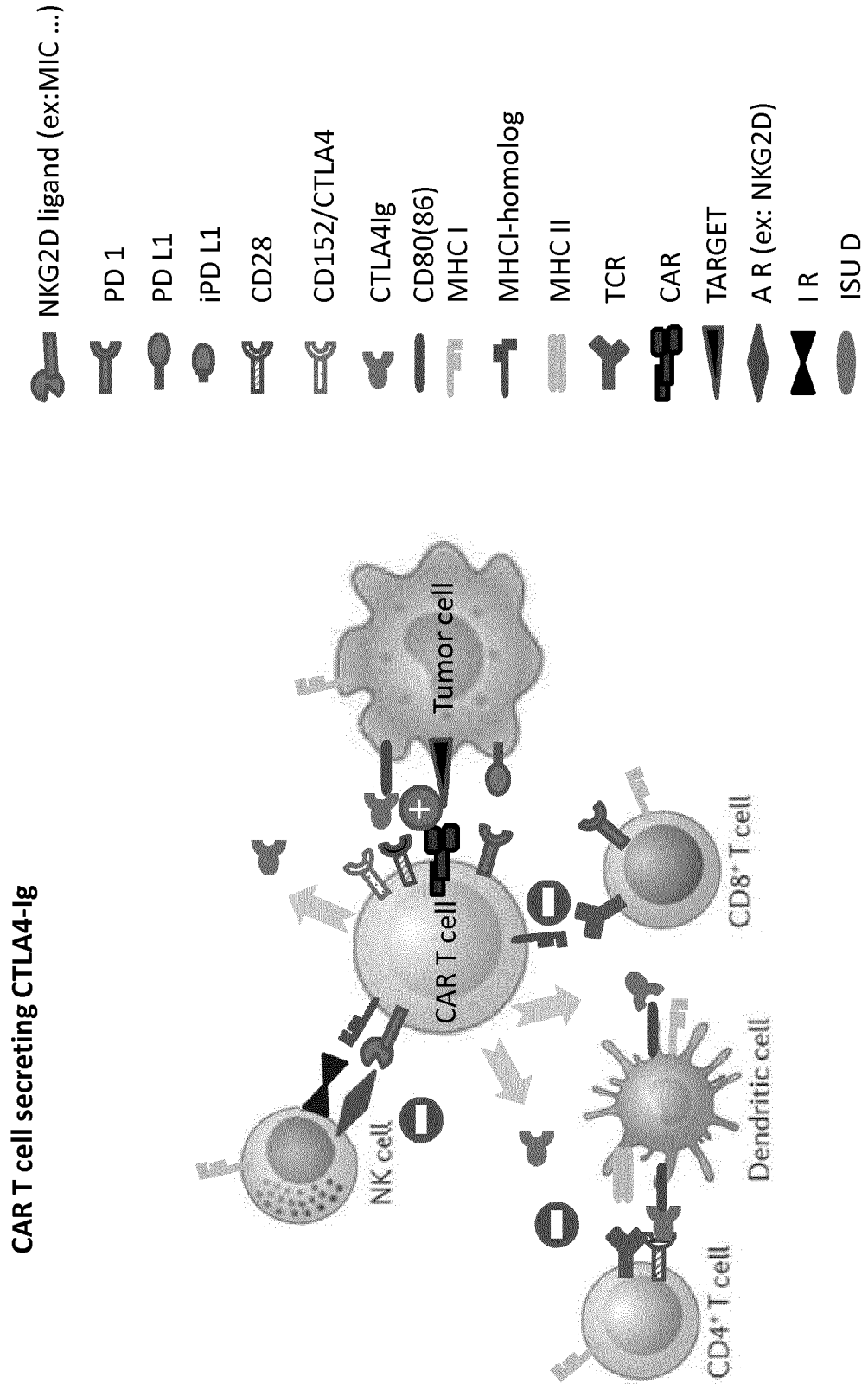

FIG. 2: Schematic representation of the potential interactions between an allogeneic CAR T cell with diverse host immune cells (CD8+ and CD4+ T cell, APC such as dendritic cell and NK cell); the CAR T cell expressing secreted CTLA-4 Igs. Sign (+) represents activation and sign (−) inhibition. CAR T cell is activated by encountering targeted tumor cell which displays an antigen cell surface recognized by the scFvs of the CAR. The interaction between NK cell and CAR T cell remains unchanged. The secreted CLTA-4 Igs bind to the CD80/CD86 antigen on the surface of APC cell and tumor cell, therefore inactivating the interaction between APC cell (such a dendritic cell here) and the CAR T cell. Thus, the secretion of CLTA-4 Igs creates a local immune protection.

Figure 3:
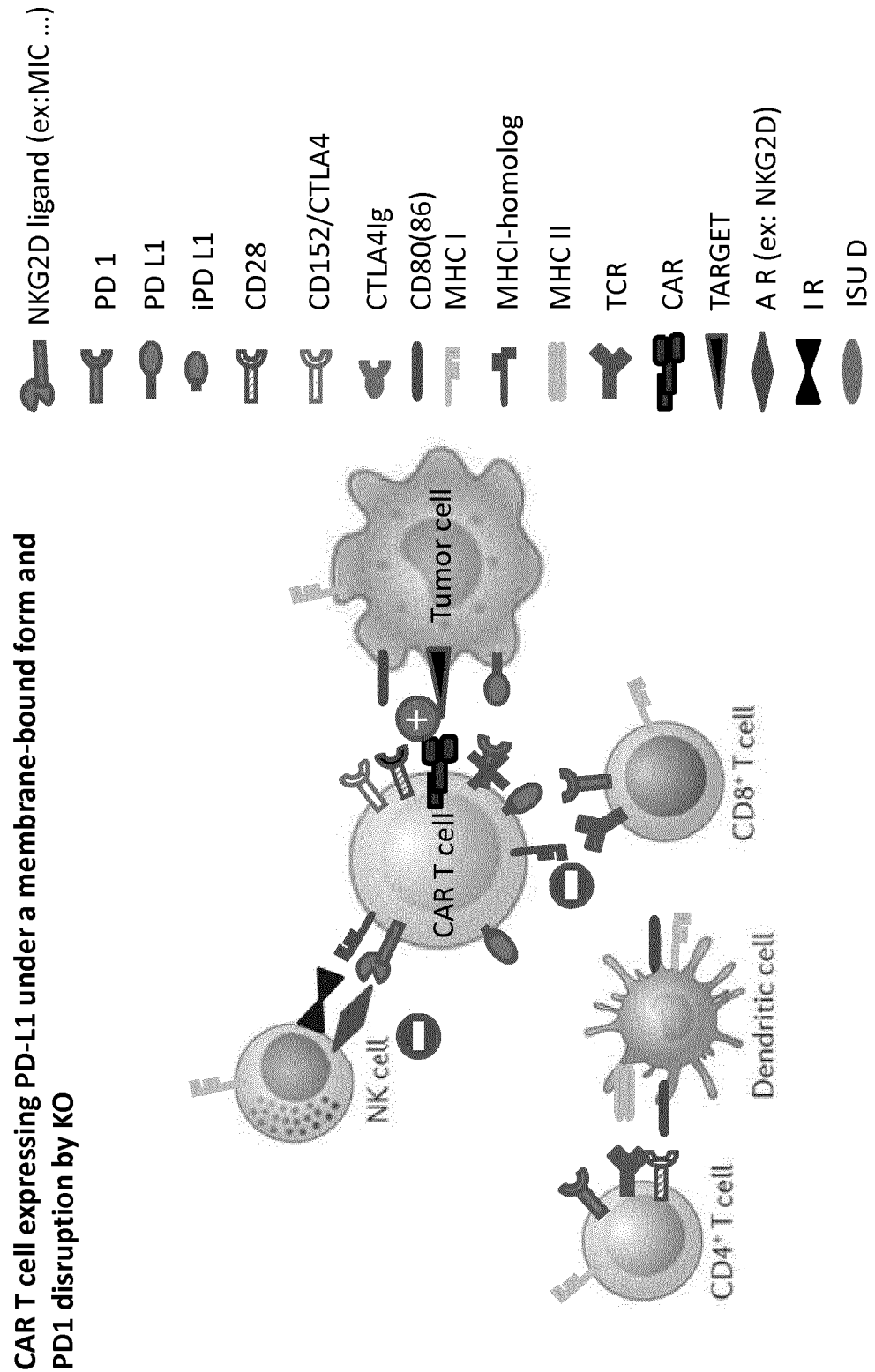

FIG. 3: Schematic representation of the potential interactions between an allogeneic CAR T cell with diverse host immune cells (CD8+ and CD4+ T cell, APC such as dendritic cell and NK cell); the CAR T cell expressing membrane-bound PD-L1 and whose PD-1 gene is inactivated by KO. Sign (+) represents activation and sign (−) inhibition. The potential interaction between CAR T cell with the tumor cell and the NK cell remain unchanged. The expression of PD-L1 by the allogeneic CAR T cell makes it insensitive to the host CD8+ T cell due to the binding PD-L1 to the PD-1 receptor of the latter. Thus, the PD-L1 triggers T cells inhibitory pathway in the patient's T cells, and this effect is more pronounced when the PD-1 gene of the allogeneic is inactivated.

Figure 4:
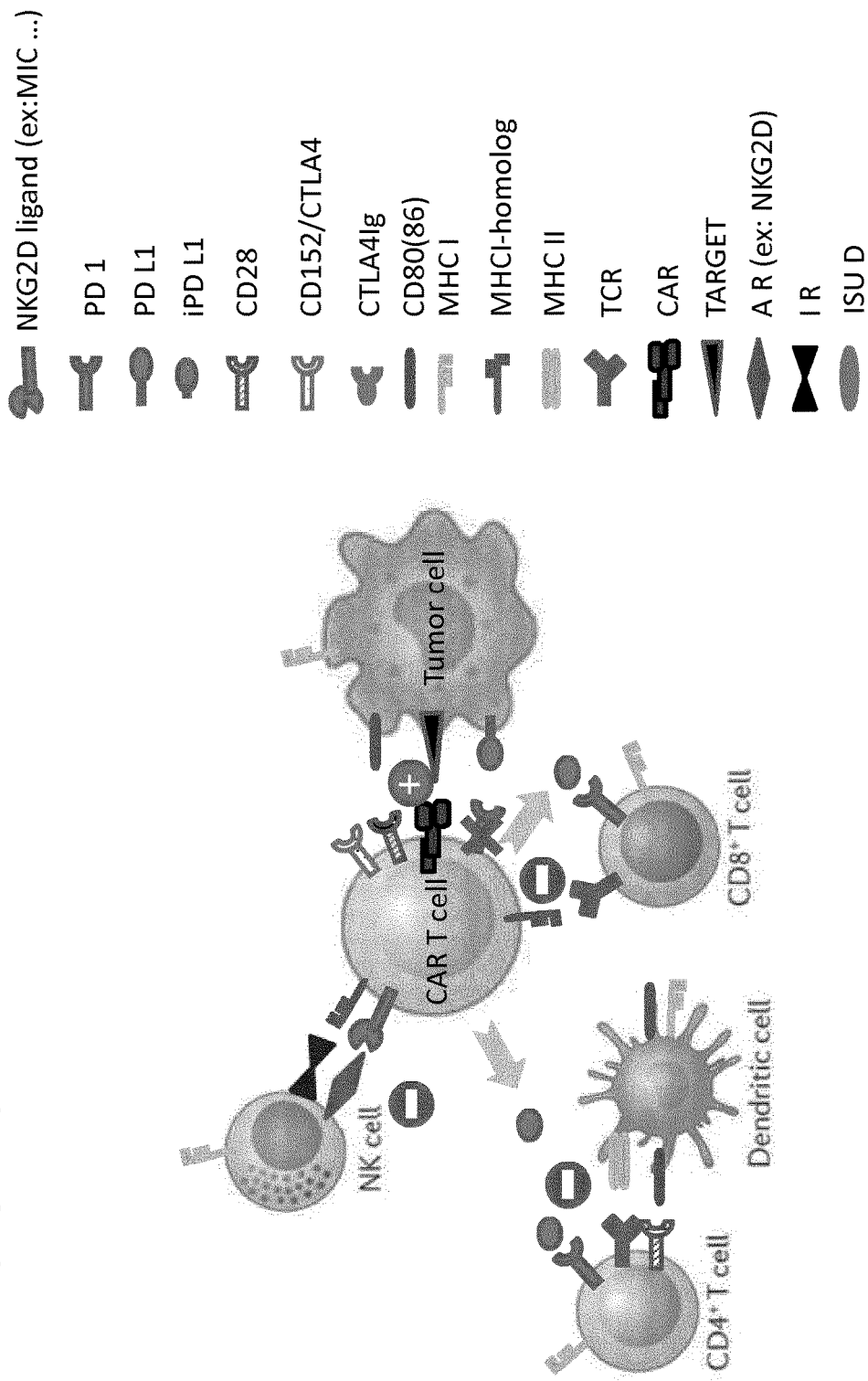

FIG. 4: Schematic representation of the potential interactions between an allogeneic CAR T cell with diverse host immune cells (CD8+ and CD4+ T cell, APC such as dendritic cell and NK cell); the CAR T cell expressing secreted PD-L1 and whose PD-1 gene is inactivated by KO. Sign (+) represents activation and sign (−) inhibition. The potential interaction between CAR T cell with the tumor cell and with the NK cell remain unchanged. The secreted PD-L1 by the allogeneic CAR T cell can bind to host CD8+ and CD4+ T cell by their PD-1 receptors, inhibiting the PD-L1/PD-1 pathway. Thus, the PD-L1 triggers T cells inhibitory pathway in the patient's T cells, and this effect is more pronounced when the PD-1 gene of the allogeneic is inactivated.

Figure 5:
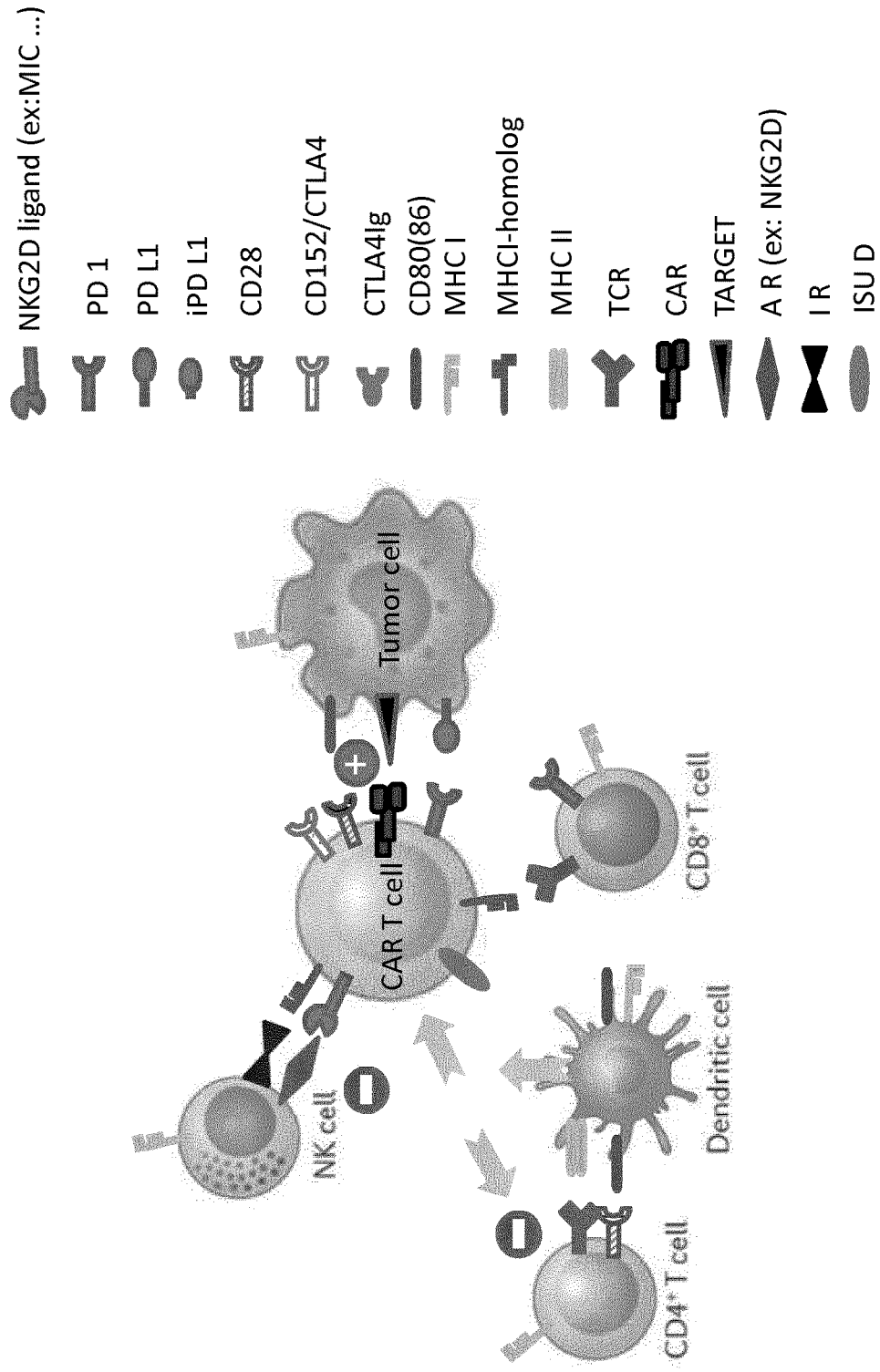

FIG. 5: Schematic representation of the potential interactions between an allogeneic CAR T cell with diverse host immune cells (CD8+ and CD4+ T cell, APC such as dendritic cell and NK cell), the CAR T cell expressing a viral env immunosuppressive domain (ISU). Sign (+) represents activation and sign (−) inhibition. The potential interaction between CAR T cell with the tumor cell and with the NK cell remain unchanged. The expression of viral ISU appears to inhibit the recognition of the allogeneic CAR T cell by the host T cells and APCs cells maybe by the reduced production of IL-10 interleukin, and thus creating an immunosuppressive effect.

Figure 6:
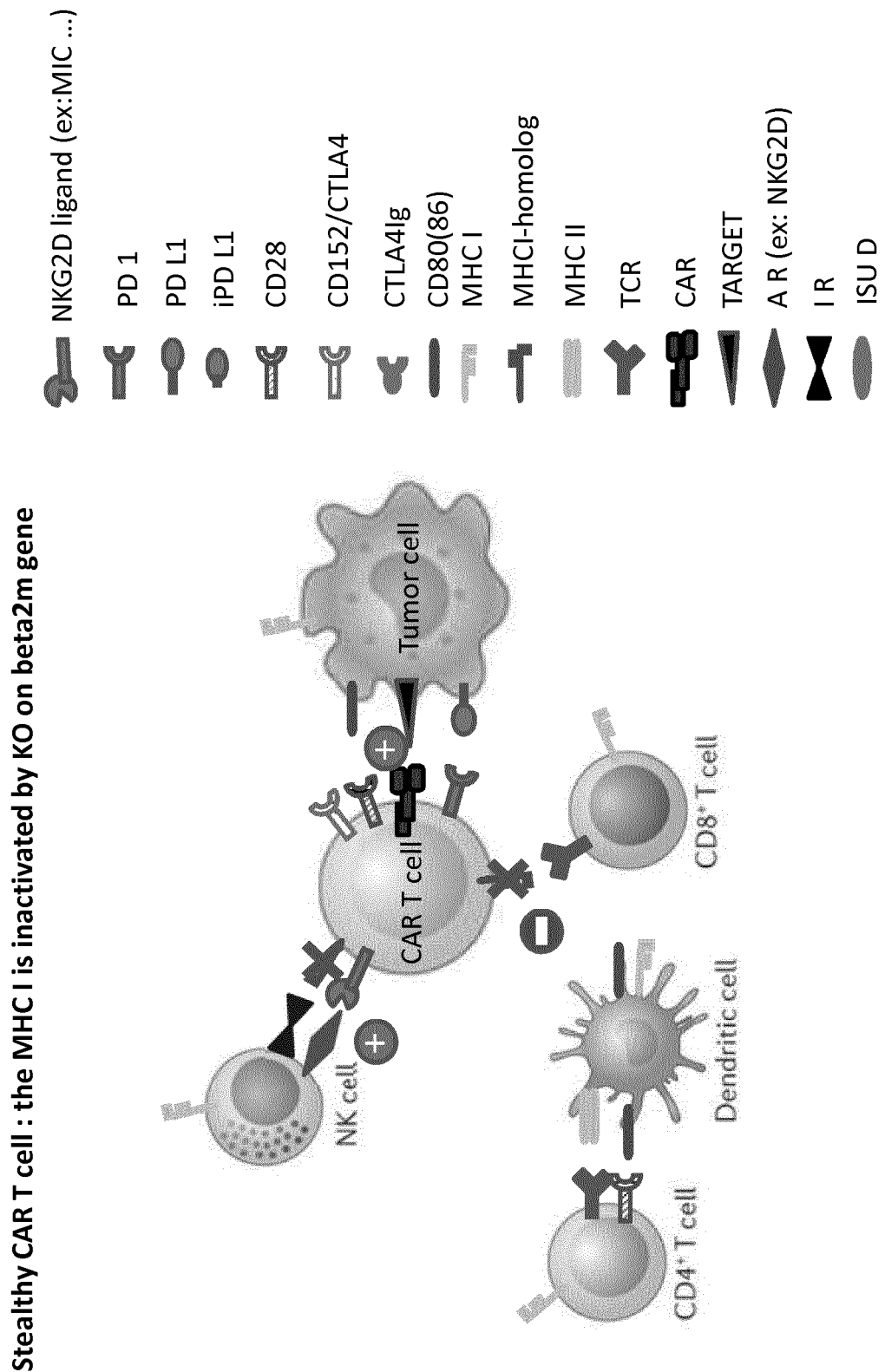

FIG. 6: Schematic representation of the potential interactions between an allogeneic CAR T cell with diverse host immune cells (CD8+ and CD4+ T cell, APC such as dendritic cell and NK cell), the CAR T cell having its B2M gene inactivated by KO. Sign (+) represents activation and sign (−) inhibition. The potential interaction between CAR T cell with the tumor cell remains unchanged. The inactivation of B2M gene which is one component of the MCHI, renders the latter non-functional in regards to the interactions with host cytotoxic T cell (CD8+) and with NK cell. Then, NK cell can exert its activation on allogeneic CART cell via activator pathway such NKG2D/NKG2D ligand.

Figure 7:
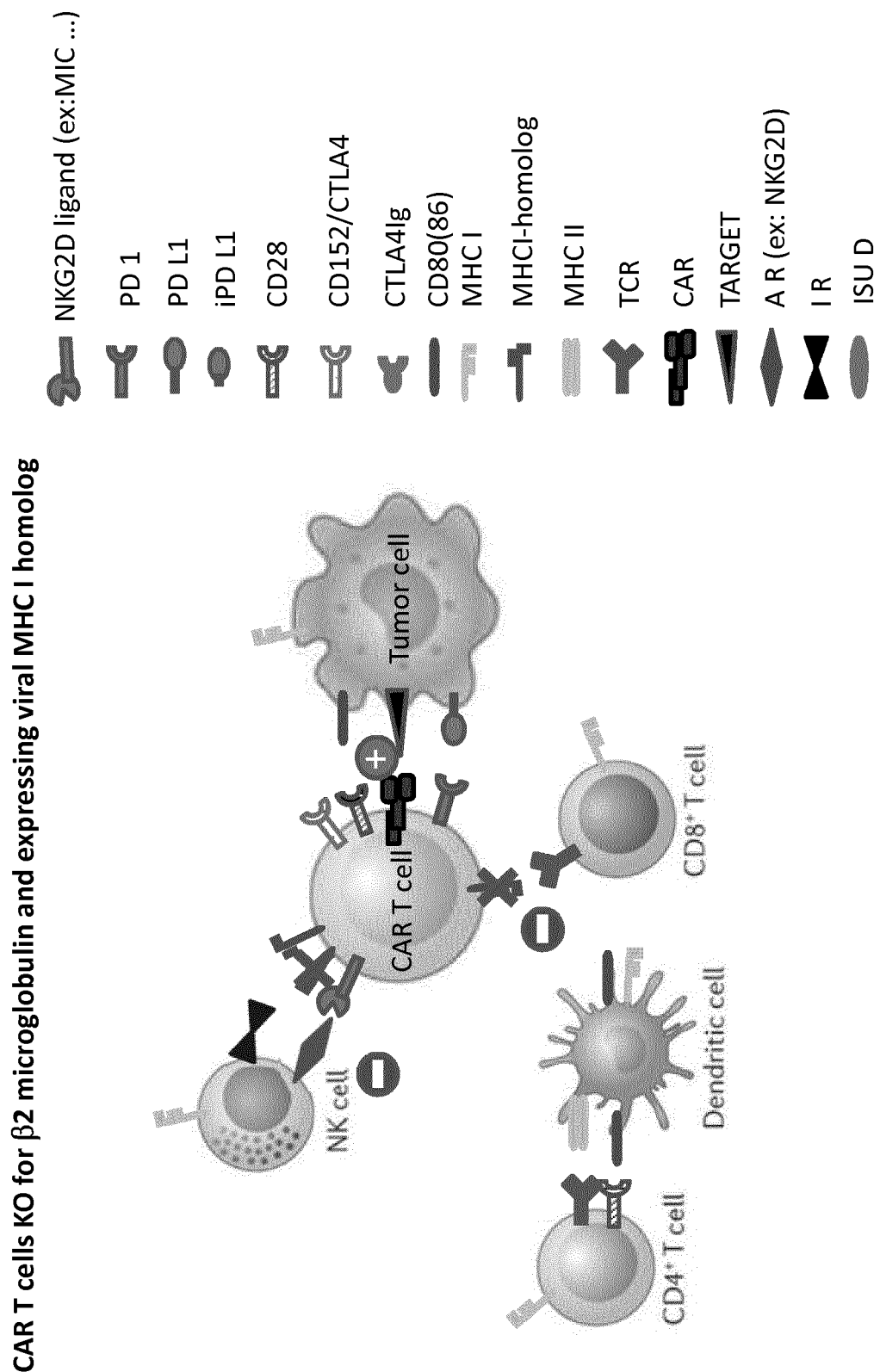

FIG. 7: Schematic representation of the potential interactions between an allogeneic CAR T cell with diverse host immune cells (CD8+ and CD4+ T cell, APC such as dendritic cell and NK cell), the CAR T cell having its B2M gene inactivated by KO and expressing viral MHCI homolog. Sign (+) represents activation and sign (−) inhibition. The potential interaction between CAR T cell with the tumor cell remains unchanged. As for the preceding figure (only B2M KO), the interaction between CAR T cell and host CD8+ T cell is alleviated. In this case, the expression of viral MHCI homolog renders the interaction with NK cell inoperative via MHCI/inhibitor receptor. The double genetic modification of allogeneic CAR T cells by KO of B2M combined with the expression of viral MHCI homolog strengthens their immunosuppressive protection.

Figure 8:
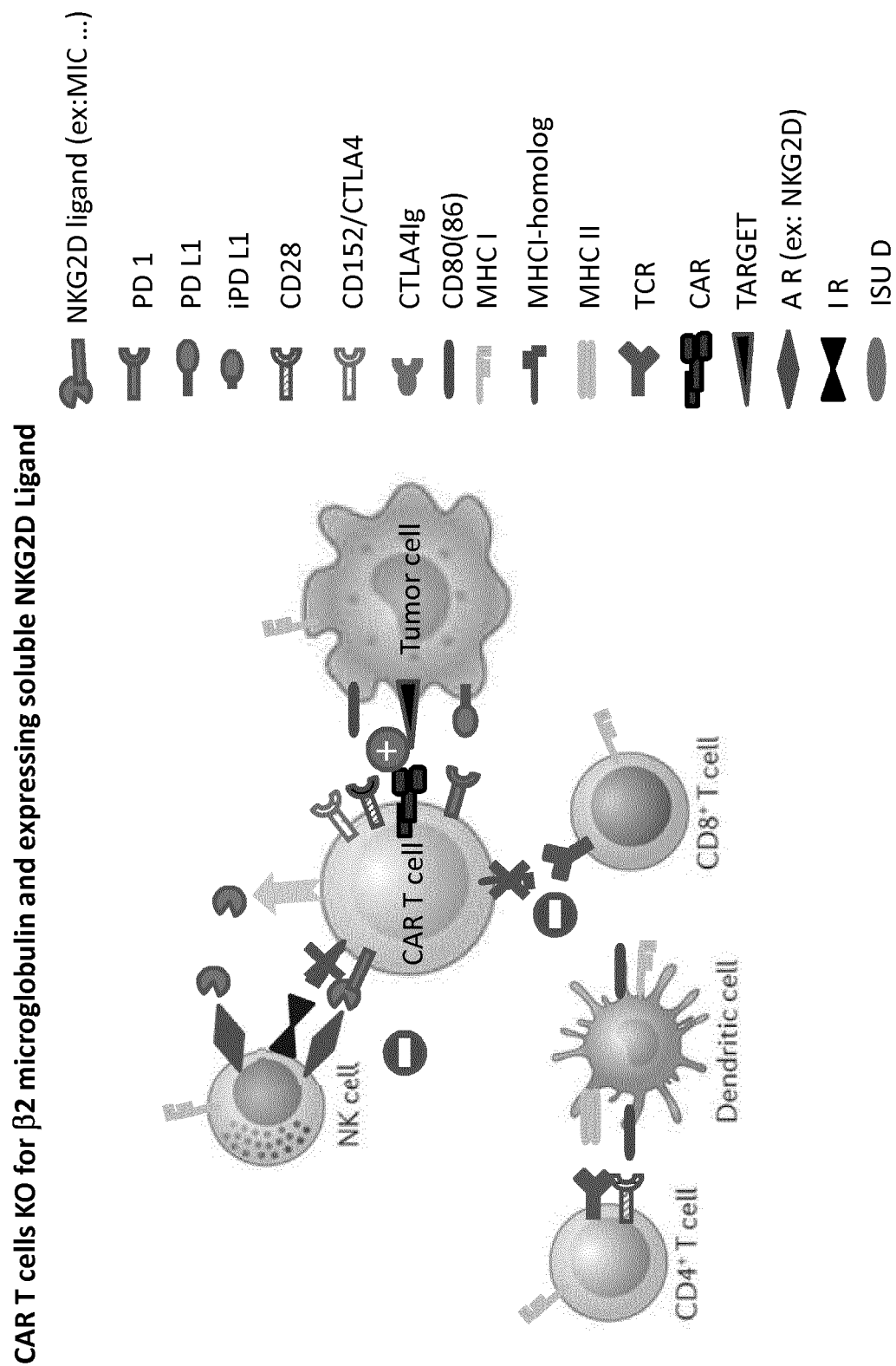

FIG. 8: Schematic representation of the potential interactions between an allogeneic CAR T cell with diverse host immune cells (CD8+ and CD4+ T cell, APC such as dendritic cell and NK cell), the CAR T cell having its B2M gene inactivated by KO and expressing a soluble NKG2D ligand. Sign (+) represents activation and sign (−) inhibition. The potential interaction between CAR T cell with the tumor cell remains unchanged. As for the preceding figure (only B2M KO), the interaction between CAR T cell and host CD8+ T cell is alleviated. The expression of soluble NKG2D ligand is another way to inactivate the interaction with NK cell. In this case, the soluble NKG2D ligand can bind to NKG2D receptor on NK cell but exerts no action, in contrast to the NKG2D ligand of CAR T cell with which it exerts an inhibitory competition. The double genetic modification of allogeneic CAR T cells by KO of B2M combined with the expression of soluble NKG2D ligand strengthens their immunosuppressive protection.

Figure 9:
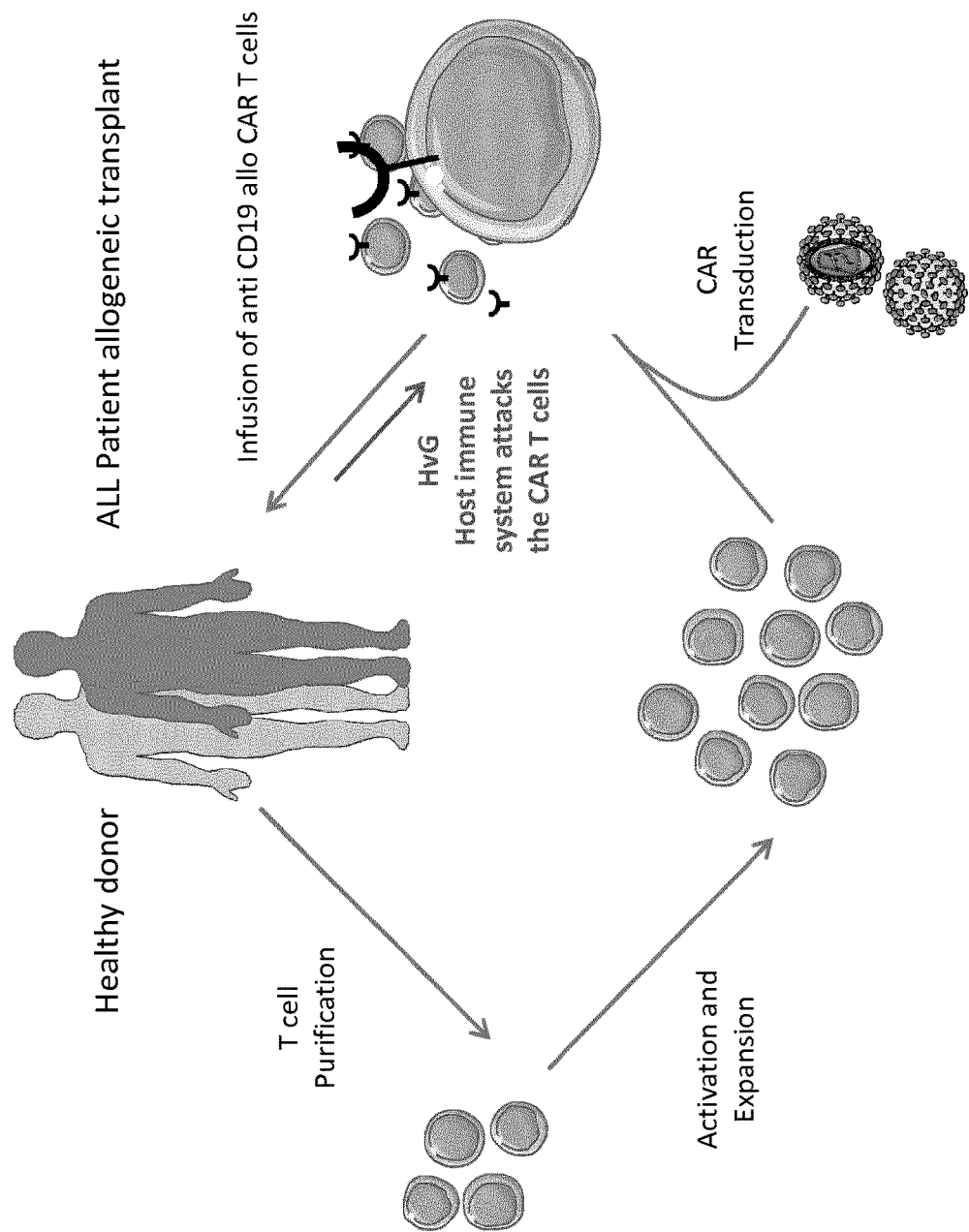

FIG. 9: General scheme of allogeneic CAR T cell adoptive immunotherapy illustrating the potential host versus graft reaction (HvG). Here is represented an example with anti-CD19 chimeric antigen receptor (CAR) which is aimed to treat patients suffering from acute lymphoblastic leukemia (ALL). After the steps of purification of allogeneic T cells from a healthy donor, their activation and expansion, the CAR transduction and finally their infusion into an ALL patient, there is a high risk of host immune attack (HvG) against these allogeneic CAR T cells.

Figure 10:
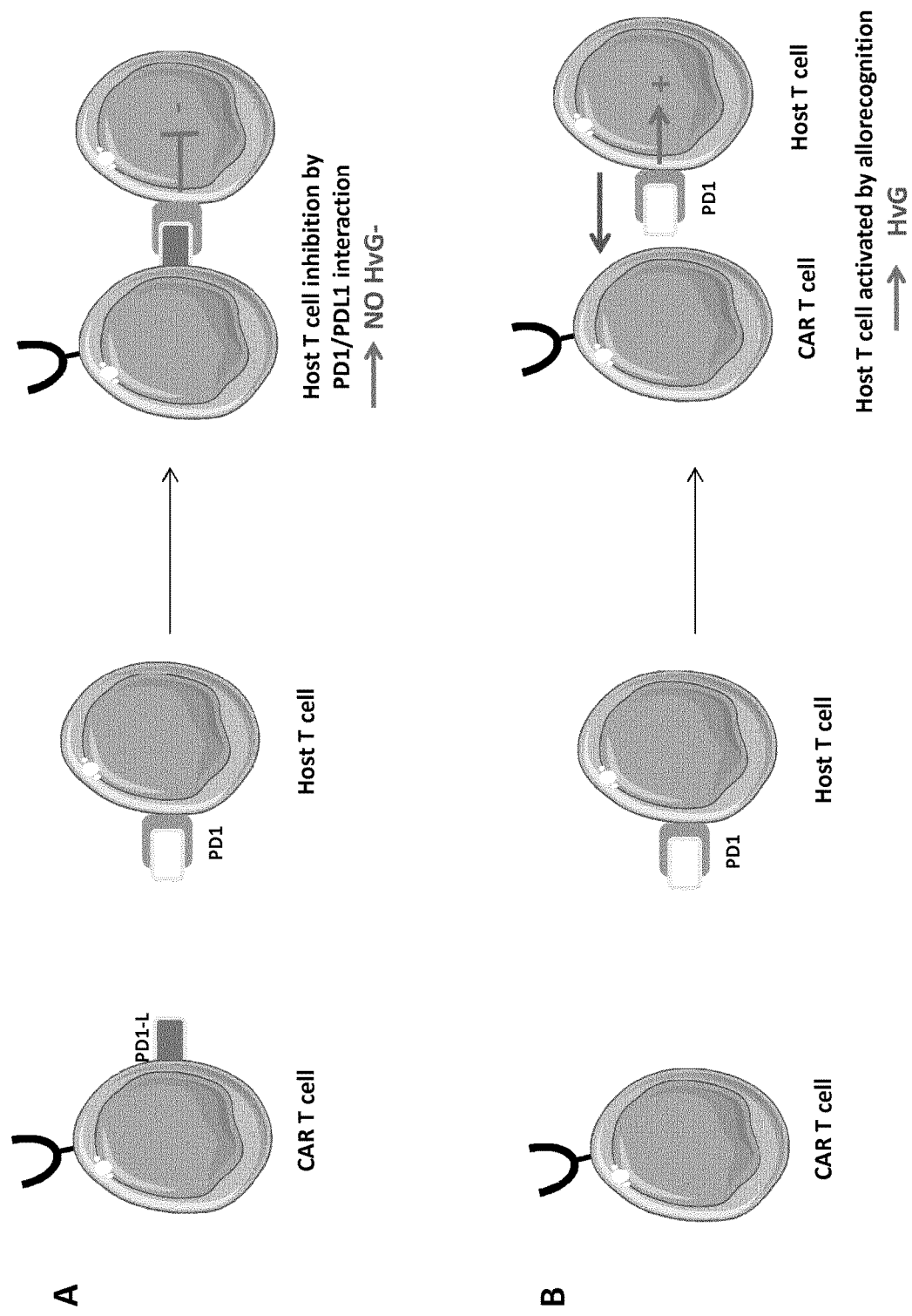

FIG. 10: Scheme describing the re-expression of PD-L1 to prevent the HvG reaction taking place in the host patient after allogeneic CAR T cells adoptive transfer. A. Scheme of HvG reaction prevention via re-expression of PD-L1 at the cell surface of primary T cells. B. Scheme of HvG reaction in the absence of PD-L1 expression.

Figure 11:
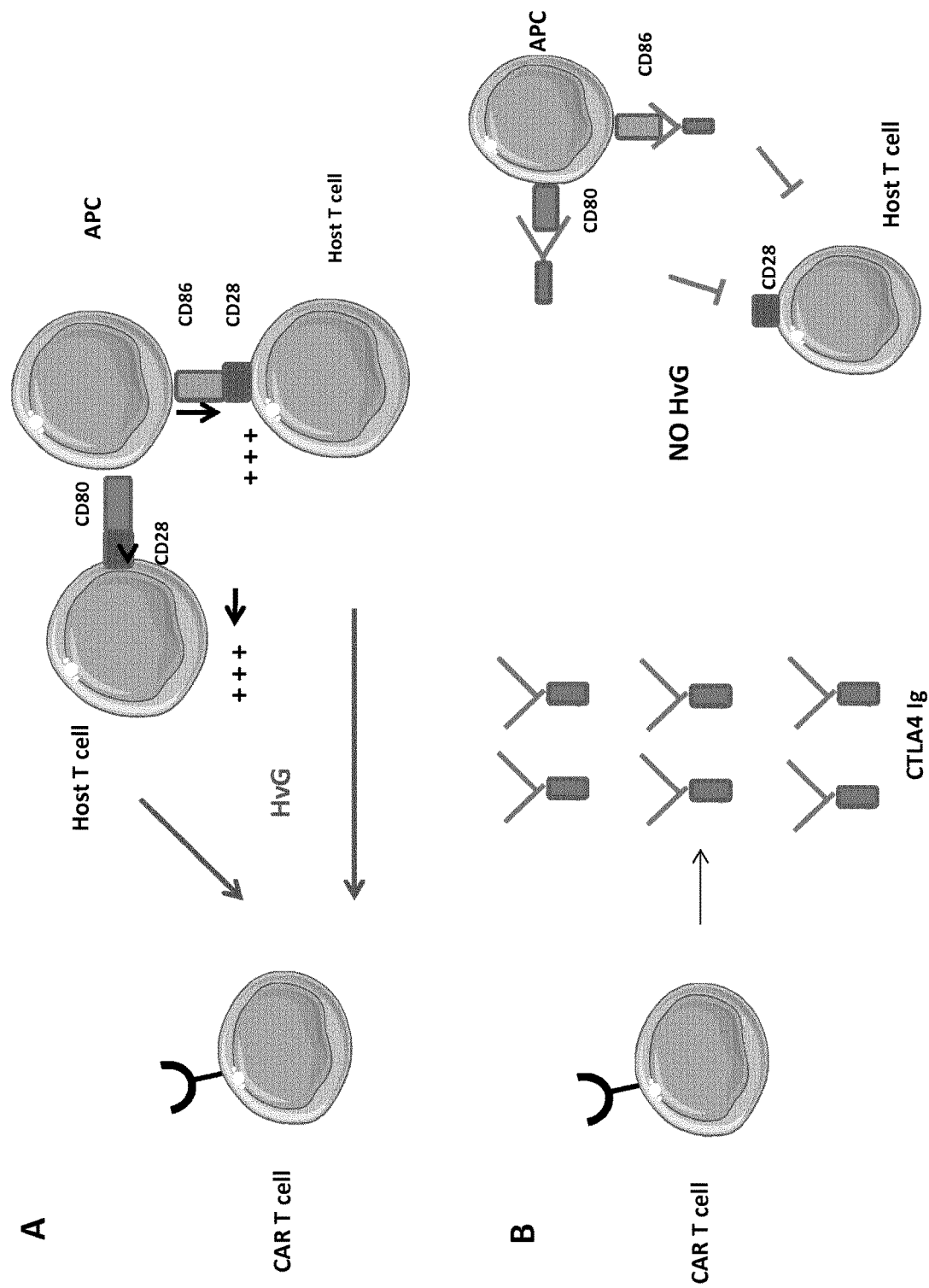

FIG. 11: Scheme describing the HvG reaction including the host antigen presenting cells (APC) and host T cells along with the names of the receptors involved in their activation in the presence of Allogeneic T cells. A. Scheme of HvG reaction. B. Scheme of HvG prevention in excretion of CTLA4-Ig by allogeneic T cells.

Figure 12A:
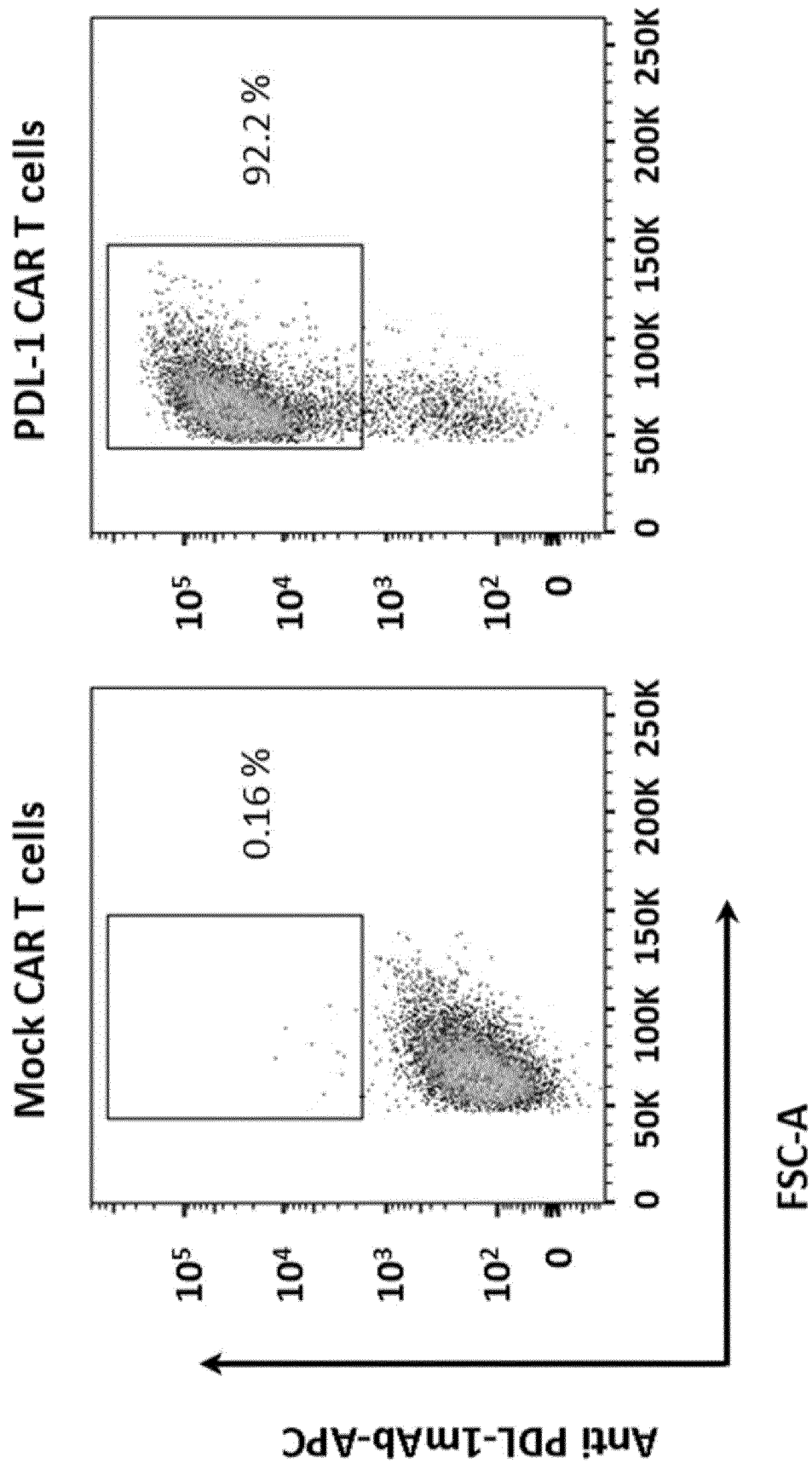
Figure 12B:
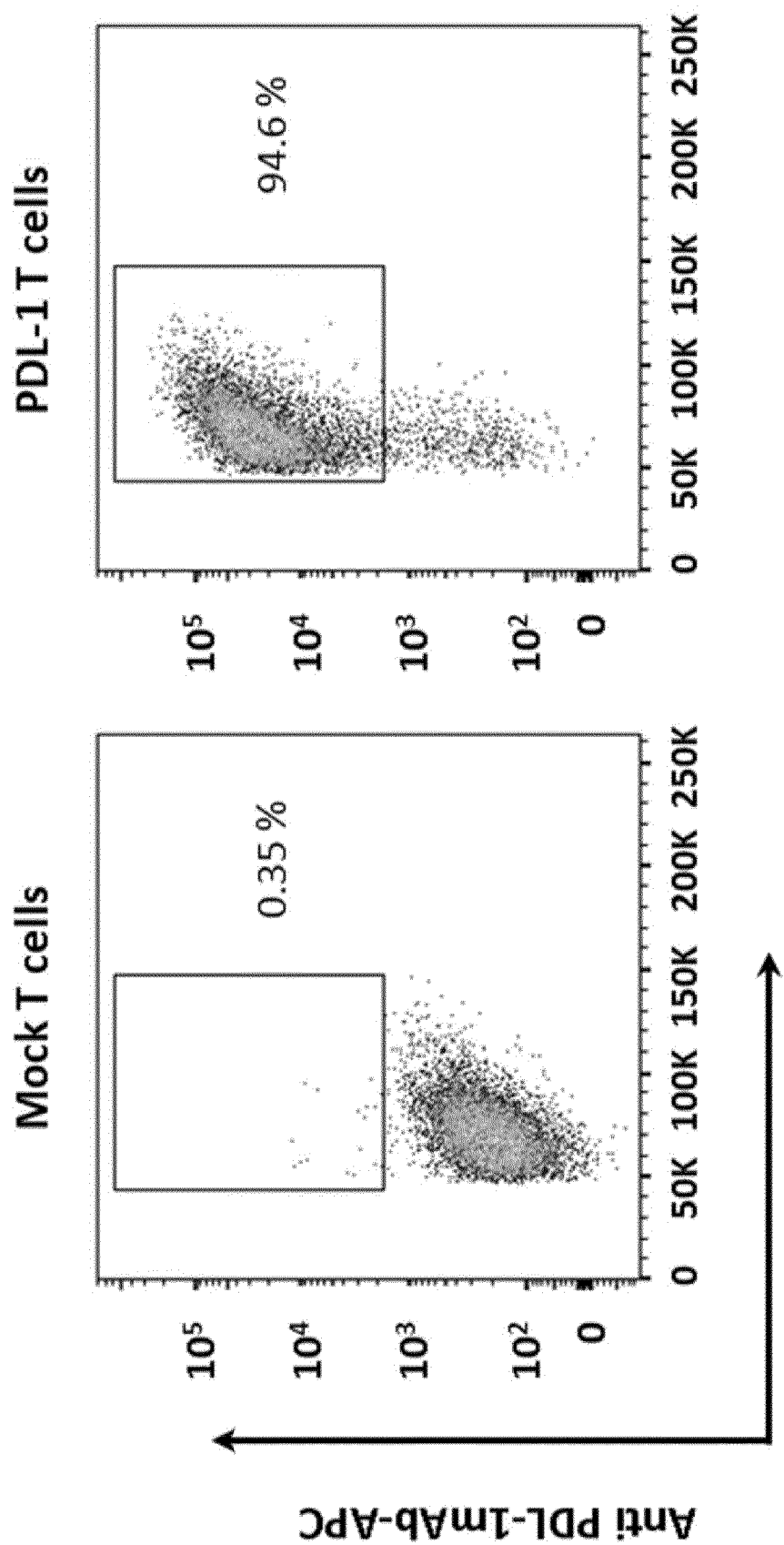
Figure 12C:
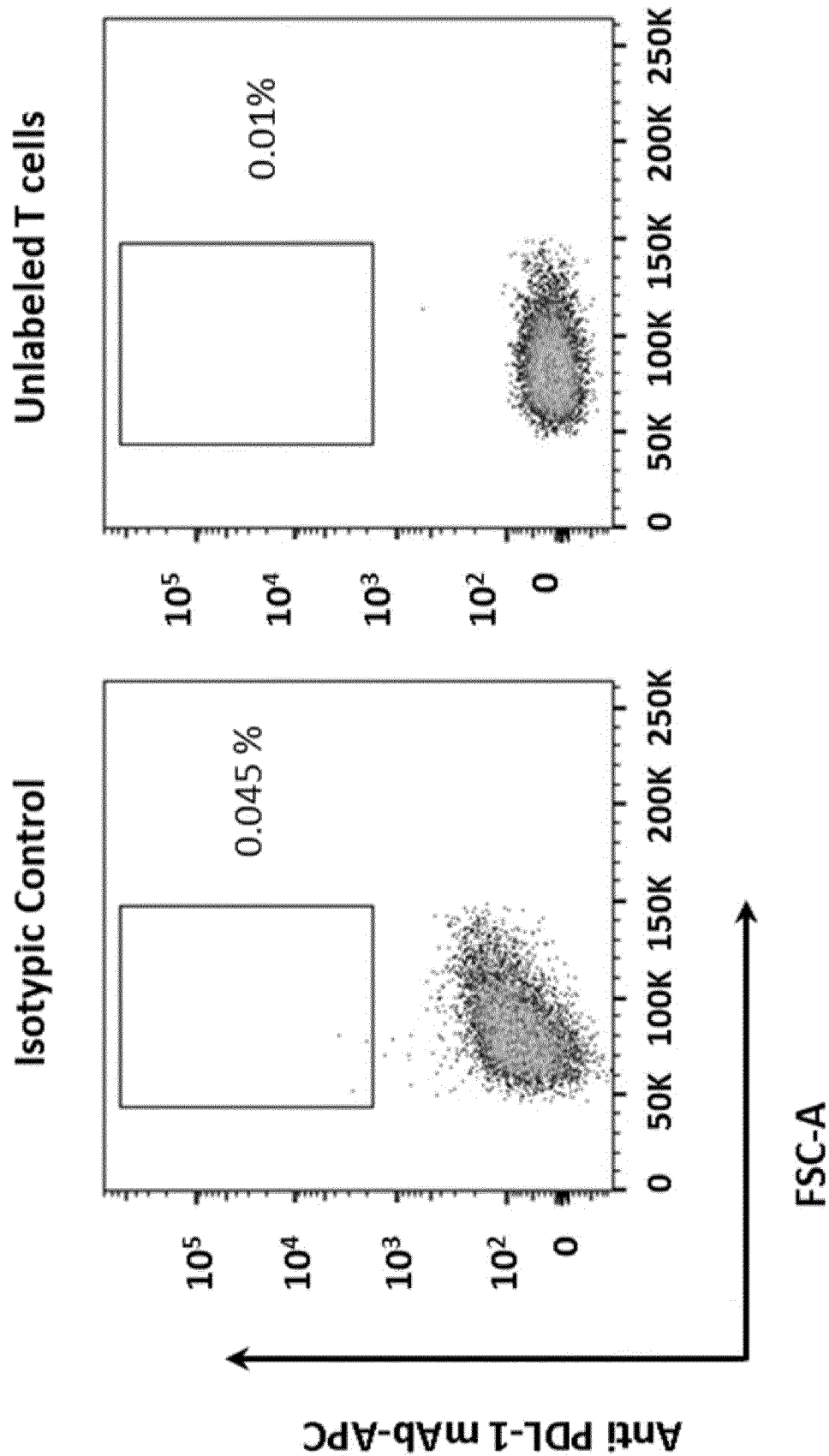

FIG. 12: A, B & C Characterization of the expression of PD-L1 at the surface of T cells or CAR tool T cells by flow cytometry.

Figure 13:

FIG. 13: Specific cell lysis activity of engineered CAR T cell expressing PD-L1 toward relevant and non-relevant tumor cells (Daudi and K562 cells respectively). A and B indicate different blood donors.

Figure 14:
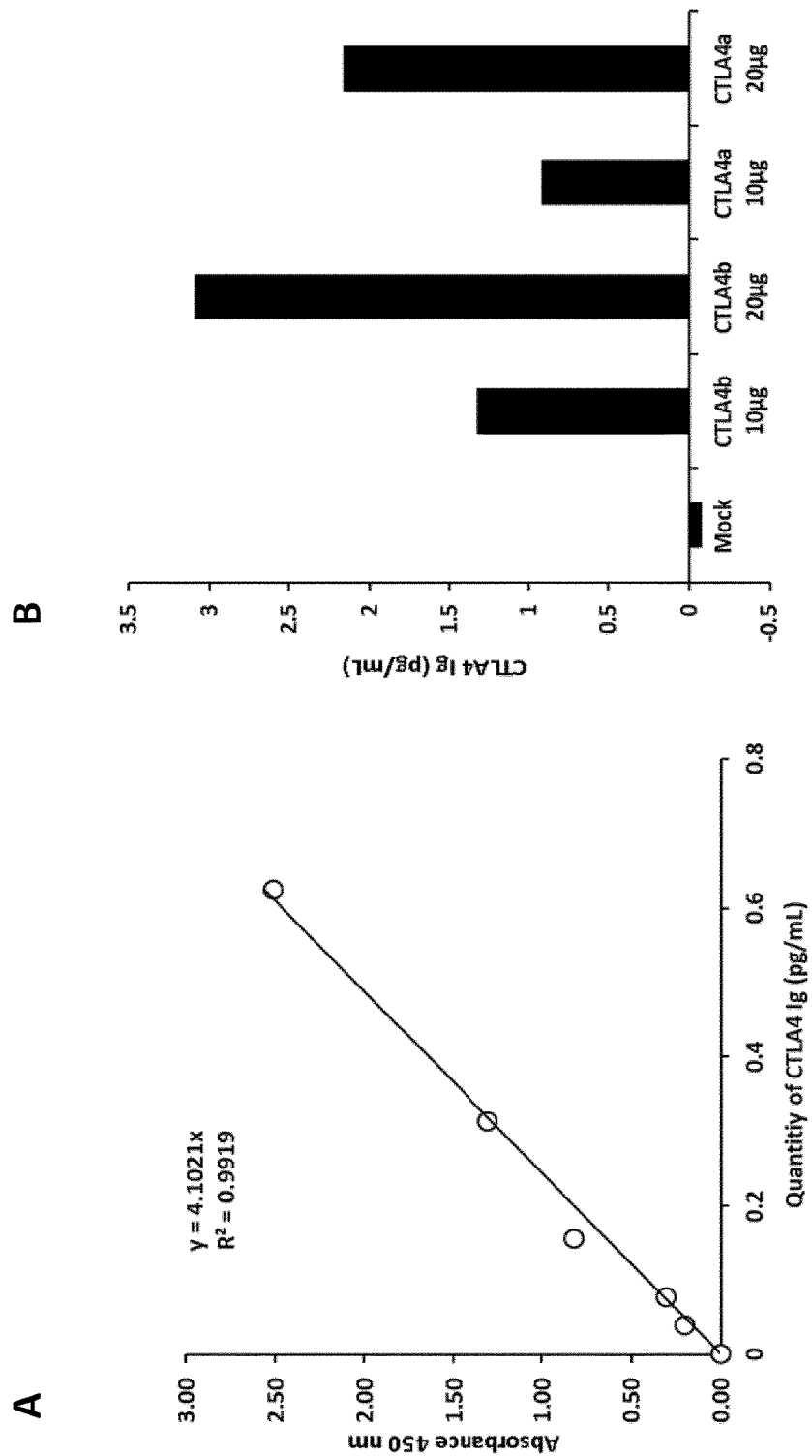

FIG. 14: ELISA detection of CTLA4a Ig and CTLA4b Ig excretion by CAR T cells in the culture media. A. Standard curve used to quantify the amount of CTLA4 Ig in the culture media. B. Detection of CTLA4 a and b Ig in the culture media supernatant of engineered CAR T cells transfected with 10 or 20 µg of mRNA encoding either CTLA4a Ig or CTLA4b Ig.

Figure 15:
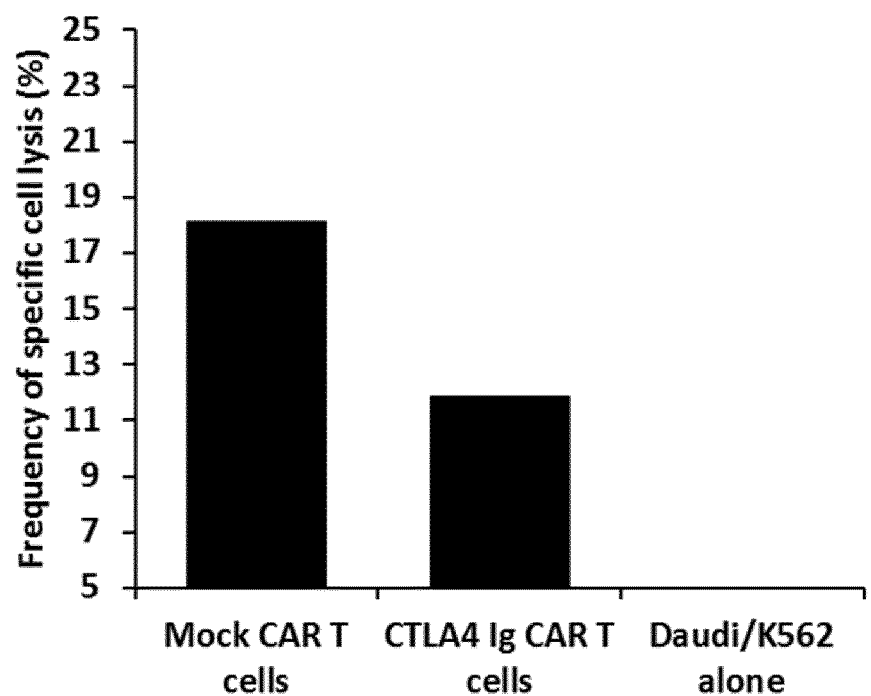

FIG. 15: Specific Cell lysis activity of Engineered CAR T cell expressing CTLA4a Ig toward relevant and non-relevant tumor cells (Daudi and K562 cells respectively).

Figure 16:
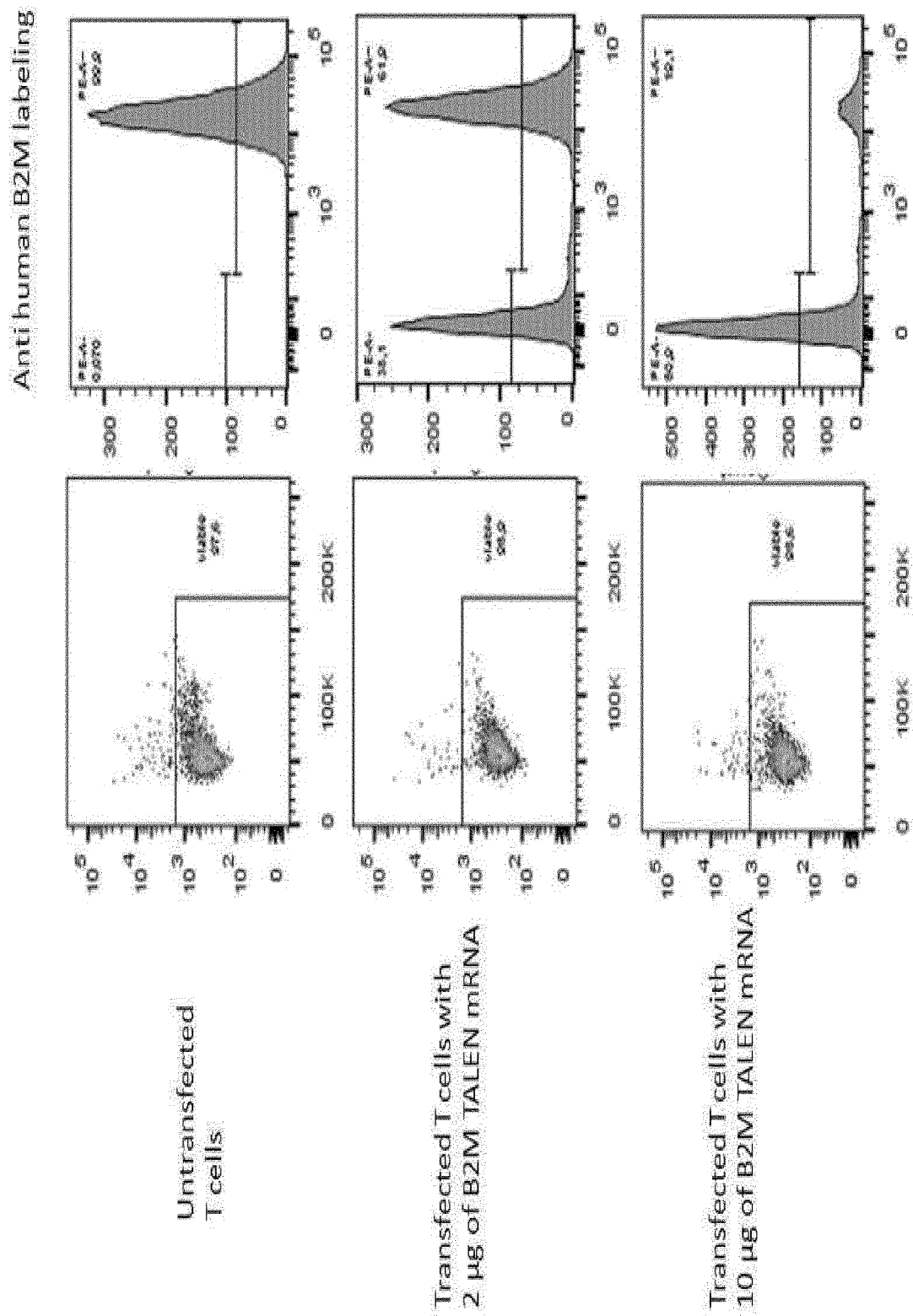

FIG. 16: FACS analysis of β2-m expression in T cells. Untransfected (top) and transfected T cells (middle and bottom) are analysed by FACS for viability (left) and β2-m expression (right).

Figure 17:
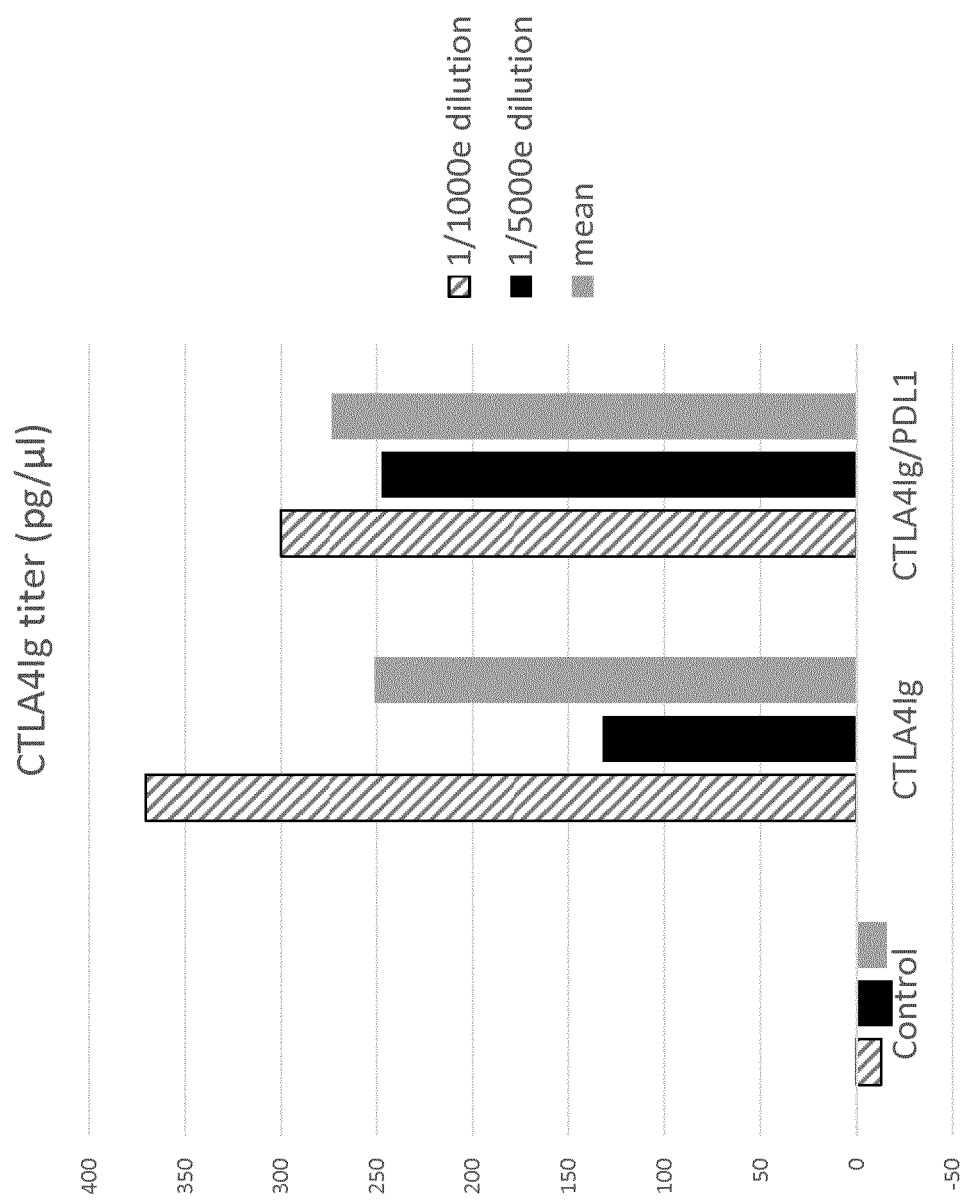

FIG. 17: Detection of CTLA4Ig in the culture media supernatant of engineered CAR T cells transduced with a control LV (PD-L1), CTLA4Ig LV alone or co transduced with PD-L1 and CTLA4Ig LV at a MOI of 5. Supernatants from 14 day old culture are tested by ELISA at 1/1000e dilution (hatched bar) or 1/5000e dilution (dark bar). The grey bar represents the mean titer from both dilution.

Figure 18:
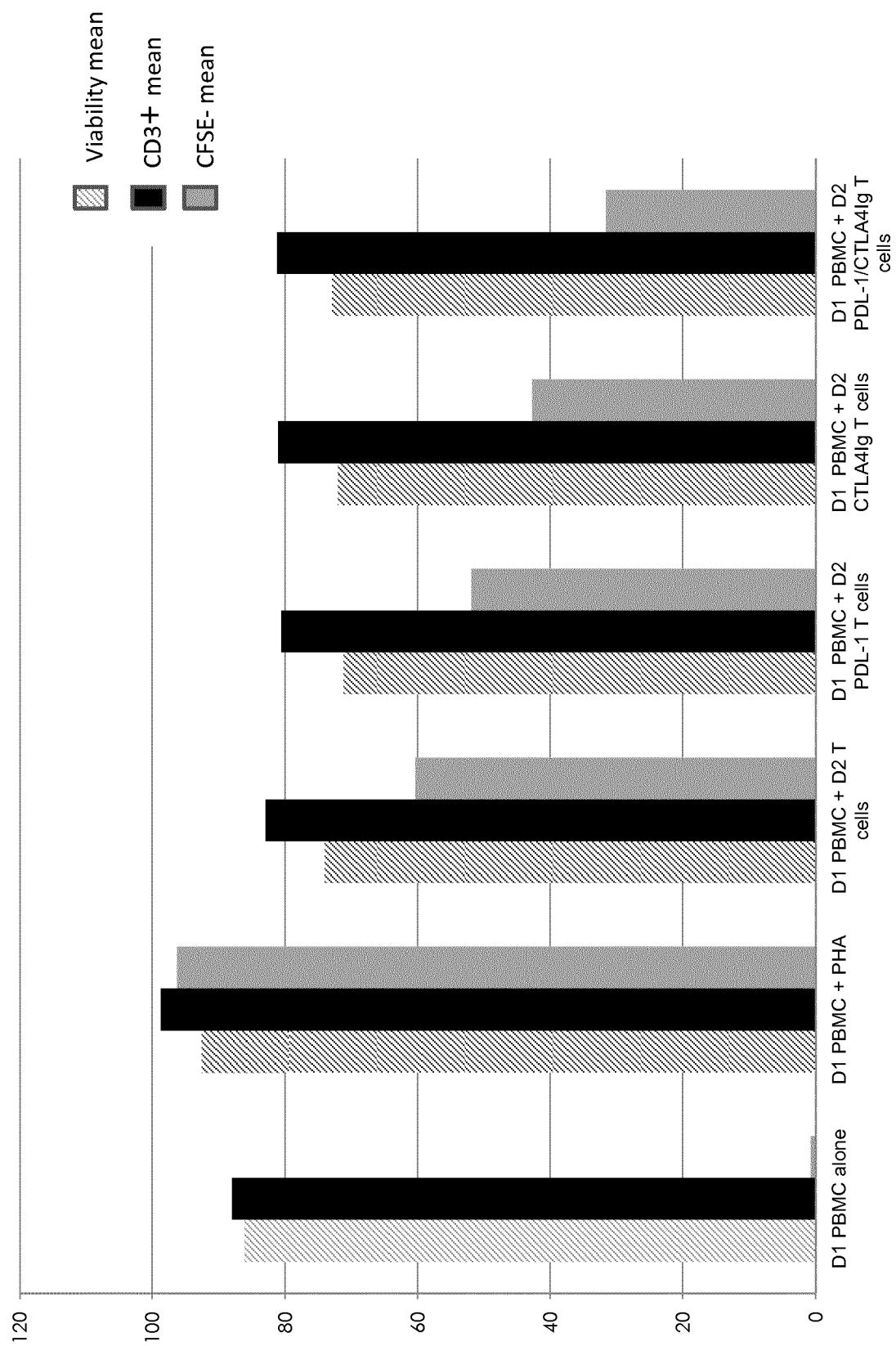

FIG. 18: Mixed Lymphocytes reaction for quantification of CFSE negative T cells from donor 1 (grey bars), quantification of CD3+ T cells (black bars) and T cells viability (hatched bars) in response to the indicated stimulations. D1 and D2 correspond to donor 1 and donor 2 respectively. From left to right: (a) PBMCs from donor 1 without any treatment have been cultured alone; (b) PBMCs from donor 1, which have been submitted to a treatment with increasing concentration of PHA (PhytoHemAgglutinin—10 μg/ml, a T cell mitogen) are cultured alone; (c) PBMCs from donor 1 are co-cultured with untransduced T cells from donor 2; (d) PBMCs from donor 1 are co-cultured with PD-L1 transduced T cells from donor 2; (e) PBMCs from donor 1 are co-cultured with CTLA4Ig transduced T cells from donor 2; (f) PBMCs from donor 1 are co-cultured with PD-L1 and CTLA4Ig co-transduced T cells from donor 2.

Figure 19:
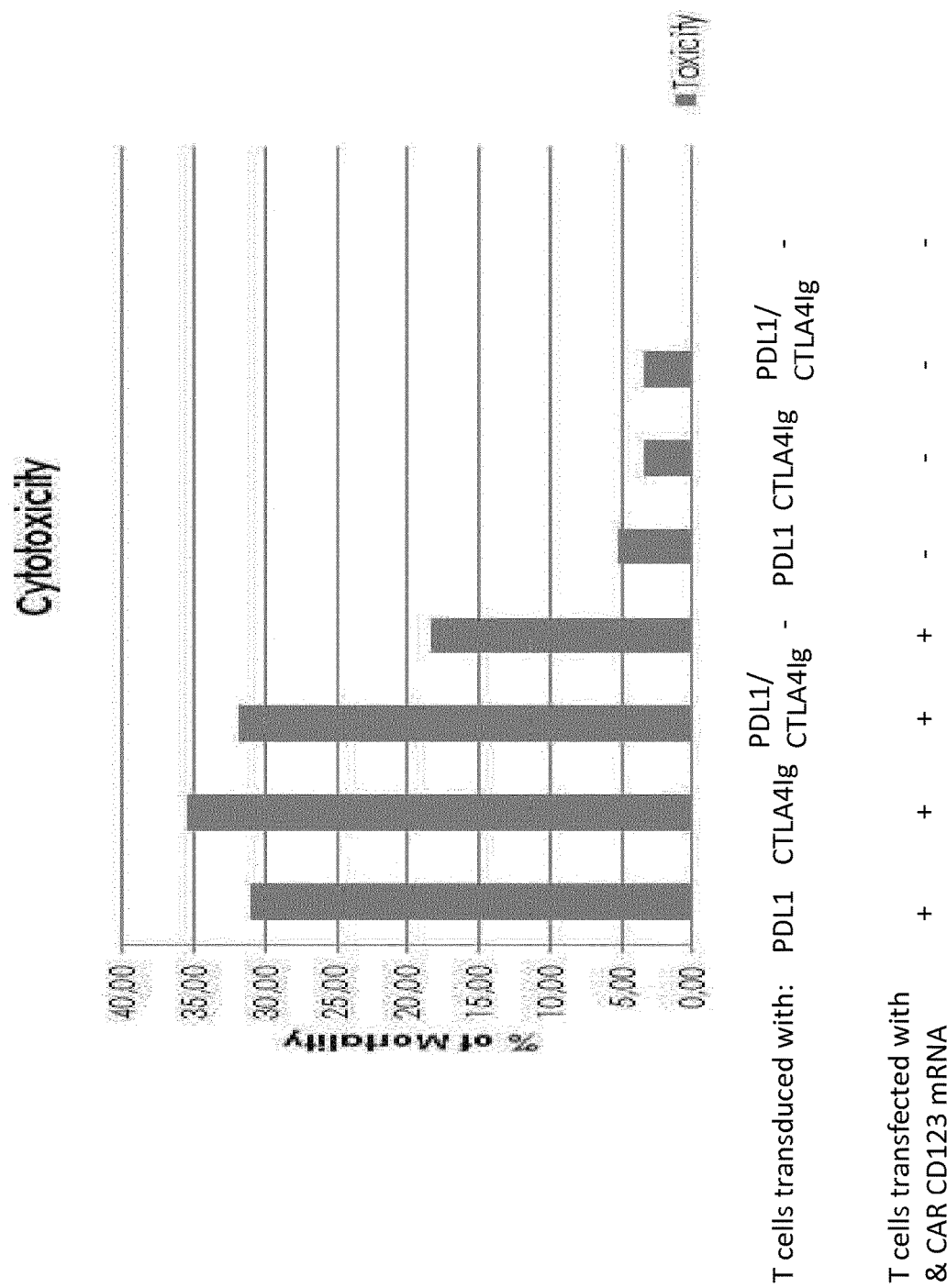

FIG. 19: Cytotoxicity assay in which indicated differently engineered CAR T cells (as shown under the graph) are incubated at a E:T ratio of 10:1 with specific target cells (MOLM-13; expressing CD123 antigen) and control negative cells (Daudi) for 4 hours. Target cell death is measured by flow cytometry and is normalized for non-specific killing (Daudi).

Figure 20:
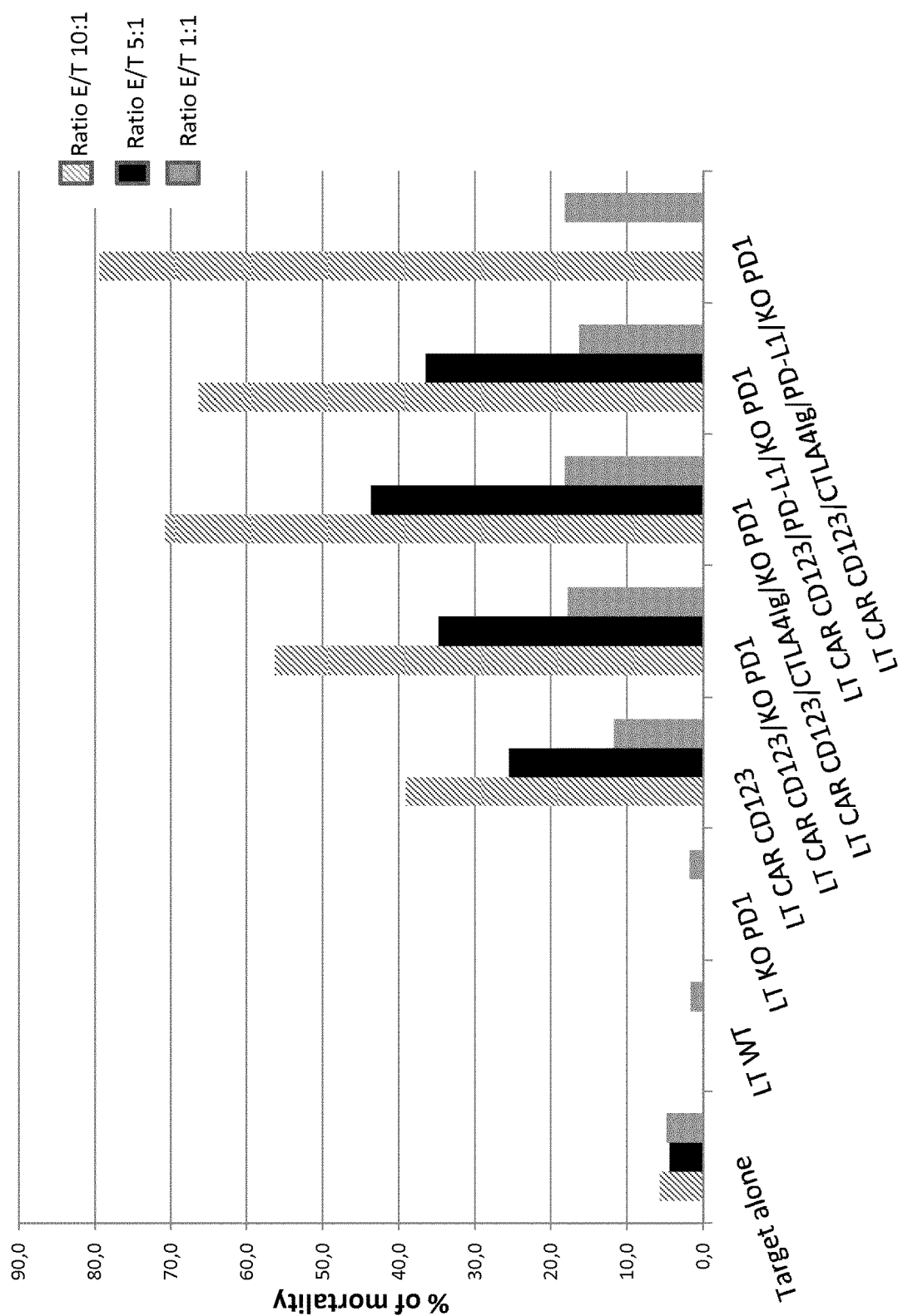

FIG. 20. Cytotoxicity assay in which Indicated differently engineered CAR T cells (as shown under the graph) are incubated at E:T ratio of 10:1 (hatched bar), 5:1 (dark bars) and 1:1 (grey bars) with specific target cells (MOLM-13) and control negative cells (Daudi) for 4 hours. Target cell death is measured by flow cytometry and is normalized for non-specific killing (Daudi).

Figure 21:
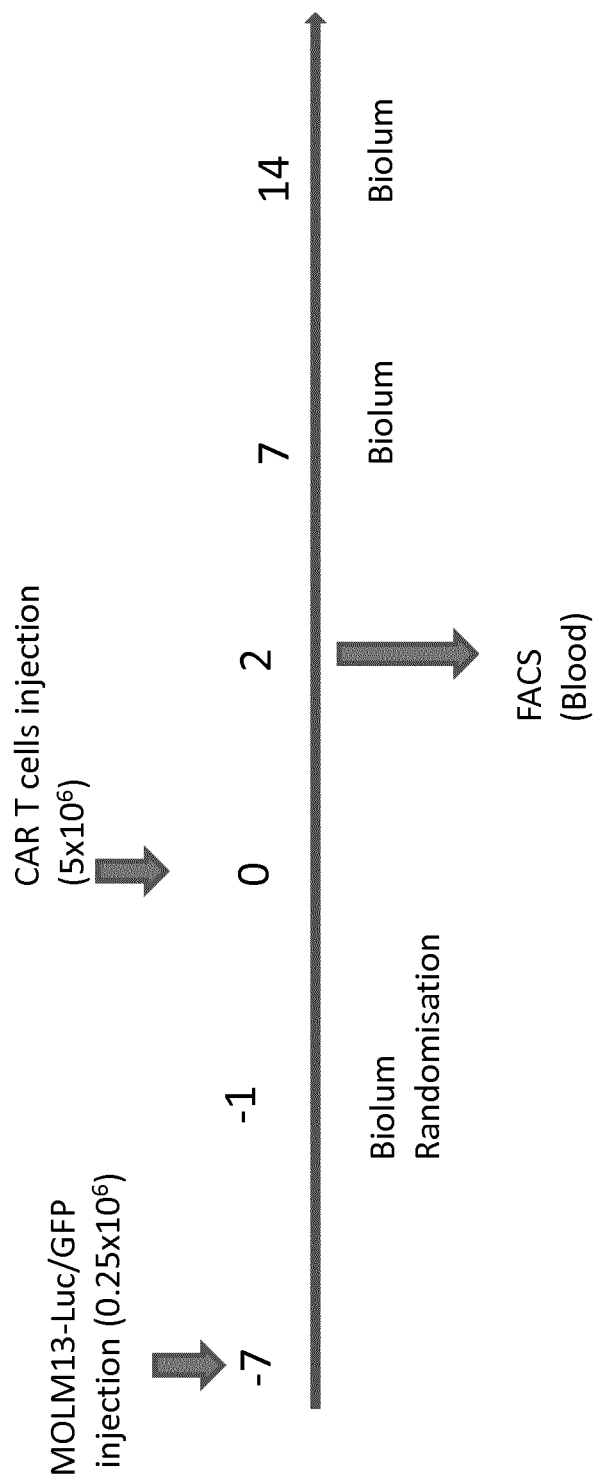

FIG. 21. Outline scheme for in vivo experiment. NOG mice are first injected with MOLM-13 (luc/GFP) tumor cell line 7 days before engineered CAR T cells injection. Tumor progression is monitored via bioluminescence (Biolum.) analysis and overall survival.

FIG. 22. Engineered T cells are monitored for the CAR CD123 and PD-L1 cell surface expression by flow cytometry.

Figure 23A:
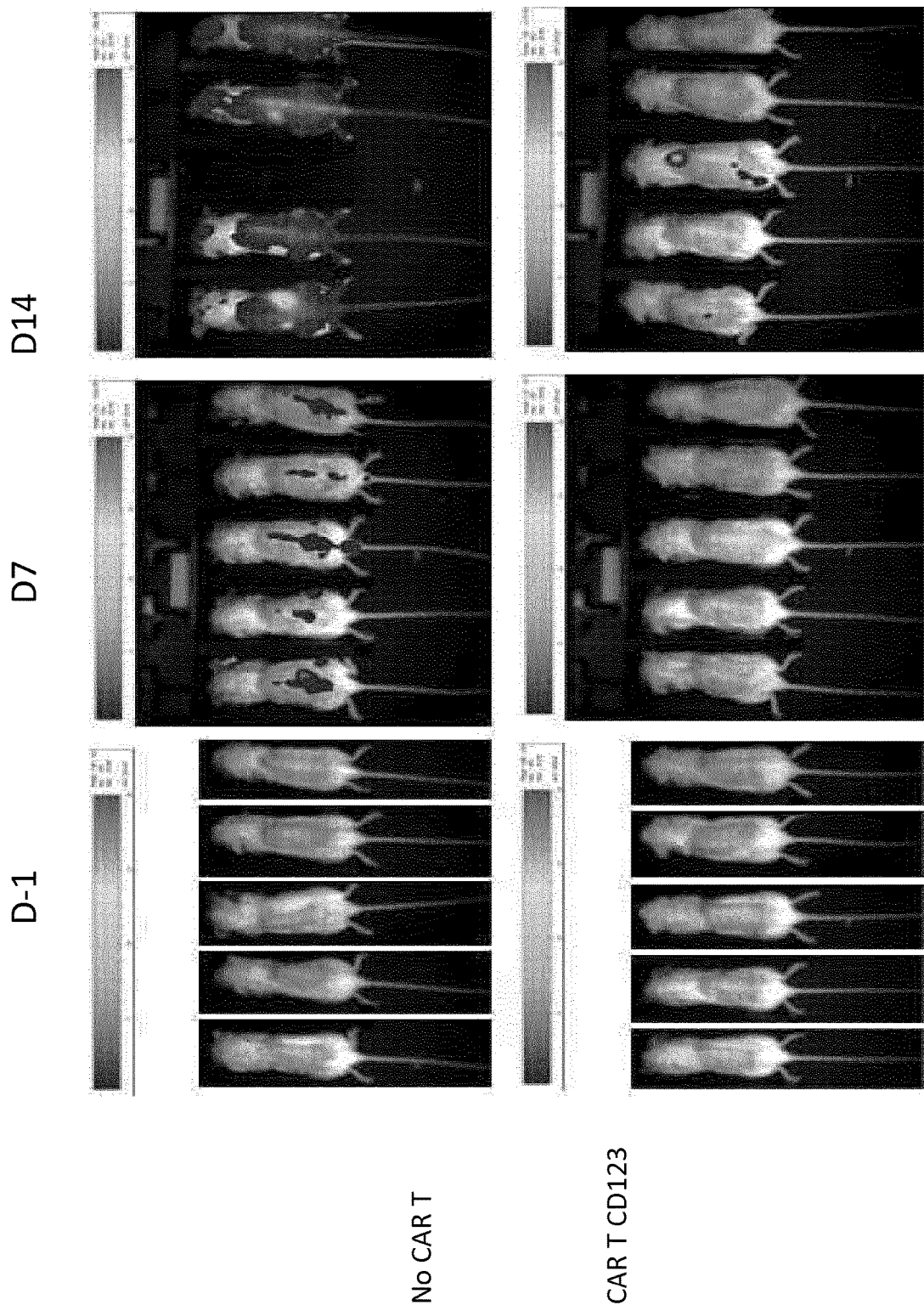
Figure 23B:
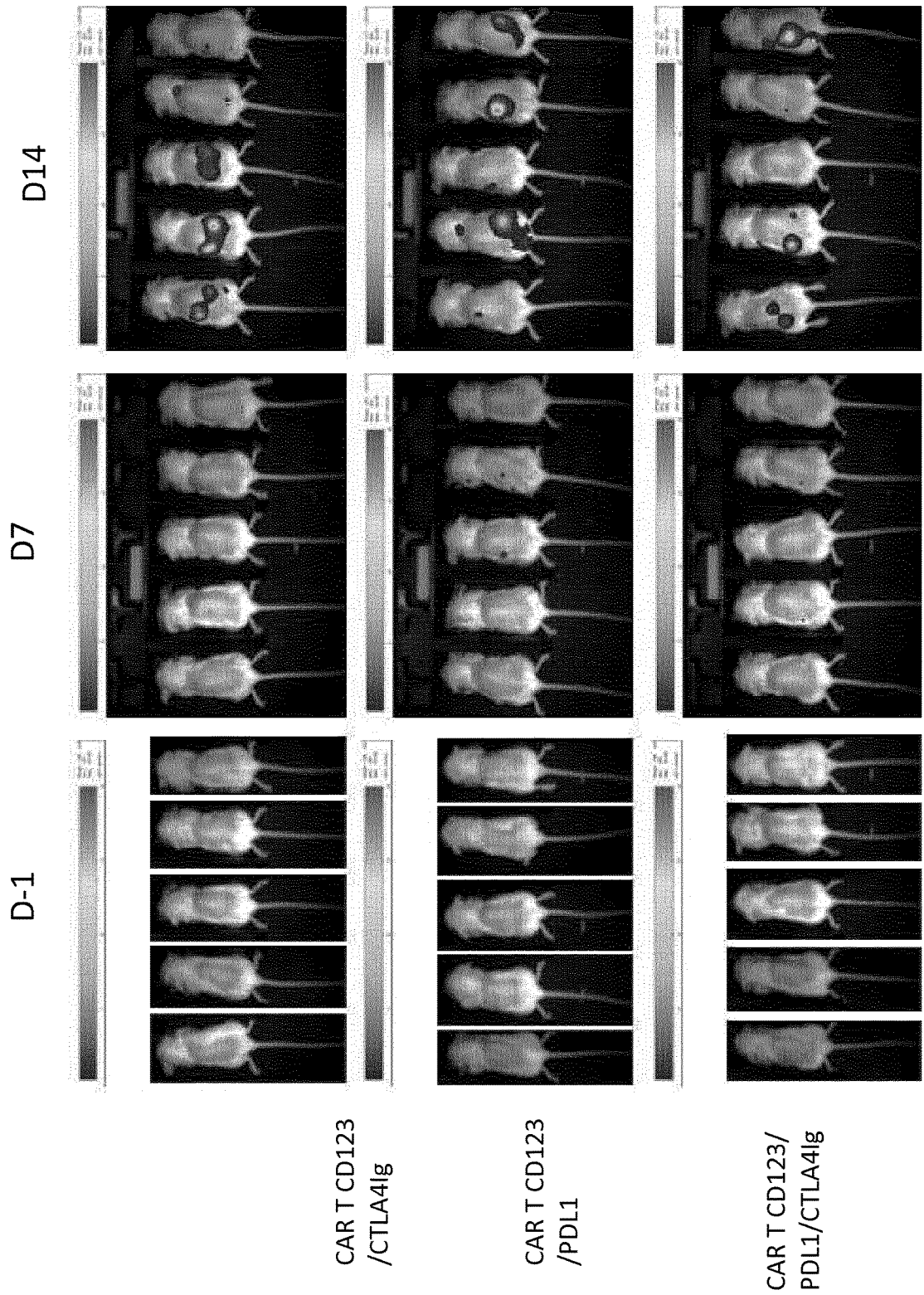

FIG. 23. Bioluminescence imaging from D-1 to D14 showing the tumors in the NOG mice. The dark spots in the photos represent the tumors. The different groups of T cells injected into the mice are presented as follows. In FIG. 23A: untransfected T cells (no CAR T cells) or T cells transfected by anti-CD123 CAR (CAR T CD123). In FIG. 23B: T cells transfected by anti-CD123 CAR and transduced with CTLA4Ig (CAR T CD123/CTLA4Ig); T cells transfected by anti-CD123 CAR and transduced with PD-L1 (CAR T CD123/PDL1); T cells transfected by anti-CD123 CAR and transduced with CTLA4Ig and with PD-L1 (CAR T CD123/PDL1/CTLA4Ig).

Figure 24:
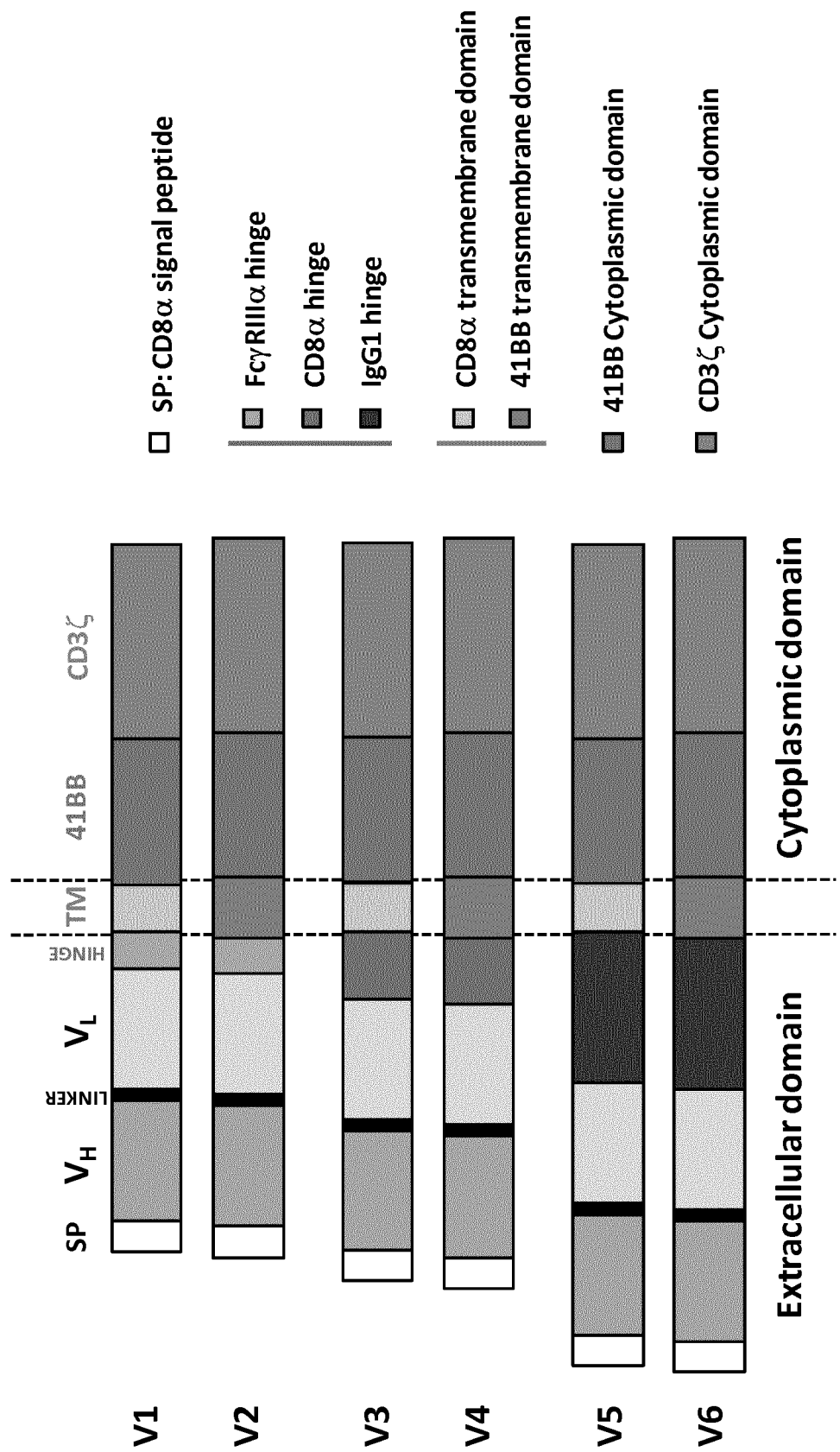

FIG. 24: Schematic representation of the different single chain chimeric antigen receptor CAR Architecture (V1 to V6) with the components: VH and VL chains specific to antigen, hinge, transmembrane domain (TM), co-stimulatory domain (4-1BB) and signaling transduction domain (CD3zeta), optionally with linker(s).

Table 1: Description of the β2m TALE-nucleases sequences

Table 2: Polynucleotide sequence of 2 pairs of TALENs are presented and for 2 different PDC1 gene targets Table 3: Polynucleotide sequences of plasmidic constructs expressing CLTA-4a, CTLA-4b and PD-L1.

Table 4: Polypeptide sequences of ISU domain variants from diverse virus.

Table 5: Polypeptide sequences of a viral MHC homolog (UL18) and a panel of NKG2D ligands.

Table 6: Aminoacid sequences of FP polypeptide from natural and artificial origins.

Table 7: Description of the TRAC and TRBC TALE-nucleases and sequences of the TALE-nucleases target sites in the human corresponding genes.

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

In a general aspect, the present invention relates to methods for new adoptive immunotherapy strategies in treating cancer and infections.

The present invention relates to the following main embodiments:

1) Method to increase the persistence and/or the engraftment of allogeneic immune cells, comprising:

a) providing allogeneic cells;

b) modifying said cells by inactivating at least one endogenous gene encoding a polypeptide involved in the self and non-self antigen recognition;

and;
  c) contacting said immune cells with at least one non-endogenous immunosuppressive polypeptide.

2) The method of embodiment 1, wherein said immune cells are hematopoietic cells.

3) The method of embodiment 1 or embodiment 2, wherein said immune cells are primary cells.

4) The method according to any one of embodiment 1 to 3, wherein said expression or contact in step c) does not specifically inhibit T regulatory cells.

5) The method of any one of embodiment 1 to 4, wherein said expression or contact in step c) does specifically inhibit CD8+ T cells.

6) The method according to embodiment 1 to embodiment 5, wherein the step c) is performed by the expression in said immune cells at least one non-endogenous polynucleotide directing the secretion of at least one non-endogenous immunosuppressive polypeptide.

7) The method according to embodiment 1 to embodiment 6, wherein the step c) contains additionally an inactivation of the expression of a gene encoding PD-1.

8) The method according to embodiment 7, wherein inactivation of PD-1 gene is performed by using a polynucleotide encoding TALE-nucleases of SEQ ID NO 11-12 and 13-14.

9) The method according to any one of embodiment 1 to 8, wherein said polypeptide in step b) is chosen amongst TCR, MHC class of class I component, b-2 microglobulin (B2M), TAP1 and large multifunctional protease 2.

10) The method according to any one of embodiment 1 to 9, wherein said polypeptide in step c) is chosen amongst PDL-1, CTLA-4, viral MHC homolog, NKG2D ligand, viral env immune suppressive domain (ISU) or the viral FP protein.

11) The method according to any one of embodiment 1 to 10, wherein step b) is performed by the inactivation of the B2M and step c) is performed by the expression of inactive PDL-1 ligand in said allogeneic immune cells.

12) The method according to any one of embodiment 1 to 11, wherein the additional modification in step c) is performed by the expression of CTLA-4 immunoglobulins in said allogeneic immune cells.

13) The method according to embodiment 12, wherein the nucleic acid molecule encoding CTLA-4 immunoglobulins to be expressed shares at least 80%, preferably 90% and more preferably 95% of identity with SEQ ID NO: 16-17.

14) The method according to any one of embodiment 1 to 13, wherein step b) is performed by the inactivation of the TCR and step c) is performed by the expression of inactive PDL-1 ligand by said allogeneic immune cells.

15) The method according to anyone of embodiment 1 to 10, wherein step c) is performed by expressing viral env immune suppressive domain (ISU) chosen from FeLV, MLV, HERV or the viral FP protein.

16) The method of anyone of embodiment 1 to 10, wherein step b) is performed by the inactivation of the B2M and step c) is performed by the expression of viral env immune suppressive domain (ISU) by said allogeneic immune cells.

17) The method of anyone of embodiment 1 to 10, wherein step b) is performed by the inactivation of the TCR and step c) is performed by the expression of viral env immune suppressive domain (ISU) by said allogeneic immune cells.

18) The method according to embodiment 16 or 17, wherein the nucleic acid molecule encoding viral env immune suppressive domain (ISU) to be expressed shares at least 80%, preferably 90% and more preferably 95% of identity with SEQ ID NO: 19-38.

19) The method of anyone of embodiment 1 to 10, wherein step b) is performed by the inactivation of the B2M and step c) is performed by the expression of viral FP protein by said allogeneic immune cells.

20) The method of anyone of embodiment 1 to 10, wherein step b) is performed by the inactivation of the TCR and step c) is performed by the expression of viral FP protein by said allogeneic immune cells.

21) The method according to embodiment 19 or 20, wherein the nucleic acid molecule encoding viral FP protein to be expressed shares at least 80%, preferably 90% and more preferably 95% of identity with SEQ ID NO: 48-50.

22) The method of anyone of embodiment 1 to 10, wherein step b) is performed by the inactivation of the B2M and step c) is performed by the expression of NKG2G ligand by said allogeneic immune cells.

23) The method of anyone of embodiment 1 to 10, wherein step b) is performed by the inactivation of the TCR and step c) is performed by the expression of NKG2G ligand by said allogeneic immune cells.

24) The method according to embodiment 22 or 23, wherein the nucleic acid molecule encoding NKG2G ligand to be expressed shares at least 80%, preferably 90% and more preferably 95% of identity with SEQ ID NO: 40-47.

25) The method according to anyone of embodiment 1 to 10, wherein the viral MHC homolog in step b) ii) is UL18.

26) The method of anyone of embodiment 1 to 10, wherein step b) is performed by the inactivation of the B2M and step c) is performed by the expression of viral MHC homolog UL18 protein by said allogeneic immune cells.

27) The method of anyone of embodiment 1 to 10, wherein step b) is performed by the inactivation of the TCR and step c) is performed by the expression of viral MHC homolog UL18 protein by said allogeneic immune cells.

28) The method according to embodiment 26 or 27, wherein the nucleic acid molecule encoding viral MHC homolog UL18 to be expressed shares at least 80%, preferably 90% and more preferably 95% of identity with SEQ ID NO: 39.

29) The method according to any one of embodiment 1 to 5 or embodiments 8-9, wherein the step c) is performed by the incubation of said immune in at least one non-endogenous immunosuppressive polypeptide.

30) The method according to embodiment 29, wherein said non-endogenous immunosuppressive polypeptide is anti-CD80 or anti-CD86 mAbs.

31) The method according to anyone of embodiment 1 or 30, wherein gene inactivation in step b) is performed by using a TAL-nuclease, meganuclease, zing-finger nuclease (ZFN), or RNA guided endonuclease.

32) The method according to anyone of embodiment 1 or 31, wherein gene inactivation in step b) is performed using a TAL-nuclease.

33) The method according to any one of embodiment 1 to 31, wherein gene inactivation in step b) is performed by using a RNA-guided endonucleases.

34) The method according to embodiment 33, wherein the RNA-guided endonuclease is Cas9.

35) The method according to any one of embodiment 1-10, 11-15, 17-18, 20-21, 23-25 or 27-34 wherein gene inactivation in step b) is performed by using a nucleic acid molecule that inhibits the expression of a gene encoding TCR.

36) The method according to embodiment 32, wherein inactivation of TCR gene is performed by using the TALE-nucleases of SEQ ID NO 52-53, 55-56, 62-63 and 65-66.

37) The method according to any one of embodiments 1-12, 13-16, 18-19, 21-22, 24-26 or 28-34 wherein inactivation gene in step b) is performed by using a nucleic acid molecule that inhibits the expression of a gene encoding B2M.

38) The method according to embodiment 32, wherein inactivation of B2M gene is performed by using the TALE-nucleases of SEQ ID NO 2-3, 5-6 and 8-9.

39) The method according to any one of embodiments 1 to 38, further comprising the step of:
d) introducing into said T-cell an exogenous nucleic acid molecule comprising a nucleotide sequence coding for a Chimeric Antigen Receptor (CAR) directed against at least one antigen expressed at the surface of a malignant or infected cell.

40) The method according to embodiment 39 wherein said Chimeric Antigen Receptor comprises scFv (VH and VL chains) having as antigenic target sequence of over 80% identity, preferably over 90%, and more preferably over 95% with SEQ ID NO 67 (CD19 antigen), SEQ ID NO 68 (CD38 antigen), SEQ ID NO 69 (CD123 antigen), SEQ ID NO 70 (CS1 antigen), SEQ ID NO 71 (BCMA antigen), SEQ ID NO 72 (FLT-3 antigen), SEQ ID NO 73 (CD33 antigen), SEQ ID NO 74 (CD70 antigen), SEQ ID NO 75 (EGFR-3v antigen) and SEQ ID NO 76 (WT1 antigen).

41) The method according to any one of embodiments 1 to 40, further comprising the step of:
d) expanding the resulting engineered T-cell.

42) An engineered, preferably isolated, T-cell, obtainable by using the method according to anyone of embodiment 1 to 41.

43) The engineered T-cell according to embodiment 42 for use as a medicament.

44) The engineered T-cell according to embodiment 42 or embodiment 43 for use in the treatment of a cancer or viral infection.

45) The engineered T-cell according to any one of embodiments 42 to 44 for use in the treatment of lymphoma.

46) The engineered T-cell according to any one of embodiments 42 to 45, wherein said T-cell originates from a patient to be treated.

47) The engineered T-cell according to any one of embodiments 42 to 45, wherein said T-cell originates from a donor.

48) A composition comprising at least one engineered T-cell according to any one of embodiments 42 to 47.

The Present Invention Relates More Particularly to the Following Embodiments:

1) Method to increase the persistence and/or the engraftment of allogeneic immune cells in presence of host immune cells, comprising:
a) providing allogeneic cells;
b) modifying said cells by inactivating at least one endogenous gene encoding a polypeptide involved in the response against self and non-self antigen recognition;
and;
c) contacting said host immune cells with at least one non-endogenous immunosuppressive polypeptide which has the effect to prevent them from interacting with allogeneic immune cells.

2) The method according to embodiment 1, wherein said polypeptide in step b) is chosen amongst TCR, MHC class of class I component, b-2 microglobulin (B2M), TAP1 and large multifunctional protease 2.

3) Method according to embodiment 1 or 2, wherein said immunosuppressive polypeptide in step c) is present under a membrane-bound form and/or under a secreted form.

4) Method of anyone of embodiment 1 to 3, wherein the step c) is performed by the expression in said immune cells at least one non-endogenous polynucleotide encoding for one non-endogenous immunosuppressive polypeptide bound to the membrane surface of said immune cells.

5) Method of anyone of embodiment 1 to 4, wherein said one non-endogenous immunosuppressive polypeptide bound to the membrane surface of said immune cells is a PD-L1 ligand.

6) The method according to embodiment 5, wherein the nucleic acid molecule encoding PD-L1 ligand under a membrane-bound form to be expressed shares at least 80%, preferably 90% and more preferably 95% of identity with SEQ ID NO:18.

7) Method of any one of embodiment 1 to 3, wherein said immunosuppressive polypeptide is present under a secreted form.

8) The method according to any one of embodiment 1-3 or embodiment 7, wherein the step c) is performed by the expression in said immune cells at least one non-endogenous polynucleotide encoding for one non-endogenous immunosuppressive polypeptide under a secreted form in said immune cells. 9) The method according to embodiment 8, wherein the nucleic acid molecule encoding CTLA-4 immunoglobulins to be expressed shares at least 80%, preferably 90% and more preferably 95% of identity with SEQ ID NO: 16-17.

10) The method according to any one of embodiment 1-8, wherein step c) is performed by contacting said host immune cells with both non-endogenous immunosuppressive polypeptide PD-L1 ligand and CTLA-4 immunoglobulins.

11) The method according to embodiment 10, wherein step c) is performed by the step c) is performed by the expression in said immune cells of both non-endogenous immunosuppressive polypeptide PD-L1 ligand and CTLA-4 immunoglobulins.

12) The method according to embodiment 11, wherein said secretion of at least one non-endogenous immunosuppressive polypeptide is PD-L1 ligand under a secreted form.

13) The method according to anyone of embodiment 9 to 12, wherein the nucleic acid molecules encoding PD-L1 ligand under a membrane-bound form and CTLA-4 immunoglobulins to be expressed in said allogeneic immune cells shares at least 80%, preferably 90% and more preferably 95% of identity with respectively SEQ ID NO:18 and SEQ ID NO: 16-17.

14) The method according to anyone of embodiment 1 to 13, wherein said immune cells are primary cells.

15) The method according to any one of embodiment 1 to 3, wherein said expression or contact in step c) does not specifically inhibit T regulatory cells.

16) The method according to any one of embodiment 1 to 15, wherein said expression or contact in step c) does specifically inhibit host CD8+ T cells.

17) The method according to anyone of embodiment 1 to 16, wherein the step c) contains additionally an inactivation of the expression of a PD-1 gene.

18) The method according to any one of embodiment 1 to 3, wherein the step c) is performed by the expression in said immune cells at least one non-endogenous polynucleotide encoding for PD-L1 ligand under a membrane-bound form, and a further modification of said allogeneic cells is performed by an inactivation of the expression of PD-1 gene.

19) The method according to any one of embodiment 1 to 18, wherein the step c) is performed by the expression in said immune cells at least one non-endogenous polynucleotide directing the secretion of CTLA4 Ig, and a further modification of said allogeneic cells is performed by an inactivation of the expression of PD-1 gene.

20) The method according to any one of embodiment 1 to 19, wherein step c) is performed by the step c) is performed by the expression in said immune cells of both non-endogenous immunosuppressive polypeptide PD-L1 ligand and CTLA-4 immunoglobulins, and a further modification of said allogeneic immune cells is performed by an inactivation of the expression of PD-1 gene.

21) The method according to embodiment 20, wherein inactivation of PD-1 gene is performed by using a polynucleotide encoding TALE-nucleases of SEQ ID NO 11-12 and 13-14.

22) The method according to any one of embodiment 1 to 16, wherein said polypeptide in step c) is chosen amongst PD-L1, CTLA-4, viral MHC homolog, NKG2D ligand, viral env immune suppressive domain (ISU) or the viral FP protein.

23) The method according to any one of embodiment 1 to 4, wherein step b) is performed by the inactivation of the B2M and step c) is performed by the expression of PD-L1 ligand in said allogeneic immune cells.

24) The method according to any one of embodiment 1 to 4, wherein step b) is performed by the inactivation of the TCR and step c) is performed by the expression of PD-L1 ligand by said allogeneic immune cells.

25) The method according to anyone of embodiment 1 to 4, wherein step c) is performed by expressing viral env immune suppressive domain (ISU) chosen from FeLV, MLV, HERV or the viral FP protein.

26) The method according to anyone of embodiment 1 to 4 or embodiment 25, wherein step b) is performed by the inactivation of the B2M and step c) is performed by the expression of viral env immune suppressive domain (ISU) by said allogeneic immune cells.

27) The method according to anyone of embodiment 1 to 4, wherein step b) is performed by the inactivation of the TCR and step c) is performed by the expression of viral env immune suppressive domain (ISU) by said allogeneic immune cells.

28) The method according to embodiment 26 or 27, wherein the nucleic acid molecule encoding viral env immune suppressive domain (ISU) to be expressed shares at least 80%, preferably 90% and more preferably 95% of identity with SEQ ID NO: 19-38.

29) The method according to anyone of embodiment 1 to 4, wherein step b) is performed by the inactivation of the B2M and step c) is performed by the expression of viral FP protein by said allogeneic immune cells.

30) The method according to anyone of embodiment 1 to 4 or embodiment 29, wherein step b) is performed by the inactivation of the TCR and step c) is performed by the expression of viral FP protein by said allogeneic immune cells.

31) The method according to embodiment 29 or 30, wherein the nucleic acid molecule encoding viral FP protein to be expressed shares at least 80%, preferably 90% and more preferably 95% of identity with SEQ ID NO: 48-50.

32) The method according to anyone of embodiment 1 to 4, wherein step b) is performed by the inactivation of the B2M and step c) is performed by the expression of NKG2G ligand by said allogeneic immune cells.

33) The method according to anyone of embodiment 1 to 4 or embodiment 32, wherein step b) is performed by the inactivation of the TCR and step c) is performed by the expression of NKG2G ligand by said allogeneic immune cells.

34) The method according to embodiment 32 or 33, wherein the nucleic acid molecule encoding NKG2G ligand to be expressed shares at least 80%, preferably 90% and more preferably 95% of identity with SEQ ID NO: 40-47.

35) The method according to anyone of embodiment 1 to 4, wherein the viral MHC homolog in step b) ii) is UL18.

36) The method according to anyone of embodiment 1 to 4 or embodiment 35, wherein step b) is performed by the inactivation of the B2M and step c) is performed by the expression of viral MHC homolog UL18 protein by said allogeneic immune cells.

37) The method according to anyone of embodiment 1 to 4 or embodiment 36, wherein step b) is performed by the inactivation of the TCR and step c) is performed by the expression of viral MHC homolog UL18 protein by said allogeneic immune cells.

38) The method according to embodiment 36 or 37, wherein the nucleic acid molecule encoding viral MHC homolog UL18 to be expressed shares at least 80%, preferably 90% and more preferably 95% of identity with SEQ ID NO: 39.

39) The method according to any one of embodiment 1 to 38, wherein the step c) is performed by the incubation of said immune in at least one non-endogenous immunosuppressive polypeptide.

40) The method according to embodiment 39, wherein said non-endogenous immunosuppressive polypeptide is anti-CD80 or anti-CD86 mAbs.

41) The method according to anyone of embodiment 1 to 40, wherein gene inactivation in step b) is performed by using a TAL-nuclease, meganuclease, zing-finger nuclease (ZFN), or RNA guided endonuclease.

42) The method according to embodiment 41, wherein gene inactivation in step b) is performed using a TAL-nuclease.

43) The method according to embodiment 41, wherein gene inactivation in step b) is performed by using a RNA-guided endonucleases.

44) The method according to embodiment 43 wherein the RNA-guided endonuclease is Cas9.

45) The method according to any one of embodiments 1-18, 20-22, 24-25, 27-28, 30-32 or 34-41 wherein gene inactivation in step b) is performed by using a nucleic acid molecule that inhibits the expression of a gene encoding TCR.

46) The method according to embodiment 45, wherein inactivation of TCR gene is performed by using the TALE-nucleases of SEQ ID NO 52-53, 55-56, 62-63 and 65-66.

47) The method according to any one of embodiments 1-17, 20-2, 25-26, 28-29, 31-33 or 35-41 wherein inactivation gene in step b) is performed by using a nucleic acid molecule that inhibits the expression of a gene encoding B2M.

48) The method according to embodiment 47, wherein inactivation of B2M gene is performed by using the TALE-nucleases of SEQ ID NO 2-3, 5-6 and 8-9.

49) The method according to any one of embodiments 1 to 48, further comprising the step of:
d) introducing into said T-cell an exogenous nucleic acid molecule comprising a nucleotide sequence coding for a Chimeric Antigen Receptor (CAR) directed against at least one antigen expressed at the surface of a malignant or infected cell.

50) The method according to embodiment 49 wherein said Chimeric Antigen Receptor comprises scFv (VH and VL chains) having as antigenic target sequence of over 80% identity, preferably over 90%, and more preferably over 95% with SEQ ID NO 67 (CD19 antigen), SEQ ID NO 68 (CD38 antigen), SEQ ID NO 69 (CD123 antigen), SEQ ID NO 70 (CS1 antigen), SEQ ID NO 71 (BCMA antigen), SEQ ID NO 72 (FLT-3 antigen), SEQ ID NO 73 (CD33 antigen), SEQ ID NO 74 (CD70 antigen), SEQ ID NO 75 (EGFR-3v antigen) and SEQ ID NO 76 (WT1 antigen)

51) The method according to anyone of embodiment 1 to 50, wherein step c) is performed by the step c) is performed by the expression in said allogeneic immune cells of non-endogenous immunosuppressive polypeptide PD-L1 ligand and/or CTLA-4 immunoglobulins, said allogeneic immune cells being further modified by the expression of an anti-CD123 Chimeric Antigen Receptor.

52) The method according to embodiment 51, wherein a further modification of said allogeneic immune cells is performed by an inactivation of the expression of the PD-1 gene.

53) The method according to any one of embodiments 1 to 52, further comprising the step of:
d) expanding the resulting engineered T-cell.

54) An engineered, preferably isolated, T-cell, obtainable by using the method according to anyone of embodiment 1 to 53.

55) The engineered T-cell according to embodiment 54 for use as a medicament.

56) The engineered T-cell according to embodiment 54 or embodiment 55 for use in the treatment of a cancer or viral infection.

57) The engineered T-cell according to any one of embodiments 54 to 56 for use in the treatment of lymphoma or leukemia.

58) The engineered T-cell according to any one of embodiments 54 to 57, wherein said T-cell originates from a patient to be treated.

59) The engineered T-cell according to any one of embodiments 54 to 57, wherein said T-cell originates from a donor.

60) A composition comprising at least one engineered T-cell according to any one of embodiments 54 to 59.

More details about the above aspects of the invention are provided in the description below.

Non Alloreactive and Highly Persistent T Cells for Immunotherapy

According to a first aspect of the present invention, the inventors have shown that some genes, when they are expressed in allogeneic immune cells, could allow an increase of their persistence in the host organism for a better efficacy.

The present invention relates to a method to increase the persistence and/or the engraftment of allogeneic immune cells, preferably in presence of host immune cells, comprising:
i) providing allogeneic cells;
ii) modifying said cells by inactivating at least one endogenous gene encoding a polypeptide involved in the response against self and non-self antigen recognition; and;
iii) contacting said host immune cells with at least one non-endogenous immunosuppressive polypeptide.

Said non-endogenous immunosuppressive polypeptide is expected to have the effect of preventing host immune cells from interacting with allogeneic immune cells.

"Persistence" refers to the ability of cells to resist rejection and remain and/or increase in number over time (e.g., days, weeks, months, years) in vivo. In general, the engineered immune cells of the present invention can be found in patient's blood at least 10 days, preferably at least 20 days, more preferably at least 25 days and even more preferably at least 30 days after infusion into said patient.

"Engraftment" refers to the process of cellular contact and incorporation into an existing site of interest in vivo.

By "increased persistence and/or engraftment", is meant that the number of allogeneic immune cells, engineered to render them persistent, remains higher during the course of the treatment, compared to the case where non-engineered ones (i.e non persistent) are administered to the patient. Such improved persistence and/or engraftment in allogeneic immune cells (e.g. T cells) to be injected to a patient are part of the immunological tolerance (or "tolerisation") which describes a state of unresponsiveness of the host immune system with respect to said immune cells, whereas said immune cells retain the capacity to elicit an immune response.

Inactivation of Gene Involved in the Self and Non-Self Antigen Recognition

By "self and non-self antigen recognition", it is intended the screening performed by the cellular immune system whereby peptides are presented by host cells on Major Histocompatibility Complex (MHC) molecules to assess if cells are infected by foreign organisms. This screening involves other transmembrane structures such as for instance TCR, or TAP1/TAP2 or protease 2.

By inactivating a gene it is intended that the gene of interest is not expressing a functional protein form. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. The nucleic acid strand breaks caused by the rare-cutting endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event—i.e a mutagenesis event consecutive to an NHEJ event—has occurred can be identified and/or selected by well-known method in the art.

Endonucleolytic breaks are known to stimulate the rate of homologous recombination. Thus, in another embodiment, the genetic modification step of the method further comprises a step of introduction into cells an exogeneous nucleic acid comprising at least a sequence homologous to a portion of the target nucleic acid sequence, such that homologous recombination occurs between the target nucleic acid sequence and the exogeneous nucleic acid. In particular embodiments, said exogeneous nucleic acid comprises first and second portions which are homologous to region 5' and 3' of the target nucleic acid sequence, respectively. Said exogenous nucleic acid in these embodiments also comprises a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogenous nucleic acid. Preferably, homologous sequences of at least 50 bp, preferably more than 100 bp and more preferably more than 200 bp are used within said donor matrix. Therefore, the exogenous nucleic acid is preferably from 200 bp to 6000 bp, more preferably from 1000 bp to 2000 bp. Indeed, shared nucleic acid homologies are located in regions flanking upstream and downstream the site of the break and the nucleic acid sequence to be introduced should be located between the two arms.

According to a preferred embodiment, the gene inactivation is preferably performed by using a TAL-nuclease, meganuclease, zing-finger nuclease (ZFN), or RNA/DNA guided endonuclease, such as Cas9, Cpf1 or Argonaute.

According to a more preferred embodiment, the inactivation of said gene involved in the self and non-self antigen recognition is performed by using TALE-nucleases. This can be accomplished at a precise genomic location targeted by a specific TALE-nuclease, wherein said specific TALE-nuclease catalyzes a cleavage and wherein said exogenous nucleic acid successively comprising at least a region of homology and a sequence to inactivate one targeted gene selected from the group previously cited. Several genes can be, successively or at the same time, inactivated by using several TALE-nucleases respectively and specifically targeting one defined gene and several specific. By TALE-nuclease is intended a fusion protein consisting of a DNA-binding domain derived from a Transcription Activator Like Effector (TALE) and one nuclease catalytic domain to cleave a nucleic acid target sequence. (Boch, Scholze et al. 2009; Moscou and Bogdanove 2009; Christian, Cermak et al. 2010; Cermak, Doyle et al. 2011; Geissler, Scholze et al. 2011; Huang, Xiao et al. 2011; Li, Huang et al. 2011; Mahfouz, Li et al. 2011; Miller, Tan et al. 2011; Morbitzer, Romer et al. 2011; Mussolino, Morbitzer et al. 2011; Sander, Cade et al. 2011; Tesson, Usal et al. 2011; Weber, Gruetzner et al. 2011; Zhang, Cong et al. 2011; Deng, Yan et al. 2012; Li, Piatek et al. 2012; Mahfouz, Li et al. 2012; Mak, Bradley et al. 2012).

According to another preferred embodiment, the inactivation of said gene involved in the self and non-self antigen recognition is performed by RNA-guided endonuclease such as Cas9 or DNA-guided endonuclease, such as Argonaute based techniques as described in WO2014189628.

The present invention relates to a method to increase the persistence and/or the engraftment of allogeneic cells which comprises a step of inactivation of at least one gene involved in the self/non-self recognition. By "gene involved in self/non-self recognition" is meant a gene encoding a polypeptide that is structurally part of an external receptor or ligand, which is deemed necessary for the detection and destruction of allogeneic cells by the immune system. Such genes preferably code for at least one component of TCR, MHC, in particular class I MHC, beta-2 microglobulin (B2M), TAP1 or large multifunctional protease 2.

In a preferred embodiment, the gene to be inactivated is TCR or B2M, more preferably TCR.

In the present invention new TALE-nucleases have been designed for precisely targeting relevant genes for adoptive immunotherapy strategies. Preferred TALE-nucleases according to the invention are those recognizing and cleaving the target sequence selected from the group consisting of SEQ ID NO: 2-3, 5-6 and 8-9 for inactivation of β2m and SEQ ID NO 52-53, 55-56, 62-63 and 65-66. (TCR).

TALE-Nucleases Cleaving Human β2m mRNA encoding the TALE-nucleases targeting exons of the human β2m gene were ordered from Cellectis Bioresearch (8, rue de la Croix Jarry, 75013 PARIS). Table 1 below indicates the target sequences cleaved by each of the two independent entities (called half TALE-nucleases) each containing a repeat sequence engineered to bind and cleave between target sequences consisting of two 17-bp long sequences (called half targets) separated by a 15-bp spacer.

TABLE 1

Description of the β2m TALE-nucleases sequences

| Target name | SEQ ID NO: | Half TALE-nuclease sequence |
|---|---|---|
| T01 Beta2M target | 1 | TCTCGCTCCGTGGCCTTAGCTGTGCTCGCGCTACTCTCTCTTTCTGGCCTGGAGGCTA |
| T01 TALEN Beta2M LEFT | 2 | ATGGGCGATCCTAAAAAGAAACGTAAGGTCATCGATTACCCATACGATGTTCCAGATTACGCTATCGATATCGCCGATCTACGCACGCTCGGCTACAGCCAGCAGCAACAGGAGAAGATCAAACCGAAGGTTCGTTCGACAGTGGCGCAGCACCACGAGGCACTGGTCGGCCACGGGTTTACACACGCGCACATCGTTGCGTTAAGCCAACACCCGGCAGCGTTAGGGACCGTCGCTGTCAAGTATCAGGACATGATCGCAGCGTTGCCAGAGGCGACACACGAAGCGATCGTTGGCGTCGGCAAACAGTGGTCCGGCGCACGCGCTCTGGAGGCCTTGCTCACGGTGGCGGGAGAGTTGAGAGGTCCACCGTTACAGTTGGACACAGGCCAACTTCTCAAGATTGCAAAACGTGGCGGCGTGACCGCAGTGGAGGCAGTGCATGCATGGCGCAATGCACTGACGGGTGCCCCGCTCAACTTGACCCCCCAGCAGGTGGTGGCCATCGCCAGCAATAATGGTGGCAAGCAGGCGCTGGAGACGGTCCAGCGGCTGTTGCCGGTGCTGTGCCAGGCCCACGGCTTGACCCCCCAGCAGGTGGTGGCCATCGCCAGCAATAATGGTGGCAAGCAGGCGCTGGAGACGGTCCAGCGGCTGTTGCCGGTGCTGTGCCAGGCCCACGGCTTGACCCCGGAGCAGGTGGTGGCCATCGCCAGCCACGATGGCGGCAAGCAGGCGCTGGAGACGGTCCAGCGGCTGTTGCCGGTGCTGTGCCAGGCCCACGGCTTGACCCCGGAGCAGGTGGTGGCCATCGCCAGCCACGATGGCGGCAAGCAGGCGCTGGAGACGGTCCAGCGGCTGTTGCCGGTGCTGTGCCAGGCCCACGGCTTGACCCCCAGCAGGTGGTGGCCATCGCCAGCAATGGCGGTGGCAAGCAGGCGCTGGAGACGGTCCAGCGGCTGTTGCCGGTGCTGTGCCAGGCCCACGGCTTGACCCCCAGCAGGTGGTGGCCATCGCCAGCAATGGCGGTGGCAAGCAGGCGCTGGAGACGGTCCAGCGGCTGTTGCCGGTGCTGTGCCAGGCCCACGGCTTGACCCCGG |

TABLE 1-continued

Description of the β2m TALE-nucleases sequences

| Target name | SEQ ID NO: | Half TALE-nuclease sequence |
|---|---|---|
| | | AGCAGGTGGTGGCCATCGCCAGCAATATTGGTGGCAAGCAGGCGCTGGAGACGG<br>TGCAGGCGCTGTTGCCGGTGCTGTGCCAGGCCCACGGCTTGACCCCCAGCAGGT<br>GGTGGCCATCGCCAGCAATAATGGTGGCAAGCAGGCGCTGGAGACGGTCCAGCG<br>GCTGTTGCCGGTGCTGTGCCAGGCCCACGGCTTGACCCCGGAGCAGGTGGTGGCC<br>ATCGCCAGCCACGATGGCGGCAAGCAGGCGCTGGAGACGGTCCAGCGGCTGTTGC<br>CGGTGCTGTGCCAGGCCCACGGCTTGACCCCCAGCAGGTGGTGGCCATCGCCAG<br>CAATGGCGGTGGCAAGCAGGCGCTGGAGACGGTCCAGCGGCTGTTGCCGGTGCT<br>GTGCCAGGCCCACGGCTTGACCCCCAGCAGGTGGTGGCCATCGCCAGCAATAAT<br>GGTGGCAAGCAGGCGCTGGAGACGGTCCAGCGGCTGTTGCCGGTGCTGTGCCAG<br>GCCCACGGCTTGACCCCCAGCAGGTGGTGGCCATCGCCAGCAATGGCGGTGGCA<br>AGCAGGCGCTGGAGACGGTCCAGCGGCTGTTGCCGGTGCTGTGCCAGGCCCACGG<br>CTTGACCCCCAGCAGGTGGTGGCCATCGCCAGCAATAATGGTGGCAAGCAGGCG<br>CTGGAGACGGTCCAGCGGCTGTTGCCGGTGCTGTGCCAGGCCCACGGCTTGACCC<br>CGGAGCAGGTGGTGGCCATCGCCAGCCACGATGGCGGCAAGCAGGCGCTGGAGA<br>CGGTCCAGCGGCTGTTGCCGGTGCTGTGCCAGGCCCACGGCTTGACCCCCAGCAG<br>GTGGTGGCCATCGCCAGCAATGGCGGTGGCAAGCAGGCGCTGGAGACGGTCCAG<br>CGGCTGTTGCCGGTGCTGTGCCAGGCCCACGGCTTGACCCCTCAGCAGGTGGTGG<br>CCATCGCCAGCAATGGCGGCGGCAGGCCGGCGCTGGAGAGCATTGTTGCCCAGTT<br>ATCTCGCCCTGATCCGGCGTTGGCCGCGTTGACCAACGACCACCTCGTCGCCTTGG<br>CCTGCCTCGGCGGGCGTCCTGCGCTGGATGCAGTGAAAAAGGGATTGGGGGATCC<br>TATCAGCCGTTCCCAGCTGGTGAAGTCCGAGCTGGAGGAGAAGAAATCCGAGTTG<br>AGGCACAAGCTGAAGTACGTGCCCCACGAGTACATCGAGCTGATCGAGATCGCCC<br>GGAACAGCACCCAGGACCGTATCCTGGAGATGAAGGTGATGGAGTTCTTCATGAA<br>GGTGTACGGCTACAGGGGCAAGCACCTGGGCGGCTCCAGGAAGCCCGACGGCGC<br>CATCTACACCGTGGGCTCCCCCATCGACTACGCGCGTGATCGTGGACACCAAGGCCT<br>ACTCCGGCGGCTACAACCTGCCCATCGGCCAGGCCGACGAAATGCAGAGGTACGT<br>GGAGGAGAACCAGACCAGGAACAAGCACATCAACCCCAACGAGTGGTGGAAGGT<br>GTACCCCTCCAGCGTGACCGAGTTCAAGTTCCTGTTCGTGTCCGGCCACTTCAAGG<br>GCAACTACAAGGCCCAGCTGACCAGGCTGAACCACATCACCAACTGCAACGGCGCC<br>GTGCTGTCCGTGGAGGAGCTCCTGATCGGCGGCGAGATGATCAAGGCCGGCACCC<br>TGACCCTGGAGGAGGTGAGGAGGAAGTTCAACAACGGCGAGATCAACTTCGCGG<br>CCGACTGATAA |
| T01 TALEN Beta2M RIGHT | 3 | ATGGGCGATCCTAAAAAGAAACGTAAGGTCATCGATAAGGAGACCGCCGCTGCCA<br>AGTTCGAGAGACAGCACATGGACAGCATCGATATCGCCGATCTACGCACGCTCGG<br>CTACAGCCAGCAGCAACAGGAGAAGATCAAACCGAAGGTTCGTTCGACAGTGGCG<br>CAGCACCACGAGGCACTGGTCGGCCACGGGTTTACACACGCGCACATCGTTGCGTT<br>AAGCCAACACCCGGCAGCGTTAGGGACCGTCGCTGTCAAGTATCAGGACATGATC<br>GCAGCGTTGCCAGAGGCGACACACGAAGCGATCGTTGGCGTCGGCAAACAGTGGT<br>CCGGCGCACGCGCTCTGGAGGCCTTGCTCACGGTGGCGGGAGAGTTGAGAGGTCC<br>ACCGTTACAGTTGGACACAGGCCAACTTCTCAAGATTGCAAAACGTGGCGGCGTGA<br>CCGAGTGGAGGCAGTGCATGCATGGCGCAATGCACTGACGGGTGCCCCGCTCAA<br>CTTGACCCCGGAGCAGGTGGTGGCCATCGCCAGCAATATTGGTGGCAAGCAGGCG<br>CTGGAGACGGTGCAGGCGCTGTTGCCGGTGCTGTGCCAGGCCCACGGCTTGACCC<br>CCAGCAGGTGGTGGCCATCGCCAGCAATAATGGTGGCAAGCAGGCGCTGGAGAC<br>GGTCCAGCGGCTGTTGCCGGTGCTGTGCCAGGCCCACGGCTTGACCCCGGAGCAG<br>GTGGTGGCCATCGCCAGCCACGATGGCGGCAAGCAGGCGCTGGAGACGGTCCAG<br>CGGCTGTTGCCGGTGCTGTGCCAGGCCCACGGCTTGACCCCGGAGCAGGTGGTGG<br>CCATCGCCAGCCACGATGGCGGCAAGCAGGCGCTGGAGACGGTCCAGCGGCTGTT<br>GCCGGTGCTGTGCCAGGCCCACGGCTTGACCCCCAGCAGGTGGTGGCCATCGCC<br>AGCAATGGCGGTGGCAAGCAGGCGCTGGAGACGGTCCAGCGGCTGTTGCCGGTG<br>CTGTGCCAGGCCCACGGCTTGACCCCGGAGCAGGTGGTGGCCATCGCCAGCCACG<br>ATGGCGGCAAGCAGGCGCTGGAGACGGTCCAGCGGCTGTTGCCGGTGCTGTGCCA<br>GGCCCACGGCTTGACCCCGGAGCAGGTGGTGGCCATCGCCAGCCACGATGGCGGC<br>AAGCAGGCGCTGGAGACGGTCCAGCGGCTGTTGCCGGTGCTGTGCCAGGCCCACG<br>GCTTGACCCCGGAGCAGGTGGTGGCCATCGCCAGCAATATTGGTGGCAAGCAGGC<br>GCTGGAGACGGTGCAGGCGCTGTTGCCGGTGCTGTGCCAGGCCCACGGCTTGACC<br>CCCAGCAGGTGGTGGCCATCGCCAGCAATAATGGTGGCAAGCAGGCGCTGGAGA<br>CGGTCCAGCGGCTGTTGCCGGTGCTGTGCCAGGCCCACGGCTTGACCCCCCAGCAG<br>GTGGTGGCCATCGCCAGCAATAATGGTGGCAAGCAGGCGCTGGAGACGGTCCAGC<br>GGCTGTTGCCGGTGCTGTGCCAGGCCCACGGCTTGACCCCGGAGCAGGTGGTGGC<br>CATCGCCAGCCACGATGGCGGCAAGCAGGCGCTGGAGACGGTCCAGCGGCTGTTG<br>CCGGTGCTGTGCCAGGCCCACGGCTTGACCCCGGAGCAGGTGGTGGCCATCGCCA<br>GCCACGATGGCGGCAAGCAGGCGCTGGAGACGGTCCAGCGGCTGTTGCCGGTGCT<br>GTGCCAGGCCCACGGCTTGACCCCGGAGCAGGTGGTGGCCATCGCCAGCAATATT<br>GGTGGCAAGCAGGCGCTGGAGACGGTGCAGGCGCTGTTGCCGGTGCTGTGCCAG<br>GCCCACGGCTTGACCCCCAGCAGGTGGTGGCCATCGCCAGCAATAATGGTGGCA<br>AGCAGGCGCTGGAGACGGTCCAGCGGCTGTTGCCGGTGCTGTGCCAGGCCCACGG<br>CTTGACCCCGGAGCAGGTGGTGGCCATCGCCAGCAATATTGGTGGCAAGCAGGCG<br>CTGGAGACGGTGCAGGCGCTGTTGCCGGTGCTGTGCCAGGCCCACGGCTTGACCC<br>CTCAGCAGGTGGTGGCCATCGCCAGCAATGGCGGCGGCAGGCCGGCGCTGGAGA<br>GCATTGTTGCCCAGTTATCTCGCCCTGATCCGGCGTTGGCCGCGTTGACCAACGAC<br>CACCTCGTCGCCTTGGCCTGCCTCGGCGGGCGTCCTGCGCTGGATGCAGTGAAAAA<br>GGGATTGGGGGATCCTATCAGCCGTTCCCAGCTGGTGAAGTCCGAGCTGGAGGAG<br>AAGAAATCCGAGTTGAGGCACAAGCTGAAGTACGTGCCCCACGAGTACATCGAGC |

TABLE 1-continued

Description of the β2m TALE-nucleases sequences

| Target name | SEQ ID NO: | Half TALE-nuclease sequence |
|---|---|---|
| | | TGATCGAGATCGCCCGGAACAGCACCCAGGACCGTATCCTGGAGATGAAGGTGAT<br>GGAGTTCTTCATGAAGGTGTACGGCTACAGGGGCAAGCACCTGGGCGGCTCCAGG<br>AAGCCCGACGGCGCCATCTACACCGTGGGCTCCCCCATCGACTACGGCGTGATCGT<br>GGACACCAAGGCCTACTCCGGCGGCTACAACCTGCCCATCGGCCAGGCCGACGAA<br>ATGCAGAGGTACGTGGAGGAGAACCAGACCAGGAACAAGCACATCAACCCCAACG<br>AGTGGTGGAAGGTGTACCCCTCCAGCGTGACCGAGTTCAAGTTCCTGTTCGTGTCC<br>GGCCACTTCAAGGGCAACTACAAGGCCCAGCTGACCAGGCTGAACCACATCACCAA<br>CTGCAACGGCGCCGTGCTGTCCGTGGAGGAGCTCCTGATCGGCGGCGAGATGATC<br>AAGGCCGGCACCCTGACCCTGGAGGAGGTGAGGAGGAAGTTCAACAACGGCGAG<br>ATCAACTTCGCGGCCGACTGATAA |
| T02<br>Beta2M<br>target | 4 | TCCAAAGATTCAGGTTTACTCACGTCATCCAGCAGAGAATGGAAAGTCAA |
| T02<br>TALEN<br>Beta2M<br>LEFT | 5 | ATGGGCGATCCTAAAAAGAAACGTAAGGTCATCGATTACCCATACGATGTTCCAGA<br>TTACGCTATCGATATCGCCGATCTACGCACGCTCGGCTACAGCCAGCAGCAACAGG<br>AGAAGATCAAACCGAAGGTTCGTTCGACAGTGGCGCAGCACCACGAGGCACTGGT<br>CGGCCACGGGTTTACACACGCGCACATCGTTGCGTTAAGCCAACACCCGGCAGCGT<br>TAGGGACCGTCGCTGTCAAGTATCAGGACATGATCGCAGCGTTGCCAGAGGCGAC<br>ACACGAAGCGATCGTTGGCGTCGGCAAACAGTGGTCCGGCGCACGCGCTCTGGAG<br>GCCTTGCTCACGGTGGCGGGAGAGTTGAGAGGTCCACCGTTACAGTTGGACACAG<br>GCCAACTTCTCAAGATTGCAAAACGTGGCGGCGTGACCGCAGTGGAGGCAGTGCA<br>TGCATGGCGCAATGCACTGACGGGTGCCCCGCTCAACTTGACCCCGGAGCAGGTG<br>GTGGCCATCGCCAGCCACGATGGCGGCAAGCAGGCGCTGGAGACGGTCCAGCGG<br>CTGTTGCCGGTGCTGTGCCAGGCCCACGGCTTGACCCCGGAGCAGGTGGTGGCCA<br>TCGCCAGCCACGATGGCGGCAAGCAGGCGCTGGAGACGGTCCAGCGGCTGTTGCC<br>GGTGCTGTGCCAGGCCCACGGCTTGACCCCGGAGCAGGTGGTGGCCATCGCCAGC<br>AATATTGGTGGCAAGCAGGCGCTGGAGACGGTGCAGGCGCTGTTGCCGGTGCTGT<br>GCCAGGCCCACGGCTTGACCCCGGAGCAGGTGGTGGCCATCGCCAGCAATATTGG<br>TGGCAAGCAGGCGCTGGAGACGGTGCAGGCGCTGTTGCCGGTGCTGTGCCAGGCC<br>CACGGCTTGACCCCGGAGCAGGTGGTGGCCATCGCCAGCAATATTGGTGGCAAGC<br>AGGCGCTGGAGACGGTGCAGGCGCTGTTGCCGGTGCTGTGCCAGGCCCACGGCTT<br>GACCCCCCAGCAGGTGGTGGCCATCGCCAGCAATAATGGTGGCAAGCAGGCGCTG<br>GAGACGGTCCAGCGGCTGTTGCCGGTGCTGTGCCAGGCCCACGGCTTGACCCCGG<br>AGCAGGTGGTGGCCATCGCCAGCAATATTGGTGGCAAGCAGGCGCTGGAGACGG<br>TGCAGGCGCTGTTGCCGGTGCTGTGCCAGGCCCACGGCTTGACCCCCAGCAGGT<br>GGTGGCCATCGCCAGCAATGGCGGTGGCAAGCAGGCGCTGGAGACGGTCCAGCG<br>GCTGTTGCCGGTGCTGTGCCAGGCCCACGGCTTGACCCCCAGCAGGTGGTGGCC<br>ATCGCCAGCAATGGCGGTGGCAAGCAGGCGCTGGAGACGGTCCAGCGGCTGTTGC<br>CGGTGCTGTGCCAGGCCCACGGCTTGACCCCGGAGCAGGTGGTGGCCATCGCCAG<br>CCACGATGGCGGCAAGCAGGCGCTGGAGACGGTCCAGCGGCTGTTGCCGGTGCTG<br>TGCCAGGCCCACGGCTTGACCCCGGAGCAGGTGGTGGCCATCGCCAGCAATATTG<br>GTGGCAAGCAGGCGCTGGAGACGGTGCAGGCGCTGTTGCCGGTGCTGTGCCAGG<br>CCCACGGCTTGACCCCCAGCAGGTGGTGGCCATCGCCAGCAATAATGGTGGCAA<br>GCAGGCGCTGGAGACGGTCCAGCGGCTGTTGCCGGTGCTGTGCCAGGCCCACGGC<br>TTGACCCCCCAGCAGGTGGTGGCCATCGCCAGCAATAATGGTGGCAAGCAGGCGC<br>TGGAGACGGTCCAGCGGCTGTTGCCGGTGCTGTGCCAGGCCCACGGCTTGACCCC<br>CCAGCAGGTGGTGGCCATCGCCAGCAATGGCGGTGGCAAGCAGGCGCTGGAGAC<br>GGTCCAGCGGCTGTTGCCGGTGCTGTGCCAGGCCCACGGCTTGACCCCCCAGCAG<br>GTGGTGGCCATCGCCAGCAATGGCGGTGGCAAGCAGGCGCTGGAGACGGTCCAG<br>CGGCTGTTGCCGGTGCTGTGCCAGGCCCACGGCTTGACCCCTCAGCAGGTGGTGG<br>CCATCGCCAGCAATGGCGGCGGCAGGCCGGCGCTGGAGAGCATTGTTGCCCAGTT<br>ATCTCGCCCTGATCCGGCGTTGGCCGCGTTGACCAACGACCACCTCGTCGCCTTGG<br>CCTGCCTCGGCGGGCGTCCTGCGCTGGATGCAGTGAAAAAGGGATTGGGGGATCC<br>TATCAGCCGTTCCCAGCTGGTGAAGTCCGAGCTGGAGGAGAAGAAATCCGAGTTG<br>AGGCACAAGCTGAAGTACGTGCCCCACGAGTACATCGAGCTGATCGAGATCGCCC<br>GGAACAGCACCCAGGACCGTATCCTGGAGATGAAGGTGATGGAGTTCTTCATGAA<br>GGTGTACGGCTACAGGGGCAAGCACCTGGGCGGCTCCAGGAAGCCCGACGGCGC<br>CATCTACACCGTGGGCTCCCCCATCGACTACGGCGTGATCGTGGACACCAAGGCCT<br>ACTCCGGCGGCTACAACCTGCCCATCGGCCAGGCCGACGAAATGCAGAGGTACGT<br>GGAGGAGAACCAGACCAGGAACAAGCACATCAACCCCAACGAGTGGTGGAAGGT<br>GTACCCCTCCAGCGTGACCGAGTTCAAGTTCCTGTTCGTGTCCGGCCACTTCAAGG<br>GCAACTACAAGGCCCAGCTGACCAGGCTGAACCACATCACCAACTGCAACGGCGCC<br>GTGCTGTCCGTGGAGGAGCTCCTGATCGGCGGCGAGATGATCAAGGCCGGCACCC<br>TGACCCTGGAGGAGGTGAGGAGGAAGTTCAACAACGGCGAGATCAACTTCGCGG<br>CCGACTGATAA |
| T02<br>TALEN<br>Beta2M<br>RIGHT | 6 | ATGGGCGATCCTAAAAAGAAACGTAAGGTCATCGATAAGGAGACCGCCGCTGCCA<br>AGTTCGAGAGACAGCACATGGACAGCATCGATATCGCCGATCTACGCACGCTCGG<br>CTACAGCCAGCAGCAACAGGAGAAGATCAAACCGAAGGTTCGTTCGACAGTGGCG<br>CAGCACCACGAGGCACTGGTCGGCCACGGGTTTACACACGCGCACATCGTTGCGTT<br>AAGCCAACACCCGGCAGCGTTAGGGACCGTCGCTGTCAAGTATCAGGACATGATC<br>GCAGCGTTGCCAGAGGCGACACACGAAGCGATCGTTGGCGTCGGCAAACAGTGGT<br>CCGGCGCACGCGCTCTGGAGGCCTTGCTCACGGTGGCGGGAGAGTTGAGAGGTCC |

TABLE 1-continued

Description of the β2m TALE-nucleases sequences

| Target name | SEQ ID NO: | Half TALE-nuclease sequence |
|---|---|---|
| | | ACCGTTACAGTTGGACACAGGCCAACTTCTCAAGATTGCAAAACGTGGCGGCGTGA<br>CCGCAGTGGAGGCAGTGCATGCATGGCGCAATGCACTGACGGGTGCCCCGCTCAA<br>CTTGACCCCCCAGCAGGTGGTGGCCATCGCCAGCAATAATGGTGGCAAGCAGGCG<br>CTGGAGACGGTCCAGCGGCTGTTGCCGGTGCTGTGCCAGGCCCACGGCTTGACCC<br>CGGAGCAGGTGGTGGCCATCGCCAGCAATATTGGTGGCAAGCAGGCGCTGGAGA<br>CGGTGCAGGCGCTGTTGCCGGTGCTGTGCCAGGCCCACGGCTTGACCCCGGAGCA<br>GGTGGTGGCCATCGCCAGCCACGATGGCGGCAAGCAGGCGCTGGAGACGGTCCA<br>GCGGCTGTTGCCGGTGCTGTGCCAGGCCCACGGCTTGACCCCCCAGCAGGTGGTG<br>GCCATCGCCAGCAATGGCGGTGGCAAGCAGGCGCTGGAGACGGTCCAGCGGCTG<br>TTGCCGGTGCTGTGCCAGGCCCACGGCTTGACCCCCAGCAGGTGGTGGCCATCGC<br>CAGCAATGGCGGTGGCAAGCAGGCGCTGGAGACGGTCCAGCGGCTGTTGCCGGT<br>GCTGTGCCAGGCCCACGGCTTGACCCCCAGCAGGTGGTGGCCATCGCCAGCAAT<br>GGCGGTGGCAAGCAGGCGCTGGAGACGGTCCAGCGGCTGTTGCCGGTGCTGTGC<br>CAGGCCCACGGCTTGACCCCGGAGCAGGTGGTGGCCATCGCCAGCCACGATGGCG<br>GCAAGCAGGCGCTGGAGACGGTCCAGCGGCTGTTGCCGGTGCTGTGCCAGGCCCA<br>CGGCTTGACCCCGGAGCAGGTGGTGGCCATCGCCAGCCACGATGGCGGCAAGCAG<br>GCGCTGGAGACGGTCCAGCGGCTGTTGCCGGTGCTGTGCCAGGCCCACGGCTTGA<br>CCCCGGAGCAGGTGGTGGCCATCGCCAGCAATATTGGTGGCAAGCAGGCGCTGGA<br>GACGGTGCAGGCGCTGTTGCCGGTGCTGTGCCAGGCCCACGGCTTGACCCCCCAG<br>CAGGTGGTGGCCATCGCCAGCAATGGCGGTGGCAAGCAGGCGCTGGAGACGGTC<br>CAGCGGCTGTTGCCGGTGCTGTGCCAGGCCCACGGCTTGACCCCCCAGCAGGTGG<br>TGGCCATCGCCAGCAATGGCGGTGGCAAGCAGGCGCTGGAGACGGTCCAGCGGC<br>TGTTGCCGGTGCTGTGCCAGGCCCACGGCTTGACCCCGGAGCAGGTGGTGGCCAT<br>CGCCAGCCACGATGGCGGCAAGCAGGCGCTGGAGACGGTCCAGCGGCTGTTGCC<br>GGTGCTGTGCCAGGCCCACGGCTTGACCCCCAGCAGGTGGTGGCCATCGCCAGC<br>AATGGCGGTGGCAAGCAGGCGCTGGAGACGGTCCAGCGGCTGTTGCCGGTGCTGT<br>GCCAGGCCCACGGCTTGACCCGGAGCAGGTGGTGGCCATCGCCAGCCACGATGG<br>CGGCAAGCAGGCGCTGGAGACGGTCCAGCGGCTGTTGCCGGTGCTGTGCCAGGCC<br>CACGGCTTGACCCCCAGCAGGTGGTGGCCATCGCCAGCAATGGCGGTGGCAAGC<br>AGGCGCTGGAGACGGTCCAGCGGCTGTTGCCGGTGCTGTGCCAGGCCCACGGCTT<br>GACCCCTCAGCAGGTGGTGGCCATCGCCAGCAATGGCGGCGGCAGGCCGGCGCTG<br>GAGAGCATTGTTGCCCAGTTATCTCGCCCTGATCCGGCGTTGGCCGCGTTGACCAA<br>CGACCACCTCGTCGCCTTGGCCTGCCTCGGCGGGCGTCCTGCGCTGGATGCAGTGA<br>AAAAGGGGATTGGGGGATCCTATCAGCCGTTCCCAGCTGGTGAAGTCCGAGCTGGA<br>GGAGAAGAAATCCGAGTTGAGGCACAAGCTGAAGTACGTGCCCCACGAGTACATC<br>GAGCTGATCGAGATCGCCCGGAACAGCACCCAGGACCGTATCCTGGAGATGAAGG<br>TGATGGAGTTCTTCATGAAGGTGTACGGCTACAGGGGCAAGCACCTGGGCGGCTC<br>CAGGAAGCCCGACGGCGCCATCTACACCGTGGGCTCCCCCATCGACTACGGCGTG<br>ATCGTGGACACCAAGGCCTACTCCGGCGGCTACAACCTGCCCATCGGCCAGGCCGA<br>CGAAATGCAGAGGTACGTGGAGGAGAACCAGACCAGGAACAAGCACATCAACCCC<br>AACGAGTGGTGGAAGGTGTACCCCTCCAGCGTGACCGAGTTCAAGTTCCTGTTCGT<br>GTCCGGCCACTTCAAGGGCAACTACAAGGCCCAGCTGACCAGGCTGAACCACATCA<br>CCAACTGCAACGGCGCCGTGCTGTCCGTGGAGGAGCTCCTGATCGGCGGCGAGAT<br>GATCAAGGCCGGCACCCTGACCCTGGAGGAGGTGAGGAGGAAGTTCAACAACGG<br>CGAGATCAACTTCGCGGCCGACTGATAA |
| T03 Beta2M target | 7 | TTAGCTGTGCTCGCGCTACTCTCTCTTTCTGGCCTGGAGGCTATCCA |
| T03 TALEN Beta2M LEFT | 8 | ATGGGCGATCCTAAAAAGAAACGTAAGGTCATCGATTACCCATACGATGTTCCAGA<br>TTACGCTATCGATATCGCCGATCTACGCACGCTCGGCTACAGCCAGCAGCAACAGG<br>AGAAGATCAAACCGAAGGTTCGTTCGACAGTGGCGCAGCACCACGAGGCACTGGT<br>CGGCCACGGGTTTACACACGCGCACATCGTTGCGTTAAGCCAACACCCGGCAGCGT<br>TAGGGACCGTCGCTGTCAAGTATCAGGACATGATCGCAGCGTTGCCAGAGGCGAC<br>ACACGAAGCGATCGTTGGCGTCGGCAAACAGTGGTCCGGCGCACGCGCTCTGGAG<br>GCCTTGCTCACGGTGGCGGGAGAGTTGAGAGGTCCACCGTTACAGTTGGACACAG<br>GCCAACTTCTCAAGATTGCAAAACGTGGCGGCGTGACCGCAGTGGAGGCAGTGCA<br>TGCATGGCGCAATGCACTGACGGGTGCCCCGCTCAACTTGACCCCGGAGCAGGTG<br>GTGGCCATCGCCAGCAATATTGGTGGCAAGCAGGCGCTGGAGACGGTGCAGGCG<br>CTGTTGCCGGTGCTGTGCCAGGCCCACGGCTTGACCCCCCAGCAGGTGGTGGCCAT<br>CGCCAGCAATAATGGTGGCAAGCAGGCGCTGGAGACGGTCCAGCGGCTGTTGCCG<br>GTGCTGTGCCAGGCCCACGGCTTGACCCCGGAGCAGGTGGTGGCCATCGCCAGCC<br>ACGATGGCGGCAAGCAGGCGCTGGAGACGGTCCAGCGGCTGTTGCCGGTGCTGT<br>GCCAGGCCCACGGCTTGACCCCCAGCAGGTGGTGGCCATCGCCAGCAATGGCGG<br>TGGCAAGCAGGCGCTGGAGACGGTCCAGCGGCTGTTGCCGGTGCTGTGCCAGGCC<br>CACGGCTTGACCCCCAGCAGGTGGTGGCCATCGCCAGCAATAATGGTGGCAAGC<br>AGGCGCTGGAGACGGTCCAGCGGCTGTTGCCGGTGCTGTGCCAGGCCCACGGCTT<br>GACCCCCCAGCAGGTGGTGGCCATCGCCAGCAATGGCGGTGGCAAGCAGGCGCTG<br>GAGACGGTCCAGCGGCTGTTGCCGGTGCTGTGCCAGGCCCACGGCTTGACCCCCC<br>AGCAGGTGGTGGCCATCGCCAGCAATAATGGTGGCAAGCAGGCGCTGGAGACGG<br>TCCAGCGGCTGTTGCCGGTGCTGTGCCAGGCCCACGGCTTGACCCCGGAGCAGGT<br>GGTGGCCATCGCCAGCCACGATGGCGGCAAGCAGGCGCTGGAGACGGTCCAGCG<br>GCTGTTGCCGGTGCTGTGCCAGGCCCACGGCTTGACCCCCCAGCAGGTGGTGGCC<br>ATCGCCAGCAATGGCGGTGGCAAGCAGGCGCTGGAGACGGTCCAGCGGCTGTTGC |

TABLE 1-continued

Description of the β2m TALE-nucleases sequences

| Target name | SEQ ID NO: | Half TALE-nuclease sequence |
|---|---|---|
| | | CGGTGCTGTGCCAGGCCCACGGCTTGACCCCGGAGCAGGTGGTGGCCATCGCCAG<br>CCACGATGGCGGCAAGCAGGCGCTGGAGACGGTCCAGCGGCTGTTGCCGGTGCTG<br>TGCCAGGCCCACGGCTTGACCCCCCAGCAGGTGGTGGCCATCGCCAGCAATAATG<br>GTGGCAAGCAGGCGCTGGAGACGGTCCAGCGGCTGTTGCCGGTGCTGTGCCAGGC<br>CCACGGCTTGACCCCGGAGCAGGTGGTGGCCATCGCCAGCCACGATGGCGGCAAG<br>CAGGCGCTGGAGACGGTCCAGCGGCTGTTGCCGGTGCTGTGCCAGGCCCACGGCT<br>TGACCCCCCAGCAGGTGGTGGCCATCGCCAGCAATAATGGTGGCAAGCAGGCGCT<br>GGAGACGGTCCAGCGGCTGTTGCCGGTGCTGTGCCAGGCCCACGGCTTGACCCCG<br>GAGCAGGTGGTGGCCATCGCCAGCCACGATGGCGGCAAGCAGGCGCTGGAGACG<br>GTCCAGCGGCTGTTGCCGGTGCTGTGCCAGGCCCACGGCTTGACCCCCAGCAGGT<br>GGTGGCCATCGCCAGCAATGGCGGTGGCAAGCAGGCGCTGGAGACGGTCCAGCG<br>GCTGTTGCCGGTGCTGTGCCAGGCCCACGGCTTGACCCCTCAGCAGGTGGTGGCC<br>ATCGCCAGCAATGGCGGCGGCAGGCCGGCGCTGGAGAGCATTGTTGCCCAGTTAT<br>CTCGCCCTGATCCGGCGTTGGCCGCGTTGACCAACGACCACCTCGTCGCCTTGGCC<br>TGCCTCGGCGGCGTCCTGCGCTGGATGCAGTGAAAAAGGGATTGGGGGATCCTA<br>TCAGCCGTTCCCAGCTGGTGAAGTCCGAGCTGGAGGAGAAGAAATCCGAGTTGAG<br>GCACAAGCTGAAGTACGTGCCCCACGAGTACATCGAGCTGATCGAGATCGCCCGG<br>AACAGCACCCAGGACCGTATCCTGGAGATGAAGGTGATGGAGTTCTTCATGAAGG<br>TGTACGGCTACAGGGGCAAGCACCTGGGCGGCTCCAGGAAGCCCGACGGCGCCAT<br>CTACACCGTGGGCTCCCCCATCGACTACGGCGTGATCGTGGACACCAAGGCCTACT<br>CCGGCGGCTACAACCTGCCCATCGGCCAGGCCGACGAAATGCAGAGGTACGTGGA<br>GGAGAACCAGACCAGGAACAAGCACATCAACCCCAACGAGTGGTGGAAGGTGTAC<br>CCCTCCAGCGTGACCGAGTTCAAGTTCCTGTTCGTGTCCGGCCACTTCAAGGGCAA<br>CTACAAGGCCCAGCTGACCAGGCTGAACCACATCACCAACTGCAACGGCGCCGTGC<br>TGTCCGTGGAGGAGCTCCTGATCGGCGGCGAGATGATCAAGGCCGGCACCCTGAC<br>CCTGGAGGAGGTGAGGAGGAAGTTCAACAACGGCGAGATCAACTTCGCGGCCGA<br>CTGATAA |
| T03 TALEN Beta2M RIGHT | 9 | ATGGGCGATCCTAAAAAGAAACGTAAGGTCATCGATAAGGAGACCGCCGCTGCCA<br>AGTTCGAGAGACAGCACATGGACAGCATCGATATCGCCGATCTACACGCTCGG<br>CTACAGCCAGCAGCAACAGGAGAAGATCAAACCGAAGGTTCGTTCGACAGTGGCG<br>CAGCACCACGAGGCACTGGTCGGCCACGGGTTTACACACGCGCACATCGTTGCGTT<br>AAGCCAACACCCGGCAGCGTTAGGGACCGTCGCTGTCAAGTATCAGGACATGATC<br>GCAGCGTTGCCAGAGGCGACACACGAAGCGATCGTTGGCGTCGGCAAACAGTGGT<br>CCGGCGCACGCGCTCTGGAGGCCTTGCTCACGGTGGCGGGAGAGTTGAGAGGTCC<br>ACCGTTACAGTTGGACACAGGCCAACTTCTCAAGATTGCAAAACGTGGCGGCGTGA<br>CCGCAGTGGAGGCAGTGCATGCATGGCGCAATGCACTGACGGGTGCCCCGCTCAA<br>CTTGACCCCCCAGCAGGTGGTGGCCATCGCCAGCAATAATGGTGGCAAGCAGGCG<br>CTGGAGACGGTCCAGCGGCTGTTGCCGGTGCTGTGCCAGGCCCACGGCTTGACCC<br>CCAGCAGGTGGTGGCCATCGCCAGCAATAATGGTGGCAAGCAGGCGCTGGAGAC<br>GGTCCAGCGGCTGTTGCCGGTGCTGTGCCAGGCCCACGGCTTGACCCCGGAGCAG<br>GTGGTGGCCATCGCCAGCAATATTGGTGGCAAGCAGGCGCTGGAGACGGTGCAG<br>GCGCTGTTGCCGGTGCTGTGCCAGGCCCACGGCTTGACCCCCAGCAGGTGGTGG<br>CCATCGCCAGCAATGGCGGTGGCAAGCAGGCGCTGGAGACGGTCCAGCGGCTGTT<br>GCCGGTGCTGTGCCAGGCCCACGGCTTGACCCCGGAGCAGGTGGTGGCCATCGCC<br>AGCAATATTGGTGGCAAGCAGGCGCTGGAGACGGTGCAGGCGCTGTTGCCGGTGC<br>TGTGCCAGGCCCACGGCTTGACCCCCAGCAGGTGGTGGCCATCGCCAGCAATAAT<br>GGTGGCAAGCAGGCGCTGGAGACGGTCCAGCGGCTGTTGCCGGTGCTGTGCCAG<br>GCCCACGGCTTGACCCCGGAGCAGGTGGTGGCCATCGCCAGCCACGATGGCGGCA<br>AGCAGGCGCTGGAGACGGTCCAGCGGCTGTTGCCGGTGCTGTGCCAGGCCCACGG<br>CTTGACCCCGGAGCAGGTGGTGGCCATCGCCAGCCACGATGGCGGCAAGCAGGCG<br>CTGGAGACGGTCCAGCGGCTGTTGCCGGTGCTGTGCCAGGCCCACGGCTTGACCC<br>CCAGCAGGTGGTGGCCATCGCCAGCAATGGCGGTGGCAAGCAGGCGCTGGAGA<br>CGGTCCAGCGGCTGTTGCCGGTGCTGTGCCAGGCCCACGGCTTGACCCCGGAGCA<br>GGTGGTGGCCATCGCCAGCCACGATGGCGGCAAGCAGGCGCTGGAGACGGTCCA<br>GCGGCTGTTGCCGGTGCTGTGCCAGGCCCACGGCTTGACCCCGGAGCAGGTGGTG<br>GCCATCGCCAGCCACGATGGCGGCAAGCAGGCGCTGGAGACGGTCCAGCGGCTGT<br>TGCCGGTGCTGTGCCAGGCCCACGGCTTGACCCCGGAGCAGGTGGTGGCCATCGC<br>CAGCAATATTGGTGGCAAGCAGGCGCTGGAGACGGTGCAGGCGCTGTTGCCGGTG<br>CTGTGCCAGGCCCACGGCTTGACCCCCAGCAGGTGGTGGCCATCGCCAGCAATAA<br>TGGTGGCAAGCAGGCGCTGGAGACGGTCCAGCGGCTGTTGCCGGTGCTGTGCCAG<br>GCCCACGGCTTGACCCCCAGCAGGTGGTGGCCATCGCCAGCAATAATGGTGGCA<br>AGCAGGCGCTGGAGACGGTCCAGCGGCTGTTGCCGGTGCTGTGCCAGGCCCACGG<br>CTTGACCCCGGAGCAGGTGGTGGCCATCGCCAGCCACGATGGCGGCAAGCAGGCG<br>CTGGAGACGGTCCAGCGGCTGTTGCCGGTGCTGTGCCAGGCCCACGGCTTGACCC<br>CTCAGCAGGTGGTGGCCATCGCCAGCAATGGCGGCGGCAGGCCGGCGCTGGAGA<br>GCATTGTTGCCCAGTTATCTCGCCCTGATCCGGCGTTGGCCGCGTTGACCAACGAC<br>CACCTCGTCGCCTTGGCCTGCCTCGGCGGCGTCCTGCGCTGGATGCAGTGAAAAA<br>GGGATTGGGGGATCCTATCAGCCGTTCCCAGCTGGTGAAGTCCGAGCTGGAGGAG<br>AAGAAATCCGAGTTGAGGCACAAGCTGAAGTACGTGCCCCACGAGTACATCGAGC<br>TGATCGAGATCGCCCGGAACAGCACCCAGGACCGTATCCTGGAGATGAAGGTGAT<br>GGAGTTCTTCATGAAGGTGTACGGCTACAGGGGCAAGCACCTGGGCGGCTCCAGG<br>AAGCCCGACGGCGCCATCTACACCGTGGGCTCCCCCATCGACTACGGCGTGATCGT<br>GGACACCAAGGCCTACTCCGGCGGCTACAACCTGCCCATCGGCCAGGCCGACGAA<br>ATGCAGAGGTACGTGGAGGAGAACCAGACCAGGAACAAGCACATCAACCCCAACG |

TABLE 1-continued

Description of the β2m TALE-nucleases sequences

| Target name | SEQ ID NO: | Half TALE-nuclease sequence |
|---|---|---|
| | | AGTGGTGGAAGGTGTACCCCTCCAGCGTGACCGAGTTCAAGTTCCTGTTCGTGTCC GGCCACTTCAAGGGCAACTACAAGGCCCAGCTGACCAGGCTGAACCACATCACCAA CTGCAACGGCGCCGTGCTGTCCGTGGAGGAGCTCCTGATCGGCGGCGAGATGATC AAGGCCGGCACCCTGACCCTGGAGGAGGTGAGGAGGAAGTTCAACAACGGCGAG ATCAACTTCGCGGCCGACTGATAA |

TALE-Nucleases Cleaving Human PD-1 Gene

In addition to the inactivation of said gene involved in the self and non-self antigen recognition, further genetic engineering may be sought such as the inactivation of one or several genes encoding immune checkpoints as described in WO2014/184744, In a preferred embodiment, to the inactivation of at least one gene involved in self/non self recognition, an additional inactivation is performed on a gene encoding PD-1. PD-1 corresponds to the human Programmed Death 1 (also known as PDCD1 or CD279, RefSeq accession number: NM_005018 for the human gene). This PD-1 inhibition, preferably by TALEN-mediated disruption, has the objective to render allogeneic immune cells resistant to their self or reciprocal inhibition by PD-L1 (also known as CD274 or B7 homolog 1 (B7-H1), and has RefSeq No. NM_001267706 for human gene).

According to a preferred embodiment, said inactivation of PD-1 gene is performed by using a polynucleotide encoding TALE-nucleases as presented in the following Table 2.

TABLE 2

Polynucleotide sequences of 2 pairs of TALENs are presented for 2 different PDC1 (or PD-1) gene targets

| Target | Target sequence | Half TALE-nuclease |
|---|---|---|
| PDCD1_T01 | TTCTCCCCAGCCCTG CT cgtggtgaccgaagg GGACAACGCCACCTTCA (SEQ ID NO: 10) | PDCD1_T01-L TALEN (SEQ ID NO: 11) PDCD1_T01-R TALEN (SEQ ID NO: 12) |
| PDCD1_T03 | TACCTCTGTGGGGC CAT ctccctggcccccaa GGCGCAGATCAAAGAGA (SEQ ID NO: 13) | PDCD1_T03-L TALEN (SEQ ID NO: 14) PDCD1_T03-R TALEN (SEQ ID NO: 15 |

According to one embodiment of the present invention, said step c) of the method is performed by the expression in said immune cells of at least one non-endogenous polynucleotide encoding for PD-L1 ligand bound to the membrane, and a further modification of said allogeneic cells is performed by an inactivation of the expression of PD-1 gene.

According to another embodiment of the present invention, said step c) is performed by the expression in said immune cells at least one non-endogenous polynucleotide corresponding to secreted CTLA4 immunoglobulins, and a further modification of said allogeneic cells is performed by an inactivation of the expression of a gene encoding PD-1.

According to a preferred embodiment of the present invention, said step c) is performed by the step c) is performed by the expression in said immune cells of both non-endogenous immunosuppressive polypeptide PD-L1 ligand and CTLA-4 immunoglobulins, and a further modification of said allogeneic immune cells is performed by an inactivation of the expression of a gene encoding PD-1.

Expression of Non-Endogenous Immunosuppressive Polypeptide

According to a preferred embodiment, said step c) of the method of the invention is performed by the expression in said immune cells of at least one non-endogenous polynucleotide encoding for one non-endogenous immunosuppressive polypeptide bound to the membrane of said immune cells.

According to one embodiment, said non endogenous immunosuppressive polypeptide is present under a membrane-bound form and/or under a secreted form.

By "non-endogenous polypeptide" is meant a polypeptide not normally expressed by a donor's immune cell, preferably a polypeptide expressed by an exogenous polynucleotide that has been imported into the immune's cell genome. For instance, IL12 is not considered hereby as being a non-endogenous polypeptide because it is expressed from a preexisting gene from the donor's immune cell.

By "not naturally expressed" is meant that the polynucleotide sequence encoding said polypeptide is either not originally present in the genome of the immune cell (e.g.: CTLA4 Ig), or said polynucleotide sequence is present in the genome but the polypeptide is expressed in the native immune cell (i.e. non-engineered) at a much lower level—generally at least 50%, preferably at least 75%, more preferably at least 100% and even more preferably 200% lower than the expression level observed into the engineered immune cell in the same experimental or treatment conditions.

By "immunosuppressive" is meant that the expression of said non-endogenous polypeptide has the effect of alleviating the immune response of the patient host against the donor's immune cells.

According to a preferred aspect of the invention, said non endogenous immunosuppressive polypeptide is selected amongst PD-L1, CTLA-4-Ig, viral MHC homolog, NKG2D ligand, viral env immune suppressive domain (ISU) or the viral FP protein.

According to one embodiment, the method comprises as step c) an expression in immune cells at least one non-endogenous polynucleotide corresponding to a non-endogenous secreted immunosuppressive polypeptide.

According to a more preferred embodiment, said one non-endogenous immunosuppressive polypeptide bound to the membrane of said immune cells is a PD-L1 ligand under a membrane-bound form.

Expression of CTLA-4-Ig

According to one embodiment, the non-endogenous immunosuppressive polypeptide to be expressed in said allogeneic immune cells is a ligand of CTLA-4 protein, preferably a CTLA4 immunoglobulin. Cytotoxic T-Lymphocyte Antigen 4 (CTLA-4) is also known as CD152, GenBank accession number AF414120.1).

According to a preferred embodiment, the polypeptide corresponding to CTLA-4 immunoglobulin to be expressed in said allogeneic immune cells comprises SEQ ID NO: 16 (CTLA-4a) or SEQ ID NO:17 (CTLA4b), or shares at least 80%, preferably 90% and more preferably 95% identity with SEQ ID NO: 16 or SEQ ID NO:17.

The interaction between the allogeneic T cell and host immune cells is schematically represented in FIG. 2 (expression of CTLA4-Ig) in regard to the situation in FIG. 1 (no expression).

According to one preferred embodiment, the nucleic acid molecule encoding CTLA-4a Ig and CTLA-4b Ig to be expressed shares respectively at least 80%, preferably 90% and more preferably 95% of identity with SEQ ID NO: 16 and SEQ ID NO: 17 as presented in the following Table 3.

under a truncated form such as, for instance, by removing the intracellular domain, or with one or more mutation(s) (Wang S et al, 2003, J Exp Med. 2003; 197(9): 1083-1091). PD1 is not considered as being a membrane-bound form of PD-L1 ligand according to the present invention.

According to a more preferred embodiment, the nucleic acid molecule encoding PD-L1 ligand under a membrane-bound form to be expressed is of SEQ ID NO:18, or shares at least 80%, preferably 90% and more preferably 95% of identity with SEQ ID NO:18 (corresponding to the wild-type form of PDL1-ligand).

According to another embodiment, said at least one non-endogenous immunosuppressive polypeptide is PD-L1 ligand under a secreted form. Such recombinant secreted PD-L1 (or soluble PD-L1) may be generated by fusing the extracellular domain of PD-L1 to the Fc portion of immunogubuline (Haile S T et al, 2014, Cancer Immunol Res. 2(7): 610-615; Song M Y et al, 2015, Gut. 64(2):260-71). This recombinant PD-L1 neutralizes PD-1 and abrogates PD-1-mediated T-cell inhibition.

The interaction between the allogeneic T cell and host immune cells is schematically represented in FIG. 3 (expres-

TABLE 3 polynucleotide sequences of plasmidic constructs expressing CLTA-4a, CTLA-4b and PD-L1.

| Name of construct | Expression | SEQ ID NO: | Polypeptide sequence |
|---|---|---|---|
| pCLS27068 | CTLA4a expression plasmid | 16 | MGGVLLTQRTLLSLVLALLFPSMASMAMHVAQPAVVLASSRGIASFVCEYAS PGKATEVRVTVLRQADSQVTEVCAATYMMGNELTFLDDSICTGTSSGNQVN LTIQGLRAMDTGLYICKVELMYPPPYYLGIGNGTQIYVIDPEPCPDSDQEPKSS DKTHTSPPSPAPELLGGSSVFLFPPKPKDTLMISRTPEVTCVVVDVSHEDPEVK FNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIAV EWESNGQPENNYKTTPPVLDSDGSFFLYSKLTVDKSRWQQGNVFSCSVMHE ALHNHYTQKSLSLSPGKGS |
| pCLS27066 | CTLA4b expression plasmid | 17 | MGGVLLTQRTLLSLVLALLFPSMASMAMHVAQPAVVLASSRGIASFVCEYAS PGKYTEVRVTVLRQADSQVTEVCAATYMMGNELTFLDDSICTGTSSGNQVN LTIQGLRAMDTGLYICKVELMYPPPYYEGIGNGTQIYVIDPEPCPDSDQEPKSS DKTHTSPPSPAPELLGGSSVFLFPPKPKDTLMISRTPEVTCVVVDVSHEDPEVK FNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIAV EWESNGQPENNYKTTPPVLDSDGSFFLYSKLTVDKSRWQQGNVFSCSVMHE ALHNHYTQKSLSLSPGKGS |
| pCLS27069 | PD-L1 expression plasmid | 18 | MGRIFAVFIFMTYWHLLNAFTVTVPKDLYVVEYGSNMTIECKFPVEKQLDLA ALIVYWEMEDKNIIQFVHGEEDLKVQHSSYRQRARLLKDQLSLGNAALQITDV KLQDAGVYRCMISYGGADYKRITVKVNAPYNKINQRILVVDPVTSEHELTCQA EGYPKAEVIWTSSDHQVLSGKTTTTNSKREEKLFNVTSTLRINTTTNEIFYCTFR RLDPEENHTAELVIPELPLAHPPNERTHLVILGAILLCLGVALTFIFRLRKGRMM DVKKCGIQDTNSKKQSDTHLEETGS |

According to one embodiment, the engineered immune cells are incubated with a non-endogenous immunosuppressive polypeptide which is anti-CD80 or anti-CD86 mAbs.

Expression of PD-L1

PD-L1 (other names: CD274, Programmed cell death 1 ligand; ref. UniProt for the human polypeptide sequence Q9NZQ7) encodes a type I transmembrane protein of 290 amino acids consisting of a Ig V-like domain, a Ig C-like domain, a hydrophobic transmembrane domain and a cytoplasmic tail of 30 amino acids.

According to a preferred embodiment of the invention, the non-endogenous immunosuppressive polypeptide to be expressed in said allogeneic immune cells is a ligand of PD-L1, more especially under a membrane-bound form.

Such membrane-bound form of PD-L1 ligand is meant in the present invention under a native form (wild-type) or sion of membrane-bound PD-L1) in regard to the situation to FIG. 1 (no expression). FIG. 3 represents also the situation when the PD-1 gene is disrupted by KO.

According to an alternative to the precedent embodiment, the non-endogenous immunosuppressive polypeptide to be expressed in said allogeneic immune cells is a PD-L1 ligand under a secreted form. The interaction between the allogeneic T cell and host immune cells is schematically represented in FIG. 4 (expression of secreted PD-L1 ligand) in regard to the situation to FIG. 1 (no expression). FIG. 4 represents also the situation when the PD-1 gene is disrupted by KO.

According to one preferred embodiment, the nucleic acid molecule encodes formembrane-bound PD-L1 to be expressed which is of SEQ ID NO: 18, or shares at least 80%, preferably 90% and more preferably 95% of identity with SEQ ID NO: 18.

Co-Expression of PD-L1 Ligand with CTLA4 Ig

The present invention relates also to a method to increase the persistence and/or the engraftment of allogeneic immune cells in presence of host immune cells, wherein step c) is performed by contacting said host immune cells with both non-endogenous immunosuppressive polypeptide PD-L1 ligand and CTLA-4 immunoglobulins.

According to a preferred embodiment, step c) of the method is performed by the step c) is performed by the expression in said immune cells of both non-endogenous immunosuppressive polypeptide PD-L1 ligand and CTLA-4 immunoglobulins.

According to a preferred embodiment, the nucleic acid molecules encode for PD-L1 ligand under a membrane-bound form and for CTLA-4 immunoglobulins to be expressed during step c) of the method in said allogeneic immune cells, said PD-L1 ligand and CTLA-4 Ig having respectively SEQ ID NO:18 and SEQ ID NO: 16-17, or sharing at least 80%, preferably 90% and more preferably 95% of identity with respectively SEQ ID NO:18 and SEQ ID NO: 16-17.

Expression of ISU Domain

According to another embodiment, the non-endogenous immunosuppressive polypeptide to be expressed in said allogeneic immune cells is a viral env immusuppressive domain (ISU), which is derived for instance from HIV-1, HIV-2, SIV, MoMuLV, HTLV-I, -II, MPMV, SRV-1, Syncitin 1 or 2, HERV-K or FELV.

The interaction between the allogeneic T cell and host immune cells is schematically represented in FIG. 5 (expression of viral ISU domain) in regard to the situation to FIG. 1 (no expression).

The following Table 4 shows variants of ISU domain from diverse virus which can be expressed within the present invention.

Expression of Viral MHC Homolog

According to another embodiment, the non-endogenous immunosuppressive polypeptide to be expressed in said allogeneic immune cells is a viral MHC homolog, such as for instance UL18.

In one embodiment, said non-endogenous immunosuppressive polypeptide is a MHC homolog comprising a chimeric beta2m-UL18 of SEQ ID NO.39, or sharing at least 80%, preferably 90% and more preferably 95% of identity with respectively SEQ ID NO:39.

The interaction between the allogeneic T cell and host immune cells is schematically represented in FIG. 7 (expression of viral MHC homolog) in regard to the situation to FIG. 6 (no expression). In both figures, the MHC class I is inactivated by disrupting (KO) the beta2M gene.

Expression of NKG2D Ligand

Some viruses such as cytomegaloviruses have acquired mechanisms to avoid NK cell mediate immune surveillance and interfere with the NKG2D pathway by secreting a protein able to bind NKG2D ligands and prevent their surface expression (Welte, S. A.; Sinzger, C.; Lutz, S. Z.; Singh-Jasuja, H.; Sampaio, K. L.; Eknigk, U.; Rammensee, H. G.; Steinle, A. 2003 "Selective intracellular retention of virally induced NKG2D ligands by the human cytomegalovirus UL16 glycoprotein". Eur. J. Immunol., 33, 194-203). In tumors cells, some mechanisms have evolved to evade NKG2D response by secreting NKG2D ligands such as ULBP2, MICB or MICA (Salih H R, Antropius H, Gieseke F, Lutz S Z, Kanz L, et al. (2003) Functional expression and release of ligands for the activating immunoreceptor NKG2D in leukemia. Blood 102: 1389-1396)

According to another embodiment, the non-endogenous immunosuppressive polypeptide to be expressed in said allogeneic immune cells is an NKG2D ligand. The interaction between the allogeneic T cell and host immune cells is

TABLE 4

ISU domain variants from diverse viruses

| SEQ ID # | Position | | | | | | | | | | | | | | virus Origin |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | |
| SEQ ID No 19-24 | L | Q | A | R | I/V | L | A | V | E | R | Y | L | K/R/Q | D | HIV-1 |
| SEQ ID No 25-30 | L | Q | A | R | V | T | A | I | E | K | Y | L | K/A/Q | D/H | HIV-2 |
| SEQ ID No 31 | L | Q | A | R | L | L | A | V | E | R | Y | L | K | D | SIV |
| SEQ ID No 32 | L | Q | N | R | R | G | L | D | L | L | F | L | K | E | MoMuLV |
| SEQ ID No 33 | A | Q | N | R | R | G | L | D | L | L | F | W | E | Q | HTLV-I, -II |
| SEQ ID No 34 | L | Q | N | R | R | G | L | D | L | L | T | A | E | Q | MPMV, SRV-1 |
| SEQ ID No 35 | L | Q | N | R | R | A | L | D | L | L | T | A | E | R | Syncitin 1 |
| SEQ ID No 36 | L | Q | N | R | R | G | L | D | M | L | T | A | A | Q | Syncitin 2 |
| SEQ ID No 37 | L | A | N | Q | I | N | D | L | R | Q | T | V | I | W | HERV-K |
| SEQ ID No 38 | L | Q | N | R | R | G | L | D | I | L | F | L | Q | E | FELV |

Accordingly, in certain embodiments, the non-endogenous immunosuppressive polypeptide to be expressed in said allogeneic immune cells is an ISU domain of SEQ ID NO.19-38.

schematically represented in FIG. 8 (expression of soluble NKG2D ligand) in regard to the situation to FIG. 6 (no expression). In both figures, the MHC class I is inactivated by disrupting (KO) the beta2M gene.

The following Table 5 represents a viral MHC homolog (UL18) and a panel of NKG2D ligands and their polypeptide sequence to be expressed according to the present invention.

TABLE 5

Polypeptide sequence of a viral MHC homolog (UL18) and a panel of NKG2D ligands.

| | SEQ ID NO: | Polypeptide sequence |
|---|---|---|
| Chimeric B2M-UL18 | 39 | MALPVTALLLPLALLLHAARPSRSVALAVLALLSLSGLEAIQRTPKIQVYSRHPAENGKSNFLN CYVSGFHPSDIEVDLLKNGERIEKVEHSDLSFSKDWSFYLLYYTEFTPTEKDEYACRVNHVTLS QPKIVKWDRDMGGGGSGGGGSGGGGSGGGGSMTMWCLTLFVLWMLRVVGMHVLRY GYTGIFDDTSHMTLTVVGIFDGQHFFTYHVNSSDKASSRANGTISWMANVSAAYPTYLDGE RAKGDLIFNQTEQNLLELEIALGYRSQSVLTWTHECNTTENGSFVAGYEGFGWDGETLMELK DNLTLWTGPNYEISWLKQNKTYIDGKIKNISEGDTTIQRNYLKGNCTQWSVIYSGFQTPVTH PVVKGGVRNQNDNRAEAFCTSYGFFPGEINITFIHYGNKAPDDSEPQCNPLLPTFDGTFHQG CYVAIFCNQNYTCRVTHGNWTVEIPISVTSPDDSSSGEVPDHPTANKRYNTMTISSVLLALLL CALLFAFLHYFTTLKQYLRNLAFAWRYRKVRSS |
| SP-MICAed | 40 | MGGVLLTQRTLLSLVLALLFPSMASMEPHSLRYNLTVLSWDGSVQSGFLTEVHLDGQPFLRC DRQKCRAKPQGQWAEDVLGNKTWDRETRDLTGNGKDLRMTLAHIKDQKEGLHSLQEIRV CEIHEDNSTRSSQHFYYDGELFLSQNLETKEWTMPQSSRAQTLAMNVRNFLKEDAMKTKTH YHAMHADCLQELRRYLKSGVVLRRIVPPMVNVTRSEASEGNITVTCRASGFYPWNITLSWR QDGVSLSHDTQQWGDVLPDGNGTYQTWVATRICQGEEQRFTCYMEHSGNHSTHPVPSG KVLVLQSHW |
| SP-MICBed | 41 | MGGVLLTQRTLLSLVLALLFPSMASMAEPHSLRYNLMVLSQDESVQSGFLAEGHLDGQPFL RYDRQKRRAKPQGQWAEDVLGAKTWDTETEDLTENGQDLRRTLTHIKDQKGGLHSLQEIR VCEIHEDSSTRGSRHFYYDGELFLSQNLETQESTVPQSSRAQTLAMNVTNFWKEDAMKTKT HYRAMQADCLQKLQRYLKSGVAIRRTVPPMVNVTCSEVSEGNITVTCRASSFYPRNITLTWR QDGVSLSHNTQQWGDVLPDGNGTYQTWVATRIRQGEEQRFTCYMEHSGNHGTHPVPSG KVLVLQSQRTD |
| SP-ULBP1ed | 42 | MGGVLLTQRTLLSLVLALLFPSMASMGWVDTHCLCYDFIIITPKSRPEPQWCEVQGLVDERP FLHYDCVNHKAKAFASLGKKVNVTKTWEEQTETLRDVVDFLKGQLLDIQVENLIPIEPLTLQA RMSCEHEAHGHGRGSWQFLFNGQKFLLFDSNNRKWTALHPGAKKMTEKWEKNRDVTMF FQKISLGDCKMWLEEFLMYWEQMLDPT |
| SP-ULBP2ed | 43 | MGGVLLTQRTLLSLVLALLFPSMASMGRADPHSLCYDITVIPKFRPGPRWCAVQGQVDEKT FLHYDCGNKTVTPVSPLGKKLNVTTAWKAQNPVLREVVDILTEQLRDIQLENYTPKEPLTLQA RMSCEQKAEGHSSGSWQFSFDGQIFLLFDSEKRMWTTVHPGARKMKEKWENDKVVAMS FHYFSMGDCIGWLEDFLMGMDSTLEPSAG |
| SP-ULBP3ed | 44 | MGGVLLIQRILLSLVLALLFPSMASMDAHSLWYNFTIIHLPRHGQQWCEVQSQVDQKNFL SYDCGSDKVLSMGHLEEQLYATDAWGKQLEMLREVGQRLRLELADTELEDFTPSGPLTLQV RMSCECEADGYIRGSWQFSFDGRKFLLFDSNNRKWTVVHAGARRMKEKWEKDSGLTTFFK MVSMRDCKSWLRDFLMHRKKRLEPT |
| SP-N2DL4ed | 45 | MGGVLLTQRTLLSLVLALLFPSMASMHSLCFNFTIKSLSRPGQPWCEAQVFLNKNLFLQYNS DNNMVKPLGLLGKKVYATSTWGELTQTLGEVGRDLRMLLCDIKPQIKTSDPSTLQVEMFCQ REAERCTGASWQFATNGEKSLLFDAMNMTWTVINHEASKIKETWKKDRGLEKYFRKLSKG DCDHWLREFLGHWEAMPEPTVSPVNASDIHWSSSSLPD |
| SP-RET1Ged | 46 | MGGVLLTQRTLLSLVLALLFPSMASMGLADPHSLCYDITVIPKFRPGPRWCAVQGQVDEKTF LHYDCGSKTVIPVSPLGKKLNVITAWKAQNPVLREVVDILTEQLLDIQLENYIPKEPLTLQAR MSCEQKAEGHGSGSWQLSFDGQIFLLFDSENRMWTTVHPGARKMKEKWENDKDMTMS FHYISMGDCTGWLEDFLMGMDSTLEPSAGAPPTMSSGTAQPR |
| SP-RAETILed | 47 | MGGVLLTQRTLLSLVLALLFPSMASMRRDDPHSLCYDITVIPKFRPGPRWCAVQGQVDEKT FLHYDCGNKTVTPVSPLGKKLNVTMAWKAQNPVLREVVDILTEQLLDIQLENYTPKEPLTLQ ARMSCEQKAEGHSSGSWQFSIDGQTFLLFDSEKRMWTTVHPGARKMKEKWENDKDVAM SFHYISMGDCIGWLEDFLMGMDSTLEPSAG |

Accordingly, in certain embodiments, said non-endogenous immunosuppressive polypeptide to be expressed in engineered immune cells comprises or consists of a NKG2D ligand of SEQ ID NO.40-47, or sharing at least 80%, preferably 90% and more preferably 95% of identity with respectively SEQ ID NO:40-47.

Expression of FP Polypeptide

According to another embodiment, the non-endogenous immunosuppressive polypeptide to be expressed in said allogeneic immune cells is a FP polypeptide such as gp41. The following Table 6 represents several FP polypeptide from natural and artificial origins.

TABLE 6

Amino acid sequences of FP polypeptide from natural and artificial origins

| | Position | | | | | | | | | Origin |
|---|---|---|---|---|---|---|---|---|---|---|
| | 1 | 2 | 3 | 4 | 5 | 6 | 7 | 8 | 9 | |
| SEQ ID No 48 | G | A | L | F | L | G | F | L | G | HIV-1 gp41 |
| SEQ ID No 49 | A | G | F | G | L | L | L | G | F | Synthetic |

TABLE 6-continued

Amino acid sequences of FP polypeptide from
natural and artificial origins

| | Position | | | | | | | | | |
|---|---|---|---|---|---|---|---|---|---|---|
| | 1 | 2 | 3 | 4 | 5 | 6 | 7 | 8 | 9 | Origin |
| SEQ ID No 50 | A | G | L | F | L | G | F | L | G | Synthetic |

Accordingly, in certain embodiments, said non-endogenous immunosuppressive polypeptide to be expressed in engineered immune cells is a FP polypeptide comprising or consisting of SEQ ID NO.48-50, or sharing at least 80%, preferably 90% and more preferably 95% of identity with respectively SEQ ID NO:48-50.

Non Alloreactive and Immunosuppressive Resistant T Cells

Combinations of Gene Inactivation with Gene Expression

The inventors present here a method for increasing the persistence and/or the engraftment to apply on allogeneic immune cells, wherein a series of genetic modifications may be performed. Amongst those, are encompassed diverse combinations of both at least one inactivation gene involved in the self/non self-recognition and at least one expression of non-endogenous immunosuppressive polypeptide.

According to a preferred embodiment, the genetic modifications are performed by the inactivation of the B2M and/or TCR gene combined with the expression in said allogeneic immune cells of PD-L1 ligand and/or CTLA-4 immunoglobulins and/or viral env immune suppressive domain (ISU) and/or viral FP protein and/or NKG2G ligand viral MHC homolog such as for instance UL18.

Are also comprised in the scope of the present invention, polynucleotides, vectors encoding the above described rare-cutting endonucleases according to the invention.

In the scope of the present invention are also encompassed isolated cells or cell lines susceptible to be obtained by said method to engineer cells, in particular allogeneic immune cells such as T cells, in which at least one endogenous gene encoding a polypeptide involved in the self and non-self antigen recognition is inactivated and at least one non-endogenous immunosuppressive polypeptide is allowed to contact said all allogeneic immune cells.

In a particular aspect, the present invention relates to a method of engineering immune cells such as T-cells, especially for immunotherapy.

In a particular embodiment, the method comprises:
i) providing allogeneic cells;
ii) modifying said cells by inactivating at least one endogenous gene encoding a polypeptide involved in the self and non-self antigen recognition;
and;
iii) contacting said immune cells with at least one non-endogenous immunosuppressive polypeptide.

In another particular aspect, the present invention relates to a method of engineering immune cells such as T-cells, especially for immunotherapy.

In a particular embodiment, the method comprises:
i) providing allogeneic cells;
ii) modifying said cells by inactivating at least one endogenous gene encoding a polypeptide involved in the self and non-self antigen recognition;
and;
iii) expressing in said immune cells at least one non-endogenous immunosuppressive polypeptide.

T cell-mediated immunity includes multiple sequential steps involving the clonal selection of antigen specific cells, their activation and proliferation in secondary lymphoid tissue, their trafficking to sites of antigen and inflammation, the execution of direct effector function and the provision of help (through cytokines and membrane ligands) for a multitude of effector immune cells. Each of these steps is regulated by counterbalancing stimulatory and inhibitory signal that fine-tunes the response.

For example, CTLA-4 is a cell-surface protein expressed on certain CD4 and CD8 T cells; when engaged by its ligands (B7-1 and B7-2) on antigen presenting cells, T-cell activation and effector function are inhibited. Thus the present invention relates to a method of engineering T-cells, especially for immunotherapy, comprising genetically modifying T-cells by inactivating at least one protein involved in the immune check-point, in particular PD1 and/or CTLA-4.

In another embodiment, the genetic modification step of the method relies on the inactivation of more than two genes. The genetic modification is preferably operated ex-vivo.

TALE-Nucleases Cleaving Human TCR Genes (TRAC and TRBC)

The human genome contains two functional T-cell receptor beta chains (TRBC1 and TRBC2). During the development of alpha/beta T lymphocytes, one of these two constant chains is selected in each cell to be spliced to the variable region of TCR-beta and form a functional full length beta chain. The 2 TRBC targets were chosen in sequences conserved between TRBC1 and TRBC2 so that the corresponding TALE-nuclease would cleave both TRBC1 and TRBC2 at the same time.

Although human TCR genes may be disrupted in allogeneic immune cells as taught in WO WO2013176915, the present invention encompasses the situation where such inactivation is combined with any of the foregoing inactivation of self/non-self recognition genes and ectopic expression of at least one non-endogenous immunosuppressive polypeptide previously mentioned.

The following Table 7 presents nucleotide sequences for 5 TRAC and 2 TRBC targets and some of their corresponding left and right TALEN. Additional sequences can be found in the applications WO2014/184741 and WO2014/184744.

TABLE 7

Description of the TRAC and TRBC TALE-nucleases and sequences of
the TALE-nucleases target sites in the human corresponding
genes.

| Target | Target sequence | Half TALE-nuclease |
|---|---|---|
| TRAC_T00 | TGATCCTCTTGTCCCACAGATATCC Agaaccctgaccctg CCGTGTACCAGCTGAGAGA (SEQ ID NO 51) | TRAC_T00-L TALEN (SEQ ID NO: 52) TRAC_T00-R TALEN (SEQ ID NO: 53) |

TABLE 7-continued

Description of the TRAC and TRBC TALE-nucleases and sequences of the TALE-nucleases target sites in the human corresponding genes.

| Target | Target sequence | Half TALE-nuclease |
|---|---|---|
| TRAC_T01 | TTGTCCCACAGATATCC Agaaccctgaccctg CCGTGTACCAGCTGAGA (SEQ ID NO: 54) | TRAC_T01-L TALEN (SEQ ID NO: 55) TRAC_T01-R TALEN (SEQ ID NO: 56) |
| TRAC_T02 | TTTAGAAAGTTCCTGTG atgtcaagctggtcg AGAAAAGCTTTGAAACA (SEQ ID NO: 57) | |
| TRAC_T03 | TCCAGTGACAAGTCTGT ctgcctattcaccga TTTTGATTCTCAAACAA (SEQ ID NO: 58) | |
| TRAC_T04 | TATATCACAGACAAAAC tgtgctagacatgag GTCTATGGACTTCAAGA (SEQ ID NO: 59) | |
| TRAC_T05 | TGAGGTCTATGGACTTC aagagcaacagtgct GTGGCCTGGAGCAACAA (SEQ ID NO: 60) | |
| TRBC_T01 | TGTGTTTGAGCCATCAG aagcagagatctccc ACACCCAAAAGGCCACA (SEQ ID NO: 61) | TRBC_T01-L TALEN (SEQ ID NO: 62) TRBC_T01-R TALEN (SEQ ID NO: 63) |
| TRBC_T02 | TTCCCACCCGAGGTCGC tgtgtttgagccatca GAAGCAGAGATCTCCCA (SEQ ID NO: 64) | TRBC_T02-L TALEN (SEQ ID NO: 65) TRBC_T02-R TALEN (SEQ ID NO: 66) |

Single Chain CAR

According to one aspect of the invention, the method comprises the step of introducing into said T-cell an exogenous nucleic acid molecule comprising a nucleotide sequence coding for a Chimeric Antigen Receptor (CAR) directed against at least one antigen expressed at the surface of a malignant or infected cell. They may be designed according to single-chain or multi-chain architectures.

In one embodiment, the Chimeric Antigen Receptor (CAR) is a single-chain CAR.

In a preferred embodiment, said extracellular ligand-binding domain is a scFv. Other binding domain than scFv can also be used for predefined targeting of lymphocytes, such as camelid single-domain antibody fragments or receptor ligands like a vascular endothelial growth factor polypeptide, an integrin-binding peptide, heregulin or an IL-13 mutein, antibody binding domains, antibody hypervariable loops or CDRs as non limiting examples.

As preferred examples of scFv according to the invention, VH and VL chains have as antigenic target sequence of over 80% identity, preferably over 90%, and more preferably over 95% with SEQ ID NO 67 (CD19 antigen), SEQ ID NO 68 (CD38 antigen), SEQ ID NO 69 (CD123 antigen), SEQ ID NO 70 (CS1 antigen), SEQ ID NO 71 (BCMA antigen), SEQ ID NO 72 (FLT-3 antigen), SEQ ID NO 73 (CD33 antigen), SEQ ID NO 74 (CD70 antigen), SEQ ID NO 75 (EGFR-3v antigen) and SEQ ID NO 76 (WT1 antigen). Other examples of surface antigens of tumoral cells to be targeted are CLL1, Hsp70, CD22, MUC16, PRAME, TSPAN10, ROR1, GD3, CT83 and mesothelin.

According to an embodiment, the present invention relates to a method as described above, wherein step c) is performed by the step c) is performed by the expression in said allogeneic immune cells of non-endogenous immunosuppressive polypeptide PD-L1 ligand and/or CTLA-4 immunoglobulins, said allogeneic immune cells being further modified by the expression of an anti-CD123 Chimeric Antigen Receptor.

According to a preferred embodiment, said anti-CD123 CAR/PD-L1 ligand/CTLA-4 Ig expressed allogeneic immune cells are further modified during step c) of the method to undergo an inactivation of the expression of the PD-1 gene.

Said polypeptide of a) further may comprise a stalk region between said extracellular ligand-binding domain and said transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence.

Said polypeptide may further comprise at least one signal-transducing domain. In a most preferred embodiment, said signal-transducing domain is selected from the group consisting of CD28, OX40, ICOS, CD137 and CD8.

Said C-terminal cytoplasmic tail of FcERI alpha, beta and/or gamma chain fragment further comprises TNFR-associated Factor 2 (TRAF2) binding motifs. In a most preferred embodiment, said C-terminal cytoplasmic tail of FcERI alpha, beta and/or gamma chain is replaced by intracytoplasmic tail of costimulatory TNFR member family. Cytoplasmic tail of costimulatory TNFR family member contains TRAF2 binding motifs consisting of the major conserved motif (P/S/A)X(Q/E)E) or the minor motif (PXQXXD), wherein X is any amino acid. TRAF proteins are recruited to the intracellular tails of many TNFRs in response to receptor trimerization.

Said intracytoplasmic domain of FcERI alpha, beta and/or gamma chain is replaced by intracytoplasmic domain of TCR zeta chain (also named CD3 zeta). In another preferred embodiment, said intracytoplasmic domain of FcERI alpha, beta and/or gamma chain comprises at least one additional immunoreceptor tyrosine-based activation motif (ITAM). ITAMs are well defined signaling motifs found in the intracytoplasmic tail of a variety of receptors that serve as binding sites for syk/zap70 class tyrosine kinases. Examples of ITAM used in the invention include those derived from TCRzeta, FCRgamma, FCRbeta, CD3gamma, CD3delta, CD3epsilon, CD5, CD22, CD79a, CD79b, and CD66d.

For instance, an example of single-chain CAR is depicted by the SEQ ID NO: 77.

In a preferred embodiment, said above CAR is single-chain CAR chosen in the group consisting of anti-CD123 single-chain CAR, anti-CS1 single-chain CAR, anti-CD38 single-chain CAR, anti-CLL1 single-chain CAR, anti-Hsp70 single-chain CAR, anti-EGFRvIII single-chain CAR, anti-BCMA single-chain CAR, anti-CD33 single-chain CAR, anti-FLT3 single-chain CAR, anti-CD70 single-chain CAR, anti-WT1 single-chain CAR, anti-MUC16 single-chain CAR, anti-PRAME single-chain CAR, anti-TSPAN10 single-chain CAR, anti-ROR1 single-chain CAR, anti-GD3 single-chain CAR, anti-CT83 single-chain CAR and mesothelin single-chain CAR;

said CAR being expressed in an immune cell has one of the polypeptide structure selected from V1, V3 or V5, as illustrated in FIG. 24;
said structure comprising:
an extra cellular ligand binding-domain comprising VH and VL from a monoclonal antibody selected in the group consisting of anti-CD123 mAb, anti-CS1 mAb, anti-CD38 mAb, anti-CLL1 mAb, anti-Hsp70 mAb, anti-EGFRvIII mAb, anti-BCMA mAb, anti-CD33 mAb, anti-FLT3 mAb, anti-CD70 mAb, anti-WT1 mAb, anti-MUC16 mAb, anti-PRAME mAb, anti-TSPAN10 mAb, anti-ROR1 mAb, anti-GD3 mAb, anti-CT83 mAb and anti-mesothelin mAb respectively;
a hinge chosen in the group consisting of CD8alpha, FcERIllgamma and IgG1;
a CD8α transmembrane domain;
a cytoplasmic domain including a CD3 zeta signaling domain and;
a 4-1BB co-stimulatory domain.

All the other components chosen in the architecture of the CAR including transmembrane domain (i.e CD8αTM), co-stimulatory domain (ie. 4-1BB), hinge (CD8alpha, FcER-lllgamma, IgG1), cytoplasmic signaling domain (ITAM CD3zeta) may be those already described in the above WO2015140268 and WO2015121454 applications.

As examples, VH and VL may be those described in the applications WO2015140268 for anti-CD123, WO2015121454 for anti-CS1 and anti-CD38.

Multi-Chain Chimeric Antigen Receptor (CAR)

In another embodiment, the invention relates to a multi-chain chimeric antigen receptor (CAR) particularly adapted to the production and expansion of engineered immune cells such as T-cells of the present invention. The multi-chain CAR comprising at least two of the following components:

a) one polypeptide comprising the transmembrembrane domain of FcERI alpha chain and an extracellular ligand-binding domain, b) one polypeptide comprising a part of N- and C-terminal cytoplasmic tail and the transmembrane domain of FcERI beta chain and/or c) two polypeptides comprising each a part of intracytoplasmic tail and the transmembrane domain of FcERI gamma chain, whereby different polypeptides multimerize together spontaneously to form dimeric, trimeric or tetrameric CAR.

CAR of the present invention can also be "multi-chain CARs" as previously mentioned, which means that the extracellular binding domain and the signaling domains are preferably located on different polypeptide chains, whereas co-stimulatory domains may be located on the same or a third polypeptide. Such multi-chain CARs can be derived from FcERI (Ravetch et al, 1989), by replacing the high affinity IgE binding domain of FcERI alpha chain by an extracellular ligand-binding domain such as scFv, whereas the N and/or C-termini tails of FcERI beta and/or gamma chains are fused to signal transducing domains and co-stimulatory domains respectively. The extracellular ligand binding domain has the role of redirecting T-cell specificity towards cell targets, while the signal transducing domains activate or reduce the immune cell response. The fact that the different polypeptides derive from the alpha, beta and gamma polypeptides from FcERI are transmembrane polypeptides sitting in juxtamembrane position provides a more flexible architecture to CARs, improving specificity towards the targeted molecule and reducing background activation of immune cells. Multi-chain architectures are more particularly disclosed in WO2014039523.

In another embodiment, said CAR which are expressed in the immune cell such as described earlier is chosen in the group consisting of anti-CD123 multi-chain CAR, anti-CS1 multi-chain CAR, anti-CD38 multi-chain CAR, anti-CLL1 multi-chain CAR or anti-Hsp70 multi-chain CAR.

In another preferred embodiment, said above CAR is multi-chain CAR chosen in the group consisting of anti-CD123 multi-chain CAR, anti-CS1 multi-chain CAR, anti-CD38 multi-chain CAR, anti-CLL1 multi-chain CAR, anti-Hsp70 multi-chain CAR, anti-EGFRvIII multi-chain CAR, anti-BCMA multi-chain CAR, anti-CD33 multi-chain CAR, anti-FLT3 multi-chain CAR, anti-CD70 multi-chain CAR, anti-WT1 multi-chain CAR, anti-MUC16 multi-chain CAR, anti-PRAME multi-chain CAR, anti-TSPAN10 multi-chain CAR, anti-ROR1 multi-chain CAR, anti-GD3 multi-chain CAR, anti-CT83 multi-chain CAR and mesothelin multi-chain CAR.

Such multi-chain CAR architectures are disclosed in WO2014/039523, especially in FIGS. 2 to 4, and from page 14 to 21, which are herein incorporated by reference.

The term "a part of" used herein refers to any subset of the molecule, that is a shorter peptide. Alternatively, amino acid sequence functional variants of the polypeptide can be prepared by mutations in the DNA which encodes the polypeptide. Such functional variants include, for example, deletions from, or insertions or substitutions of, residues within the amino acid sequence. Any combination of deletion, insertion, and substitution may also be made to arrive at the final construct, provided that the final construct possesses the desired activity, especially to exhibit a specific anti-target cellular immune activity.

Are also comprised in the scope of the present invention, polynucleotides, vectors encoding the above described multi-chain CAR according to the invention.

In a particular embodiment, the invention relates to a method of preparing immune cells such as T-cells for immunotherapy comprising introducing into said T-cells the different polypeptides composing said multi-chain CAR and expanding said cells.

The present invention also relates isolated cells or cell lines susceptible to be obtained by said method to engineer cells. In particular said isolated cell comprises exogenous polynucleotide sequences encoding polypeptides composing said multi-chain CAR.

Bispecific Antibodies

According to a further embodiment, engineered immune cells such as T cells obtained by the different methods as previously described can be further exposed with bispecific antibodies. Said T-cells could be exposed to bispecific antibodies ex vivo prior to administration to a patient or in vivo following administration to a patient. Said bispecific antibodies comprise two variable regions with distinct antigen properties that allow bringing the engineered cells into proximity to a target antigen. As a non-limiting example, said bispecific antibody is directed against a tumor marker and lymphocyte antigen such as CD3 and has the potential to redirect and activate any circulating T cells against tumors.

Delivery Methods

The different methods described above involve introducing pTalpha or functional variants thereof, rare cutting endonuclease, TALE-nuclease, CAR or multi-chain CAR optionally with DNA-end processing enzyme or exogenous nucleic acid into a cell.

As non-limiting example, rare cutting endonucleases, TALE-nucleases, gene encoding non-endogenous immunosuppressive polypeptide, CAR or multi-chain CAR optionally with DNA-end processing enzyme or exogenous nucleic acid can be introduced as transgenes encoded by one or as different plasmidic vectors. Different transgenes can be included in one vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA. As non-limiting example, in the present invention, 2A peptides have been used to express into the cell the rare-cutting endonuclease and a DNA end-processing enzyme or the different polypeptides of the multi-chain CAR.

Said plasmid vector can contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into animal cells are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Electroporation

Polynucleotides encoding polypeptides according to the present invention can be mRNA which is introduced directly into the cells, for example by electroporation. The inventors determined the optimal condition for mRNA electroporation in T-cell.

The inventor used the cytoPulse technology which allows, by the use of pulsed electric fields, to transiently permeabilize living cells for delivery of material into the cells. The technology, based on the use of PulseAgile (Cellectis property) electroporation waveforms grants the precise control of pulse duration, intensity as well as the interval between pulses (U.S. Pat. No. 6,010,613 and International PCT application WO2004083379). All these parameters can be modified in order to reach the best conditions for high transfection efficiency with minimal mortality. Basically, the first high electric field pulses allow pore formation, while subsequent lower electric field pulses allow to move the polynucleotide into the cell. In one aspect of the present invention, the inventor describe the steps that led to achievement of >95% transfection efficiency of mRNA in T cells, and the use of the electroporation protocol to transiently express different kind of proteins in T cells. In particular the invention relates to a method of transforming T cell comprising contacting said T cell with RNA and applying to T cell an agile pulse sequence consisting of:

(a) one electrical pulse with a voltage range from 2250 to 3000 V per centimeter, a pulse width of 0.1 ms and a pulse interval of 0.2 to 10 ms between the electrical pulses of step (a) and (b);

(b) one electrical pulse with a voltage range from 2250 to 3000 V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

The method of transforming T cell may comprise contacting said T cell with RNA and applying to T cell an agile pulse sequence consisting of:

(a) one electrical pulse with a voltage of 2250, 2300, 2350, 2400, 2450, 2500, 2550, 2400, 2450, 2500, 2600, 2700, 2800, 2900 or 3000V per centimeter, a pulse width of 0.1 ms and a pulse interval of 0.2, 0.5, 1, 2, 3, 4, 5, 6, 7, 8, 9 or 10 ms between the electrical pulses of step (a) and (b);

(b) one electrical pulse with a voltage range from 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

Any values included in the value range described above are disclosed in the present application. Electroporation medium can be any suitable medium known in the art. Preferably, the electroporation medium has conductivity in a range spanning 0.01 to 1.0 milliSiemens.

As non-limiting examples, said RNA encodes a rare-cutting endonuclase, one monomer of the rare-cutting endonuclase such as Half-TALE-nuclease, a Chimeric Antigen Receptor, at least one component of the multi-chain chimeric antigen receptor, an exogenous nucleic acid, one additional catalytic domain.

Activation and Expansion of Immune Cells

Whether prior to or after genetic modification of the immune cells such as T cells, the immune cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with a surface having attached thereto an agent that stimulates a CD3 TCR complex associated signal and a ligand that stimulates a co-stimulatory molecule on the surface of the T cells.

In particular, immune cells such as T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of immune cells can be contacted with an anti-CD3 antibody and an anti-CD28 antibody, under conditions appropriate for stimulating proliferation of the immune cells. To stimulate proliferation of either CD4+ T cells or CD8+ T cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell. In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. Cell surface proteins may be ligated by allowing paramagnetic beads to which anti-CD3 and anti-CD28 are attached (3×28 beads) to contact the T cells. In one embodiment the cells (for example, 4 to 10 T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. The mixture may be cultured for several hours (about 3 hours) to about 14 days or any hourly integer value in between. In another embodiment, the mixture may be cultured for 21 days. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). Immune cells such as T cells that have been exposed to varied stimulation times may exhibit different characteristics.

In another particular embodiment, said cells can be expanded by co-culturing with tissue or cells. Said cells can also be expanded in vivo, for example in the subject's blood after administrating said cell into the subject.

Engineered Immune Cells and Their Interaction with Host Immune Cells

In the scope of the present invention is also encompassed an isolated immune cell obtained according to any one of the methods previously described. Said immune cell according to the present invention can be derived from a hematopoietic stem cell. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells.

According to an embodiment, said immune cells are hematopoietic cells, and more preferably primary cells.

According to a preferred embodiment, the engineered allogeneic immune cells, after contacting at least one non-endogenous immunosuppressive polypeptide, do not induce specifically the inhibition of T regulatory cells.

According to a more preferred embodiment, the engineered allogeneic immune cells, after contacting at least one non-endogenous immunosuppressive polypeptide, induce specifically an inhibition of CD8+ T cells.

Prior to expansion and genetic modification of the cells of the invention, a source of cells can be obtained from a subject through a variety of non-limiting methods. Immune cells such as T cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. Any number of immune cell lines available and known to those skilled in the art, may be used. In another embodiment, said cell can be derived from a healthy donor, from a patient diagnosed with cancer or from a patient diagnosed with an infection. Said cell is part of a mixed population of cells which present different phenotypic characteristics. In the scope of the present invention is also encompassed a cell line obtained from a transformed immune cell such as T-cell according to the method previously described. Modified cells resistant to an immunosuppressive treatment and susceptible to be obtained by the previous method are encompassed in the scope of the present invention.

In another embodiment, said isolated cell according to the present invention comprises one inactivated endogenous gene encoding a polypeptide involved in the self and non-self antigen recognition, such as TCR, MHC class of class I component, b-2 microglobulin (B2M), TAP1 and large multifunctional protease 2. Furthermore, said engineered allogeneic immune cells are contacted with at least one non-endogenous immunosuppressive polypeptide, either by expressing at least one secreted non-endogenous immunosuppressive polypeptide or by incubating said immune cells with at least one non-endogenous immunosuppressive polypeptide.

Therapeutic Applications

In another embodiment, isolated cell obtained by the different methods or cell line derived from said isolated cell as previously described can be used as a medicament. In another embodiment, said medicament can be used for treating cancer or infections in a patient in need thereof. In another embodiment, said isolated cell according to the invention or cell line derived from said isolated cell can be used in the manufacture of a medicament for treatment of a cancer or a viral infection in a patient in need thereof.

In another aspect, the present invention relies on methods for treating patients in need thereof, said method comprising at least one of the following steps:

(a) providing an immune cell such as T-cell obtainable by any one of the methods previously described;

(b) Administrating said transformed immune cell such as T-cells to said patient, On one embodiment, said immune cell such as T cells of the invention can undergo robust in vivo immune cell such as T cell expansion and can persist for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immunotherapy, insofar as it enables the transformation of immune cells such as T-cells, typically obtained from donors, into non-alloreactive cells. This may be done under standard protocols and reproduced as many times as needed. The resulted modified immune cells may be pooled and administrated to one or several patients, being made available as an "off the shelf" therapeutic product.

Cells that can be used with the disclosed methods are described in the previous section. Said treatment can be used to treat patients diagnosed with cancer, viral infection, autoimmune disorders or Graft versus Host Disease (GvHD). Cancers that may be treated include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

It can be a treatment in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery. Said modified cells obtained by any one of the methods described here can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

by "DNA target", "DNA target sequence", "target DNA sequence", "nucleic acid target sequence", "target sequence", or "processing site" is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of TALE-nuclease targets, targeted genomic sequences generally consist of two 17-bp long sequences (called half targets) separated by a 15-bp spacer. Each half-target is recognized by repeats of TALE-nucleases listed in tables 2, 7 and 11 as non-limiting examples, encoded in plasmids, under the control of EF1-alpha promoter or T7 promoter. The nucleic acid target sequence is defined by the 5' to 3' sequence of one strand of said target, as indicated in tables 2 and 7.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFvFc) fused to the intracellular signaling domain of the T cell antigen receptor complex zeta chain (scFvFc:ζ) and have the ability, when expressed in T cells, to redirect antigen recognition based on the monoclonal antibody's specificity. One example of CAR used in the present invention is a CAR directing against CD19 antigen and can comprise as non-limiting example the amino acid sequence: SEQ ID NO: 6

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non limiting example, that are able to integrate the genome of a target cell. At the opposite by "non integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non limiting examples cell lines can be selected from the group consisting of CHO-K1 cells; HEK293 cells; Caco2 cells; U2-OS cells; NIH 3T3 cells; NSO cells; SP2 cells; CHO—S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, fourty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "locus" is the specific physical location of a DNA sequence (e.g. of a gene) on a chromosome. The term "locus" can refer to the specific physical location of a rare-cutting endonuclease target sequence on a chromosome. Such a locus can comprise a target sequence that is recognized and/or cleaved by a rare-cutting endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

Rare-cutting endonucleases can also be for example TALE-nucleases, a new class of chimeric nucleases using a FokI catalytic domain and a DNA binding domain derived from Transcription Activator Like Effector (TALE), a family of proteins used in the infection process by plant pathogens of the Xanthomonas genus (Boch, Scholze et al. 2009; Moscou and Bogdanove 2009; Christian, Cermak et al. 2010; Li, Huang et al.). The functional layout of a FokI-based TALE-nuclease (TALE-nuclease) is essentially that of a ZFN, with the Zinc-finger DNA binding domain being replaced by the TALE domain. As such, DNA cleavage by a TALE-nuclease requires two DNA recognition regions flanking an unspecific central region. Rare-cutting endonucleases encompassed in the present invention can also be derived from TALE-nucleases.

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant.

By a "TALE-nuclease" is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-I. In a particular embodiment, the TALE domain can be fused to a meganuclease like for instance I-CreI and I-OnuI or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species Xanthomonas comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Boch, Scholze et al. 2009; Moscou and Bogdanove 2009; Christian, Cermak et al. 2010; Li, Huang et al.). Engineered TAL-nucleases are commercially available under the trade name TALEN™ (Cellectis, 8 rue de la Croix Jarry, 75013 Paris, France).

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"similarity" describes the relationship between the amino acid sequences of two or more polypeptides. BLASTP may also be used to identify an amino acid sequence having at least 70%, 75%, 80%, 85%, 87.5%, 90%, 92.5%, 95%, 97.5%, 98%, 99% sequence similarity to a reference amino acid sequence using a similarity matrix such as BLOSUM45, BLOSUM62 or BLOSUM80. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

The inventors propose to explore three different strategies to prevent allogeneic CAR T cells depletion via HvG (FIG. 9). As presented in Example 1, the first one consists of expressing PD-L1 at the surface of CAR T cell. The presence of such antigen is likely to inhibit host T cells via PD1/PD-L1 inhibition pathway and thus decrease their cytolytic activity toward CAR T cell (FIG. 10A). Without such decoy system and after a certain length of time, host T cells are expected to attack and deplete allogeneic CAR T cells (FIG. 10B). The second strategy consists of engineering CAR T cells to make them excrete CTLA4 Ig, a chimeric construction made out of CTLA4 protein fused the constant region of IgG. Release of CTLA4 Ig in the extracellular medium is likely to bind to CD86/CD80 exposed at the surface of antigen presenting cells (APC) and prevent them to activate host T cells via CD28/CD80 or CD28/CD86 interactions. The HvG reaction, involving host APC and host T cells interaction/activation, is displayed in FIG. 11A and the prevention of CAR T cell rejection via excretion of CTLA4 Ig is displayed in FIG. 11B. The third strategy, consisting of combining the two aforementioned strategies, could also been used to prevent HvG reaction and allow CAR T cells to proliferate in the setting of an allogeneic cell adoptive transfer.

In the following Examples 3 to 7, to prolong their survival and enhance their therapeutic activity, the inventors describe a method to prevent NK-cell mediated rejection of therapeutic allogeneic T cells by engineering the allogenic T cells through the inactivation of the B2M gene using specific TALEN, combined to either: i) the expression of a chimeric single chain molecule composed of UL18 and β2-m (B2M-UL18) or ii) the secretion of NKG2D ligands. The particularity resides in applying to primary T cells a mechanism occurring normally in tumor cells or virally infected cells. Thus, the mechanism of action is potentially different: in tumor cells, shedding NKG2D ligands leads to their decreased presence at the surface whereas in engineered cells, secreted the NKG2D ligand(s) would serve as a decoy for several other NKG2D ligands potentially still present at the T cell surface.

In the following Examples 8 to 11, are presented a method where allogenic CAR T cells are engineered in order to express immunosuppressive polypeptides from viral proteins (ISU or FP as membrane-bound or secreted peptides), allowing inhibition of patient T cells and therefore allowing efficient persistence of allogenic CAR T cells infused into patient.

General Methods

Primary T-Cell Cultures

T cells were purified from Buffy coat samples provided by EFS (Etablissement Francais du Sang, Paris, France) using Ficoll gradient density medium. The PBMC layer was recovered and T cells were purified using a commercially available T-cell enrichment kit. Purified T cells were activated in X-Vivo™-15 medium (Lonza) supplemented with 20 ng/mL Human IL-2, 5% Human, and Dynabeads Human T activator CD3/CD28 at a bead:cell ratio 1:1 (Life Technologies).

scCAR mRNA Transfection

Transfections were done at Day 4 or Day 11 after T-cell purification and activation. 5 millions of cells were transfected with 15 µg of mRNA encoding the different scCAR constructs. scCAR mRNAs were produced using T7 mRNA polymerase transfections done using Cytopulse technology, by applying two 0.1 mS pulses at 3000V/cm followed by four 0.2 mS pulses at 325V/cm in 0.4 cm gap cuvettes in a final volume of 200 µl of "Cytoporation buffer T" (BTX Harvard Apparatus). Cells were immediately diluted in X-Vivo™-15 media and incubated at 37° C. with 5% $CO_2$. IL-2 was added 2 h after electroporation at 20 ng/mL.

Cytotoxicity Assay

T-cells were incubated in 96-well plates (100,000 cells/well), together with 10,000 target cells (expressing CD123) and 10,000 control (CD123neg) cells in the same well. Target and control cells were labelled with fluorescent intracellular dyes (CFSE or Cell Trace Violet) before co-culturing them with CD123 CAR+ T-cells. The co-cultures were incubated for 4 hours at 37° C. with 5% $CO_2$. After this incubation period, cells were labelled with a fixable viability dye and analyzed by flow cytometry. Viability of each cellular population (target cells or CD123 control cells) was determined and the % of specific cell lysis was calculated. Cytotoxicity assays were carried out 48 h after mRNA transfection.

T-Cell Transduction

Transduction of T-cells with recombinant lentiviral vectors expression the scCAR was carried out three days after T-cell purification/activation. scCAR detection at the surface of T-cells was done using a recombinant protein consisting on the fusion of the extracellular domain of the human CD123 protein, together with a murine IgG1 Fc fragment. Binding of this protein to the scCAR molecule was detected with a fluorochrome-conjugated secondary antibody targeting the mouse Fc portion of the protein, and analyzed by flow cytometry.

Example 1. Transgenic Expression of PD-L1 at the Surface of Primary T Cells and CAR T Cells In these experiments, it is shown that—human activated T cells, transfected or transduced with PD-L1 encoding vectors (mRNA or lentivirus) express detectable levels of PD-L1 at the cell surface.

Expression of PD-L1

This example describes expression of PD-L1 at the surface of T cells or CAR T cells along with the impact of such expression on their cytolytic activity toward tumor cells. To express PD-L1 at the surface of primary T cells, primary T cells were first purified from buffy-coat samples, activated transduced by a lentiviral particle containing an anti-CD19 CAR tool (pCLS23856, SEQ ID NO 77) and transfected according to the procedure described in Galetto R et al. (2014) Molecular Therapy—Methods & Clinical Development 1, Article number: 14021 doi:10.1038/mtm.2014.2.

Briefly regarding transduction, 2 days post activation by Dynabeads human T activator CD3/CD28, T cells were incubated with lentiviral particles containing anti-CD19 CAR tool at 5 MOI.

Transfection of mRNA

Regarding transfection, 5 days after their activation, 5 million of CAR T cells or T cells were transfected with 20 µg of mRNA encoding PD-L1 (pCLS27069, SEQ ID NO 18). Transfection was performed using Agilpulse technology, by applying two 0.1 mS pulses at 3,000 V/cm followed by four 0.2 mS pulses at 325 V/cm in 0.4 cm gap cuvettes and a final volume of 200 µl of Cytoporation buffer T (BTX Harvard Apparatus, Holliston, Mass.). Cells were then immediately diluted in X-Vivo-15 media supplemented by 20 ng/ml IL-2 (final concentration) and 5% human serum AB. Transfected T cells were eventually diluted at $1 \times 10^6$/ml and kept in culture at 37° C. in the presence of 5% $CO_2$ and 20 ng/ml IL-2 (final concentration) and 5% human AB serum for further characterization. One day post transfection, CAR T cells were recovered to characterize the expression of PD-L1 at their cell surface and to determine the impact of such expression on their specific cytolytic activity toward relevant tumor cells targeted by their anti CD19 tool CAR.

Our results showed that PD-L1 is expressed in CAR T cell transfected with mRNA encoding PD-L1 (>90% of cells express PD-L1, FIG. 12) whereas no expression could be detected in mock transfected T cells or CAR T cells. Similar results were obtained with untransduced T cells indicating that PD-L1 is successfully expressed on CAR T cells and T cells (FIG. 12).

Transfection with Lentivirus Vector (LV)

A LV vector containing the PD-L1 cDNA was produced. Primary T cells were first purified from buffy-coat samples, activated, transduced either with a lentiviral particle containing PD-L1 (pCLS27062 of SEQ ID NO.18) at a MOI of 5. Three days post transduction, transduced T cells were recovered to characterize the expression of PD-L1 at their cell surface.

The results showed that PD-L1 is expressed in T cell transduced with LV vector encoding PD-L1 alone (>70% of cells express PD-L1, result not shown) whereas no expression could be detected in untransduced T cells.

Specific Cell Lysis

Regarding the specific cell lysis activity of CAR T cells toward relevant tumor cells (Daudi) determined using the flow-based assay described in Zhao, Y. et al. (2010) Cancer Res 70, 9053-9061, our result showed that the re-expression of PD-L1 at the surface of CAR T cell does not markedly affect their activity (FIG. 13). This result is reproducible with CAR T cells engineered out of different blood donor (FIG. 13, see results obtained with Mock CAR T cells B and PD-L1 CAR T cells B).

Example 2. Transgenic Expression and Excretion of Abatacept and Belatacept (CTLA4 Ig) by Primary T Cells and CART Cells Transfection of mRNA and with Lentivirus Vector (LV)

Abatacept and belatacept (marketed as Orencia and Nulojix respectively) are fusion proteins composed of the Fc region of the immunoglobulin IgG1 fused to the extracellular domain of CTLA-4.

This example describes the expression and excretion of CTLA4a Ig and CTLA4b Ig (Abatacept, or Belatacept pCLS27068 SEQ ID NO 3 and pCLS27066, SEQ ID NO 4 respectively) and by LV containing the CTLA4Ig (pCLS27064 of SEQ ID NO.16) at a MOI of 5 by primary T cells in the culture media. Abatacept is described in Moreland L et al; (2006) Nature Reviews Drug Discovery 5, 185-186. Belatacept is described by Larsen C P et al. (2005) "*Rational development of LEA29Y (belatacept), a high-affinity variant of CTLA4-Ig with potent immunosuppressive properties*". Am J Transplant. 5(3):443-53.

CTLA4 a/b Ig Expression

To express CTLA4 Ig by primary T cells, primary T cells were first purified from buffy-coat samples, activated transduced by a lentiviral particle containing an anti-CD19 CAR tool (pCLS23856, SEQ ID NO 77) and transfected according to the procedure described as in example 1. Regarding transfection, 5 days after their activation, 5 million of CAR T cells or T cells were transfected with 20 µg of mRNA encoding CTLA4a or b Ig (Abatacept, or Belatacept pCLS27068 SEQ ID NO:16 and pCLS27066, SEQ ID NO:17 respectively) and cultured according to the protocol described in example 1. One day post transfection, CAR T cells were recovered to characterize their ability to excrete CTLA4 Ig in the culture media via ELISA and to determine the impact of such expression/excretion on their specific cytolytic activity toward relevant and non-relevant tumor cells targeted (Daudi and K562 respectively).

Our results showed that transfection of primary T cells by mRNA encoding CTLA4 a or b Ig resulted in the appearance of the corresponding fusion proteins in the culture media. The quantity of CTLA4 Ig in the culture media was approximatively proportional to the amount of mRNA transfected with a maximum of CTLA4a Ig and CTLA4b Ig of 2.1 and 3.1 pg/mL respectively in our experimental condition. As expected, the culture media of mock transfected T cell did not contain any detectable CTLA4 Ig protein. These results indicated that CTLA4a Ig and CTLA4b Ig were successfully expressed by primary T cells and excreted in the culture media.

Specific Cytolytic Activity

To study the impact of CTLA4 Ig on the activity of CAR T cells, their cytolytic activity toward relevant and non-relevant tumor cell lines was determined using a flow based assay described in Example 1. Our results showed that the Mock transfected CAR T cell and CTLA4 Ig CAR T cells displayed significant cytolytic activity toward Daudi cells. Altogether, these results indicated that primary T cells successfully expressed and excreted CTLA4 Ig while retaining their antitumor activity.

Example 3. Transgenic Expression and Excretion of CTLA4 Ig and CTLA4 Ig/PD-L1 Ligand by Primary T Cells In this experiment, in T cells co-transduced with LV vectors encoding PD-L1 and CTLA4Ig as described before. FIG. 17 shows the level of CTLA4 Ig secreted in the supernatant by T cell transduced with LV vector encoding CTLA4Ig alone (mean=250 pg/µl) or in T cells co transduced with LV vectors encoding PD-L1 and CTLA4Ig (mean=270 pg/µl) whereas no expression could be detected in PD-L1-transduced T cells. The results showed that PD-L1 is expressed in T cell transduced with LV vector encoding PD-L1 alone (>70% of cells express PD-L1, FIG. 17) or in T cells co transduced with LV vectors encoding PD-L1 and CTLA4Ig (59%) whereas no expression could be detected in untransduced T cells or CTLA4Ig-transduced T cells.

Example 4: Mixed Reaction Assay (MLR) to Test Allogeneic T Cells Response

Rationale and Protocol of the Experiment

In order to test whether overexpression of PD-L1 and/or CTLA4Ig by CAR T cells would have an impact on the host immune system, it was set up an in vitro assay in which naïve PBMCs from donor 1 are co-cultured with T cell from an HLA-mismatched donor 2. Briefly, PBMCs (donor 1) are labeled with CFSE and mixed with unlabeled, mitomycin-treated or irradiated engineered T cells (donor 2) meaning that they cannot proliferate. After a period of 6 days, flow cytometry analysis is performed with the following gating strategy: FSC/SSC→viable cells→CD3+ (T cells from donor 1 PBMCs)→CFSE. Decrease of CFSE staining is indicative of cell division and thus of allogeneic response of donor 1's T cells due to the presence of HLA mismatched donor 2's T cells.

A series of experiments has been set as follows from left to right in FIG. 18:
  (a) PBMCs from donor 1 without any treatment have been cultured alone,
  (b) PBMCs from donor 1, which have been submitted to a treatment with increasing concentration of PHA (PhytoHemAgglutinin), a T cell mitogen are cultured alone;
  (c) PBMCs from donor 1 are co-cultured with untransduced T cells from donor 2
  (d) PBMCs from donor 1 are co-cultured with PD-L1 transduced T cells from donor 2;
  (e) PBMCs from donor 1 are co-cultured with CTLA4Ig transduced T cells from donor 2;
  (f) PBMCs from donor 1 are co-cultured with PD-L1 and CTLA4Ig co-transduced T cells from donor 2.

Results

From FIG. 18, it appears that CD3+ T cells do not proliferate when not co-cultured (a) or in the presence au autologous T cells (c). As a control (b), PBMCs from donor 1, as expected CFSE positive population is decreasing as PHA concentration increases. CD3+ T cells do proliferate (disappearance of CFSE positive population) in the presence of allogeneic T cells (c). When allogeneic T cells are engineered to express PD-L1 (d), CTLA4Ig (e) or both (f), it is observed that responder T cells keep a bright CFSE staining, leading to the conclusion that the expression PD-L1 and/or CTLA4Ig by engineered T cells inhibit the responder proliferation. Thus, the results obtained in FIG. 18 show that engineered T cells expressing PD-L1, CTLA4Ig or both are less prone to stimulate allogeneic T cells response in an in vitro mixed lymphocytes reaction (MLR) assay. Moreover, the results show a cumulative effect when both PD-L1, CTLA4Ig are expressed.

Example 5: Cytotoxicity Assay Testing Anti-CD123 CAR T Cells Expressing PD-L1 and/or CTLA4Ig for their Capacity to Kill MOLM13 Target Cells This experiment is aimed to test T cells expressing PD-L1 and/or CTLA4Ig for their capacity to kill specific target cells through the expression of a CAR molecule.

T cells that have transduced with PD-L1 LV, CTLA4IG or both, have been transfected with 20 µg of mRNA encoding anti-CD123 CAR (SEQ ID NO.69) After a period of 2 days, the cytotoxic assay is performed using MOLM13 cell line as specific target cells.

Results from cytotoxicity assays, FIG. 19 and FIG. 20 show that engineered T cells expressing PD-L1, CTLA4Ig or both, and further engineered to express a CD123 CAR molecule, sustain their capacity to kill specific target. Furthermore, these data suggest that expression of PD-L1, CTLA4Ig or both, increase their intrinsic cytolytic activity.

Example 6: In Vivo Experiments

The aim of these experiments is to verify that modified T cells are still able to eradicate cognate tumor cells in vivo. Thus, an in vivo experiment has been conducted to investigate whether the expression of PD-L1, CTLA4Ig or both impact the CAR T cells anti-tumor activity. The protocol outline is shown in FIG. 21.

Activated T cells were obtained for the following groups of treatment:
Non-transduced T cells;
T cells transduced with CD123 CAR lentivirus (LV);
T cells transduced with CD123 CAR LV and PD-L1 LV;
T cells transduced with CD123 CAR LV, CTLA4Ig LV;
T cells transduced with CD123 CAR LV, PD-L1 LV and CTLA4Ig LV.

After 2 days of transduction, T cells were amplified in G-Rex for in vivo experiments. After 19 days cells were recovered and counted.

FIG. 22 shows that engineered T cells expressing PD-L1, CTLA4Ig or both, and further engineered to express a CD123 CAR molecule sustain similar proliferative capacity as compared to CAR CD123 engineered T cells.

T cells thus obtained were injected in NOG mice for in vivo experiment.

Anti-Tumor Mouse Model

Immunodeficient NOG mice were intravenously (iv) injected with (CD123 expressing_MOLM13-Luciferase cells as an AML xenograft mouse model. Mice were then iv injected (either 2 or 7 days after injection of the tumor cell line) with different doses of CD123 CAR+ T-cells to be tested, or with T-cells that were not transduced with the CD123 CAR lentiviral vector. Bioluminescent signals were determined at the day of T-cell injection (D0), at D7 and D14 after T-cell injection in order to follow tumoral progression on the different animals.

Bioluminescence analysis results from FIG. 23A and FIG. 23B indicate that all groups of mice injected with engineered CAR T cells eradicate efficiently the tumor as compared to control group, and a clear anti-tumor activity of engineered CAR T cells in vivo.

Example 7 Efficient B2M Gene Knock Out Using Specific B2M TALEN

Specific TALEN targeting a sequence (SEQ ID NO 1) within the first coding exon of the B2M gene (GenBank accession number NC_000015) has been produced (Left DNA binding domain RVDs: NN-NN-HD-HD-NG-NG-NI-NN-HD-NG-NN-NG-NN-HD-NG-NG with SEQ ID NO: 2, and Right DNA binding domain RVDs: NI-NN-HD-HD-NG-HD-HD-NI-NN-NN-HD-HD-NI-NN-NI-NG with SEQ ID NO: 3).

To test the ability of this B2M specific TALEN to promote error-prone NHEJ events at the B2M locus, 2 or 10 µg of mRNA encoding TALEN were electroporated in Primary T cells using Pulse Agile technology according to the manufacturer protocol. Three days post transfection, cells were recovered and labeled with a specific β2-microglobulin antibody coupled to the PhycoErythrin fluorochrome. Cells are then analyzed by flow cytometry for viability and β2-m expression. The results are shown on FIG. 16. On the top panel, nearly 100% of untransfected T cells express β2-m (top right panel). Transfection of T cells with the specific B2M TALEN reduces dramatically β2-m expression since 38% (middle right) and 80% of T cells (bottom right panel) become beta2-m negative when transfected with 2 µg or 10 µg of TALEN mRNA respectively. These data indicates that B2M knock-out in T cells can be achieved with high efficacy.

Example 8: Production and Expression of the Single Chain Molecule B2M-UL18 in T Cells HCMV UL18 encodes a type I transmembrane glycoprotein that shares a high level of AA sequence identity with MHC Class I molecules that associates with beta2-m and binds endogenous peptides. Since our goal is to express this molecule in T cells where B2M gene has been invalidated, our strategy is to produce a chimeric molecule where beta2-m and UL18 is fused as a single chain polypeptide. SEQ ID NO 39 shows the amino-acid sequence of the chimeric protein. Lentiviral particles containing the chimeric B2M-UL18 are transduced into T cells. Expression of transgene is monitored by FACS analysis using a beta2-m antibody. The results from this experiment aim to show that a B2M-UL18 chimeric protein is efficiently expressed in T cells.

Example 9: Production and Expression of NKG2D Ligands in T Cells

NKG2D natural ligands are transmembrane or GPI-anchored proteins. In order to achieve secretion of these molecules by T cells, the extra-cellular domains of NKG2D ligands have been fused in their N-terminus to a secretory peptide form. Amino-acid sequences of secreted chimeric NKG2D ligands are listed below (SEQ ID NO:40 to SEQ ID NO:47). Lentiviral particles containing the chimeric NKG2D ligands are transduced into T cells. Expression of transgene in culture supernatant is monitored by Western Blot analysis using specific antibodies. The results from this experiment aim to show that chimeric NKG2D ligand proteins are efficiently expressed in T cells.

Example 10: Beta2-M Deficient CAR T Cells are not Recognized by Allogenic T Cells PBMCs from healthy donor A is co-cultured with irradiated or mitomycin-treated engineered beta2-m deficient T cells from donor B. As a control, PBMCs from healthy donor A is co-cultured with irradiated or mitomycin-treated engineered beta2-m positive T cells from donor B. 7 days later, cells proliferation from donor A is measured by XTT colorimetric assay or by CFSE dilution (FACS analysis). Although cell proliferation is observed in control, no or limited cell proliferation is observed when engineered T cells do not express beta2-m. The results from this experiment aim to show that alloreactive T cells are not able to recognize and proliferate against beta2-m deficient T cells.

Example 11: Efficient Inhibition of NK Mediated Engineered T Cells Lysis

NK cells are purified from healthy donor A PBMCs. As targets, engineered T cells from healthy donor B are produced and listed below. a) engineered T cells (negative control), b) beta2-m deficient engineered T cells (positive control), c) beta2-m deficient engineered T cells expressing B2M-UL18 (SEQ ID NO 39), d-k) beta2-m deficient engineered T cells expressing respectively SP-MICAed (SEQ ID No. 40), SP-MICBed (SEQ ID No 41), SP-ULBP1ed (SEQ ID NO 42), SP-ULBP2ed (SEQ ID NO 43), SP-ULBP3ed (SEQ ID NO 44), SP-N2DL4ed (SEQ ID NO 45), SP-RET1Ged (SEQ ID NO 46), SP-RAETILed (SEQ ID No 47). Cytotoxicity mediated by NK cells was determined by a CFSE labeling assay. Target cells were labeled with CFSE, washed in PBS, mixed with NK cells at various E:T cell ratios and incubated for 4 h at 37° C. Cells are then analysed by flow cytometry and percentages of CFSE positive engineered T cells are measured, indicating the survival of engineered T cells in the presence of NK cells. It is intended that although NK mediated cell lysis is observed in the positive control (beta2-m deficient engineered T cells), no or limited NK mediated cell lysis is observed when beta2-m deficient engineered T cells engineered T cells express B2M-UL18 (SEQ ID NO 39) or secreted NKG2D ligands (SP-MICAed (SEQ ID NO 40), SP-MICBed (SEQ ID NO 41), SP-ULBP1ed (SEQ ID NO 42), SP-ULBP2ed (SEQ ID No. 43), SP-ULBP3ed (SEQ ID NO 44), SP-N2DL4ed (SEQ ID NO 45), SP-RET1Ged (SEQ ID NO 46), SP-RAETILed (SEQ ID NO 47)). The results from this experiment aim to show that allogenic NK cells cytotoxicity activity is impaired when chimeric molecules, express in engineered T cells, act as decoy either for inhibitory signal receptor (B2M-UL18) or for stimulatory signal receptor (NKG2D ligands).

Example 12: Expression of ISU in Engineered T Cells

Lentiviral particles bearing either the envelope protein from Moloney Murine Leukemia Virus (MMLV) (SEQ ID NO 78), a transmembrane truncated form of the envelope protein from MMLV (SEQ ID No. 79) or secreted 14-mer ISU peptides (6 variants from HIV-1 virus SEQ ID NO 19 to 24; 6 variants from HIV-2 virus SEQ ID NO 25 to 30; from SIV, MoMuLV, HTLV-1, MPMV, Syncitin 1, Syncitin 2, HERV-K and FELV virus with respectively SEQ ID NO 32, 33, 34, 35, 36, 37, and 38) are transduced into T cells. Expression of membrane bound transgene is monitored by FACS analysis whereas expression of secreted ISU peptide is monitored in cell culture supernatant by western blot. The results from this experiment aim to show that both forms of ISU are efficiently expressed in T cells.

Example 13: Expression of FP Peptides in Engineered T Cells

Lentiviral particles bearing secreted 9-mer FP polypeptides (1 from HIV-1 virus and 2 from artificial sequence with respective SEQ ID NO 48 and 49-50) are transduced into T cells. Expression of secreted FP peptides is monitored in cell culture supernatant by western blot. The results from this experiment aim to show that secreted FP peptides are efficiently expressed in T cells.

Example 14: Efficient Inhibition of T Cells Proliferation Towards Engineered T Cells Expressing ISU PBMCs from healthy donor A is co-cultured with irradiated or mitomycin-treated engineered T cells from donor B, expressing ISU. As a control, PBMCs from healthy donor A is co-cultured with irradiated or mitomycin-treated engineered T cells from donor B that do not express ISU. 7 days later, cells proliferation from donor A is measured by XTT colorimetric assay or by CFSE dilution (FACS analysis). Although cell proliferation is observed in control, no or limited cell proliferation is observed when engineered T cells express membrane bound or secreted ISU. The results from this experiment aim to show that alloreactive T cells proliferation is inhibited when engineered T cells express ISU.

Example 15: Efficient Inhibition of T Cells Proliferation Towards Engineered T Cells Expressing FP PBMCs from healthy donor A is co-cultured with irradiated or mitomycin-treated engineered T cells from donor B, expressing FP. As a control, PBMCs from healthy donor A is co-cultured with irradiated or mitomycin-treated engineered T cells from donor B that do not express FP. 7 days later, cells proliferation from donor A is measured by XTT colorimetric assay or by CFSE dilution (FACS analysis). Although cell proliferation is observed in control, no or limited cell proliferation is observed when engineered T cells express secreted FP. The results from this experiment aim to show that alloreactive T cells proliferation is inhibited when engineered T cells express FP.

LIST OF REFERENCES CITED IN THE DESCRIPTION

Arimondo, P. B., C. J. Thomas, et al. (2006). "Exploring the cellular activity of camptothecin-triple-helix-forming oligonucleotide conjugates." Mol Cell Biol 26(1): 324-33.
Arnould, S., P. Chames, et al. (2006). "Engineering of large numbers of highly specific homing endonucleases that induce recombination on novel DNA targets." J Mol Biol 355(3): 443-58.
Ashwell, J. D. and R. D. Klusner (1990). "Genetic and mutational analysis of the T-cell antigen receptor." Annu Rev Immunol 8: 139-67.
Boch, J., H. Scholze, et al. (2009). "Breaking the code of DNA binding specificity of TAL-type III effectors." Science 326(5959): 1509-12.
Boni, A., P. Muranski, et al. (2008). "Adoptive transfer of allogeneic tumor-specific T cells mediates effective regression of large tumors across major histocompatibility barriers." Blood 112(12): 4746-54.
Brahmer, J. R., C. G. Drake, et al. (2010). "Phase I study of single-agent anti-programmed death-1 (MDX-1106) in refractory solid tumors: safety, clinical activity, pharmacodynamics, and immunologic correlates." J Clin Oncol 28(19): 3167-75.
Cermak, T., E. L. Doyle, et al. (2011). "Efficient design and assembly of custom TALEN and other TAL effector-based constructs for DNA targeting." Nucleic Acids Res 39(12): e82.
Choulika, A., A. Perrin, et al. (1995). "Induction of homologous recombination in mammalian chromosomes by using the I-Scel system of *Saccharomyces cerevisiae*." Mol Cell Biol 15(4): 1968-73.
Christian, M., T. Cermak, et al. (2010). "Targeting DNA double-strand breaks with TAL effector nucleases." Genetics 186(2): 757-61.
Coutinho, A. E. and K. E. Chapman (2011). "The anti-inflammatory and immunosuppressive effects of glucocorticoids, recent developments and mechanistic insights." Mol Cell Endocrinol 335(1): 2-13.

Critchlow, S. E. and S. P. Jackson (1998). "DNA end-joining: from yeast to man." Trends Biochem Sci 23(10): 394-8.

Deng, D., C. Yan, et al. (2012). "Structural basis for sequence-specific recognition of DNA by TAL effectors." Science 335(6069): 720-3.

Eisenschmidt, K., T. Lanio, et al. (2005). "Developing a programmed restriction endonuclease for highly specific DNA cleavage." Nucleic Acids Res 33(22): 7039-47.

EGeissler, R., H. Scholze, et al. (2011). "Transcriptional activators of human genes with programmable DNA-specificity." PLoS One 6(5): e19509.

Huang, P., A. Xiao, et al. (2011). "Heritable gene targeting in zebrafish using customized TALENs." Nat Biotechnol 29(8): 699-700.

Jena, B., G. Dotti, et al. (2010). "Redirecting T-cell specificity by introducing a tumor-specific chimeric antigen receptor." Blood 116(7): 1035-44.

Kalish, J. M. and P. M. Glazer (2005). "Targeted genome modification via triple helix formation." Ann N Y Acad Sci 1058: 151-61.

Li, L., M. J. Piatek, et al. (2012). "Rapid and highly efficient construction of TALE-based transcriptional regulators and nucleases for genome modification." Plant Mol Biol 78(4-5): 407-16.

Li, T., S. Huang, et al. (2011). "TAL nucleases (TALNs): hybrid proteins composed of TAL effectors and FokI DNA-cleavage domain." Nucleic Acids Res 39(1): 359-72.

Li, T., S. Huang, et al. (2011). "Modularly assembled designer TAL effector nucleases for targeted gene knock-out and gene replacement in eukaryotes." Nucleic Acids Res 39(14): 6315-25.

Ma, J. L., E. M. Kim, et al. (2003). "Yeast Mre11 and Rad1 proteins define a Ku-independent mechanism to repair double-strand breaks lacking overlapping end sequences." Mol Cell Biol 23(23): 8820-8.

Mahfouz, M. M., L. Li, et al. (2012). "Targeted transcriptional repression using a chimeric TALE-SRDX repressor protein." Plant Mol Biol 78(3): 311-21.

Mahfouz, M. M., L. Li, et al. (2011). "De novo-engineered transcription activator-like effector (TALE) hybrid nuclease with novel DNA binding specificity creates double-strand breaks." Proc Natl Acad Sci USA 108(6): 2623-8.

Mak, A. N., P. Bradley, et al. (2012). "The crystal structure of TAL effector PthXo1 bound to its DNA target." Science 335(6069): 716-9.

Miller, J. C., S. Tan, et al. (2011). "A TALE nuclease architecture for efficient genome editing." Nat Biotechnol 29(2): 143-8.

Morbitzer, R., P. Romer, et al. (2011). "Regulation of selected genome loci using de novo-engineered transcription activator-like effector (TALE)-type transcription factors." Proc Natl Acad Sci USA 107(50): 21617-22.

Moscou, M. J. and A. J. Bogdanove (2009). "A simple cipher governs DNA recognition by TAL effectors." Science 326(5959): 1501.

Mussolino, C., R. Morbitzer, et al. (2011). "A novel TALE nuclease scaffold enables high genome editing activity in combination with low toxicity." Nucleic Acids Res 39(21): 9283-93.

Paques, F. and P. Duchateau (2007). "Meganucleases and DNA double-strand break-induced recombination: perspectives for gene therapy." Curr Gene Ther 7(1): 49-66.

Pardoll, D. and C. Drake (2012). "Immunotherapy earns its spot in the ranks of cancer therapy." J Exp Med 209(2): 201-9.

Pardoll, D. M. (2012). "The blockade of immune checkpoints in cancer immunotherapy." Nat Rev Cancer 12(4): 252-64.

Park, T. S., S. A. Rosenberg, et al. (2011). "Treating cancer with genetically engineered T cells." Trends Biotechnol 29(11): 550-7.

Pegram H J, Lee J C, Hayman E G, Imperato G H, Tedder T F, Sadelain M, Brentjens R J. (2012). "Tumor-targeted T cells modified to secrete IL-12 eradicate systemic tumors without need for prior conditioning". Blood 119 (18):4133-41)

Pingoud, A. and G. H. Silva (2007). "Precision genome surgery." Nat Biotechnol 25(7): 743-4.

Porteus, M. H. and D. Carroll (2005). "Gene targeting using zinc finger nucleases." Nat Biotechnol 23(8): 967-73.

Robert, C. and C. Mateus (2011). "[Anti-CTLA-4 monoclonal antibody: a major step in the treatment of metastatic melanoma]." Med Sci (Paris) 27(10): 850-8.

Rong Z, Wang M, Hu Z, Stradner M, Zhu S, Kong H, Yi H, Goldrath A, Yang Y G, Xu Y and Fu X. (2014). "An Effective Approach to Prevent Immune Rejection of Human ESC-Derived Allografts." Cell Stem Cell. 14(1): 121-30.

Rouet, P., F. Smih, et al. (1994). "Introduction of double-strand breaks into the genome of mouse cells by expression of a rare-cutting endonuclease." *Mol Cell Biol* 14(12): 8096-106.

Sander, J. D., L. Cade, et al. (2011). "Targeted gene disruption in somatic zebrafish cells using engineered TAL-ENs." *Nat Biotechnol* 29(8): 697-8.

Stoddard, B. L. (2005). "Homing endonuclease structure and function." *Q Rev Biophys* 38(1): 49-95.

Tesson, L., C. Usal, et al. (2011). "Knockout rats generated by embryo microinjection of TALENs." *Nat Biotechnol* 29(8): 695-6.

Waldmann, H. and G. Hale (2005). "CAMPATH: from concept to clinic." *Philos Trans R Soc Lond B Biol Sci* 360(1461): 1707-11.

Weber, E., R. Gruetzner, et al. (2011). "Assembly of designer TAL effectors by Golden Gate cloning." *PLoS One* 6(5): e19722.

Zhang, F., L. Cong, et al. (2011). "Efficient construction of sequence-specific TAL effectors for modulating mammalian transcription." *Nat Biotechnol* 29(2): 149-53.

The invention claimed is:

1. An isolated engineered primary T cell not having the PD-1 gene inactivated, wherein the T cell contains an exogenous nucleic acid molecule expressing PD-L1 under a membrane-bound form that has at least 85% amino acid identity with SEQ ID NO: 18 and an exogenous nucleic acid molecule expressing a CTLA-4 immunoglobulin that has at least 85% amino acid identity with SEQ ID NO: 16 or SEQ ID NO: 17.

2. The isolated engineered primary T cell of claim 1, wherein the PD-L1 under the membrane-bound form has at least 90% amino acid identity with SEQ ID NO: 18 and the CTLA-4 immunoglobulin has at least 90% amino acid identity with SEQ ID NO: 16.

3. The isolated engineered primary T cell of claim 1, wherein the PD-L1 under the membrane-bound form has at least 90% amino acid identity with SEQ ID NO: 18 and the CTLA-4 immunoglobulin has at least 90% amino acid identity with SEQ ID NO: 17.

4. The isolated engineered primary T cell of claim 1, wherein the PD-L1 under the membrane-bound form has at least 95% amino acid identity with SEQ ID NO: 18 and the CTLA-4 immunoglobulin has at least 95% amino acid identity with SEQ ID NO: 16.

5. The isolated engineered primary T cell of claim 1, wherein the PD-L'1 under the membrane-bound form has at least 95% amino acid identity with SEQ ID NO: 18 and the CTLA-4 immunoglobulin has at least 95% amino acid identity with SEQ ID NO: 17.

6. The isolated engineered primary T cell of claim 1, wherein the PD-L1 under the membrane-bound form comprises the amino acid sequence of SEQ ID NO: 18 and the CTLA-4 immunoglobulin comprises the amino acid sequence of SEQ ID NO: 16.

7. The isolated engineered primary T cell of claim 1, wherein the PD-L1 under the membrane-bound form comprises the amino acid sequence of SEQ ID NO: 18 and the CTLA-4 immunoglobulin comprises the amino acid sequence of SEQ ID NO: 17.

8. The isolated engineered primary T cell of claim 1, wherein B2M is inactivated.

9. The isolated engineered primary T cell of claim 1, wherein B2M is inactivated with a TALEN targeting SEQ ID NO:1 within the first coding exon of the B2M gene.

10. The isolated engineered primary T cell of claim 9, wherein the TALEN comprises SEQ ID NO: 2 and SEQ ID NO: 3.

11. The isolated engineered primary T cell of claim 8, further expressing a B2M-UL18 chimeric protein.

12. The isolated engineered primary T cell of claim 11, wherein the B2M-UL18 chimeric protein comprises the amino acid sequence of SEQ ID NO:39.

13. The isolated engineered primary T cell of claim 8, further expressing an NKG2D ligand.

14. The isolated engineered primary T cell of claim 13, wherein the NKG2D ligand comprises an amino acid sequence selected from the group consisting of the amino acid sequences of SEQ ID NO:40-47.

15. The isolated engineered primary T cell of claim 1, wherein TCR is inactivated.

16. The isolated engineered primary T cell of claim 8, wherein TCR is inactivated.

17. The isolated engineered primary T cell of claim 1, wherein the isolated engineered primary T cell expresses a Chimeric Antigen Receptor (CAR).

18. The isolated engineered primary T cell of claim 8, wherein the isolated engineered primary T cell expresses a Chimeric Antigen Receptor (CAR).

19. A composition comprising the isolated engineered primary T cell of claim 1 and an anti-CD80 or anti-CD86 monoclonal antibody.

20. An isolated engineered primary T cell not having the PD-1 gene inactivated, wherein the isolated engineered primary T cell contains an exogenous nucleic acid molecule expressing PD-L1 under a membrane-bound form that has at least 95% amino acid identity with SEQ ID NO: 18, and wherein the isolated engineered primary T cell expresses a Chimeric Antigen Receptor (CAR).

21. The isolated engineered primary T cell of claim 1, wherein the isolated engineered primary T cell does not have the CTLA-4 gene inactivated.

22. The isolated engineered primary T cell of claim 20, wherein the isolated engineered primary T cell does not have the CTLA-4 gene inactivated.

* * * * *

SEQUENCE LISTING

<160> NUMBER OF SEQ ID NOS: 79

<210> SEQ ID NO 1
<211> LENGTH: 58
<212> TYPE: DNA
<213> ORGANISM: homo sapiens
<220> FEATURE:
<223> OTHER INFORMATION: B2M TALEN T01targeting sequence

<400> SEQUENCE: 1

```
tctcgctccg tggccttagc tgtgctcgcg ctactctctc tttctggcct ggaggcta      58
```

<210> SEQ ID NO 2
<211> LENGTH: 2814
<212> TYPE: DNA
<213> ORGANISM: artificial sequence
<220> FEATURE:
<223> OTHER INFORMATION: Beta2M T01- TALEN - LEFT

<400> SEQUENCE: 2

```
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa cacccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480 ttgaccccccc agcaggtggt ggccatcgcc agcaataatg gtggcaagca ggcgctggag     540
acggtccagc ggctgttgcc ggtgctgtgc caggcccacg gcttgacccc ccagcaggtg     600
gtggccatcg ccagcaataa tggtggcaag caggcgctgg agacggtcca gcggctgttg     660
ccggtgctgt gccaggccca cggcttgacc ccggagcagg tggtggccat cgccagccac     720
gatggcggca agcaggcgct ggagacggtc agcggctgt tgccggtgct gtgccaggcc     780
cacggcttga ccccggagca ggtggtggcc atcgccagcc acgatggcgg caagcaggcg     840
ctggagacgg tccagcggct gttgccggtg ctgtgccagg cccacggctt gacccccag     900 caggtggtgg ccatcgccag caatggcggt ggcaagcagg cgctggagac ggtccagcgg     960
ctgttgccgg tgctgtgcca ggcccacggc ttgaccccccc agcaggtggt ggccatcgcc    1020
agcaatggcg gtggcaagca ggcgctggag acggtccagc ggctgttgcc ggtgctgtgc    1080
caggcccacg gcttgacccc ggagcaggtg gtggccatcg ccagcaatat ggtggcaag    1140 caggcgctgg agacggtgca ggcgctgttt ccggtgctgt gccaggccca cggcttgacc    1200
ccccagcagg tggtggccat cgccagcaat aatggtggca agcaggcgct ggagacggtc    1260
cagcggctgt tgccggtgct gtgccaggcc cacggcttga ccccggagca ggtggtggcc    1320
atcgccagcc acgatggcgg caagcaggcg ctggagacgg tccagcggct gttgccggtg    1380
ctgtgccagg cccacggctt gacccccccag caggtggtgg ccatcgccag caatggcggt    1440
ggcaagcagg cgctggagac ggtccagcgg ctgttgccgg tgctgtgcca ggcccacggc    1500 ttgaccccccc agcaggtggt ggccatcgcc agcaataatg gtggcaagca ggcgctggag    1560
acggtccagc ggctgttgcc ggtgctgtgc caggcccacg gcttgacccc ccagcaggtg    1620
gtggccatcg ccagcaatgg cgtggcaag caggcgctgg agacggtcca gcggctgttg    1680
ccggtgctgt gccaggccca cggcttgacc ccccagcagg tggtggccat cgccagcaat    1740
aatggtggca agcaggcgct ggagacggtc agcggctgt tgccggtgct gtgccaggcc    1800
cacggcttga ccccggagca ggtggtggcc atcgccagcc acgatggcgg caagcaggcg    1860
ctggagacgg tccagcggct gttgccggtg ctgtgccagg cccacggctt gacccccag    1920
```

```
caggtggtgg ccatcgccag caatggcggt ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg gctcccccca tcgactacgg cgtgatcgtg    2460
gacaccaagg cctactccgg cggctacaac ctgcccatcg gccaggccga cgaaatgcag    2520
aggtacgtgg aggagaacca gaccaggaac aagcacatca accccaacga gtggtggaag    2580
gtgtacccct ccagcgtgac cgagttcaag ttcctgttcg tgtccggcca cttcaagggc    2640
aactacaagc ccagctgacc aggctgaacc acatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814
```

<210> SEQ ID NO 3
<211> LENGTH: 2832
<212> TYPE: DNA
<213> ORGANISM: artificial sequence
<220> FEATURE:
<223> OTHER INFORMATION: Beta2M T01 TALEN -RIGHT

<400> SEQUENCE: 3

```
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccc tcgctgtcaa gtatcaggac atgatcgcag cgttgccaga ggcgacacac     300
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gaccccggag caggtggtgg ccatcgccag caatattggt     540
ggcaagcagg cgctggagac ggtgcaggcg ctgttgccgg tgctgtgcca ggcccacggc     600
ttgaccccca gcaggtggt ggccatcgcc agcaataatg gtggcaagca ggcgctggag     660
acggtccagc ggctgttgcc ggtgctgtgc caggcccacg gcttgacccc ggagcaggtg     720
gtggccatcg ccagccacga tggcggcaag caggcgctgg agacggtcca gcggctgttg     780
ccggtgctgt gccaggccca cggcttgacc ccggagcagg tggtggccat cgccagccac     840
gatggcggca gcaggcgct ggagacggtc agcggctgt tgccggtgct gtgccaggcc     900
cacggcttga ccccccagca ggtggtggcc atcgccagca atggcggtgg caagcaggcg     960
ctggagacgg tccagcggct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgacccccg gagcaggtgg tggccatcgcc   1140 agccacgatg gcggcaagca ggcgctggag acggtccagc ggctgttgcc ggtgctgtgc    1200
```

```
caggcccacg gcttgacccc ggagcaggtg gtggccatcg ccagcaatat tggtggcaag    1260
caggcgctgg agacggtgca ggcgctgttg ccggtgctgt gccaggccca cggcttgacc    1320
ccccagcagg tggtggccat cgccagcaat aatggtggca agcaggcgct ggagacggtc    1380
cagcggctgt tgccggtgct gtgccaggcc cacggcttga ccccccagca ggtggtggcc    1440
atcgccagca ataatggtgg caagcaggcg ctggagacgg tccagcggct gttgccggtg    1500
ctgtgccagg cccacggctt gaccccggag caggtggtgg ccatcgccag ccacgatggc    1560
ggcaagcagg cgctggagac ggtccagcgg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccccagcagg tggtggccat cgccagcaat    1860
aatggtggca agcaggcgct ggagacggtc agcggctgt tgccggtgct gtgccaggcc    1920
cacggcttga ccccggagca ggtggtggcc atcgccagca atattggtgg caagcaggcg    1980
ctggagacgg tgcaggcgct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag    2280 ctgaagtacg tgccccacga gtacatcgag ctgatcgaga tcgcccggaa cagcacccag    2340
gaccgtatcc tggagatgaa ggtgatgag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg    2640
tccggccact tcaagggcaa ctacaaggcc agctgacca ggctgaacca catcaccaac    2700
tgcaacggcg ccgtgctgtc cgtggaggag ctcctgatcg gcggcgagat gatcaaggcc    2760 ggcacctga cctggagga ggtgaggagg aagttcaaca acggcgagat caacttcgcg    2820
gccgactgat aa                                                       2832
```

<210> SEQ ID NO 4  
<211> LENGTH: 50  
<212> TYPE: DNA  
<213> ORGANISM: artificial sequence  
<220> FEATURE:  
<223> OTHER INFORMATION: B2M T02- TALEN targeting sequence

<400> SEQUENCE: 4

```
tccaaagatt caggtttact cacgtcatcc agcagagaat ggaaagtcaa                   50
```

<210> SEQ ID NO 5  
<211> LENGTH: 2814  
<212> TYPE: DNA  
<213> ORGANISM: artificial sequence  
<220> FEATURE:  
<223> OTHER INFORMATION: Beta2M T02-TALEN - LEFT

<400> SEQUENCE: 5

```
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa caccccggcag cgttagggac cgtcgctgtc    240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480
ttgaccccgg agcaggtggt ggccatcgcc agccacgatg gcggcaagca ggcgctggag     540
acggtccagc ggctgttgcc ggtgctgtgc caggcccacg gcttgacccc ggagcaggtg     600
gtggccatcg ccagccacga tggcggcaag caggcgctgg acggtccag cggctgttg      660 ccggtgctgt gccaggccca cggcttgacc ccggagcagg tggtggccat cgccagcaat    720
attggtggca agcaggcgct ggagacggtg caggcgctgt tgccggtgct gtgccaggcc    780
cacggcttga ccccggagca ggtggtggcc atcgccagca atattggtgg caagcaggcg    840
ctggagacgt gcaggcgct gttgccggtg ctgtgccagg cccacggctt gaccccggag     900
caggtggtgg ccatcgccag caatattggt ggcaagcagg cgctggagac ggtgcaggcg    960
ctgttgccgg tgctgtgcca ggcccacggc ttgaccccc agcaggtggt ggccatcgcc    1020
agcaataatg gtggcaagca ggcgctggag acggtccagc ggctgttgcc ggtgctgtgc   1080
caggcccacg gcttgacccc ggagcaggtg gtggccatcg ccagcaatat tggtggcaag   1140
caggcgctgg agacggtgca ggcgctgttg ccggtgctgt gccaggccca cggcttgacc   1200
ccccagcagg tggtggccat cgccagcaat ggcggtggca agcaggcgct ggagacggtc   1260
cagcggctgt tgccggtgct gtgccaggcc cacggcttga ccccccagca ggtggtggcc   1320
atcgccagca atggcggtgg caagcaggcg ctggagacgg tccagcggct gttgccggtg   1380
ctgtgccagg cccacggctt gaccccggag caggtggtgg ccatcgccag ccacgatggc   1440
ggcaagcagg cgctggagac ggtccagcgg ctgttgccgg tgctgtgcca ggcccacggc   1500
ttgaccccgg agcaggtggt ggccatcgcc agcaatattg gtggcaagca ggcgctggag   1560
acggtgcagg cgctgttgcc ggtgctgtgc caggcccacg gcttgacccc ccagcaggtg   1620
gtggccatcg ccagcaataa tggtggcaag caggcgctgg agacggtcca gcggctgttg   1680
ccggtgctgt gccaggccca cggcttgacc ccccagcagg tggtggccat cgccagcaat   1740
aatggtggca agcaggcgct ggagacggtc agcggctgt tgccggtgct gtgccaggcc    1800
cacggcttga ccccccagca ggtggtggcc atcgccagca atggcggtgg caagcaggcg   1860
ctggagacgg tccagcggct gttgccggtg ctgtgccagg cccacggctt gacccccag    1920 caggtggtgg ccatcgccag caatggcggt ggcaagcagg cgctggagac ggtccagcgg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg ggggatccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
```

-continued

```
aggaagcccg acggcgccat ctacaccgtg ggctccccca tcgactacgg cgtgatcgtg    2460
gacaccaagg cctactccgg cggctacaac ctgcccatcg ccaggccga cgaaatgcag    2520 aggtacgtgg aggagaacca gaccaggaac aagcacatca accccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814
```

<210> SEQ ID NO 6
<211> LENGTH: 2832
<212> TYPE: DNA
<213> ORGANISM: artificial sequence
<220> FEATURE:
<223> OTHER INFORMATION: Beta2M T02-TALEN RIGHT

<400> SEQUENCE: 6

```
atgggcgatc ctaaaaagaa acgtaaggtc atcgataagg agaccgccgc tgccaagttc      60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gacccccag caggtggtgg ccatcgccag caataatggt    540
ggcaagcagg cgctggagac ggtccagcg ctgttgccgg tgctgtgcca ggcccacggc    600
ttgacccggg agcaggtggt ggccatcgcc agcaatattg gtggcaagca ggcgctggag    660
acggtgcagg cgctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc cccagcagg tggtggccat cgccagcaat    840 ggcgtggca gcaggcgct ggagacggtc agcggctgt gccggtgct gtgccaggcc    900 cacggcttga ccccccagca ggtggtggcc atcgccagca atggcggtgg caagcaggcg    960
ctggagacgt ccagcggct gttgccgtg ctgtgccagg cccacggctt gaccccccag   1020
caggtggtgg ccatcgccag caatggcggt ggcaagcagg cgctggagac ggtccagcgg   1080
ctgttgccgg tgctgtgcca ggcccacggc ttgaccccgg agcaggtggt ggccatcgcc   1140
agccacgatg gcggcaagca ggcgctggag acggtccagc ggctgttgcc ggtgctgtgc   1200
caggcccacg gcttgacccc ggagcaggtg gtggccatcg ccagccacga tggcggcaag   1260
caggcgctgg agacggtcca gcggctgttg ccggtgctgt gccaggccca cggcttgacc   1320
ccggagcagg tggtggccat cgccagcaat attggtggca agcaggcgct ggagacggtg   1380
caggcgctgt tgccggtgct gtgccaggcc acggcttga ccccccagca ggtggtggcc   1440
atcgccagca atggcggtgg caagcaggcg ctggagacgg tccagcggct gttgccggtg   1500
ctgtgccagg cccacggctt gaccccccag caggtggtgg ccatcgccag caatggcggt   1560
ggcaagcagg cgctggagac ggtccagcgg ctgttgccgg tgctgtgcca ggcccacggc   1620
```

```
ttgaccccgg agcaggtggt ggccatcgcc agccacgatg gcggcaagca ggcgctggag    1680
acggtccagc ggctgttgcc ggtgctgtgc caggcccacg gcttgacccc ccagcaggtg    1740
gtggccatcg ccagcaatgg cggtggcaag caggcgctgg agacggtcca gcggctgttg    1800
ccggtgctgt gccaggccca cggcttgacc ccggagcagg tggtggccat cgccagccac    1860
gatggcggca gcaggcgct ggagacggtc agcggctgt tgccggtgct gtgccaggcc    1920
cacggcttga ccccccagca ggtggtggcc atcgccagca atggcggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg aggagaaga atccgagtt gaggcacaag    2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccccctcc agcgtgaccg agttcaagtt cctgttcgtg    2640
tccggccact tcaagggcaa ctacaaggcc cagctgacca ggctgaacca catcaccaac    2700
tgcaacggcg ccgtgctgtc cgtggaggag ctcctgatcg gcggcgagat gatcaaggcc    2760 ggcacccctga ccctggagga ggtgaggagg aagttcaaca acggcgagat caacttcgcg    2820
gccgactgat aa                                                        2832

<210> SEQ ID NO 7
<211> LENGTH: 47
<212> TYPE: DNA
<213> ORGANISM: artificial sequence
<220> FEATURE:
<223> OTHER INFORMATION: B2M T03- TALEN targeting sequence

<400> SEQUENCE: 7
ttagctgtgc tcgcgctact ctctctttct ggcctggagg ctatcca                   47

<210> SEQ ID NO 8
<211> LENGTH: 2814
<212> TYPE: DNA
<213> ORGANISM: artificial sequence
<220> FEATURE:
<223> OTHER INFORMATION: Beta2M T03-TALEN - LEFT

<400> SEQUENCE: 8
atgggcgatc ctaaaaagaa acgtaaggtc atcgattacc catacgatgt tccagattac     60
gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa cacccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca gattgcaaa acgtggcggc    420 gtgaccgcag tggaggcagt gcatgcatgg cgcaatgcac tgacgggtgc cccgctcaac    480
```

```
ttgaccccgg agcaggtggt ggccatcgcc agcaatattg gtggcaagca ggcgctggag      540
acggtgcagg cgctgttgcc ggtgctgtgc caggcccacg gcttgacccc ccagcaggtg      600
gtggccatcg ccagcaataa tggtggcaag caggcgctgg agacggtcca gcggctgttg      660
ccggtgctgt gccaggccca cggcttgacc ccggagcagg tggtggccat cgccagccac      720
gatggcggca agcaggcgct ggagacggtc agcggctgt tgccggtgct gtgccaggcc      780
cacggcttga ccccccagca ggtggtggcc atcgccagca atggcggtgg caagcaggcg      840
ctggagacgg tccagcggct gttgccggtg ctgtgccagg cccacggctt gacccccag      900 caggtggtgg ccatcgccag caataatggt ggcaagcagg cgctggagac ggtccagcgg      960
ctgttgccgg tgctgtgcca ggcccacggc ttgacccccc agcaggtggt ggccatcgcc     1020
agcaatggcg gtggcaagca ggcgctggag acggtccagc ggctgttgcc ggtgctgtgc     1080
caggcccacg gcttgacccc cagcaggtg gtggccatcg ccagcaataa tggtggcaag     1140
caggcgctgg agacggtcca gcggctgttg ccggtgctgt gccaggccca cggcttgacc     1200
ccggagcagg tggtggccat cgccagccac gatggcggca agcaggcgct ggagacggtc     1260
cagcggctgt tgccggtgct gtgccaggcc cacggcttga ccccccagca ggtggtggcc     1320
atcgccagca atggcggtgg caagcaggcg ctggagacgg tccagcggct gttgccggtg     1380
ctgtgccagg cccacggctt gaccccggag caggtggtgg ccatcgccag ccacgatggc     1440
ggcaagcagg cgctggagac ggtccagcgg ctgttgccgg tgctgtgcca ggcccacggc     1500 ttgaccccc agcaggtggt ggccatcgcc agcaataatg gtggcaagca ggcgctggag     1560
acggtccagc ggctgttgcc ggtgctgtgc caggcccacg gcttgacccc ggagcaggtg     1620
gtggccatcg ccagccacga tggcggcaag caggcgctgg agacggtcca gcggctgttg     1680
ccggtgctgt gccaggccca cggcttgacc cccagcagg tggtggccat cgccagcaat     1740
aatggtggca agcaggcgct ggagacggtc agcggctgt tgccggtgct gtgccaggcc     1800
cacggcttga ccccggagca ggtggtggcc atcgccagcc acgatggcgg caagcaggcg     1860
ctggagacgg tccagcggct gttgccggtg ctgtgccagg cccacggctt gacccccag     1920 caggtggtgg ccatcgccag caatggcggt ggcaagcagg cgctggagac ggtccagcgg     1980
ctgttgccgg tgctgtgcca ggcccacggc ttgacccctc agcaggtggt ggccatcgcc     2040
agcaatggcg gcggcaggcc ggcgctggag agcattgttg cccagttatc tcgccctgat     2100
ccggcgttgg ccgcgttgac caacgaccac ctcgtcgcct tggcctgcct cggcgggcgt     2160
cctgcgctgg atgcagtgaa aaagggattg ggggatccta tcagccgttc ccagctggtg     2220
aagtccgagc tggaggagaa gaaatccgag ttgaggcaca agctgaagta cgtgccccac     2280
gagtacatcg agctgatcga gatcgcccgg aacagcaccc aggaccgtat cctggagatg     2340
aaggtgatgg agttcttcat gaaggtgtac ggctacaggg gcaagcacct gggcggctcc     2400
aggaagcccg acgcgccat ctacaccgtg gcctcccca tcgactacgg cgtgatcgtg     2460
gacaccaagg cctactccgg cggctacaac ctgcccatcg ccaggccga cgaaatgcag     2520 aggtacgtgg aggagaacca gaccaggaac aagcacatca ccccaacga gtggtggaag     2580 gtgtacccct ccagcgtgac cgagttcaag ttcctgttcg tgtccggcca cttcaagggc     2640
aactacaagg cccagctgac caggctgaac cacatcacca actgcaacgg cgccgtgctg     2700
tccgtggagg agctcctgat cggcggcgag atgatcaagg ccggcacccct gaccctggag     2760 gaggtgagga ggaagttcaa caacggcgag atcaacttcg cggccgactg ataa            2814
```

<210> SEQ ID NO 9
<211> LENGTH: 2832
<212> TYPE: DNA
<213> ORGANISM: artificial sequence
<220> FEATURE:
<223> OTHER INFORMATION: Beta2M T03-TALEN -RIGHT

<400> SEQUENCE: 9

| | | | | | |
|---|---|---|---|---|---:|
| atgggcgatc | ctaaaaagaa | acgtaaggtc | atcgataagg | agaccgccgc | tgccaagttc | 60 |
| gagagacagc | acatggacag | catcgatatc | gccgatctac | gcacgctcgg | ctacagccag | 120 |
| cagcaacagg | agaagatcaa | accgaaggtt | cgttcgacag | tggcgcagca | ccacgaggca | 180 |
| ctggtcggcc | acgggtttac | acacgcgcac | atcgttgcgt | taagccaaca | cccggcagcg | 240 |
| ttagggaccg | tcgctgtcaa | gtatcaggac | atgatcgcag | cgttgccaga | ggcgacacac | 300 |
| gaagcgatcg | ttggcgtcgg | caaacagtgg | tccggcgcac | gcgctctgga | ggccttgctc | 360 |
| acggtggcgg | gagagttgag | aggtccaccg | ttacagttgg | acacaggcca | acttctcaag | 420 |
| attgcaaaac | gtggcggcgt | gaccgcagtg | gaggcagtgc | atgcatggcg | caatgcactg | 480 |
| acgggtgccc | cgctcaactt | gaccccccag | caggtggtgg | ccatcgccag | caataatggt | 540 |
| ggcaagcagg | cgctggagac | ggtccagcgg | ctgttgccgg | tgctgtgcca | ggcccacggc | 600 |
| ttgacccccc | agcaggtggt | ggccatcgcc | agcaataatg | gtggcaagca | ggcgctggag | 660 |
| acggtccagc | ggctgttgcc | ggtgctgtgc | caggcccacg | gcttgacccc | ggagcaggtg | 720 |
| gtggccatcg | ccagcaatat | tggtggcaag | caggcgctgg | agacggtgca | ggcgctgttg | 780 |
| ccggtgctgt | gccaggccca | cggcttgacc | cccagcagg | tggtggccat | cgccagcaat | 840 |
| ggcggtggca | agcaggcgct | ggagacggtc | cagcggctgt | tgccggtgct | gtgccaggcc | 900 |
| cacggcttga | ccccggagca | ggtggtggcc | atcgccagca | atattggtgg | caagcaggcg | 960 |
| ctggagacgg | tgcaggcgct | gttgccggtg | ctgtgccagg | cccacggctt | gacccccag | 1020 |
| caggtggtgg | ccatcgccag | caataatggt | ggcaagcagg | cgctggagac | ggtccagcgg | 1080 |
| ctgttgccgg | tgctgtgcca | ggcccacggc | ttgaccccgg | agcaggtggt | ggccatcgcc | 1140 |
| agccacgatg | gcggcaagca | ggcgctggag | acggtccagc | ggctgttgcc | ggtgctgtgc | 1200 |
| caggcccacg | gcttgacccc | ggagcaggtg | gtggccatcg | ccagccacga | tggcggcaag | 1260 |
| caggcgctgg | agacggtcca | gcggctgttg | ccggtgctgt | gccaggccca | cggcttgacc | 1320 |
| ccccagcagg | tggtggccat | cgccagcaat | ggcggtggca | agcaggcgct | ggagacggtc | 1380 |
| cagcggctgt | tgccggtgct | gtgccaggcc | cacggcttga | ccccggagca | ggtggtggcc | 1440 |
| atcgccagcc | acgatggcgg | caagcaggcg | ctggagacgg | tccagcggct | gttgccggtg | 1500 |
| ctgtgccagg | cccacggctt | gaccccggag | caggtggtgg | ccatcgccag | ccacgatggc | 1560 |
| ggcaagcagg | cgctggagac | ggtccagcgg | ctgttgccgg | tgctgtgcca | ggcccacggc | 1620 |
| ttgaccccgg | agcaggtggt | ggccatcgcc | agcaatattg | gtggcaagca | ggcgctggag | 1680 |
| acggtgcagg | cgctgttgcc | ggtgctgtgc | caggcccacg | gcttgacccc | cagcaggtg | 1740 |
| gtggccatcg | ccagcaataa | tggtggcaag | caggcgctgg | agacggtcca | gcggctgttg | 1800 |
| ccggtgctgt | gccaggccca | cggcttgacc | cccagcagg | tggtggccat | cgccagcaat | 1860 |
| aatggtggca | agcaggcgct | ggagacggtc | cagcggctgt | tgccggtgct | gtgccaggcc | 1920 |
| cacggcttga | ccccggagca | ggtggtggcc | atcgccagcc | acgatggcgg | caagcaggcg | 1980 |
| ctggagacgg | tccagcggct | gttgccggtg | ctgtgccagg | cccacggctt | gacccctcag | 2040 |
| caggtggtgg | ccatcgccag | caatggcggc | ggcaggccgg | cgctggagag | cattgttgcc | 2100 |

```
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga atccgagtt gaggcacaag    2280 ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtaccccctc cagcgtgaccg agttcaagtt cctgttcgtg   2640
tccggccact tcaagggcaa ctacaaggcc cagctgacca ggctgaacca catcaccaac   2700
tgcaacggcg ccgtgctgtc cgtggaggag ctcctgatcg gcggcgagat gatcaaggcc   2760 ggcacccctga ccctggagga ggtgaggagg aagttcaaca acggcgagat caacttcgcg   2820
gccgactgat aa                                                       2832

<210> SEQ ID NO 10
<211> LENGTH: 49
<212> TYPE: DNA
<213> ORGANISM: artificial sequence
<220> FEATURE:
<223> OTHER INFORMATION: PDCD1_T01

<400> SEQUENCE: 10
ttctccccag ccctgctcgt ggtgaccgaa ggggacaacg ccaccttca              49

<210> SEQ ID NO 11
<211> LENGTH: 2814
<212> TYPE: DNA
<213> ORGANISM: artificial sequence
<220> FEATURE:
<223> OTHER INFORMATION: PDCD1_T01-L TALEN

<400> SEQUENCE: 11
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa cacccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480
ttgacccccc agcaggtggt ggccatcgcc agcaatggcg gtggcaagca ggcgctggag   540
acggtccagc ggctgttgcc ggtgctgtgc caggcccacg gcttgacccc ggagcaggtg   600
gtggccatcg ccagccacga tggcggcaag caggcgctgg agacggtcca gcggctgttg   660
ccggtgctgt gccaggccca cggcttgacc ccccagcagg tggtggccat cgccagcaat   720
ggcggtggca agcaggcgct ggagacggtc cagcggctgt tgccggtgct gtgccaggcc   780
cacggcttga ccccggagca ggtggtggcc atcgccagcc acgatggcgg caagcaggcg   840
ctggagacgg tccagcggct gttgccggtg ctgtgccagc ccacggcttt gaccccggag   900
```

| | |
|---|---:|
| caggtggtgg ccatcgccag ccacgatggc ggcaagcagg cgctggagac ggtccagcgg | 960 |
| ctgttgccgg tgctgtgcca ggcccacggc ttgaccccgg agcaggtggt ggccatcgcc | 1020 |
| agccacgatg gcggcaagca ggcgctggag acggtccagc ggctgttgcc ggtgctgtgc | 1080 |
| caggcccacg gcttgacccc ggagcaggtg gtggccatcg ccagccacga tggcggcaag | 1140 |
| caggcgctgg agacggtcca gcggctgttg ccggtgctgt gccaggccca cggcttgacc | 1200 |
| ccggagcagg tggtggccat cgccagcaat attggtggca agcaggcgct ggagacggtg | 1260 |
| caggcgctgt tgccggtgct gtgccaggcc cacggcttga ccccccagca ggtggtggcc | 1320 |
| atcgccagca ataatggtgg caagcaggcg ctggagacgg tccagcggct gttgccggtg | 1380 |
| ctgtgccagg cccacggctt gaccccggag caggtggtgg ccatcgccag ccacgatggc | 1440 |
| ggcaagcagg cgctggagac ggtccagcgg ctgttgccgg tgctgtgcca ggcccacggc | 1500 |
| ttgaccccgg agcaggtggt ggccatcgcc agccacgatg gcggcaagca ggcgctggag | 1560 |
| acggtccagc ggctgttgcc ggtgctgtgc caggcccacg gcttgacccc ggagcaggtg | 1620 |
| gtggccatcg ccagccacga tggcggcaag caggcgctgg agacggtcca gcggctgttg | 1680 |
| ccggtgctgt gccaggccca cggcttgacc cccagcagg tggtggccat cgccagcaat | 1740 |
| ggcggtggca agcaggcgct ggagacggtc agcggctgt tgccggtgct gtgccaggcc | 1800 |
| cacggcttga ccccccagca ggtggtggcc atcgccagca ataatggtgg caagcaggcg | 1860 |
| ctggagacgg tccagcggct gttgccggtg ctgtgccagg cccacggctt gaccccggag | 1920 |
| caggtggtgg ccatcgccag ccacgatggc ggcaagcagg cgctggagac ggtccagcgg | 1980 |
| ctgttgccgg tgctgtgcca ggcccacggc ttgaccccctc agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctgg atgcagtgaa aaagggattg ggggatccta tcagccgttc ccagctggtg | 2220 |
| aagtccgagc tggaggagaa gaaatccgag ttgaggcaca agctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acggcgccat ctacaccgtg ggctccccca tcgactacgg cgtgatcgtg | 2460 |
| gacaccaagg cctactccgg cggctacaac ctgcccatcg ccaggccgga cgaaatgcag | 2520 |
| aggtacgtgg aggagaacca gaccaggaac aagcacatca ccccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gacccctggag | 2760 |
| gaggtgagga ggaagttcaa caacggcgag atcaacttcg cggccgactg ataa | 2814 |

<210> SEQ ID NO 12
<211> LENGTH: 2829
<212> TYPE: DNA
<213> ORGANISM: artificial sequence
<220> FEATURE:
<223> OTHER INFORMATION: PDCD1_T01-R TALEN

<400> SEQUENCE: 12

| | |
|---|---:|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |

```
ctggtcggcc acgggtttac acacgcgcac atcgttgcgt taagccaaca cccggcagcg     240
ttagggaccg tcgctgtcaa gtatcaggac atgatcgcag cgttgccaga ggcgacacac     300
gaagcgatcg ttggcgtcgg caaacagtgg tccggcgcac gcgctctgga ggccttgctc     360 acggtggcg gagagttgag aggtccaccg ttacagttgg acacaggcca acttctcaag      420
attgcaaaac gtggcggcgt gaccgcagtg gaggcagtgc atgcatggcg caatgcactg     480
acgggtgccc cgctcaactt gacccccgag caagtcgtcg caatcgccag ccatgatgga     540
gggaagcaag ccctcgaaac cgtgcagcgg ttgcttcctg tgctctgcca ggcccacggc     600
cttacccctc agcaggtggt ggccatcgca agtaacggag gaggaaagca agccttggag     660
acagtgcagc gcctgttgcc cgtgctgtgc caggcacacg gcctcacacc agagcaggtc     720
gtggccattg cctcccatga cgggggggaaa caggctctgg agaccgtcca gaggctgctg     780
cccgtcctct gtcaagctca cggcctgact ccccaacaag tggtcgccat cgcctctaat    840
ggcggcggga agcaggcact ggaaacagtg cagagactgc tccctgtgct ttgccaagct     900
catgggttga ccccccaaca ggtcgtcgct attgcctcaa acggggggg caagcaggcc     960 cttgagactg tgcagaggct gttgccagtg ctgtgtcagg ctcacgggct cactccacaa    1020
caggtggtcg caattgccag caacggcggc ggaaagcaag ctcttgaaac cgtgcaacgc    1080
ctcctgcccg tgctctgtca ggctcatggc ctgacaccac aacaagtcgt ggccatcgcc    1140
agtaataatg gcgggaaaca ggctcttgag accgtccaga ggctgctccc agtgctctgc    1200
caggcacacg gctgaccccc cgagcaggtg gtggctatcg ccagcaatat tgggggcaag    1260
caggccctgg aaacagtcca ggccctgctg ccagtgcttt gccaggctca cgggctcact    1320
ccccagcagg tcgtggcaat cgcctccaac ggcggaggga agcaggctct ggagaccgtg    1380
cagagactgc tgcccgtctt gtgccaggcc acggactca cacctgaaca ggtcgtcgcc     1440
attgcctctc acgatggggg caaacaagcc ctggagacag tgcagcggct gttgcctgtg    1500
ttgtgccaag cccacggctt gactcctcaa caagtggtcg ccatcgcctc aaatggcggc    1560
ggaaaacaag ctctggagac agtgcagagg ttgctgcccg tcctctgcca gcccacggc    1620 ctgactcccc aacaggtcgt cgccattgcc agcaacaacg gaggaaagca ggctctcgaa    1680
actgtgcagc ggctgcttcc tgtgctgtgt caggctcatg gctgaccccc gagcaagtg    1740 gtggctattg cctctaatgg aggcaagcaa gcccttgaga cagtccagag gctgttgcca    1800
gtgctgtgcc aggcccacgg gctcacaccc cagcaggtgg tcgccatcgc cagtaacaac    1860
gggggcaaac aggcattgga aaccgtccag cgcctgcttc cagtgctctg ccaggcacac    1920
ggactgacac ccgaacaggt ggtggccatt gcatcccatg atgggggcaa gcaggccctg    1980
gagaccgtga gagactcct gccagtgttg tgccaagctc acggcctcac ccctcagcaa    2040
gtcgtggcca tcgcctcaaa cggggggggc cggcctgcac tggagagcat gttgcccag    2100 ttatctcgcc ctgatccggc gttggccgcg ttgaccaacg accacctcgt cgccttggcc    2160
tgcctcggcg ggcgtcctgc gctggatgca gtgaaaaagg gattggggga tcctatcagc    2220
cgttcccagc tggtgaagtc cgagctggag gagaagaaat ccgagttgag gcacaagctg    2280
aagtacgtgc cccacgagta catcgagctg atcgagatcg cccggaacag cacccaggac    2340
cgtatcctgg agatgaaggt gatggagttc ttcatgaagg tgtacggcta caggggcaag    2400
cacctgggcg gctccaggaa gcccgacggc gccatctaca ccgtgggctc ccccatcgac    2460
tacggcgtga tcgtggacac caaggcctac tccggcggct acaacctgcc catcggccag    2520
```

```
gccgacgaaa tgcagaggta cgtggaggag aaccagacca ggaacaagca catcaacccc    2580
aacgagtggt ggaaggtgta cccctccagc gtgaccgagt tcaagttcct gttcgtgtcc    2640
ggccacttca agggcaacta caaggcccag ctgaccaggc tgaaccacat caccaactgc    2700
aacggcgccg tgctgtccgt ggaggagctc ctgatcggcg gcgagatgat caaggccggc    2760
accctgaccc tggaggaggt gaggaggaag ttcaacaacg gcgagatcaa cttcgcggcc    2820
gactgataa                                                            2829

<210> SEQ ID NO 13
<211> LENGTH: 49
<212> TYPE: DNA
<213> ORGANISM: artificial sequence
<220> FEATURE:
<223> OTHER INFORMATION: PDCD1_T03

<400> SEQUENCE: 13
tacctctgtg gggccatctc cctggccccc aaggcgcaga tcaaagaga               49

<210> SEQ ID NO 14
<211> LENGTH: 2814
<212> TYPE: DNA
<213> ORGANISM: artificial sequence
<220> FEATURE:
<223> OTHER INFORMATION: PDCD1_T03-L TALEN

<400> SEQUENCE: 14
atgggcgatc ctaaaaagaa acgtaaggtc atcgattacc atacgatgt tccagattac     60 gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa caccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgaccccgg agcaggtggt ggccatcgcc agcaatattg tggcaagca ggcgctggag    540 acggtgcagg cgctgttgcc ggtgctgtgc caggcccacg gcttgacccc ggagcaggtg    600
gtggccatcg ccagccacga tggcggcaag caggcgctgg agacggtcca gcggctgttg    660
ccggtgctgt gccaggccca cggcttgacc cggagcagg tggtggccat cgccagccac    720
gatggcggca gcaggcgct ggagacggtc agcggctgt tgccggtgct gtgccaggcc    780
cacggcttga ccccccagca ggtggtggcc atcgccagca atggcggtgg caagcaggcg    840
ctggagacgg tccagcggct gttgccggtg ctgtgccagg cccacggctt gaccccggag    900
caggtggtgg ccatcgccag ccacgatggc ggcaagcagg cgctggagac ggtccagcgg    960
ctgttgccgg tgctgtgcca ggcccacggc ttgaccccc agcaggtggt ggccatcgcc   1020
agcaatggcg gtggcaagca ggcgctggag acggtccagc ggctgttgcc ggtgctgtgc   1080
caggcccacg gcttgacccc ccagcaggtg gtggccatcg ccagcaataa tggtggcaag   1140
caggcgctgg agacggtcca gcggctgttg ccggtgctgt gccaggccca cggcttgacc   1200
ccccagcagg tggtggccat cgccagcaat ggcggtggca agcaggcgct ggagacggtc   1260
cagcggctgt tgccggtgct gtgccaggcc cacggcttga ccccccagca ggtggtggcc   1320
atcgccagca ataatggtgg caagcaggcg ctggagacgg tccagcggct gttgccggtg   1380
```

```
ctgtgccagg cccacggctt gacccccag caggtggtgg ccatcgccag caataatggt    1440
ggcaagcagg cgctggagac ggtccagcgg ctgttgccgg tgctgtgcca ggcccacggc    1500 ttgaccccc agcaggtggt ggccatcgcc agcaataatg gtggcaagca ggcgctggag    1560
acggtccagc ggctgttgcc ggtgctgtgc caggcccacg gcttgacccc ccagcaggtg    1620
gtggccatcg ccagcaataa tggtggcaag caggcgctgg agacggtcca gcggctgttg    1680
ccggtgctgt gccaggccca cggcttgacc ccggagcagg tggtggccat cgccagccac    1740
gatggcggca gcaggcgct ggagacggtc cagcggctgt tgccggtgct gtgccaggcc    1800
cacggcttga ccccggagca ggtggtggcc atcgccagcc acgatggcgg caagcaggcg    1860
ctggagacgg tccagcggct gttgccggtg ctgtgccagg cccacggctt gaccccggag    1920
caggtggtgg ccatcgccag caatattggt ggcaagcagg cgctggagac ggtgcaggcg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctga tgcagtgaaa aagggattgg gggatcctat cagccgttc ccagctggtg    2220 aagtccgagc tggaggagaa gaaatccgag ttgaggcaca gctgaagta cgtgcccac    2280 gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctcccccca tcgactacgg cgtgatcgtg    2460
gacaccaagg cctactccgg cggctacaac ctgcccatcg ccaggccga cgaaatgcag    2520 aggtacgtgg aggagaacca gaccaggaac aagcacatca ccccaacga gtggtggaag    2580 gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814
```

<210> SEQ ID NO 15
<211> LENGTH: 2829
<212> TYPE: DNA
<213> ORGANISM: artificial sequence
<220> FEATURE:
<223> OTHER INFORMATION: PDCD1_T03-R TALEN

<400> SEQUENCE: 15

```
atgggcgatc ctaaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360 acggtggcg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gacccccgag caagtcgtcg caatcgccag ccatgatgga    540
gggaagcaag ccctcgaaac cgtgcagcgg ttgcttcctg tgctctgcca ggcccacggc    600
```

-continued

| | |
|---|---|
| cttacccctc agcaggtggt ggccatcgca agtaacggag gaggaaagca agccttggag | 660 |
| acagtgcagc gcctgttgcc cgtgctgtgc caggcacacg gcctcacacc agagcaggtc | 720 |
| gtggccattg cctcccatga cgggggggaaa caggctctgg agaccgtcca gaggctgctg | 780 |
| cccgtcctct gtcaagctca cggcctgact ccccaacaag tggtcgccat cgcctctaat | 840 |
| ggcggcggga agcaggcact ggaaacagtg cagagactgc tccctgtgct ttgccaagct | 900 |
| catgggttga ccccccaaca ggtcgtcgct attgcctcaa acgggggggg caagcaggcc | 960 |
| cttgagactg tgcagaggct gttgccagtg ctgtgtcagg ctcacgggct cactccacaa | 1020 |
| caggtggtcg caattgccag caacggcggc ggaaagcaag ctcttgaaac cgtgcaacgc | 1080 |
| ctcctgcccg tgctctgtca ggctcatggc ctgacaccac aacaagtcgt ggccatcgcc | 1140 |
| agtaataatg gcgggaaaca ggctcttgag accgtccaga ggctgctccc agtgctctgc | 1200 |
| caggcacacg gctgaccccc cgagcaggtg gtggctatcg ccagcaatat tgggggcaag | 1260 |
| caggccctgg aaacagtcca ggccctgctg ccagtgcttt gccaggctca cgggctcact | 1320 |
| ccccagcagg tcgtggcaat cgcctccaac ggcgagggga agcaggctct ggagaccgtg | 1380 |
| cagagactgc tgcccgtctt gtgccaggcc cacggactca cacctgaaca ggtcgtcgcc | 1440 |
| attgcctctc acgatggggg caaacaagcc ctggagacag tgcagcggct gttgcctgtg | 1500 |
| ttgtgccaag cccacggctt gactcctcaa caagtggtcg ccatcgcctc aaatggcggc | 1560 |
| ggaaaacaag ctctggagac agtgcagagg ttgctgcccg tcctctgcca gcccacggc | 1620 |
| ctgactcccc aacaggtcgt cgccattgcc agcaacaacg gaggaaagca ggctctcgaa | 1680 |
| actgtgcagc ggctgcttcc tgtgctgtgt caggctcatg gctgaccccc cgagcaagtg | 1740 |
| gtggctattg cctctaatgg aggcaagcaa gcccttgaga cagtccagag gctgttgcca | 1800 |
| gtgctgtgcc aggcccacgg gctcacaccc cagcaggtgg tcgccatcgc cagtaacaac | 1860 |
| gggggcaaac aggcattgga aaccgtccag cgcctgcttc cagtgctctg ccaggcacac | 1920 |
| ggactgacac ccgaacaggt ggtggccatt gcatcccatg atgggggcaa gcaggccctg | 1980 |
| agaccgtgc agagactcct gccagtgttg tgccaagctc acggcctcac ccctcagcaa | 2040 |
| gtcgtggcca tcgcctcaaa cggggggggc cggcctgcac tggagagcat tgttgcccag | 2100 |
| ttatctcgcc ctgatccggc gttggccgcg ttgaccaacg accacctcgt cgccttggcc | 2160 |
| tgcctcggcg ggcgtcctgc gctggatgca gtgaaaaagg gattggggga tcctatcagc | 2220 |
| cgttcccagc tggtgaagtc cgagctggag gagaagaaat ccgagttgag gcacaagctg | 2280 |
| aagtacgtgc cccacgagta catcgagctg atcgagatcg cccggaacag cacccaggac | 2340 |
| cgtatcctgg agatgaaggt gatggagttc ttcatgaagg tgtacggcta caggggcaag | 2400 |
| cacctggggcg gctccaggaa gcccgacggc gccatctaca ccgtgggctc ccccatcgac | 2460 |
| tacggcgtga tcgtggacac caaggcctac tccggcggct acaacctgcc catcggccag | 2520 |
| gccgacgaaa tgcagaggta cgtggaggag aaccagacca ggaacaagca catcaacccc | 2580 |
| aacgagtggt ggaaggtgta ccccctccagc gtgaccgagt tcaagttcct gttcgtgtcc | 2640 |
| ggccacttca agggcaacta caaggcccag ctgaccaggc tgaaccacat caccaactgc | 2700 |
| aacgcgccc tgctgtccgt ggaggagctc ctgatcggcg gcgagatgat caaggccggc | 2760 |
| accctgaccc tggaggaggt gaggaggaag ttcaacaacg gcgagatcaa cttcgcggcc | 2820 |
| gactgataa | 2829 |

<210> SEQ ID NO 16
<211> LENGTH: 386

<212> TYPE: PRT
<213> ORGANISM: artificial sequence
<220> FEATURE:
<223> OTHER INFORMATION: pCLS27068: CTLA4a expression plasmid

<400> SEQUENCE: 16

Met Gly Gly Val Leu Leu Thr Gln Arg Thr Leu Leu Ser Leu Val Leu
1               5                   10                  15

Ala Leu Leu Phe Pro Ser Met Ala Ser Met Ala Met His Val Ala Gln
            20                  25                  30

Pro Ala Val Val Leu Ala Ser Ser Arg Gly Ile Ala Ser Phe Val Cys
        35                  40                  45

Glu Tyr Ala Ser Pro Gly Lys Ala Thr Glu Val Arg Val Thr Val Leu
    50                  55                  60

Arg Gln Ala Asp Ser Gln Val Thr Glu Val Cys Ala Ala Thr Tyr Met
65                  70                  75                  80

Met Gly Asn Glu Leu Thr Phe Leu Asp Asp Ser Ile Cys Thr Gly Thr
                85                  90                  95

Ser Ser Gly Asn Gln Val Asn Leu Thr Ile Gln Gly Leu Arg Ala Met
            100                 105                 110

Asp Thr Gly Leu Tyr Ile Cys Lys Val Glu Leu Met Tyr Pro Pro Pro
        115                 120                 125

Tyr Tyr Leu Gly Ile Gly Asn Gly Thr Gln Ile Tyr Val Ile Asp Pro
    130                 135                 140

Glu Pro Cys Pro Asp Ser Asp Gln Glu Pro Lys Ser Ser Asp Lys Thr
145                 150                 155                 160

His Thr Ser Pro Pro Ser Pro Ala Pro Glu Leu Leu Gly Gly Ser Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
        275                 280                 285

Pro Pro Ser Arg Asp Glu Leu Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
    370                 375                 380

Gly Ser
385

<210> SEQ ID NO 17
<211> LENGTH: 386
<212> TYPE: PRT
<213> ORGANISM: artificial sequence
<220> FEATURE:
<223> OTHER INFORMATION: pCLS27066: CTLA4b expression plasmid

<400> SEQUENCE: 17

Met Gly Gly Val Leu Leu Thr Gln Arg Thr Leu Leu Ser Leu Val Leu
1               5                   10                  15

Ala Leu Leu Phe Pro Ser Met Ala Ser Met Ala Met His Val Ala Gln
                20                  25                  30

Pro Ala Val Val Leu Ala Ser Ser Arg Gly Ile Ala Ser Phe Val Cys
            35                  40                  45

Glu Tyr Ala Ser Pro Gly Lys Tyr Thr Glu Val Arg Val Thr Val Leu
        50                  55                  60

Arg Gln Ala Asp Ser Gln Val Thr Glu Val Cys Ala Ala Thr Tyr Met
65                  70                  75                  80

Met Gly Asn Glu Leu Thr Phe Leu Asp Asp Ser Ile Cys Thr Gly Thr
                85                  90                  95

Ser Ser Gly Asn Gln Val Asn Leu Thr Ile Gln Gly Leu Arg Ala Met
            100                 105                 110

Asp Thr Gly Leu Tyr Ile Cys Lys Val Glu Leu Met Tyr Pro Pro Pro
        115                 120                 125

Tyr Tyr Glu Gly Ile Gly Asn Gly Thr Gln Ile Tyr Val Ile Asp Pro
130                 135                 140

Glu Pro Cys Pro Asp Ser Asp Gln Glu Pro Lys Ser Ser Asp Lys Thr
145                 150                 155                 160

His Thr Ser Pro Pro Ser Pro Ala Pro Glu Leu Leu Gly Gly Ser Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
        275                 280                 285

Pro Pro Ser Arg Asp Glu Leu Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

```
Arg Trp Gln Gln Gly Asn Val Phe Ser Cys Ser Val Met His Glu Ala
            355                 360                 365

Leu His Asn His Tyr Thr Gln Lys Ser Leu Ser Leu Ser Pro Gly Lys
    370                 375                 380

Gly Ser
385

<210> SEQ ID NO 18
<211> LENGTH: 293
<212> TYPE: PRT
<213> ORGANISM: artificial sequence
<220> FEATURE:
<223> OTHER INFORMATION: pCLS27069: PDL-1 expression plasmid

<400> SEQUENCE: 18

Met Gly Arg Ile Phe Ala Val Phe Ile Phe Met Thr Tyr Trp His Leu
1               5                   10                  15

Leu Asn Ala Phe Thr Val Thr Val Pro Lys Asp Leu Tyr Val Val Glu
            20                  25                  30

Tyr Gly Ser Asn Met Thr Ile Glu Cys Lys Phe Pro Val Glu Lys Gln
        35                  40                  45

Leu Asp Leu Ala Ala Leu Ile Val Tyr Trp Glu Met Glu Asp Lys Asn
    50                  55                  60

Ile Ile Gln Phe Val His Gly Glu Glu Asp Leu Lys Val Gln His Ser
65                  70                  75                  80

Ser Tyr Arg Gln Arg Ala Arg Leu Leu Lys Asp Gln Leu Ser Leu Gly
                85                  90                  95

Asn Ala Ala Leu Gln Ile Thr Asp Val Lys Leu Gln Asp Ala Gly Val
            100                 105                 110

Tyr Arg Cys Met Ile Ser Tyr Gly Gly Ala Asp Tyr Lys Arg Ile Thr
        115                 120                 125

Val Lys Val Asn Ala Pro Tyr Asn Lys Ile Asn Gln Arg Ile Leu Val
    130                 135                 140

Val Asp Pro Val Thr Ser Glu His Glu Leu Thr Cys Gln Ala Glu Gly
145                 150                 155                 160

Tyr Pro Lys Ala Glu Val Ile Trp Thr Ser Ser Asp His Gln Val Leu
                165                 170                 175

Ser Gly Lys Thr Thr Thr Thr Asn Ser Lys Arg Glu Glu Lys Leu Phe
            180                 185                 190

Asn Val Thr Ser Thr Leu Arg Ile Asn Thr Thr Thr Asn Glu Ile Phe
        195                 200                 205

Tyr Cys Thr Phe Arg Arg Leu Asp Pro Glu Glu Asn His Thr Ala Glu
    210                 215                 220

Leu Val Ile Pro Glu Leu Pro Leu Ala His Pro Pro Asn Glu Arg Thr
225                 230                 235                 240

His Leu Val Ile Leu Gly Ala Ile Leu Leu Cys Leu Gly Val Ala Leu
                245                 250                 255

Thr Phe Ile Phe Arg Leu Arg Lys Gly Arg Met Met Asp Val Lys Lys
            260                 265                 270

Cys Gly Ile Gln Asp Thr Asn Ser Lys Lys Gln Ser Asp Thr His Leu
        275                 280                 285

Glu Glu Thr Gly Ser
    290

<210> SEQ ID NO 19
<211> LENGTH: 14
```

```
<212> TYPE: PRT
<213> ORGANISM: HIV-1 virus
<220> FEATURE:
<223> OTHER INFORMATION: ISU peptide n°1 from gp41 env protein

<400> SEQUENCE: 19

Leu Gln Ala Arg Ile Leu Ala Val Glu Arg Tyr Leu Lys Asp
1               5                   10

<210> SEQ ID NO 20
<211> LENGTH: 14
<212> TYPE: PRT
<213> ORGANISM: HIV-1 virus
<220> FEATURE:
<223> OTHER INFORMATION: ISU peptide n°2 from gp41 env protein

<400> SEQUENCE: 20

Leu Gln Ala Arg Val Leu Ala Val Glu Arg Tyr Leu Lys Asp
1               5                   10

<210> SEQ ID NO 21
<211> LENGTH: 14
<212> TYPE: PRT
<213> ORGANISM: HIV-1 virus
<220> FEATURE:
<223> OTHER INFORMATION: ISU peptide n°3 from gp41 env protein

<400> SEQUENCE: 21

Leu Gln Ala Arg Ile Leu Ala Val Glu Arg Tyr Leu Ala Asp
1               5                   10

<210> SEQ ID NO 22
<211> LENGTH: 14
<212> TYPE: PRT
<213> ORGANISM: HIV-1 virus
<220> FEATURE:
<223> OTHER INFORMATION: ISU peptide n°4 from gp41 env protein

<400> SEQUENCE: 22

Leu Gln Ala Arg Val Leu Ala Val Glu Arg Tyr Leu Ala Asp
1               5                   10

<210> SEQ ID NO 23
<211> LENGTH: 14
<212> TYPE: PRT
<213> ORGANISM: HIV-1 virus
<220> FEATURE:
<223> OTHER INFORMATION: ISU peptide n°5 from gp41 env protein

<400> SEQUENCE: 23

Leu Gln Ala Arg Ile Leu Ala Val Glu Arg Tyr Leu Gln Asp
1               5                   10

<210> SEQ ID NO 24
<211> LENGTH: 14
<212> TYPE: PRT
<213> ORGANISM: HIV-1 virus
<220> FEATURE:
<223> OTHER INFORMATION: ISU peptide n°6 from gp41 env protein

<400> SEQUENCE: 24

Leu Gln Ala Arg Val Leu Ala Val Glu Arg Tyr Leu Gln Asp
1               5                   10

<210> SEQ ID NO 25
<211> LENGTH: 14
<212> TYPE: PRT
```

<213> ORGANISM: HIV-2 virus
<220> FEATURE:
<223> OTHER INFORMATION: ISU peptide n°1 from gp41 env protein

<400> SEQUENCE: 25

Leu Gln Ala Arg Val Leu Ala Val Glu Arg Tyr Leu Gln Asp
1 5 10

<210> SEQ ID NO 26
<211> LENGTH: 13
<212> TYPE: PRT
<213> ORGANISM: HIV-2 virus
<220> FEATURE:
<223> OTHER INFORMATION: ISU peptide n°2 from gp41 env protein

<400> SEQUENCE: 26

Leu Gln Ala Arg Val Thr Ala Ile Glu Tyr Leu Ala Asp
1 5 10

<210> SEQ ID NO 27
<211> LENGTH: 14
<212> TYPE: PRT
<213> ORGANISM: HIV-2 virus
<220> FEATURE:
<223> OTHER INFORMATION: ISU peptide n°3 from gp41 env protein

<400> SEQUENCE: 27

Leu Gln Ala Arg Val Thr Ala Ile Glu Lys Tyr Leu Gln Asp
1 5 10

<210> SEQ ID NO 28
<211> LENGTH: 14
<212> TYPE: PRT
<213> ORGANISM: HIV-2 virus
<220> FEATURE:
<223> OTHER INFORMATION: ISU peptide n°4 from gp41 env protein

<400> SEQUENCE: 28

Leu Gln Ala Arg Val Leu Ala Val Glu Arg Tyr Leu Gln His
1 5 10

<210> SEQ ID NO 29
<211> LENGTH: 13
<212> TYPE: PRT
<213> ORGANISM: HIV-2 virus
<220> FEATURE:
<223> OTHER INFORMATION: ISU peptide n°5 from gp41 env protein

<400> SEQUENCE: 29

Leu Gln Ala Arg Val Thr Ala Ile Glu Tyr Leu Ala His
1 5 10

<210> SEQ ID NO 30
<211> LENGTH: 14
<212> TYPE: PRT
<213> ORGANISM: HIV-2 virus
<220> FEATURE:
<223> OTHER INFORMATION: ISU peptide n°6 from gp41 env protein

<400> SEQUENCE: 30

Leu Gln Ala Arg Val Thr Ala Ile Glu Lys Tyr Leu Gln His
1 5 10

<210> SEQ ID NO 31
<211> LENGTH: 13
<212> TYPE: PRT
<213> ORGANISM: SIV virus

```
<220> FEATURE:
<223> OTHER INFORMATION: ISU peptide from gp41 env protein

<400> SEQUENCE: 31

Leu Gln Ala Arg Leu Ala Val Glu Arg Tyr Leu Lys Asp
1               5                   10

<210> SEQ ID NO 32
<211> LENGTH: 14
<212> TYPE: PRT
<213> ORGANISM: MoMuLV virus
<220> FEATURE:
<223> OTHER INFORMATION: ISU peptide from gp41 env protein

<400> SEQUENCE: 32

Leu Gln Asn Arg Arg Gly Leu Asp Leu Leu Phe Leu Lys Glu
1               5                   10

<210> SEQ ID NO 33
<211> LENGTH: 14
<212> TYPE: PRT
<213> ORGANISM: HTLV-I, -2 virus
<220> FEATURE:
<223> OTHER INFORMATION: ISU peptide from gp41 env protein

<400> SEQUENCE: 33

Ala Gln Asn Arg Arg Gly Leu Asp Leu Leu Phe Trp Glu Gln
1               5                   10

<210> SEQ ID NO 34
<211> LENGTH: 14
<212> TYPE: PRT
<213> ORGANISM: MPMV,SRV-1 virus
<220> FEATURE:
<223> OTHER INFORMATION: ISU peptide from gp41 env protein

<400> SEQUENCE: 34

Leu Gln Asn Arg Arg Gly Leu Asp Leu Leu Thr Ala Glu Gln
1               5                   10

<210> SEQ ID NO 35
<211> LENGTH: 14
<212> TYPE: PRT
<213> ORGANISM: Syncitin 1 virus
<220> FEATURE:
<223> OTHER INFORMATION: ISU peptide from gp41 env protein

<400> SEQUENCE: 35

Leu Gln Asn Arg Arg Ala Leu Asp Leu Leu Thr Ala Glu Arg
1               5                   10

<210> SEQ ID NO 36
<211> LENGTH: 14
<212> TYPE: PRT
<213> ORGANISM: Syncitin 2 virus
<220> FEATURE:
<223> OTHER INFORMATION: ISU peptide from gp41 env protein

<400> SEQUENCE: 36

Leu Gln Asn Arg Arg Gly Leu Asp Met Leu Thr Ala Ala Gln
1               5                   10

<210> SEQ ID NO 37
<211> LENGTH: 14
<212> TYPE: PRT
<213> ORGANISM: HERV-K virus
<220> FEATURE:
```

-continued

<223> OTHER INFORMATION: ISU peptide from gp41 env protein

<400> SEQUENCE: 37

Leu Ala Asn Gln Ile Asn Asp Leu Arg Gln Thr Val Ile Trp
1               5                   10

<210> SEQ ID NO 38
<211> LENGTH: 14
<212> TYPE: PRT
<213> ORGANISM: FELV virus
<220> FEATURE:
<223> OTHER INFORMATION: ISU peptide from gp41 env protein

<400> SEQUENCE: 38

Leu Gln Asn Arg Arg Gly Leu Asp Ile Leu Phe Leu Gln Glu
1               5                   10

<210> SEQ ID NO 39
<211> LENGTH: 526
<212> TYPE: PRT
<213> ORGANISM: artificial sequence
<220> FEATURE:
<223> OTHER INFORMATION: Chimeric B2M-UL18

<400> SEQUENCE: 39

Met Ala Leu Pro Val Thr Ala Leu Leu Leu Pro Leu Ala Leu Leu Leu
1               5                   10                  15

His Ala Ala Arg Pro Ser Arg Ser Val Ala Leu Ala Val Leu Ala Leu
                20                  25                  30

Leu Ser Leu Ser Gly Leu Glu Ala Ile Gln Arg Thr Pro Lys Ile Gln
        35                  40                  45

Val Tyr Ser Arg His Pro Ala Glu Asn Gly Lys Ser Asn Phe Leu Asn
    50                  55                  60

Cys Tyr Val Ser Gly Phe His Pro Ser Asp Ile Glu Val Asp Leu Leu
65                  70                  75                  80

Lys Asn Gly Glu Arg Ile Glu Lys Val Glu His Ser Asp Leu Ser Phe
                85                  90                  95

Ser Lys Asp Trp Ser Phe Tyr Leu Leu Tyr Tyr Thr Glu Phe Thr Pro
            100                 105                 110

Thr Glu Lys Asp Glu Tyr Ala Cys Arg Val Asn His Val Thr Leu Ser
        115                 120                 125

Gln Pro Lys Ile Val Lys Trp Asp Arg Asp Met Gly Gly Gly Gly Ser
    130                 135                 140

Gly Gly Gly Gly Ser Gly Gly Gly Ser Gly Gly Gly Gly Ser Met
145                 150                 155                 160

Thr Met Trp Cys Leu Thr Leu Phe Val Leu Trp Met Leu Arg Val Val
                165                 170                 175

Gly Met His Val Leu Arg Tyr Gly Tyr Thr Gly Ile Phe Asp Asp Thr
            180                 185                 190

Ser His Met Thr Leu Thr Val Val Gly Ile Phe Asp Gly Gln His Phe
        195                 200                 205

Phe Thr Tyr His Val Asn Ser Ser Asp Lys Ala Ser Ser Arg Ala Asn
    210                 215                 220

Gly Thr Ile Ser Trp Met Ala Asn Val Ser Ala Ala Tyr Pro Thr Tyr
225                 230                 235                 240

Leu Asp Gly Glu Arg Ala Lys Gly Asp Leu Ile Phe Asn Gln Thr Glu
                245                 250                 255

Gln Asn Leu Leu Glu Leu Glu Ile Ala Leu Gly Tyr Arg Ser Gln Ser

```
                    260                 265                 270
Val Leu Thr Trp Thr His Glu Cys Asn Thr Thr Glu Asn Gly Ser Phe
            275                 280                 285

Val Ala Gly Tyr Glu Gly Phe Gly Trp Asp Gly Glu Thr Leu Met Glu
        290                 295                 300

Leu Lys Asp Asn Leu Thr Leu Trp Thr Gly Pro Asn Tyr Glu Ile Ser
305                 310                 315                 320

Trp Leu Lys Gln Asn Lys Thr Tyr Ile Asp Gly Lys Ile Lys Asn Ile
                325                 330                 335

Ser Glu Gly Asp Thr Thr Ile Gln Arg Asn Tyr Leu Lys Gly Asn Cys
            340                 345                 350

Thr Gln Trp Ser Val Ile Tyr Ser Gly Phe Gln Thr Pro Val Thr His
        355                 360                 365

Pro Val Val Lys Gly Gly Val Arg Asn Gln Asn Asp Asn Arg Ala Glu
    370                 375                 380

Ala Phe Cys Thr Ser Tyr Gly Phe Phe Pro Gly Glu Ile Asn Ile Thr
385                 390                 395                 400

Phe Ile His Tyr Gly Asn Lys Ala Pro Asp Asp Ser Glu Pro Gln Cys
                405                 410                 415

Asn Pro Leu Leu Pro Thr Phe Asp Gly Thr Phe His Gln Gly Cys Tyr
            420                 425                 430

Val Ala Ile Phe Cys Asn Gln Asn Tyr Thr Cys Arg Val Thr His Gly
        435                 440                 445

Asn Trp Thr Val Glu Ile Pro Ile Ser Val Thr Ser Pro Asp Asp Ser
    450                 455                 460

Ser Ser Gly Glu Val Pro Asp His Pro Thr Ala Asn Lys Arg Tyr Asn
465                 470                 475                 480

Thr Met Thr Ile Ser Ser Val Leu Leu Ala Leu Leu Cys Ala Leu
                485                 490                 495

Leu Phe Ala Phe Leu His Tyr Phe Thr Thr Leu Lys Gln Tyr Leu Arg
            500                 505                 510

Asn Leu Ala Phe Ala Trp Arg Tyr Arg Lys Val Arg Ser Ser
        515                 520                 525

<210> SEQ ID NO 40
<211> LENGTH: 310
<212> TYPE: PRT
<213> ORGANISM: artificial sequence
<220> FEATURE:
<223> OTHER INFORMATION: SP-MICAed

<400> SEQUENCE: 40

Met Gly Gly Val Leu Leu Thr Gln Arg Thr Leu Leu Ser Leu Val Leu
1               5                   10                  15

Ala Leu Leu Phe Pro Ser Met Ala Ser Met Glu Pro His Ser Leu Arg
            20                  25                  30

Tyr Asn Leu Thr Val Leu Ser Trp Asp Gly Ser Val Gln Ser Gly Phe
        35                  40                  45

Leu Thr Glu Val His Leu Asp Gly Gln Pro Phe Leu Arg Cys Asp Arg
    50                  55                  60

Gln Lys Cys Arg Ala Lys Pro Gln Gly Gln Trp Ala Glu Asp Val Leu
65                  70                  75                  80

Gly Asn Lys Thr Trp Asp Arg Glu Thr Arg Asp Leu Thr Gly Asn Gly
                85                  90                  95

Lys Asp Leu Arg Met Thr Leu Ala His Ile Lys Asp Gln Lys Glu Gly
```

```
                100              105              110
Leu His Ser Leu Gln Glu Ile Arg Val Cys Glu Ile His Glu Asp Asn
            115                  120                  125
Ser Thr Arg Ser Ser Gln His Phe Tyr Tyr Asp Gly Glu Leu Phe Leu
            130                  135                  140
Ser Gln Asn Leu Glu Thr Lys Glu Trp Thr Met Pro Gln Ser Ser Arg
145                  150                  155                  160
Ala Gln Thr Leu Ala Met Asn Val Arg Asn Phe Leu Lys Glu Asp Ala
                165                  170                  175
Met Lys Thr Lys Thr His Tyr His Ala Met His Ala Asp Cys Leu Gln
                180                  185                  190
Glu Leu Arg Arg Tyr Leu Lys Ser Gly Val Val Leu Arg Arg Thr Val
            195                  200                  205
Pro Pro Met Val Asn Val Thr Arg Ser Glu Ala Ser Glu Gly Asn Ile
            210                  215                  220
Thr Val Thr Cys Arg Ala Ser Gly Phe Tyr Pro Trp Asn Ile Thr Leu
225                  230                  235                  240
Ser Trp Arg Gln Asp Gly Val Ser Leu Ser His Asp Thr Gln Gln Trp
                245                  250                  255
Gly Asp Val Leu Pro Asp Gly Asn Gly Thr Tyr Gln Thr Trp Val Ala
                260                  265                  270
Thr Arg Ile Cys Gln Gly Glu Glu Gln Arg Phe Thr Cys Tyr Met Glu
            275                  280                  285
His Ser Gly Asn His Ser Thr His Pro Val Pro Ser Gly Lys Val Leu
            290                  295                  300
Val Leu Gln Ser His Trp
305                  310

<210> SEQ ID NO 41
<211> LENGTH: 313
<212> TYPE: PRT
<213> ORGANISM: artificial sequence
<220> FEATURE:
<223> OTHER INFORMATION: SP-MICBed

<400> SEQUENCE: 41

Met Gly Gly Val Leu Leu Thr Gln Arg Thr Leu Leu Ser Leu Val Leu
1               5                   10                  15
Ala Leu Leu Phe Pro Ser Met Ala Ser Met Ala Glu Pro His Ser Leu
                20                  25                  30
Arg Tyr Asn Leu Met Val Leu Ser Gln Asp Glu Ser Val Gln Ser Gly
            35                  40                  45
Phe Leu Ala Glu Gly His Leu Asp Gly Gln Pro Phe Leu Arg Tyr Asp
        50                  55                  60
Arg Gln Lys Arg Arg Ala Lys Pro Gln Gly Gln Trp Ala Glu Asp Val
65                  70                  75                  80
Leu Gly Ala Lys Thr Trp Asp Thr Glu Thr Glu Asp Leu Thr Glu Asn
                85                  90                  95
Gly Gln Asp Leu Arg Arg Thr Leu Thr His Ile Lys Asp Gln Lys Gly
            100                 105                 110
Gly Leu His Ser Leu Gln Glu Ile Arg Val Cys Glu Ile His Glu Asp
            115                 120                 125
Ser Ser Thr Arg Gly Ser Arg His Phe Tyr Tyr Asp Gly Glu Leu Phe
        130                 135                 140
Leu Ser Gln Asn Leu Glu Thr Gln Glu Ser Thr Val Pro Gln Ser Ser
```

-continued

```
            145                 150                 155                 160
Arg Ala Gln Thr Leu Ala Met Asn Val Thr Asn Phe Trp Lys Glu Asp
                    165                 170                 175
Ala Met Lys Thr Lys Thr His Tyr Arg Ala Met Gln Ala Asp Cys Leu
                180                 185                 190
Gln Lys Leu Gln Arg Tyr Leu Lys Ser Gly Val Ala Ile Arg Arg Thr
            195                 200                 205
Val Pro Pro Met Val Asn Val Thr Cys Ser Glu Val Ser Glu Gly Asn
        210                 215                 220
Ile Thr Val Thr Cys Arg Ala Ser Ser Phe Tyr Pro Arg Asn Ile Thr
225                 230                 235                 240
Leu Thr Trp Arg Gln Asp Gly Val Ser Leu Ser His Asn Thr Gln Gln
                245                 250                 255
Trp Gly Asp Val Leu Pro Asp Gly Asn Gly Thr Tyr Gln Thr Trp Val
                260                 265                 270
Ala Thr Arg Ile Arg Gln Gly Glu Glu Gln Arg Phe Thr Cys Tyr Met
            275                 280                 285
Glu His Ser Gly Asn His Gly Thr His Pro Val Pro Ser Gly Lys Val
        290                 295                 300
Leu Val Leu Gln Ser Gln Arg Thr Asp
305                 310

<210> SEQ ID NO 42
<211> LENGTH: 209
<212> TYPE: PRT
<213> ORGANISM: artificial sequence
<220> FEATURE:
<223> OTHER INFORMATION: SP-ULBP1ed

<400> SEQUENCE: 42

Met Gly Gly Val Leu Leu Thr Gln Arg Thr Leu Leu Ser Leu Val Leu
1               5                   10                  15
Ala Leu Leu Phe Pro Ser Met Ala Ser Met Gly Trp Val Asp Thr His
                20                  25                  30
Cys Leu Cys Tyr Asp Phe Ile Ile Thr Pro Lys Ser Arg Pro Glu Pro
            35                  40                  45
Gln Trp Cys Glu Val Gln Gly Leu Val Asp Glu Arg Pro Phe Leu His
        50                  55                  60
Tyr Asp Cys Val Asn His Lys Ala Lys Ala Phe Ala Ser Leu Gly Lys
65                  70                  75                  80
Lys Val Asn Val Thr Lys Thr Trp Glu Glu Gln Thr Glu Thr Leu Arg
                85                  90                  95
Asp Val Val Asp Phe Leu Lys Gly Gln Leu Leu Asp Ile Gln Val Glu
                100                 105                 110
Asn Leu Ile Pro Ile Glu Pro Leu Thr Leu Gln Ala Arg Met Ser Cys
            115                 120                 125
Glu His Glu Ala His Gly His Gly Arg Gly Ser Trp Gln Phe Leu Phe
        130                 135                 140
Asn Gly Gln Lys Phe Leu Leu Phe Asp Ser Asn Asn Arg Lys Trp Thr
145                 150                 155                 160
Ala Leu His Pro Gly Ala Lys Lys Met Thr Glu Lys Trp Glu Lys Asn
                165                 170                 175
Arg Asp Val Thr Met Phe Phe Gln Lys Ile Ser Leu Gly Asp Cys Lys
                180                 185                 190
Met Trp Leu Glu Glu Phe Leu Met Tyr Trp Glu Gln Met Leu Asp Pro
```

<210> SEQ ID NO 43
<211> LENGTH: 211
<212> TYPE: PRT
<213> ORGANISM: artificial sequence
<220> FEATURE:
<223> OTHER INFORMATION: SP-ULBP2ed

<400> SEQUENCE: 43

```
Met Gly Gly Val Leu Leu Thr Gln Arg Thr Leu Leu Ser Leu Val Leu
1               5                   10                  15
Ala Leu Leu Phe Pro Ser Met Ala Ser Met Gly Arg Ala Asp Pro His
                20                  25                  30
Ser Leu Cys Tyr Asp Ile Thr Val Ile Pro Lys Phe Arg Pro Gly Pro
            35                  40                  45
Arg Trp Cys Ala Val Gln Gly Gln Val Asp Glu Lys Thr Phe Leu His
    50                  55                  60
Tyr Asp Cys Gly Asn Lys Thr Val Thr Pro Val Ser Pro Leu Gly Lys
65                  70                  75                  80
Lys Leu Asn Val Thr Thr Ala Trp Lys Ala Gln Asn Pro Val Leu Arg
                85                  90                  95
Glu Val Val Asp Ile Leu Thr Glu Gln Leu Arg Asp Ile Gln Leu Glu
            100                 105                 110
Asn Tyr Thr Pro Lys Glu Pro Leu Thr Leu Gln Ala Arg Met Ser Cys
        115                 120                 125
Glu Gln Lys Ala Glu Gly His Ser Ser Gly Ser Trp Gln Phe Ser Phe
    130                 135                 140
Asp Gly Gln Ile Phe Leu Leu Phe Asp Ser Glu Lys Arg Met Trp Thr
145                 150                 155                 160
Thr Val His Pro Gly Ala Arg Lys Met Lys Glu Lys Trp Glu Asn Asp
                165                 170                 175
Lys Val Val Ala Met Ser Phe His Tyr Phe Ser Met Gly Asp Cys Ile
            180                 185                 190
Gly Trp Leu Glu Asp Phe Leu Met Gly Met Asp Ser Thr Leu Glu Pro
        195                 200                 205
Ser Ala Gly
    210
```

<210> SEQ ID NO 44
<211> LENGTH: 206
<212> TYPE: PRT
<213> ORGANISM: artificial sequence
<220> FEATURE:
<223> OTHER INFORMATION: SP-ULBP3ed

<400> SEQUENCE: 44

```
Met Gly Gly Val Leu Leu Thr Gln Arg Thr Leu Leu Ser Leu Val Leu
1               5                   10                  15
Ala Leu Leu Phe Pro Ser Met Ala Ser Met Asp Ala His Ser Leu Trp
                20                  25                  30
Tyr Asn Phe Thr Ile Ile His Leu Pro Arg His Gly Gln Gln Trp Cys
            35                  40                  45
Glu Val Gln Ser Gln Val Asp Gln Lys Asn Phe Leu Ser Tyr Asp Cys
    50                  55                  60
Gly Ser Asp Lys Val Leu Ser Met Gly His Leu Glu Glu Gln Leu Tyr
```

```
            65                  70                  75                  80
Ala Thr Asp Ala Trp Gly Lys Gln Leu Glu Met Leu Arg Glu Val Gly
                85                  90                  95

Gln Arg Leu Arg Leu Glu Leu Ala Asp Thr Glu Leu Glu Asp Phe Thr
            100                 105                 110

Pro Ser Gly Pro Leu Thr Leu Gln Val Arg Met Ser Cys Glu Cys Glu
            115                 120                 125

Ala Asp Gly Tyr Ile Arg Gly Ser Trp Gln Phe Ser Phe Asp Gly Arg
        130                 135                 140

Lys Phe Leu Leu Phe Asp Ser Asn Asn Arg Lys Trp Thr Val Val His
145                 150                 155                 160

Ala Gly Ala Arg Arg Met Lys Glu Lys Trp Glu Lys Asp Ser Gly Leu
                165                 170                 175

Thr Thr Phe Phe Lys Met Val Ser Met Arg Asp Cys Lys Ser Trp Leu
            180                 185                 190

Arg Asp Phe Leu Met His Arg Lys Lys Arg Leu Glu Pro Thr
                195                 200                 205

<210> SEQ ID NO 45
<211> LENGTH: 221
<212> TYPE: PRT
<213> ORGANISM: artificial sequence
<220> FEATURE:
<223> OTHER INFORMATION: SP-N2DL4ed

<400> SEQUENCE: 45

Met Gly Gly Val Leu Leu Thr Gln Arg Thr Leu Leu Ser Leu Val Leu
1               5                   10                  15

Ala Leu Leu Phe Pro Ser Met Ala Ser Met His Ser Leu Cys Phe Asn
            20                  25                  30

Phe Thr Ile Lys Ser Leu Ser Arg Pro Gly Gln Pro Trp Cys Glu Ala
        35                  40                  45

Gln Val Phe Leu Asn Lys Asn Leu Phe Leu Gln Tyr Asn Ser Asp Asn
    50                  55                  60

Asn Met Val Lys Pro Leu Gly Leu Leu Gly Lys Lys Val Tyr Ala Thr
65                  70                  75                  80

Ser Thr Trp Gly Glu Leu Thr Gln Thr Leu Gly Glu Val Gly Arg Asp
                85                  90                  95

Leu Arg Met Leu Leu Cys Asp Ile Lys Pro Gln Ile Lys Thr Ser Asp
            100                 105                 110

Pro Ser Thr Leu Gln Val Glu Met Phe Cys Gln Arg Glu Ala Glu Arg
            115                 120                 125

Cys Thr Gly Ala Ser Trp Gln Phe Ala Thr Asn Gly Glu Lys Ser Leu
        130                 135                 140

Leu Phe Asp Ala Met Asn Met Thr Trp Thr Val Ile Asn His Glu Ala
145                 150                 155                 160

Ser Lys Ile Lys Glu Thr Trp Lys Lys Asp Arg Gly Leu Glu Lys Tyr
                165                 170                 175

Phe Arg Lys Leu Ser Lys Gly Asp Cys Asp His Trp Leu Arg Glu Phe
            180                 185                 190

Leu Gly His Trp Glu Ala Met Pro Glu Pro Thr Val Ser Pro Val Asn
        195                 200                 205

Ala Ser Asp Ile His Trp Ser Ser Ser Leu Pro Asp
    210                 215                 220
```

```
<210> SEQ ID NO 46
<211> LENGTH: 224
<212> TYPE: PRT
<213> ORGANISM: artificial sequence
<220> FEATURE:
<223> OTHER INFORMATION: SP-RET1Ged

<400> SEQUENCE: 46

Met Gly Gly Val Leu Leu Thr Gln Arg Thr Leu Leu Ser Leu Val Leu
1               5                   10                  15

Ala Leu Leu Phe Pro Ser Met Ala Ser Met Gly Leu Ala Asp Pro His
            20                  25                  30

Ser Leu Cys Tyr Asp Ile Thr Val Ile Pro Lys Phe Arg Pro Gly Pro
        35                  40                  45

Arg Trp Cys Ala Val Gln Gly Gln Val Asp Glu Lys Thr Phe Leu His
    50                  55                  60

Tyr Asp Cys Gly Ser Lys Thr Val Thr Pro Val Ser Pro Leu Gly Lys
65                  70                  75                  80

Lys Leu Asn Val Thr Thr Ala Trp Lys Ala Gln Asn Pro Val Leu Arg
                85                  90                  95

Glu Val Val Asp Ile Leu Thr Glu Gln Leu Leu Asp Ile Gln Leu Glu
            100                 105                 110

Asn Tyr Ile Pro Lys Glu Pro Leu Thr Leu Gln Ala Arg Met Ser Cys
        115                 120                 125

Glu Gln Lys Ala Glu Gly His Gly Ser Gly Ser Trp Gln Leu Ser Phe
    130                 135                 140

Asp Gly Gln Ile Phe Leu Leu Phe Asp Ser Glu Asn Arg Met Trp Thr
145                 150                 155                 160

Thr Val His Pro Gly Ala Arg Lys Met Lys Glu Lys Trp Glu Asn Asp
                165                 170                 175

Lys Asp Met Thr Met Ser Phe His Tyr Ile Ser Met Gly Asp Cys Thr
            180                 185                 190

Gly Trp Leu Glu Asp Phe Leu Met Gly Met Asp Ser Thr Leu Glu Pro
        195                 200                 205

Ser Ala Gly Ala Pro Pro Thr Met Ser Ser Gly Thr Ala Gln Pro Arg
    210                 215                 220

<210> SEQ ID NO 47
<211> LENGTH: 211
<212> TYPE: PRT
<213> ORGANISM: artificial sequence
<220> FEATURE:
<223> OTHER INFORMATION: SP-RAETILed

<400> SEQUENCE: 47

Met Gly Gly Val Leu Leu Thr Gln Arg Thr Leu Leu Ser Leu Val Leu
1               5                   10                  15

Ala Leu Leu Phe Pro Ser Met Ala Ser Met Arg Arg Asp Asp Pro His
            20                  25                  30

Ser Leu Cys Tyr Asp Ile Thr Val Ile Pro Lys Phe Arg Pro Gly Pro
        35                  40                  45

Arg Trp Cys Ala Val Gln Gly Gln Val Asp Glu Lys Thr Phe Leu His
    50                  55                  60

Tyr Asp Cys Gly Asn Lys Thr Val Thr Pro Val Ser Pro Leu Gly Lys
65                  70                  75                  80

Lys Leu Asn Val Thr Met Ala Trp Lys Ala Gln Asn Pro Val Leu Arg
                85                  90                  95
```

```
Glu Val Val Asp Ile Leu Thr Glu Gln Leu Asp Ile Gln Leu Glu
                100                 105                 110
Asn Tyr Thr Pro Lys Glu Pro Leu Thr Leu Gln Ala Arg Met Ser Cys
            115                 120                 125
Glu Gln Lys Ala Glu Gly His Ser Ser Gly Ser Trp Gln Phe Ser Ile
        130                 135                 140
Asp Gly Gln Thr Phe Leu Leu Phe Asp Ser Glu Lys Arg Met Trp Thr
145                 150                 155                 160
Thr Val His Pro Gly Ala Arg Lys Met Lys Glu Lys Trp Glu Asn Asp
                165                 170                 175
Lys Asp Val Ala Met Ser Phe His Tyr Ile Ser Met Gly Asp Cys Ile
            180                 185                 190
Gly Trp Leu Glu Asp Phe Leu Met Gly Met Asp Ser Thr Leu Glu Pro
        195                 200                 205
Ser Ala Gly
    210

<210> SEQ ID NO 48
<211> LENGTH: 9
<212> TYPE: PRT
<213> ORGANISM: HIV-1 virus
<220> FEATURE:
<223> OTHER INFORMATION: FP polypeptide

<400> SEQUENCE: 48

Gly Ala Leu Phe Leu Gly Phe Leu Gly
1               5

<210> SEQ ID NO 49
<211> LENGTH: 9
<212> TYPE: PRT
<213> ORGANISM: artificial sequence
<220> FEATURE:
<223> OTHER INFORMATION: FP polypeptide

<400> SEQUENCE: 49

Ala Gly Phe Gly Leu Leu Leu Gly Phe
1               5

<210> SEQ ID NO 50
<211> LENGTH: 9
<212> TYPE: PRT
<213> ORGANISM: artificial sequence
<220> FEATURE:
<223> OTHER INFORMATION: FP polypeptide

<400> SEQUENCE: 50

Ala Gly Leu Phe Leu Gly Phe Leu Gly
1               5

<210> SEQ ID NO 51
<211> LENGTH: 59
<212> TYPE: DNA
<213> ORGANISM: Homo sapiens
<220> FEATURE:
<223> OTHER INFORMATION: Target TRAC

<400> SEQUENCE: 51
tgatcctctt gtcccacaga tatccagaac cctgaccctg ccgtgtacca gctgagaga      59

<210> SEQ ID NO 52
<211> LENGTH: 2832
<212> TYPE: DNA
```

<213> ORGANISM: artificial sequence
<220> FEATURE:
<223> OTHER INFORMATION: TALEN TRAC LEFT

<400> SEQUENCE: 52

```
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcag cgttgccaga ggcgacacac     300
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gacccggag caggtggtgg ccatcgccag ccacgatggc     540
ggcaagcagg cgctggagac ggtccagcgg ctgttgccgg tgctgtgcca gcccacggc     600
ttgacccccc agcaggtggt ggccatcgcc agcaatggcg gtggcaagca ggcgctggag     660
acggtccagc ggctgttgcc ggtgctgtgc caggcccacg gcttgacccc ggagcaggtg     720
gtggccatcg ccagccacga tggcggcaag caggcgctgg agacggtcca gcggctgttg     780
ccggtgctgt gccaggccca cggcttgacc ccggagcagg tggtggccat cgccagcaat     840
attggtggca gcaggcgct ggagacggtg caggcgctgt gccggtgct gtgccaggcc      900
cacggcttga ccccccagca ggtggtggcc atcgccagca ataatggtgg caagcaggcg     960
ctggagacgg tccagcggct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgacccccc agcaggtggt ggccatcgcc    1140
agcaatggcg gtggcaagca ggcgctggag acggtccagc ggctgttgcc ggtgctgtgc    1200
caggcccacg gcttgacccc ccagcaggtg gtggccatcg ccagcaataa tggtggcaag    1260
caggcgctgg agacggtcca gcggctgttg ccggtgctgt gccaggccca cggcttgacc    1320
ccccagcagg tggtggccat cgccagcaat aatggtggca gcaggcgct ggagacggtc     1380
cagcggctgt gccggtgct gtgccaggcc cacggcttga ccccccagca ggtggtggcc    1440
atcgccagca atggcggtgg caagcaggcg ctggagacgg tccagcggct gttgccggtg    1500
ctgtgccagg cccacggctt gacccccgag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccggagcagg tggtggccat cgccagccac    1860
gatggcggca gcaggcgct ggagacggtc cagcggctgt gccggtgct gtgccaggcc      1920
cacggcttga ccccccagca ggtggtggcc atcgccagca ataatggtgg caagcaggcg    1980
ctggagacgg tccagcggct gttgccggtg ctgtgccagg cccacggctt gaccccctcag   2040
caggtggtgg ccatcgccag caatggcggc ggcaggccgg cgctggagag cattgttgcc    2100
cagttatctc gccctgatcc ggcgttggcc gcgttgacca cgaccacct cgtcgccttg     2160
gcctgcctcg gcgggcgtcc tgcgctggat gcagtgaaaa agggattggg ggatcctatc    2220
```

```
agccgttccc agctggtgaa gtccgagctg gaggagaaga aatccgagtt gaggcacaag    2280
ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtacccctcc agcgtgaccg agttcaagtt cctgttcgtg    2640
tccggccact tcaagggcaa ctacaaggcc agctgacca ggctgaacca catcaccaac    2700
tgcaacggcg ccgtgctgtc cgtggaggag ctcctgatcg gcggcgagat gatcaaggcc    2760 ggcacccctga ccctggagga ggtgaggagg aagttcaaca cggcgagat caacttcgcg    2820 gccgactgat aa                                                        2832
```

<210> SEQ ID NO 53
<211> LENGTH: 2814
<212> TYPE: DNA
<213> ORGANISM: artificial sequence
<220> FEATURE:
<223> OTHER INFORMATION: TALEN TRAC RIGHT

<400> SEQUENCE: 53

```
atgggcgatc ctaaaaagaa acgtaaggtc atcgattacc catacgatgt tccagattac     60
gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa caccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgacccccc agcaggtggt ggccatcgcc agcaatggcg gtggcaagca ggcgctggag    540
acggtccagc ggctgttgcc ggtgctgtgc caggcccacg gcttgacccc ccagcaggtg    600
gtggccatcg ccagcaataa tggtggcaag caggcgctgg agacggtcca gcggctgttg    660
ccggtgctgt gccaggccca cggcttgacc ccccagcagg tggtggccat cgccagcaat    720
ggcggtggca agcaggcgct ggagacggtc agcggctgt tgccggtgct gtgccaggcc    780
cacggcttga ccccggagca ggtggtggcc atcgccagcc acgatggcgg caagcaggcg    840
ctggagacgg tccagcggct gttgccggtg ctgtgccagg cccacggctt gaccccggag    900
caggtggtgg ccatcgccag ccacgatggc ggcaagcagg cgctggagac ggtccagcgg    960
ctgttgccgg tgctgtgcca ggcccacggc ttgaccccgg agcaggtggt ggccatcgcc   1020
agccacgatg gcggcaagca ggcgctggag acggtccagc ggctgttgcc ggtgctgtgc   1080
caggcccacg gcttgacccc ggagcaggtg gtggccatcg ccagcaatat tggtggcaag   1140
caggcgctga gacggtgca ggcgctgttg ccggtgctgt gccaggccca cggcttgacc   1200
ccggagcagg tggtggccat cgccagccac gatggcggca agcaggcgct ggagacggtc   1260
cagcggctgt tgccggtgct gtgccaggcc cacggcttga ccccggagca ggtggtggcc   1320
atcgccagca atattggtgg caagcaggcg ctggagacgg tgcaggcgct gttgccggtg   1380
```

```
ctgtgccagg cccacggctt gaccccccag caggtggtgg ccatcgccag caataatggt    1440
ggcaagcagg cgctggagac ggtccagcgg ctgttgccgg tgctgtgcca ggcccacggc    1500
ttgaccccgg agcaggtggt ggccatcgcc agcaatattg gtggcaagca ggcgctggag    1560
acggtgcagg cgctgttgcc ggtgctgtgc caggcccacg gcttgacccc ccagcaggtg    1620
gtggccatcg ccagcaatgg cggtggcaag caggcgctgg agacggtcca gcggctgttg    1680
ccggtgctgt gccaggccca cggcttgacc ccggagcagg tggtggccat cgccagcaat    1740
attggtggca agcaggcgct ggagacggtg caggcgctgt tgccggtgct gtgccaggcc    1800
cacggcttga ccccccagca ggtggtggcc atcgccagca atggcggtgg caagcaggcg    1860
ctggagacgg tccagcggct gttgccggtg ctgtgccagg cccacggctt gaccccggag    1920
caggtggtgg ccatcgccag ccacgatggc ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca gctgaagta cgtgccccac    2280 gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg gccaggccga cgaaatgcag    2520
aggtacgtgg aggagaacca gaccaggaac aagcacatca ccccaacga gtggtggaag    2580 gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814

<210> SEQ ID NO 54
<211> LENGTH: 49
<212> TYPE: DNA
<213> ORGANISM: Homo sapiens
<220> FEATURE:
<223> OTHER INFORMATION: Target TRAC-T01

<400> SEQUENCE: 54
ttgtcccaca gatatccaga accctgaccc tgccgtgtac cagctgaga                  49

<210> SEQ ID NO 55
<211> LENGTH: 2814
<212> TYPE: DNA
<213> ORGANISM: artificial sequence
<220> FEATURE:
<223> OTHER INFORMATION: TALEN TRAC T01 LEFT

<400> SEQUENCE: 55
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa cacccggcag cgttagggac cgtcgctgtc     240
aagtatcagg acatgatcgc agcgttgcca gaggcgacac acgaagcgat cgttggcgtc     300
```

```
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480 ttgaccccc agcaggtggt ggccatcgcc agcaatggcg gtggcaagca ggcgctggag     540
acggtccagc ggctgttgcc ggtgctgtgc caggcccacg gcttgacccc ccagcaggtg    600
gtggccatcg ccagcaataa tggtggcaag caggcgctgg agacggtcca gcggctgttg    660
ccggtgctgt gccaggccca cggcttgacc cccagcagg tggtggccat cgccagcaat     720
ggcggtggca agcaggcgct ggagacggtc agcggctgt tgccggtgct gtgccaggcc     780
cacggcttga ccccggagca ggtggtggcc atcgccagcc acgatggcgg caagcaggcg    840
ctggagacgg tccagcggct gttgccggtg ctgtgccagg cccacggctt gaccccggag    900
caggtggtgg ccatcgccag ccacgatggc ggcaagcagg cgctggagac ggtccagcgg    960
ctgttgccgg tgctgtgcca ggcccacggc ttgaccccgg agcaggtggt ggccatcgcc   1020
agccacgatg gcggcaagca ggcgctggag acggtccagc ggctgttgcc ggtgctgtgc   1080
caggcccacg gcttgacccc ggagcaggtg gtggccatcg ccagcaatat tggtggcaag   1140
caggcgctgg agacggtgca ggcgctgttg ccggtgctgt gccaggccca cggcttgacc   1200
ccggagcagg tggtggccat cgccagccac gatggcggca agcaggcgct ggagacggtc   1260
cagcggctgt tgccggtgct gtgccaggcc cacggcttga ccccggagca ggtggtggcc   1320
atcgccagca atattggtgg caagcaggcg ctggagacgg tgcaggcgct gttgccggtg   1380
ctgtgccagg cccacggctt gaccccccag caggtggtgg ccatcgccag caataatggt   1440
ggcaagcagg cgctggagac ggtccagcgg ctgttgccgg tgctgtgcca ggcccacggc   1500
ttgaccccgg agcaggtggt ggccatcgcc agcaatattg gtggcaagca ggcgctggag   1560
acggtgcagg cgctgttgcc ggtgctgtgc caggcccacg gcttgacccc ccagcaggtg   1620
gtggccatcg ccagcaatgg cggtggcaag caggcgctgg agacggtcca gcggctgttg   1680
ccggtgctgt gccaggccca cggcttgacc ccggagcagg tggtggccat cgccagcaat   1740
attggtggca agcaggcgct ggagacggtg caggcgctgt tgccggtgct gtgccaggcc   1800
cacggcttga ccccccagca ggtggtggcc atcgccagca atggcggtgg caagcaggcg   1860
ctggagacgg tccagcggct gttgccggtg ctgtgccagg cccacggctt gaccccggag   1920
caggtggtgg ccatcgccag ccacgatggc ggcaagcagg cgctggagac ggtccagcgg   1980
ctgttgccgg tgctgtgcca ggcccacggc ttgaccccct cagcaggtggt ggccatcgcc   2040 agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg ggggatccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acgcgccat ctacaccgtg gctcccccca tcgactacgg cgtgatcgtg   2460
gacaccaagg cctactccgg cggctacaac ctgcccatcg ccaggcgcga cgaaatgcag   2520
aggtacgtgg aggagaacca gaccaggaac aagcacatca cccccaacga gtggtggaag   2580
gtgtaccccc tccagcgtga ccgagttcaag ttcctgttcg tgtccggcca cttcaagggc   2640
```

```
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814

<210> SEQ ID NO 56
<211> LENGTH: 2832
<212> TYPE: DNA
<213> ORGANISM: artificial sequence
<220> FEATURE:
<223> OTHER INFORMATION: TALEN TRAC T01 RIGHT

<400> SEQUENCE: 56
atgggcgatc ctaaaaagaa acgtaaggtc atcgataagg agaccgccgc tgccaagttc      60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcac cgttgccaga ggcgacacac    300
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccggag caggtggtgg ccatcgccag ccacgatggc    540
ggcaagcagg cgctggagac ggtccagcgg ctgttgccgg tgctgtgcca ggcccacggc    600
ttgacccccc agcaggtggt ggccatcgcc agcaatggcg gtggcaagca ggcgctggag    660
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc ccggagcagg tggtggccat cgccagcaat    840
attggtggca gcaggcgctg gagacggtg caggcgctgt tgccggtgct gtgccaggcc    900
cacggcttga ccccccagca ggtggtggcc atcgccagca ataatggtgg caagcaggcg    960
ctggagacgg tccagcggct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgacccccc agcaggtggt ggccatcgcc    1140
agcaatggcg gtggcaagca ggcgctggag acggtccagc ggctgttgcc ggtgctgtgc    1200
caggcccacg gcttgacccc ccagcaggtg gtggccatcg ccagcaataa tggtggcaag    1260
caggcgctgg agacggtcca gcggctgttg ccggtgctgt gccaggccca cggcttgacc    1320
ccccagcagg tggtggccat cgccagcaat aatggtggca agcaggcgct ggagacggtc    1380
cagcggctgt tgccggtgct gtgccaggcc cacggcttga ccccccagca ggtggtggcc    1440
atcgccagca atggcggtgg caagcaggcg ctggagacgg tccagcggct gttgccggtg    1500
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgacccccg gagcaggtgg tggccatcgc cagccacgat gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccggagcagg tggtggccat cgccagccac    1860
gatggcggca agcaggcgct ggagacggtc cagcggctgt tgccggtgct gtgccaggcc    1920
```

```
cacggcttga ccccccagca ggtggtggcc atcgccagca ataatggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag     2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtacccctcc agcgtgaccg agttcaagtt cctgttcgtg    2640
tccggccact tcaagggcaa ctacaaggcc cagctgacca ggctgaacca tcaccaac     2700 tgcaacggcg ccgtgctgtc cgtggaggag ctcctgatcg gcggcgagat gatcaaggcc    2760 ggcacccctga ccctggagga ggtgaggagg aagttcaaca acggcgagat caacttcgcg   2820
gccgactgat aa                                                        2832
```

<210> SEQ ID NO 57
<211> LENGTH: 49
<212> TYPE: DNA
<213> ORGANISM: Homo sapiens
<220> FEATURE:
<223> OTHER INFORMATION: Target TRAC-T02

<400> SEQUENCE: 57

```
tttagaaagt tcctgtgatg tcaagctggt cgagaaaagc tttgaaaca                 49
```

<210> SEQ ID NO 58
<211> LENGTH: 49
<212> TYPE: DNA
<213> ORGANISM: Homo sapiens
<220> FEATURE:
<223> OTHER INFORMATION: Target TRAC-T03

<400> SEQUENCE: 58

```
tccagtgaca agtctgtctg cctattcacc gattttgatt ctcaaacaa                 49
```

<210> SEQ ID NO 59
<211> LENGTH: 49
<212> TYPE: DNA
<213> ORGANISM: Homo sapiens
<220> FEATURE:
<223> OTHER INFORMATION: Target TRAC-T04

<400> SEQUENCE: 59

```
tatatcacag acaaaactgt gctagacatg aggtctatgg acttcaaga                 49
```

<210> SEQ ID NO 60
<211> LENGTH: 49
<212> TYPE: DNA
<213> ORGANISM: Homo sapiens
<220> FEATURE:
<223> OTHER INFORMATION: Target TRAC-T05

<400> SEQUENCE: 60
tgaggtctat ggacttcaag agcaacagtg ctgtggcctg gagcaacaa         49

<210> SEQ ID NO 61
<211> LENGTH: 49
<212> TYPE: DNA
<213> ORGANISM: Homo sapiens
<220> FEATURE:
<223> OTHER INFORMATION: Target TRBC_T01

<400> SEQUENCE: 61
tgtgtttgag ccatcagaag cagagatctc ccacacccaa aaggccaca         49

<210> SEQ ID NO 62
<211> LENGTH: 2814
<212> TYPE: DNA
<213> ORGANISM: artificial sequence
<220> FEATURE:
<223> OTHER INFORMATION: TALEN TRBC_T01 LEFT

<400> SEQUENCE: 62
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa caccggcag cgttagggac cgtcgctgtc    240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca gagattgcaaa acgtggcggc  420
gtgaccgcag tggaggcagt gcatgcatgg cgcaatgcac tgacgggtgc cccgctcaac   480
ttgaccccc agcaggtggt ggccatcgcc agcaataatg gtggcaagca ggcgctggag    540
acggtccagc ggctgttgcc ggtgctgtgc caggcccacg gcttgacccc ccagcaggtg   600
gtggccatcg ccagcaatgg cggtggcaag caggcgctgg agacggtcca gcggctgttg   660
ccggtgctgt gccaggccca cggcttgacc cccagcagg tggtggccat cgccagcaat    720
aatggtggca gcaggcgct ggagacggtc agcggctgt tgccggtgct gtgccaggcc    780
cacggcttga cccccagca ggtggtggcc atcgccagca atggcggtgg caagcaggcg   840
ctggagacgg tccagcggct gttgccggtg ctgtgccagg cccacggctt gaccccccag   900
caggtggtgg ccatcgccag caatggcggt ggcaagcagg cgctggagac ggtccagcgg   960
ctgttgccgg tgctgtgcca ggcccacggc ttgaccccc agcaggtggt ggccatcgcc   1020
agcaatggcg gtggcaagca ggcgctggag acggtccagc ggctgttgcc ggtgctgtgc   1080
caggcccacg gcttgacccc ccagcaggtg gtggccatcg ccagcaataa tggtggcaag   1140
caggcgctgg agacggtcca gcggctgttg ccggtgctgt gccaggccca cggcttgacc   1200
ccggagcagg tggtggccat cgccagcaat attggtggca gcaggcgct ggagacggtg    1260
caggcgctgt gccggtgct gtgccaggcc cacggcttga cccccagca ggtggtggcc    1320
atcgccagca ataatggtgg caagcaggcg ctggagacgg tccagcggct gttgccggtg   1380
ctgtgccagg cccacggctt gaccccggag caggtggtgg ccatcgccag ccacgatggc   1440
ggcaagcagg cgctggagac ggtccagcgg ctgttgccgg tgctgtgcca ggcccacggc   1500
ttgaccccgg agcaggtggt ggccatcgcc agcacgatg cggcaagca ggcgctggag    1560
acggtccagc ggctgttgcc ggtgctgtgc caggcccacg gcttgacccc ggagcaggtg   1620
gtggccatcg ccagcaatat tggtggcaag caggcgctgg agacggtgca ggcgctgttg   1680

```
ccggtgctgt gccaggccca cggcttgacc ccccagcagg tggtggccat cgccagcaat    1740
ggcggtggca agcaggcgct ggagacggtc agcggctgt tgccggtgct gtgccaggcc     1800
cacggcttga ccccggagca ggtggtggcc atcgccagcc acgatggcgg caagcaggcg    1860
ctggagacgg tccagcggct gttgccggtg ctgtgccagg cccacggctt gaccccggag    1920
caggtggtgg ccatcgccag caatattggt ggcaagcagg cgctggagac ggtgcaggcg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg ccaggccgga cgaaatgcag    2520
aggtacgtgg aggagaacca gaccaggaac aagcacatca accccaacga gtggtggaag    2580
gtgtacccct ccagcgtgac cgagttcaag ttcctgttcg tgtccggcca cttcaagggc    2640
aactacaagg cccagctgac caggctgaac cacatcacca ctgcaacgg cgccgtgctg    2700 tccgtggagg agctcctgat cggcggcgag atgatcaagg ccggcacct gaccctggag    2760 gaggtgagga ggaagttcaa caacggcgag atcaacttcg cggccgactg ataa        2814
```

<210> SEQ ID NO 63
<211> LENGTH: 2832
<212> TYPE: DNA
<213> ORGANISM: artificial sequence
<220> FEATURE:
<223> OTHER INFORMATION: TALEN TRBC_T01 RIGHT

<400> SEQUENCE: 63

```
atgggcgatc taaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccc tcgctgtcaa gtatcaggac atgatcgcac gttgccaga ggcgacacac     300 gaagcgatcg ttggcgtcgg caaacagtgg tccggcgcac gcgctctgga ggccttgctc    360 acggtggcg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gacccccag caggtggtgg ccatcgccag caataatggt    540
ggcaagcagg cgctggagac ggtccagcgg ctgttgccgg tgctgtgcca ggcccacggc    600
ttgacccccc agcaggtggt ggccatcgcc agcaatggcg gtggcaagca ggcgctggag    660
acggtccagc ggctgttgcc ggtgctgtgc caggcccacg gcttgacccc ccagcaggtg    720
gtggccatcg ccagcaataa tggtggcaag caggcgctgg agacggtcca gcggctgttg    780
ccggtgctgt gccaggccca cggcttgacc ccccagcagg tggtggccat cgccagcaat    840
aatggtggca agcaggcgct ggagacggtc agcggctgt tgccggtgct gtgccaggcc     900
```

```
cacggcttga ccccggagca ggtggtggcc atcgccagcc acgatggcgg caagcaggcg      960
ctggagacgg tccagcggct gttgccggtg ctgtgccagg cccacggctt gaccccggag     1020
caggtggtgg ccatcgccag ccacgatggc ggcaagcagg cgctggagac ggtccagcgg     1080
ctgttgccgg tgctgtgcca ggcccacggc ttgaccccc agcaggtggt ggccatcgcc      1140
agcaatggcg gtggcaagca ggcgctggag acggtccagc ggctgttgcc ggtgctgtgc     1200
caggcccacg gcttgacccc ccagcaggtg gtggccatcg ccagcaatgg cggtggcaag     1260
caggcgctgg agacggtcca gcggctgttg ccggtgctgt gccaggccca cggcttgacc     1320
ccccagcagg tggtggccat cgccagcaat ggcggtggca agcaggcgct ggagacggtc     1380
cagcggctgt tgccggtgct gtgccaggcc acggcttga ccccccagca ggtggtggcc      1440
atcgccagca atggcggtgg caagcaggcg ctggagacgg tccagcggct gttgccggtg     1500
ctgtgccagg cccacggctt gaccccccag caggtggtgg ccatcgccag caataatggt     1560
ggcaagcagg cgctggagac ggtccagcgg ctgttgccgg tgctgtgcca ggcccacggc     1620
ttgaccccc agcaggtggt ggccatcgcc agcaataatg gtggcaagca ggcgctggag      1680
acggtccagc ggctgttgcc ggtgctgtgc caggcccacg gcttgacccc ccagcaggtg     1740
gtggccatcg ccagcaataa tggtggcaag caggcgctgg agacggtcca gcggctgttg     1800
ccggtgctgt gccaggccca cggcttgacc ccccagcagg tggtggccat cgccagcaat     1860
ggcggtggca agcaggcgct ggagacggtc agcggctgt tgccggtgct gtgccaggcc      1920
cacggcttga ccccccagca ggtggtggcc atcgccagca ataatggtgg caagcaggcg     1980
ctggagacgg tccagcggct gttgccggtg ctgtgccagg cccacggctt gaccctcag      2040
caggtggtgg ccatcgccag caatggcggc ggcaggccgg cgctggagag cattgttgcc     2100
cagttatctc gccctgatcc ggcgttggcc gcgttgacca acgaccacct cgtcgccttg     2160
gcctgcctcg gcgggcgtcc tgcgctggat gcagtgaaaa agggattggg ggatcctatc     2220
agccgttccc agctggtgaa gtccgagctg aggagaaga aatccgagtt gaggcacaag      2280
ctgaagtacg tgccccacga gtacatcgag ctgatcgaga tcgcccggaa cagcacccag     2340
gaccgtatcc tggagatgaa ggtgatggag ttcttcatga aggtgtacgg ctacaggggc     2400
aagcacctgg gcggctccag gaagcccgac ggcgccatct acaccgtggg ctcccccatc     2460
gactacggcg tgatcgtgga caccaaggcc tactccggcg gctacaacct gcccatcggc     2520
caggccgacg aaatgcagag gtacgtggag gagaaccaga ccaggaacaa gcacatcaac     2580
cccaacgagt ggtggaaggt gtacccctcc agcgtgaccg agttcaagtt cctgttcgtg     2640
tccggccact tcaagggcaa ctacaaggcc cagctgacca ggctgaacca catcaccaac     2700
tgcaacggcg ccgtgctgtc cgtgaggag ctcctgatcg gcggcgagat gatcaaggcc      2760
ggcaccctga ccctggagga ggtgaggagg aagttcaaca cggcgagat caacttcgcg      2820
gccgactgat aa                                                        2832
```

<210> SEQ ID NO 64
<211> LENGTH: 50
<212> TYPE: DNA
<213> ORGANISM: Homo sapiens
<220> FEATURE:
<223> OTHER INFORMATION: Target TRBC_T02

<400> SEQUENCE: 64

```
ttcccacccg aggtcgctgt gtttgagcca tcagaagcag agatctccca               50
```

<210> SEQ ID NO 65
<211> LENGTH: 2814
<212> TYPE: DNA
<213> ORGANISM: artificial sequence
<220> FEATURE:
<223> OTHER INFORMATION: TALEN TRBC_T02 LEFT

<400> SEQUENCE: 65

```
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa caccccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480
ttgaccccgg agcaggtggt ggccatcgcc agccacgatg gcggcaagca ggcgctggag   540
acggtccagc ggctgttgcc ggtgctgtgc caggcccacg gcttgacccc ggagcaggtg   600
gtggccatcg ccagccacga tggcggcaag caggcgctgg agacggtcca gcggctgttg   660
ccggtgctgt gccaggccca cggcttgacc ccggagcagg tggtggccat cgccagccac   720
gatggcggca agcaggcgct ggagacggtc agcggctgt tgccggtgct gtgccaggcc   780
cacggcttga ccccggagca ggtggtggcc atcgccagca atattggtgg caagcaggcg   840
ctggagacgg tgcaggcgct gttgccggtg ctgtgccagg cccacggctt gaccccggag   900
caggtggtgg ccatcgccag ccacgatggc ggcaagcagg cgctggagac ggtccagcgg   960
ctgttgccgg tgctgtgcca ggcccacggc ttgaccccgg agcaggtggt ggccatcgcc  1020
agccacgatg gcggcaagca ggcgctggag acggtccagc ggctgttgcc ggtgctgtgc  1080
caggcccacg gcttgacccc ggagcaggtg gtggccatcg ccagccacga tggcggcaag  1140
caggcgctgg agacggtcca gcggctgttg ccggtgctgt gccaggccca cggcttgacc  1200
ccccagcagg tggtggccat cgccagcaat aatggtggca agcaggcgct ggagacggtc  1260
cagcggctgt tgccggtgct gtgccaggcc cacggcttga ccccggagca ggtggtggcc  1320
atcgccagca atattggtgg caagcaggcg ctggagacgg tgcaggcgct gttgccggtg  1380
ctgtgccagg cccacggctt gacccccag caggtggtgg ccatcgccag caataatggt  1440
ggcaagcagg cgctggagac ggtccagcgg ctgttgccgg tgctgtgcca ggcccacggc  1500
ttgacccccc agcaggtggt ggccatcgcc agcaataatg gtggcaagca ggcgctggag  1560
acggtccagc ggctgttgcc ggtgctgtgc caggcccacg gcttgacccc ccagcaggtg  1620
gtggccatcg ccagcaatgg cggtggcaag caggcgctgg agacggtcca gcggctgttg  1680
ccggtgctgt gccaggccca cggcttgacc ccggagcagg tggtggccat cgccagccac  1740
gatggcggca agcaggcgct ggagacggtc agcggctgt tgccggtgct gtgccaggcc  1800
cacggcttga ccccccagca ggtggtggcc atcgccagca ataatggtgg caagcaggcg  1860
ctggagacgg tccagcggct gttgccggtg ctgtgccagg cccacggctt gaccccggag  1920
caggtggtgg ccatcgccag ccacgatggc ggcaagcagg cgctggagac ggtccagcgg  1980
ctgttgccgg tgctgtgcca ggcccacggc ttgacccctc agcaggtggt ggccatcgcc  2040
agcaatggcg gcggcaggcc ggcgctggag agcattgttg cccagttatc tcgccctgat  2100
```

```
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg gctcccccca tcgactacgg cgtgatcgtg    2460
gacaccaagg cctactccgg cggctacaac ctgcccatcg gccaggccga cgaaatgcag    2520
aggtacgtgg aggagaacca gaccaggaac aagcacatca cccccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcacccc tgaccctgga g   2760 gaggtgagga ggaagttcaa caacggcgag atcaacttcg cggccgactg ataa          2814
```

<210> SEQ ID NO 66
<211> LENGTH: 2832
<212> TYPE: DNA
<213> ORGANISM: artificial sequence
<220> FEATURE:
<223> OTHER INFORMATION: TALEN TRBC_T02 RIGHT

<400> SEQUENCE: 66

```
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcag cgttgccaga ggcgacacac     300
gaagcgatct tggcgtcgg caaacagtgg tccggcgcac gcgctctgga ggccttgctc     360
acggtggcgg gagagttgag aggtccaccg ttacagttgg acacaggcca acttctcaag     420
attgcaaaac gtgccggcgt gaccgcagtg gaggcagtgc atgcatggcg caatgcactg     480
acgggtgccc cgctcaactt gaccccccag caggtggtgg ccatcgccag caataatggt     540
ggcaagcagg cgctggagac ggtccagcgg ctgttgccgg tgctgtgcca ggcccacggc     600 ttgaccccc agcaggtggt ggccatcgcc agcaataatg gtggcaagca ggcgctggag     660
acggtccagc ggctgttgcc ggtgctgtgc caggcccacg gcttgacccc ccagcaggtg     720
gtggccatcg ccagcaataa tggtggcaag caggcgctgg agacggtcca gcggctgttg     780
ccggtgctgt gccaggccca cggcttgacc ccggagcagg tggtggccat cgccagcaat     840
attggtggca gcaggcgct ggagacggtg caggcgctgt gccggtgct gtgccaggcc       900 cacggcttga ccccccagca ggtggtggcc atcgccagca ataatggtgg caagcaggcg     960
ctggagacgg tccagcggct gttgccgtg ctgtgccagg cccacggctt gaccccggag     1020
caggtggtgg ccatcgccag caatattggt ggcaagcagg cgctggagac ggtgcaggcg    1080
ctgttgccgg tgctgtgcca ggcccacggc ttgaccccc agcaggtggt ggccatcgcc     1140
agcaatggcg gtggcaagca ggcgctggag acggtccagc ggctgttgcc ggtgctgtgc    1200
caggcccacg gcttgacccc ggagcaggtg gtggccatcg ccagccacga tggcggcaag    1260
caggcgctga gacggtcca gcggctgttg ccggtgctgt gccaggccca cggcttgacc    1320
ccccagcagg tggtggccat cgccagcaat ggcggtggca agcaggcgct ggagacggtc    1380
```

```
cagcggctgt tgccggtgct gtgccaggcc cacggcttga ccccggagca ggtggtggcc    1440
atcgccagcc acgatggcgg caagcaggcg ctggagacgg tccagcggct gttgccggtg    1500
ctgtgccagg cccacggctt gaccccccag caggtggtgg ccatcgccag caatggcggt    1560
ggcaagcagg cgctggagac ggtccagcgg ctgttgccgg tgctgtgcca ggcccacggc    1620 ttgaccccccc agcaggtggt ggccatcgcc agcaataatg gtggcaagca ggcgctggag    1680
acggtccagc ggctgttgcc ggtgctgtgc caggcccacg gcttgacccc ggagcaggtg    1740
gtggccatcg ccagccacga tggcggcaag caggcgctgg agacggtcca gcggctgttg    1800
ccggtgctgt gccaggccca cggcttgacc cccagcagg tggtggccat cgccagcaat    1860
ggcggtggca agcaggcgct ggagacggtc agcggctgt tgccggtgct gtgccaggcc    1920
cacggcttga ccccccagca ggtggtggcc atcgccagca atggcggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg aggagaaga atccgagtt gaggcacaag    2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacagggc    2400 aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg    2640
tccggccact tcaagggcaa ctacaaggcc cagctgacca ggctgaacca tcaccaac    2700 tgcaacggcg ccgtgctgtc cgtggaggag ctcctgatcg gcggcgagat gatcaaggcc    2760 ggcacctga ccctggagga ggtgaggagg aagttcaaca cggcgagat caacttcgcg    2820 gccgactgat aa    2832
```

<210> SEQ ID NO 67
<211> LENGTH: 557
<212> TYPE: PRT
<213> ORGANISM: murine
<220> FEATURE:
<223> OTHER INFORMATION: CD19 antigen

<400> SEQUENCE: 67

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95
```

-continued

```
Cys Gln Pro Gly Pro Pro Ser Glu Lys Ala Trp Gln Pro Gly Trp Thr
                100                 105                 110
Val Asn Val Glu Gly Ser Gly Glu Leu Phe Arg Trp Asn Val Ser Asp
            115                 120                 125
Leu Gly Gly Leu Gly Cys Gly Leu Lys Asn Arg Ser Ser Glu Gly Pro
        130                 135                 140
Ser Ser Pro Ser Gly Lys Leu Met Ser Pro Lys Leu Tyr Val Trp Ala
145                 150                 155                 160
Lys Asp Arg Pro Glu Ile Trp Glu Gly Glu Pro Pro Cys Leu Pro Pro
                165                 170                 175
Arg Asp Ser Leu Asn Gln Ser Leu Ser Gln Asp Leu Thr Met Ala Pro
            180                 185                 190
Gly Ser Thr Leu Trp Leu Ser Cys Gly Val Pro Pro Asp Ser Val Ser
        195                 200                 205
Arg Gly Pro Leu Ser Trp Thr His Val His Pro Lys Gly Pro Lys Ser
210                 215                 220
Leu Leu Ser Leu Glu Leu Lys Asp Asp Arg Pro Ala Arg Asp Met Trp
225                 230                 235                 240
Val Met Glu Thr Gly Leu Leu Leu Pro Arg Ala Thr Ala Gln Asp Ala
                245                 250                 255
Gly Lys Tyr Tyr Cys His Arg Gly Asn Leu Thr Met Ser Phe His Leu
            260                 265                 270
Glu Ile Thr Ala Arg Pro Val Leu Trp His Trp Leu Leu Arg Thr Gly
        275                 280                 285
Gly Trp Lys Val Ser Ala Val Thr Leu Ala Tyr Leu Ile Phe Cys Leu
    290                 295                 300
Cys Ser Leu Val Gly Ile Leu His Leu Gln Arg Ala Leu Val Leu Arg
305                 310                 315                 320
Arg Lys Arg Lys Arg Met Thr Asp Pro Thr Arg Arg Phe Phe Lys Val
                325                 330                 335
Thr Pro Pro Pro Gly Ser Gly Pro Gln Asn Gln Tyr Gly Asn Val Leu
            340                 345                 350
Ser Leu Pro Thr Pro Thr Ser Gly Leu Gly Arg Ala Gln Arg Trp Ala
        355                 360                 365
Ala Gly Leu Gly Gly Thr Ala Pro Ser Tyr Gly Asn Pro Ser Ser Asp
    370                 375                 380
Val Gln Ala Asp Gly Ala Leu Gly Ser Arg Ser Pro Pro Gly Val Gly
385                 390                 395                 400
Pro Glu Glu Glu Glu Gly Glu Gly Tyr Glu Glu Pro Asp Ser Glu Glu
                405                 410                 415
Asp Ser Glu Phe Tyr Glu Asn Asp Ser Asn Leu Gly Gln Asp Gln Leu
            420                 425                 430
Ser Gln Asp Gly Ser Gly Tyr Glu Asn Pro Glu Asp Glu Pro Leu Gly
        435                 440                 445
Pro Glu Asp Glu Asp Ser Phe Ser Asn Ala Glu Ser Tyr Glu Asn Glu
    450                 455                 460
Asp Glu Glu Leu Thr Gln Pro Val Ala Arg Thr Met Asp Phe Leu Ser
465                 470                 475                 480
Pro His Gly Ser Ala Trp Asp Pro Ser Arg Glu Ala Thr Ser Leu Ala
                485                 490                 495
Gly Ser Gln Ser Tyr Glu Asp Met Arg Gly Ile Leu Tyr Ala Ala Pro
            500                 505                 510
Gln Leu Arg Ser Ile Arg Gly Gln Pro Gly Pro Asn His Glu Glu Asp
```

```
                515                 520                 525
Ala Asp Ser Tyr Glu Asn Met Asp Asn Pro Asp Gly Pro Asp Pro Ala
530                 535                 540

Trp Gly Gly Gly Gly Arg Met Gly Thr Trp Ser Thr Arg
545                 550                 555

<210> SEQ ID NO 68
<211> LENGTH: 300
<212> TYPE: PRT
<213> ORGANISM: murine
<220> FEATURE:
<223> OTHER INFORMATION: CD38 antigen

<400> SEQUENCE: 68

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
                20                  25                  30

Leu Ile Leu Val Val Leu Ala Val Val Val Pro Arg Trp Arg Gln Gln
35                  40                  45

Gln Trp Ser Gly Pro Gly Thr Thr Lys Arg Phe Pro Glu Thr Val Leu
50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
                100                 105                 110

Gly Thr Gln Thr Val Pro Cys Asn Lys Ile Leu Leu Trp Ser Arg Ile
                115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
                180                 185                 190

Ser Arg Arg Phe Ala Glu Ala Ala Cys Asp Val Val His Val Met Leu
                195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
                260                 265                 270

Phe Ser Cys Lys Asn Ile Tyr Arg Pro Asp Lys Phe Leu Gln Cys Val
                275                 280                 285

Lys Asn Pro Glu Asp Ser Ser Cys Thr Ser Glu Ile
290                 295                 300

<210> SEQ ID NO 69
<211> LENGTH: 378
<212> TYPE: PRT
```

<213> ORGANISM: murine
<220> FEATURE:
<223> OTHER INFORMATION: CD123 antigen

<400> SEQUENCE: 69

```
Met Val Leu Leu Trp Leu Thr Leu Leu Ile Ala Leu Pro Cys Leu
1               5                   10                  15

Leu Gln Thr Lys Glu Asp Pro Asn Pro Ile Thr Asn Leu Arg Met
            20                  25                  30

Lys Ala Lys Ala Gln Gln Leu Thr Trp Asp Leu Asn Arg Asn Val Thr
            35                  40                  45

Asp Ile Glu Cys Val Lys Asp Ala Asp Tyr Ser Met Pro Ala Val Asn
            50                  55                  60

Asn Ser Tyr Cys Gln Phe Gly Ala Ile Ser Leu Cys Glu Val Thr Asn
65                  70                  75                  80

Tyr Thr Val Arg Val Ala Asn Pro Pro Phe Ser Thr Trp Ile Leu Phe
                85                  90                  95

Pro Glu Asn Ser Gly Lys Pro Trp Ala Gly Ala Glu Asn Leu Thr Cys
            100                 105                 110

Trp Ile His Asp Val Asp Phe Leu Ser Cys Ser Trp Ala Val Gly Pro
            115                 120                 125

Gly Ala Pro Ala Asp Val Gln Tyr Asp Leu Tyr Leu Asn Val Ala Asn
            130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

Ile Pro Cys Thr Asp Lys Phe Val Val Phe Ser Gln Ile Glu Ile Leu
            195                 200                 205

Thr Pro Pro Asn Met Thr Ala Lys Cys Asn Lys Thr His Ser Phe Met
210                 215                 220

His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270

Arg Ala Arg Glu Arg Val Tyr Glu Phe Leu Ser Ala Trp Ser Thr Pro
            275                 280                 285

Gln Arg Phe Glu Cys Asp Gln Glu Glu Gly Ala Asn Thr Arg Ala Trp
            290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335

Arg Ile Pro His Met Lys Asp Pro Ile Gly Asp Ser Phe Gln Asn Asp
            340                 345                 350

Lys Leu Val Val Trp Glu Ala Gly Lys Ala Gly Leu Glu Glu Cys Leu
            355                 360                 365

Val Thr Glu Val Gln Val Gln Lys Thr
            370                 375
```

```
<210> SEQ ID NO 70
<211> LENGTH: 335
<212> TYPE: PRT
<213> ORGANISM: murine
<220> FEATURE:
<223> OTHER INFORMATION: CS1 antigen

<400> SEQUENCE: 70

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205

Ile Leu Ala Arg Lys Leu Cys Glu Gly Ala Ala Asp Asp Pro Asp Ser
    210                 215                 220

Ser Met Val Leu Leu Cys Leu Leu Val Pro Leu Leu Leu Ser Leu
225                 230                 235                 240

Phe Val Leu Gly Leu Phe Leu Trp Phe Leu Lys Arg Glu Arg Gln Glu
                245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
        275                 280                 285

His Thr Asn Arg Thr Ile Leu Lys Glu Asp Pro Ala Asn Thr Val Tyr
    290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 71
<211> LENGTH: 184
<212> TYPE: PRT
<213> ORGANISM: murine
<220> FEATURE:
<223> OTHER INFORMATION: BCMA antigen
```

<400> SEQUENCE: 71

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

<210> SEQ ID NO 72
<211> LENGTH: 993
<212> TYPE: PRT
<213> ORGANISM: murine
<220> FEATURE:
<223> OTHER INFORMATION: FLT3 antigen

<400> SEQUENCE: 72

```
Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
            20                  25                  30

Ile Lys Cys Val Leu Ile Asn His Lys Asn Asn Asp Ser Ser Val Gly
        35                  40                  45

Lys Ser Ser Ser Tyr Pro Met Val Ser Glu Ser Pro Glu Asp Leu Gly
    50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160
```

-continued

```
Arg Asn Thr Leu Leu Tyr Thr Leu Arg Arg Pro Tyr Phe Arg Lys Met
                165                 170                 175
Glu Asn Gln Asp Ala Leu Val Cys Ile Ser Glu Ser Val Pro Glu Pro
            180                 185                 190
Ile Val Glu Trp Val Leu Cys Asp Ser Gln Gly Glu Ser Cys Lys Glu
        195                 200                 205
Glu Ser Pro Ala Val Val Lys Lys Glu Lys Val Leu His Glu Leu
    210                 215                 220
Phe Gly Thr Asp Ile Arg Cys Cys Ala Arg Asn Glu Leu Gly Arg Glu
225                 230                 235                 240
Cys Thr Arg Leu Phe Thr Ile Asp Leu Asn Gln Thr Pro Gln Thr Thr
                245                 250                 255
Leu Pro Gln Leu Phe Leu Lys Val Gly Glu Pro Leu Trp Ile Arg Cys
            260                 265                 270
Lys Ala Val His Val Asn His Gly Phe Gly Leu Thr Trp Glu Leu Glu
        275                 280                 285
Asn Lys Ala Leu Glu Glu Gly Asn Tyr Phe Glu Met Ser Thr Tyr Ser
    290                 295                 300
Thr Asn Arg Thr Met Ile Arg Ile Leu Phe Ala Phe Val Ser Ser Val
305                 310                 315                 320
Ala Arg Asn Asp Thr Gly Tyr Tyr Thr Cys Ser Ser Ser Lys His Pro
                325                 330                 335
Ser Gln Ser Ala Leu Val Thr Ile Val Glu Lys Gly Phe Ile Asn Ala
            340                 345                 350
Thr Asn Ser Ser Glu Asp Tyr Glu Ile Asp Gln Tyr Glu Glu Phe Cys
        355                 360                 365
Phe Ser Val Arg Phe Lys Ala Tyr Pro Gln Ile Arg Cys Thr Trp Thr
    370                 375                 380
Phe Ser Arg Lys Ser Phe Pro Cys Glu Gln Lys Gly Leu Asp Asn Gly
385                 390                 395                 400
Tyr Ser Ile Ser Lys Phe Cys Asn His Lys His Gln Pro Gly Glu Tyr
                405                 410                 415
Ile Phe His Ala Glu Asn Asp Asp Ala Gln Phe Thr Lys Met Phe Thr
            420                 425                 430
Leu Asn Ile Arg Arg Lys Pro Gln Val Leu Ala Glu Ala Ser Ala Ser
        435                 440                 445
Gln Ala Ser Cys Phe Ser Asp Gly Tyr Pro Leu Pro Ser Trp Thr Trp
    450                 455                 460
Lys Lys Cys Ser Asp Lys Ser Pro Asn Cys Thr Glu Glu Ile Thr Glu
465                 470                 475                 480
Gly Val Trp Asn Arg Lys Ala Asn Arg Lys Val Phe Gly Gln Trp Val
                485                 490                 495
Ser Ser Ser Thr Leu Asn Met Ser Glu Ala Ile Lys Gly Phe Leu Val
            500                 505                 510
Lys Cys Cys Ala Tyr Asn Ser Leu Gly Thr Ser Cys Glu Thr Ile Leu
        515                 520                 525
Leu Asn Ser Pro Gly Pro Phe Pro Phe Ile Gln Asp Asn Ile Ser Phe
    530                 535                 540
Tyr Ala Thr Ile Gly Val Cys Leu Leu Phe Ile Val Val Leu Thr Leu
545                 550                 555                 560
Leu Ile Cys His Lys Tyr Lys Lys Gln Phe Arg Tyr Glu Ser Gln Leu
                565                 570                 575
Gln Met Val Gln Val Thr Gly Ser Ser Asp Asn Glu Tyr Phe Tyr Val
```

-continued

Asp Phe Arg Glu Tyr Glu Tyr Asp Leu Lys Trp Glu Phe Pro Arg Glu
         580                 585                 590
Asn Leu Glu Phe Gly Lys Val Leu Gly Ser Gly Ala Phe Gly Lys Val
    595                 600                 605
Met Asn Ala Thr Ala Tyr Gly Ile Ser Lys Thr Gly Val Ser Ile Gln
610                 615                 620
625                 630                 635                 640
Val Ala Val Lys Met Leu Lys Glu Lys Ala Asp Ser Ser Glu Arg Glu
                645                 650                 655
Ala Leu Met Ser Glu Leu Lys Met Met Thr Gln Leu Gly Ser His Glu
            660                 665                 670
Asn Ile Val Asn Leu Leu Gly Ala Cys Thr Leu Ser Gly Pro Ile Tyr
        675                 680                 685
Leu Ile Phe Glu Tyr Cys Cys Tyr Gly Asp Leu Leu Asn Tyr Leu Arg
    690                 695                 700
Ser Lys Arg Glu Lys Phe His Arg Thr Trp Thr Glu Ile Phe Lys Glu
705                 710                 715                 720
His Asn Phe Ser Phe Tyr Pro Thr Phe Gln Ser His Pro Asn Ser Ser
                725                 730                 735
Met Pro Gly Ser Arg Glu Val Gln Ile His Pro Asp Ser Asp Gln Ile
            740                 745                 750
Ser Gly Leu His Gly Asn Ser Phe His Ser Glu Asp Glu Ile Glu Tyr
        755                 760                 765
Glu Asn Gln Lys Arg Leu Glu Glu Glu Asp Leu Asn Val Leu Thr
    770                 775                 780
Phe Glu Asp Leu Leu Cys Phe Ala Tyr Gln Val Ala Lys Gly Met Glu
785                 790                 795                 800
Phe Leu Glu Phe Lys Ser Cys Val His Arg Asp Leu Ala Ala Arg Asn
                805                 810                 815
Val Leu Val Thr His Gly Lys Val Lys Ile Cys Asp Phe Gly Leu
            820                 825                 830
Ala Arg Asp Ile Met Ser Asp Ser Asn Tyr Val Val Arg Gly Asn Ala
        835                 840                 845
Arg Leu Pro Val Lys Trp Met Ala Pro Glu Ser Leu Phe Glu Gly Ile
    850                 855                 860
Tyr Thr Ile Lys Ser Asp Val Trp Ser Tyr Gly Ile Leu Leu Trp Glu
865                 870                 875                 880
Ile Phe Ser Leu Gly Val Asn Pro Tyr Pro Gly Ile Pro Val Asp Ala
                885                 890                 895
Asn Phe Tyr Lys Leu Ile Gln Asn Gly Phe Lys Met Asp Gln Pro Phe
            900                 905                 910
Tyr Ala Thr Glu Glu Ile Tyr Ile Ile Met Gln Ser Cys Trp Ala Phe
        915                 920                 925
Asp Ser Arg Lys Arg Pro Ser Phe Pro Asn Leu Thr Ser Phe Leu Gly
    930                 935                 940
Cys Gln Leu Ala Asp Ala Glu Glu Ala Met Tyr Gln Asn Val Asp Gly
945                 950                 955                 960
Arg Val Ser Glu Cys Pro His Thr Tyr Gln Asn Arg Arg Pro Phe Ser
                965                 970                 975
Arg Glu Met Asp Leu Gly Leu Leu Ser Pro Gln Ala Gln Val Glu Asp
            980                 985                 990
Ser

<210> SEQ ID NO 73
<211> LENGTH: 364
<212> TYPE: PRT
<213> ORGANISM: murine
<220> FEATURE:
<223> OTHER INFORMATION: CD33 antigen

<400> SEQUENCE: 73

```
Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360
```

```
<210> SEQ ID NO 74
<211> LENGTH: 193
<212> TYPE: PRT
<213> ORGANISM: murine
<220> FEATURE:
<223> OTHER INFORMATION: CD70 antigen

<400> SEQUENCE: 74

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 75
<211> LENGTH: 943
<212> TYPE: PRT
<213> ORGANISM: murine
<220> FEATURE:
<223> OTHER INFORMATION: EGFRvIII

<400> SEQUENCE: 75

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110
```

```
Ser Phe Thr His Thr Pro Pro Leu Asp Pro Gln Glu Leu Asp Ile Leu
            115                 120                 125
Lys Thr Val Lys Glu Ile Thr Gly Phe Leu Leu Ile Gln Ala Trp Pro
130                 135                 140
Glu Asn Arg Thr Asp Leu His Ala Phe Glu Asn Leu Glu Ile Ile Arg
145                 150                 155                 160
Gly Arg Thr Lys Gln His Gly Gln Phe Ser Leu Ala Val Val Ser Leu
                165                 170                 175
Asn Ile Thr Ser Leu Gly Leu Arg Ser Leu Lys Glu Ile Ser Asp Gly
            180                 185                 190
Asp Val Ile Ile Ser Gly Asn Lys Asn Leu Cys Tyr Ala Asn Thr Ile
            195                 200                 205
Asn Trp Lys Lys Leu Phe Gly Thr Ser Gly Gln Lys Thr Lys Ile Ile
210                 215                 220
Ser Asn Arg Gly Glu Asn Ser Cys Lys Ala Thr Gly Gln Val Cys His
225                 230                 235                 240
Ala Leu Cys Ser Pro Glu Gly Cys Trp Gly Pro Glu Pro Arg Asp Cys
                245                 250                 255
Val Ser Cys Arg Asn Val Ser Arg Gly Arg Glu Cys Val Asp Lys Cys
            260                 265                 270
Asn Leu Leu Glu Gly Glu Pro Arg Glu Phe Val Glu Asn Ser Glu Cys
            275                 280                 285
Ile Gln Cys His Pro Glu Cys Leu Pro Gln Ala Met Asn Ile Thr Cys
            290                 295                 300
Thr Gly Arg Gly Pro Asp Asn Cys Ile Gln Cys Ala His Tyr Ile Asp
305                 310                 315                 320
Gly Pro His Cys Val Lys Thr Cys Pro Ala Gly Val Met Gly Glu Asn
                325                 330                 335
Asn Thr Leu Val Trp Lys Tyr Ala Asp Ala Gly His Val Cys His Leu
            340                 345                 350
Cys His Pro Asn Cys Thr Tyr Gly Cys Thr Gly Pro Gly Leu Glu Gly
            355                 360                 365
Cys Pro Thr Asn Gly Pro Lys Ile Pro Ser Ile Ala Thr Gly Met Val
370                 375                 380
Gly Ala Leu Leu Leu Leu Leu Val Val Ala Leu Gly Ile Gly Leu Phe
385                 390                 395                 400
Met Arg Arg Arg His Ile Val Arg Lys Arg Thr Leu Arg Arg Leu Leu
                405                 410                 415
Gln Glu Arg Glu Leu Val Glu Pro Leu Thr Pro Ser Gly Glu Ala Pro
            420                 425                 430
Asn Gln Ala Leu Leu Arg Ile Leu Lys Glu Thr Glu Phe Lys Lys Ile
            435                 440                 445
Lys Val Leu Gly Ser Gly Ala Phe Gly Thr Val Tyr Lys Gly Leu Trp
450                 455                 460
Ile Pro Glu Gly Glu Lys Val Lys Ile Pro Val Ala Ile Lys Glu Leu
465                 470                 475                 480
Arg Glu Ala Thr Ser Pro Lys Ala Asn Lys Glu Ile Leu Asp Glu Ala
                485                 490                 495
Tyr Val Met Ala Ser Val Asp Asn Pro His Val Cys Arg Leu Leu Gly
            500                 505                 510
Ile Cys Leu Thr Ser Thr Val Gln Leu Ile Thr Gln Leu Met Pro Phe
            515                 520                 525
Gly Cys Leu Leu Asp Tyr Val Arg Glu His Lys Asp Asn Ile Gly Ser
```

-continued

```
            530                 535                 540
Gln Tyr Leu Leu Asn Trp Cys Val Gln Ile Ala Lys Gly Met Asn Tyr
545                 550                 555                 560

Leu Glu Asp Arg Arg Leu Val His Arg Asp Leu Ala Ala Arg Asn Val
                565                 570                 575

Leu Val Lys Thr Pro Gln His Val Lys Ile Thr Asp Phe Gly Leu Ala
            580                 585                 590

Lys Leu Leu Gly Ala Glu Glu Lys Glu Tyr His Ala Glu Gly Gly Lys
        595                 600                 605

Val Pro Ile Lys Trp Met Ala Leu Glu Ser Ile Leu His Arg Ile Tyr
    610                 615                 620

Thr His Gln Ser Asp Val Trp Ser Tyr Gly Val Thr Val Trp Glu Leu
625                 630                 635                 640

Met Thr Phe Gly Ser Lys Pro Tyr Asp Gly Ile Pro Ala Ser Glu Ile
                645                 650                 655

Ser Ser Ile Leu Glu Lys Gly Glu Arg Leu Pro Gln Pro Ile Cys
            660                 665                 670

Thr Ile Asp Val Tyr Met Ile Met Val Lys Cys Trp Met Ile Asp Ala
        675                 680                 685

Asp Ser Arg Pro Lys Phe Arg Glu Leu Ile Ile Glu Phe Ser Lys Met
690                 695                 700

Ala Arg Asp Pro Gln Arg Tyr Leu Val Ile Gln Gly Asp Glu Arg Met
705                 710                 715                 720

His Leu Pro Ser Pro Thr Asp Ser Asn Phe Tyr Arg Ala Leu Met Asp
                725                 730                 735

Glu Glu Asp Met Asp Asp Val Val Asp Ala Asp Glu Tyr Leu Ile Pro
            740                 745                 750

Gln Gln Gly Phe Phe Ser Ser Pro Ser Thr Ser Arg Thr Pro Leu Leu
        755                 760                 765

Ser Ser Leu Ser Ala Thr Ser Asn Asn Ser Thr Val Ala Cys Ile Asp
    770                 775                 780

Arg Asn Gly Leu Gln Ser Cys Pro Ile Lys Glu Asp Ser Phe Leu Gln
785                 790                 795                 800

Arg Tyr Ser Ser Asp Pro Thr Gly Ala Leu Thr Glu Asp Ser Ile Asp
                805                 810                 815

Asp Thr Phe Leu Pro Val Pro Glu Tyr Ile Asn Gln Ser Val Pro Lys
            820                 825                 830

Arg Pro Ala Gly Ser Val Gln Asn Pro Val Tyr His Asn Gln Pro Leu
        835                 840                 845

Asn Pro Ala Pro Ser Arg Asp Pro His Tyr Gln Asp Pro His Ser Thr
    850                 855                 860

Ala Val Gly Asn Pro Glu Tyr Leu Asn Thr Val Gln Pro Thr Cys Val
865                 870                 875                 880

Asn Ser Thr Phe Asp Ser Pro Ala His Trp Ala Gln Lys Gly Ser His
                885                 890                 895

Gln Ile Ser Leu Asp Asn Pro Asp Tyr Gln Gln Asp Phe Phe Pro Lys
            900                 905                 910

Glu Ala Lys Pro Asn Gly Ile Phe Lys Gly Ser Thr Ala Glu Asn Ala
        915                 920                 925

Glu Tyr Leu Arg Val Ala Pro Gln Ser Ser Glu Phe Ile Gly Ala
    930                 935                 940

<210> SEQ ID NO 76
```

```
<211> LENGTH: 497
<212> TYPE: PRT
<213> ORGANISM: murine
<220> FEATURE:
<223> OTHER INFORMATION: WT1

<400> SEQUENCE: 76
```

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
        115                 120                 125

Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly His Ser Thr
305                 310                 315                 320

Gly Tyr Glu Ser Asp Asn His Thr Thr Pro Ile Leu Cys Gly Ala Gln
                325                 330                 335

Tyr Arg Ile His Thr His Gly Val Phe Arg Gly Ile Gln Asp Val Arg
            340                 345                 350

Arg Val Pro Gly Val Ala Pro Thr Leu Val Arg Ser Ala Ser Glu Thr
        355                 360                 365

Ser Glu Lys Arg Pro Phe Met Cys Ala Tyr Pro Gly Cys Asn Lys Arg
    370                 375                 380

```
Tyr Phe Lys Leu Ser His Leu Gln Met His Ser Arg Lys His Thr Gly
385                 390                 395                 400

Glu Lys Pro Tyr Gln Cys Asp Phe Lys Asp Cys Glu Arg Phe Ser
            405                 410                 415

Arg Ser Asp Gln Leu Lys Arg His Gln Arg Arg His Thr Gly Val Lys
            420                 425                 430

Pro Phe Gln Cys Lys Thr Cys Gln Arg Lys Phe Ser Arg Ser Asp His
            435                 440                 445

Leu Lys Thr His Thr Arg Thr His Thr Gly Glu Lys Pro Phe Ser Cys
450                 455                 460

Arg Trp Pro Ser Cys Gln Lys Lys Phe Ala Arg Ser Asp Glu Leu Val
465                 470                 475                 480

Arg His His Asn Met His Gln Arg Asn Met Thr Lys Leu Gln Leu Ala
                485                 490                 495

Leu
```

<210> SEQ ID NO 77
<211> LENGTH: 671
<212> TYPE: PRT
<213> ORGANISM: artificial sequence
<220> FEATURE:
<223> OTHER INFORMATION: pCLS23856:anti-CD19 CAR

<400> SEQUENCE: 77

```
Met Leu Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
            35                  40                  45

Thr Asn Val Ser Pro Ala Lys Pro Thr Thr Thr Ala Cys Pro Tyr Ser
50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
            115                 120                 125

Gly Val Leu Leu Leu Ser Leu Val Ile Thr Leu Tyr Cys Asn His Arg
130                 135                 140

Asn Arg Arg Arg Val Cys Lys Cys Pro Arg Pro Val Val Arg Ala Glu
145                 150                 155                 160

Gly Arg Gly Ser Leu Leu Thr Cys Gly Asp Val Glu Glu Asn Pro Gly
                165                 170                 175

Pro Met Glu Thr Asp Thr Leu Leu Leu Trp Val Leu Leu Leu Trp Val
            180                 185                 190

Pro Gly Ser Thr Gly Asp Ile Gln Met Thr Gln Thr Thr Ser Ser Leu
            195                 200                 205

Ser Ala Ser Leu Gly Asp Arg Val Thr Ile Ser Cys Arg Ala Ser Gln
210                 215                 220

Asp Ile Ser Lys Tyr Leu Asn Trp Tyr Gln Gln Lys Pro Asp Gly Thr
225                 230                 235                 240
```

```
Val Lys Leu Leu Ile Tyr His Thr Ser Arg Leu His Ser Gly Val Pro
                245                 250                 255

Ser Arg Phe Ser Gly Ser Gly Ser Gly Thr Asp Tyr Ser Leu Thr Ile
            260                 265                 270

Ser Asn Leu Glu Gln Glu Asp Ile Ala Thr Tyr Phe Cys Gln Gln Gly
        275                 280                 285

Asn Thr Leu Pro Tyr Thr Phe Gly Gly Gly Thr Lys Leu Glu Ile Thr
    290                 295                 300

Lys Ala Gly Gly Gly Ser Gly Gly Gly Ser Gly Gly Gly Gly
305                 310                 315                 320

Ser Gly Gly Gly Ser Glu Val Lys Leu Gln Glu Ser Gly Pro Gly
            325                 330                 335

Leu Val Ala Pro Ser Gln Ser Leu Ser Val Thr Cys Thr Val Ser Gly
            340                 345                 350

Val Ser Leu Pro Asp Tyr Gly Val Ser Trp Ile Arg Gln Pro Pro Arg
        355                 360                 365

Lys Gly Leu Glu Trp Leu Gly Val Ile Trp Gly Ser Glu Thr Thr Tyr
    370                 375                 380

Tyr Asn Ser Ala Leu Lys Ser Arg Leu Thr Ile Ile Lys Asp Asn Ser
385                 390                 395                 400

Lys Ser Gln Val Phe Leu Lys Met Asn Ser Leu Gln Thr Asp Asp Thr
            405                 410                 415

Ala Ile Tyr Tyr Cys Ala Lys His Tyr Tyr Gly Gly Ser Tyr Ala
            420                 425                 430

Met Asp Tyr Trp Gly Gln Gly Thr Ser Val Thr Val Ser Ser Asp Pro
    435                 440                 445

Thr Thr Thr Pro Ala Pro Arg Pro Pro Thr Pro Ala Pro Thr Ile Ala
    450                 455                 460

Ser Gln Pro Leu Ser Leu Arg Pro Glu Ala Cys Arg Pro Ala Ala Gly
465                 470                 475                 480

Gly Ala Val His Thr Arg Gly Leu Asp Phe Ala Cys Asp Ile Tyr Ile
            485                 490                 495

Trp Ala Pro Leu Ala Gly Thr Cys Gly Val Leu Leu Leu Ser Leu Val
            500                 505                 510

Ile Thr Leu Tyr Cys Lys Arg Gly Arg Lys Lys Leu Leu Tyr Ile Phe
        515                 520                 525

Lys Gln Pro Phe Met Arg Pro Val Gln Thr Thr Gln Glu Glu Asp Gly
    530                 535                 540

Cys Ser Cys Arg Phe Pro Glu Glu Glu Glu Gly Gly Cys Glu Leu Arg
545                 550                 555                 560

Val Lys Phe Ser Arg Ser Ala Asp Ala Pro Ala Tyr Gln Gln Gly Gln
            565                 570                 575

Asn Gln Leu Tyr Asn Glu Leu Asn Leu Gly Arg Arg Glu Glu Tyr Asp
            580                 585                 590

Val Leu Asp Lys Arg Arg Gly Arg Asp Pro Glu Met Gly Gly Lys Pro
        595                 600                 605

Arg Arg Lys Asn Pro Gln Glu Gly Leu Tyr Asn Glu Leu Gln Lys Asp
    610                 615                 620

Lys Met Ala Glu Ala Tyr Ser Glu Ile Gly Met Lys Gly Glu Arg Arg
625                 630                 635                 640

Arg Gly Lys Gly His Asp Gly Leu Tyr Gln Gly Leu Ser Thr Ala Thr
            645                 650                 655

Lys Asp Thr Tyr Asp Ala Leu His Met Gln Ala Leu Pro Pro Arg
```

<210> SEQ ID NO 78
<211> LENGTH: 665
<212> TYPE: PRT
<213> ORGANISM: MMLV virus
<220> FEATURE:
<223> OTHER INFORMATION: Env protein from MMLV virus

<400> SEQUENCE: 78

```
Met Ala Arg Ser Thr Leu Ser Lys Pro Leu Lys Asn Lys Val Asn Pro
1               5                   10                  15

Arg Gly Pro Leu Ile Pro Leu Ile Leu Leu Met Leu Arg Gly Val Ser
            20                  25                  30

Thr Ala Ser Pro Gly Ser Ser Pro His Gln Val Tyr Asn Ile Thr Trp
        35                  40                  45

Glu Val Thr Asn Gly Asp Arg Glu Thr Ile Trp Ala Ile Ser Gly Asn
    50                  55                  60

His Pro Leu Trp Thr Trp Trp Pro Asp Leu Thr Pro Asp Leu Cys Met
65                  70                  75                  80

Leu Ala His His Gly Pro Ser Tyr Trp Gly Leu Glu Tyr Gln Ser Pro
                85                  90                  95

Phe Ser Ser Pro Pro Gly Pro Pro Cys Cys Ser Gly Gly Ser Ser Pro
            100                 105                 110

Gly Cys Ser Arg Asp Cys Glu Glu Pro Leu Thr Ser Leu Thr Pro Arg
        115                 120                 125

Cys Asn Thr Ala Trp Asn Arg Leu Lys Leu Asp Gln Thr Thr His Lys
130                 135                 140

Ser Asn Glu Gly Phe Tyr Val Cys Pro Gly Pro His Arg Pro Arg Glu
145                 150                 155                 160

Ser Lys Ser Cys Gly Gly Pro Asp Ser Phe Tyr Cys Ala Tyr Trp Gly
                165                 170                 175

Cys Glu Thr Thr Gly Arg Ala Tyr Trp Lys Pro Ser Ser Ala Trp Asp
            180                 185                 190

Phe Ile Thr Val Asn Asn Asn Leu Thr Ser Asp Gln Ala Val Gln Val
        195                 200                 205

Cys Lys Asp Asn Lys Trp Cys Asn Pro Leu Val Ile Arg Phe Thr Asp
210                 215                 220

Ala Gly Arg Arg Val Thr Ser Trp Thr Thr Gly His Tyr Trp Gly Leu
225                 230                 235                 240

Arg Leu Tyr Val Ser Gly Gln Asp Pro Gly Leu Thr Phe Gly Ile Arg
                245                 250                 255

Leu Arg Tyr Gln Asn Leu Gly Pro Arg Val Pro Ile Gly Pro Asn Pro
            260                 265                 270

Val Leu Ala Gly Gln Gln Pro Leu Ser Lys Pro Lys Pro Val Lys Ser
        275                 280                 285

Pro Ser Val Thr Lys Pro Pro Ser Gly Thr Pro Leu Ser Pro Thr Gln
290                 295                 300

Leu Pro Pro Ala Gly Thr Glu Asn Arg Leu Leu Asn Leu Val Asp Gly
305                 310                 315                 320

Ala Tyr Gln Ala Leu Asn Leu Thr Ser Pro Asp Lys Thr Gln Glu Cys
                325                 330                 335

Trp Leu Cys Leu Val Ala Gly Pro Pro Tyr Tyr Glu Gly Val Ala Val
            340                 345                 350

Leu Gly Thr Tyr Ser Asn His Thr Ser Ala Pro Ala Asn Cys Ser Val
```

```
                355                 360                 365
Ala Ser Gln His Lys Leu Thr Leu Ser Glu Val Thr Gly Gln Gly Leu
    370                 375                 380
Cys Ile Gly Ala Val Pro Lys Thr His Gln Ala Leu Cys Asn Thr Thr
385                 390                 395                 400
Gln Thr Ser Ser Arg Gly Pro Tyr Tyr Leu Val Ala Pro Thr Gly Thr
                405                 410                 415
Met Trp Ala Cys Asn Thr Gly Leu Thr Pro Cys Ile Ser Thr Thr Ile
            420                 425                 430
Leu Asn Leu Thr Thr Asp Tyr Cys Val Leu Val Glu Leu Trp Pro Arg
        435                 440                 445
Val Thr Tyr His Ser Pro Ser Tyr Val Tyr Gly Leu Phe Glu Lys Ser
    450                 455                 460
Asn Arg His Lys Arg Glu Pro Val Ser Leu Thr Leu Ala Leu Leu Leu
465                 470                 475                 480
Gly Gly Leu Thr Met Gly Gly Ile Ala Ala Gly Val Gly Thr Gly Thr
                485                 490                 495
Thr Ala Leu Met Ala Thr Gln Gln Phe Gln Gln Leu His Ala Ala Val
            500                 505                 510
Gln Asp Asp Leu Arg Glu Val Glu Lys Ser Ile Ser Asn Leu Glu Lys
        515                 520                 525
Ser Leu Thr Ser Leu Ser Glu Val Val Leu Gln Asn Arg Arg Gly Leu
    530                 535                 540
Asp Leu Leu Phe Leu Lys Glu Gly Gly Leu Cys Ala Ala Leu Lys Glu
545                 550                 555                 560
Glu Cys Cys Phe Tyr Ala Asp His Thr Gly Leu Val Arg Asp Ser Met
                565                 570                 575
Ala Lys Leu Arg Glu Arg Leu Asn Gln Arg Gln Lys Leu Phe Glu Ser
            580                 585                 590
Thr Gln Gly Trp Phe Glu Gly Leu Phe Asn Arg Ser Pro Trp Phe Thr
        595                 600                 605
Thr Leu Ile Ser Thr Ile Met Gly Pro Leu Ile Val Leu Leu Met Ile
    610                 615                 620
Leu Leu Phe Gly Pro Cys Ile Leu Asn Arg Leu Val Gln Phe Val Lys
625                 630                 635                 640
Asp Arg Ile Ser Val Val Gln Ala Leu Val Leu Thr Gln Gln Tyr His
                645                 650                 655
Gln Leu Lys Pro Ile Glu Tyr Glu Pro
            660                 665

<210> SEQ ID NO 79
<211> LENGTH: 229
<212> TYPE: PRT
<213> ORGANISM: MMLV virus
<220> FEATURE:
<223> OTHER INFORMATION: Truncated env protein from MMLV virus

<400> SEQUENCE: 79

Met Ala Arg Ser Thr Leu Ser Lys Pro Leu Lys Asn Lys Val Asn Pro
1               5                   10                  15
Arg Gly Pro Leu Ile Pro Leu Ile Leu Leu Met Leu Arg Gly Val Ser
                20                  25                  30
Arg Glu Pro Val Ser Leu Thr Leu Ala Leu Leu Leu Gly Gly Leu Thr
            35                  40                  45
Met Gly Gly Ile Ala Ala Gly Val Gly Thr Gly Thr Thr Ala Leu Met
```

-continued

```
            50                  55                  60
Ala Thr Gln Gln Phe Gln Gln Leu His Ala Ala Val Gln Asp Asp Leu
65                      70                  75                  80

Arg Glu Val Glu Lys Ser Ile Ser Asn Leu Glu Lys Ser Leu Thr Ser
                85                  90                  95

Leu Ser Glu Val Val Leu Gln Asn Arg Arg Gly Leu Asp Leu Leu Phe
                100                 105                 110

Leu Lys Glu Gly Gly Leu Cys Ala Ala Leu Lys Glu Glu Cys Cys Phe
            115                 120                 125

Tyr Ala Asp His Thr Gly Leu Val Arg Asp Ser Met Ala Lys Leu Arg
        130                 135                 140

Glu Arg Leu Asn Gln Arg Gln Lys Leu Phe Glu Ser Thr Gln Gly Trp
145                 150                 155                 160

Phe Glu Gly Leu Phe Asn Arg Ser Pro Trp Phe Thr Thr Leu Ile Ser
                165                 170                 175

Thr Ile Met Gly Pro Leu Ile Val Leu Leu Met Ile Leu Leu Phe Gly
                180                 185                 190

Pro Cys Ile Leu Asn Arg Leu Val Gln Phe Val Lys Asp Arg Ile Ser
        195                 200                 205

Val Val Gln Ala Leu Val Leu Thr Gln Gln Tyr His Gln Leu Lys Pro
    210                 215                 220

Ile Glu Tyr Glu Pro
225
```